US012558303B2

(12) United States Patent
Harris et al.

(10) Patent No.: US 12,558,303 B2
(45) Date of Patent: Feb. 24, 2026

(54) MANUFACTURE, ISOLATION, PURIFICATION, AND USES OF SMALL PARTICLE SIZE CELLULOSE PARTICLES AND COMPOSITIONS

(71) Applicant: Renmatix, Inc., Wayne, PA (US)

(72) Inventors: Stephen Herbert Harris, Kennett Square, PA (US); Matyas Kosa, Vancouver (CA); Charles Sebastian Sanderson, Wayne, PA (US); Marie Jane Chorley, Beeston (GB); Derek Alexander Carlson, Marietta, GA (US); Jeremy R. Austin, Malvern, PA (US); Konstantinos M. Lahanas, Ramsey, NJ (US); Frederick J. Moesler, Berwyn, PA (US); David Lee Breeden, Missouri City, TX (US); Orlando Jose D'Elia, The Woodlands, TX (US)

(73) Assignee: RENMATIX, INC., Wayne, PA (US)

( * ) Notice: Subject to any disclaimer, the term of this patent is extended or adjusted under 35 U.S.C. 154(b) by 0 days.

(21) Appl. No.: 18/209,925

(22) Filed: Jun. 14, 2023

(65) Prior Publication Data
US 2023/0381086 A1     Nov. 30, 2023

Related U.S. Application Data

(63) Continuation of application No. 16/028,359, filed on Jul. 5, 2018, now abandoned.
(Continued)

(51) Int. Cl.
| | |
|---|---|
| *A61K 8/73* | (2006.01) |
| *A01N 43/16* | (2006.01) |
| *A21D 2/18* | (2006.01) |
| *A21D 13/047* | (2017.01) |
| *A21D 13/066* | (2017.01) |
| *A21D 13/068* | (2017.01) |
(Continued)

(52) U.S. Cl.
CPC .............. *A61K 8/731* (2013.01); *A01N 43/16* (2013.01); *A21D 2/188* (2013.01); *A21D 13/047* (2017.01); *A21D 13/066* (2013.01); *A21D 13/068* (2013.01); *A23D 7/0053* (2013.01); *A23D 7/0056* (2013.01); *A23D 7/015* (2013.01); *A23D 9/007* (2013.01); *A23G 9/34* (2013.01); *A23L 7/109* (2016.08); *A23L 13/422* (2016.08); *A23L 13/426* (2016.08); *A23L 27/60* (2016.08); *A23L 29/262* (2016.08); *A23L 33/10* (2016.08); *A61K 8/0245* (2013.01); *A61K 9/10* (2013.01); *A61K 31/60* (2013.01); *A61K 47/38* (2013.01); *A61P 17/10* (2018.01); *A61Q 17/04* (2013.01); *A61Q 19/00* (2013.01); *A61Q 19/007* (2013.01); *A61Q 19/10* (2013.01); *C10M*

*145/40* (2013.01); *A23V 2002/00* (2013.01); *A61K 2800/10* (2013.01); *A61K 2800/28* (2013.01); *A61K 2800/412* (2013.01); *C10M 2201/02* (2013.01); *C10M 2209/12* (2013.01); *C10N 2020/06* (2013.01); *C10N 2040/20* (2013.01); *C10N 2050/01* (2020.05); *C10N 2050/015* (2020.05); *C10N 2050/10* (2013.01)

(58) Field of Classification Search
None
See application file for complete search history.

(56) References Cited

U.S. PATENT DOCUMENTS

| | | | |
|---|---|---|---|
| 2,781,328 A | 2/1957 | Ayers et al. | |
| 4,652,363 A | 3/1987 | Miller | |
(Continued)

FOREIGN PATENT DOCUMENTS

| | | |
|---|---|---|
| AU | 2013290013 | 1/2017 |
| AU | 2015320328 | 4/2019 |
(Continued)

OTHER PUBLICATIONS

Abdullah et al. (2014) "Hydrothermal decomposition of various crystalline celluloses as treated by semi-flow hot-compressed water," Journal of Wood Science 60: 278-286.
Avicel PH-200. FMC BioPolymer: Certificate of Analysis-Avicel® Microcrystalline Cellulose, NF, Ph. Eur, JP. FMC International (1 page).
Avicel® PH-200—Microcrystalline Cellulose NF, Ph. Eur., JP. Product Specification Bulletin. FMC International: FMC BioPolymer (2 pages).
Avicel® RC-591—Microcrystalline Cellulose and Carboxymethylcellulose Sodium, NF, BP. Pharmaceutical Emulsions and Suspensions: Stabilization Technology for Liquid and Semi-Solid Dosage Forms. FMC International: FMC BioPolymer (1994) (20 pages).
(Continued)

*Primary Examiner* — David J Blanchard
*Assistant Examiner* — Sarah J Chickos
(74) *Attorney, Agent, or Firm* — Ballard Spahr LLP

(57) ABSTRACT
This invention relates to compositions comprising cellulose particles and methods for making and using same. This invention also relates to compositions comprising a fluid and particles comprising cellulose. Thus, disclosed herein are methods of manufacture, isolation, purification, and handling of cellulose particles. Also disclosed are uses for cellulose particles as additives in leavened or leavenable food products, or in an emulsion or emulsifiable product, or as a suspension aid, or in a thickened composition, or in a meat or meat analog product, or in a personal care formulation, or in a beauty formulation, or in a cosmetic formulation, or in a skin care formulation. Also disclosed are uses for cellulose particles in subterranean treatment compositions. Also disclosed are uses for cellulose particles in metal working compositions, cutting compositions, and stamping compositions. Also disclosed herein are resuspendable particles comprising cellulose. This abstract is intended as a scanning tool for purposes of searching in the particular art and is not intended to be limiting of the present invention.

22 Claims, 17 Drawing Sheets

Related U.S. Application Data

(60) Provisional application No. 62/671,026, filed on May 14, 2018, provisional application No. 62/628,443, filed on Feb. 9, 2018, provisional application No. 62/587,472, filed on Nov. 16, 2017, provisional application No. 62/528,838, filed on Jul. 5, 2017.

(51) Int. Cl.

| | |
|---|---|
| *A23D 7/005* | (2006.01) |
| *A23D 7/015* | (2006.01) |
| *A23D 9/007* | (2006.01) |
| *A23G 9/34* | (2006.01) |
| *A23L 7/109* | (2016.01) |
| *A23L 13/40* | (2023.01) |
| *A23L 27/60* | (2016.01) |
| *A23L 29/262* | (2016.01) |
| *A23L 33/10* | (2016.01) |
| *A61K 8/02* | (2006.01) |
| *A61K 9/10* | (2006.01) |
| *A61K 31/60* | (2006.01) |
| *A61K 47/38* | (2006.01) |
| *A61P 17/10* | (2006.01) |
| *A61Q 17/04* | (2006.01) |
| *A61Q 19/00* | (2006.01) |
| *A61Q 19/10* | (2006.01) |
| *C10M 145/40* | (2006.01) |
| *C10N 20/06* | (2006.01) |
| *C10N 40/20* | (2006.01) |
| *C10N 50/00* | (2006.01) |
| *C10N 50/10* | (2006.01) |

(56) References Cited

U.S. PATENT DOCUMENTS

| | | | |
|---|---|---|---|
| 4,946,953 | A | 8/1990 | Okuma et al. |
| 5,104,520 | A | 4/1992 | Maronde et al. |
| 5,123,962 | A | 6/1992 | Komuro et al. |
| 5,413,802 | A | 5/1995 | Baumanis et al. |
| 6,921,820 | B2 | 7/2005 | Arai et al. |
| 7,144,972 | B2 | 12/2006 | Hayes |
| 7,507,474 | B2 | 3/2009 | Varlet et al. |
| 7,901,663 | B2 | 3/2011 | Lenglet |
| 7,955,508 | B2 | 6/2011 | Allan et al. |
| 8,057,639 | B2 | 11/2011 | Pschorn et al. |
| 8,075,629 | B2 | 12/2011 | Pschorn et al. |
| 8,282,738 | B2 | 10/2012 | Kilambi |
| 8,372,899 | B2 | 2/2013 | Kotzev et al. |
| 8,729,325 | B2 | 5/2014 | Powell |
| 8,747,561 | B2 | 6/2014 | Tao |
| 8,999,065 | B2 | 4/2015 | Vitalyevich et al. |
| 9,169,523 | B2 | 10/2015 | Vitalyevich et al. |
| 9,399,782 | B2 | 7/2016 | Smith et al. |
| 10,385,140 | B2 | 8/2019 | Capanema et al. |
| 11,440,974 | B2 | 9/2022 | Capanema et al. |
| 2002/0172650 | A1 | 11/2002 | Cannell et al. |
| 2003/0017187 | A1 | 1/2003 | Brode et al. |
| 2003/0018187 | A1 | 1/2003 | Arai et al. |
| 2004/0074615 | A1 | 4/2004 | Nguyen |
| 2007/0093654 | A1 | 4/2007 | Yabusaki |
| 2007/0148750 | A1 | 6/2007 | Hoshino et al. |
| 2007/0196471 | A1 | 8/2007 | Thosar et al. |
| 2009/0221814 | A1 | 9/2009 | Pschorn et al. |
| 2010/0043782 | A1 | 2/2010 | Kilambi et al. |
| 2010/0048884 | A1 | 2/2010 | Kilambi |
| 2010/0063271 | A1 | 3/2010 | Allan et al. |
| 2010/0069626 | A1 | 3/2010 | Kilambi |
| 2010/0170504 | A1 | 7/2010 | Zhang |
| 2010/0206499 | A1 | 8/2010 | Lasonde et al. |
| 2010/0285295 | A1 | 11/2010 | Wang et al. |
| 2011/0182990 | A1 | 7/2011 | Su et al. |
| 2011/0219679 | A1 | 9/2011 | Budarin et al. |

| | | | |
|---|---|---|---|
| 2012/0100585 | A1 | 4/2012 | Ropars et al. |
| 2012/0108127 | A1 | 5/2012 | Yuan et al. |
| 2012/0108798 | A1 | 5/2012 | Wenger et al. |
| 2012/0145094 | A1 | 6/2012 | Simard |
| 2012/0205059 | A1 | 8/2012 | Senturk-Ozer et al. |
| 2012/0285445 | A1 | 11/2012 | Kilambi et al. |
| 2012/0291774 | A1 | 11/2012 | Kilambi et al. |
| 2013/0115358 | A1 | 5/2013 | Seeley et al. |
| 2013/0172546 | A1 | 7/2013 | Floyd et al. |
| 2013/0172547 | A1 | 7/2013 | Floyd et al. |
| 2013/0239954 | A1 | 9/2013 | Kilambi et al. |
| 2014/0014092 | A1 | 1/2014 | Kazachkin et al. |
| 2014/0039144 | A1 | 2/2014 | Simard et al. |
| 2014/0134219 | A1* | 5/2014 | Bonner ............... A61Q 19/10 |
| | | | 424/401 |
| 2014/0200335 | A1 | 7/2014 | Olkowski et al. |
| 2014/0275501 | A1 | 9/2014 | Capanema et al. |
| 2015/0176091 | A1 | 6/2015 | Kazachkin et al. |
| 2015/0191499 | A1 | 7/2015 | Floyd et al. |
| 2015/0191500 | A1 | 7/2015 | Floyd et al. |
| 2015/0291786 | A1 | 10/2015 | Sumnicht et al. |
| 2015/0320057 | A1 | 11/2015 | Cha et al. |
| 2016/0108182 | A1 | 4/2016 | Kilambi et al. |
| 2016/0244852 | A1 | 8/2016 | Kilambi et al. |
| 2016/0319186 | A1 | 11/2016 | Chopade et al. |
| 2017/0275385 | A1 | 9/2017 | Capanema et al. |
| 2018/0142071 | A1 | 5/2018 | Ju et al. |
| 2019/0008749 | A1 | 1/2019 | Harris et al. |

FOREIGN PATENT DOCUMENTS

| | | |
|---|---|---|
| CA | 2816250 | 5/2012 |
| CA | 2962606 C | 3/2016 |
| CA | 3068830 | 2/2024 |
| CN | 101395320 A | 3/2009 |
| CN | 101787398 | 7/2010 |
| CN | 102388144 | 3/2012 |
| CN | 104817836 | 8/2015 |
| CN | 106010155 | 10/2015 |
| CN | 104592753 | 3/2017 |
| CN | 104592753 B | 3/2017 |
| CN | 107074981 | 8/2017 |
| CN | 104411830 | 3/2020 |
| EP | 0 425 477 A2 | 5/1991 |
| EP | 0 537 554 A2 | 4/1993 |
| EP | 1547170 A1 | 6/2005 |
| EP | 2042519 | 4/2009 |
| EP | 2872643 | 5/2015 |
| EP | 2949707 | 12/2015 |
| EP | 3186286 | 7/2017 |
| GB | 1003537 A | 9/1965 |
| IN | 51/2015 | 12/2015 |
| JP | 2000-127152 A | 5/2000 |
| JP | 2001262162 | 9/2001 |
| JP | 2002233400 | 8/2002 |
| JP | 2003213037 A | 7/2003 |
| JP | 2004121055 | 4/2004 |
| JP | 2006136263 | 6/2006 |
| JP | 2007163574 | 6/2007 |
| JP | 2008248202 A | 10/2008 |
| JP | 2010531668 | 9/2010 |
| JP | 2011032388 | 2/2011 |
| JP | 2012201767 A | 10/2012 |
| KR | 2015-0036368 | 4/2015 |
| KR | 10-2571674 | 8/2023 |
| MY | 168280 A | 10/2018 |
| NZ | 628964 | 11/2016 |
| PH | 1-2015-500040 | 8/2019 |
| RU | 2651509 | 4/2019 |
| SG | 201400907.0 | 8/2017 |
| WO | WO 1999/028350 | 6/1999 |
| WO | WO 2009/003167 A1 | 12/2008 |
| WO | WO 2010/113129 | 10/2010 |
| WO | WO 2011/091044 | 7/2011 |
| WO | WO-2011/091044 A1 | 7/2011 |
| WO | WO 2012/060767 | 5/2012 |
| WO | WO 2012/106808 | 8/2012 |
| WO | WO 2013/070160 | 5/2013 |
| WO | WO-2013/101397 A1 | 7/2013 |

(56) References Cited

FOREIGN PATENT DOCUMENTS

| WO | WO-2013/101402 A1 | 7/2013 | |
| WO | WO-2013/101403 A1 | 7/2013 | |
| WO | WO-2013/165308 A1 | 11/2013 | |
| WO | WO 2014/012030 | 1/2014 | |
| WO | WO-2014/012030 A1 | 1/2014 | |
| WO | WO 2014/089170 A1 | 6/2014 | |
| WO | WO-2014/144746 A1 | 9/2014 | |
| WO | WO-2015/104459 A1 | 7/2015 | |
| WO | WO-2015179072 A1 * | 11/2015 | ............ A61K 47/38 |
| WO | WO 2015/199482 A1 | 12/2015 | |
| WO | WO-2016/049564 A1 | 3/2016 | |
| WO | WO-2016/049567 A1 | 3/2016 | |
| WO | WO-2016/049569 A1 | 3/2016 | |
| WO | WO 2019/010336 | 1/2019 | |
| WO | WO 2019/195033 | 10/2019 | |
| ZA | 2015/00209 | 10/2016 | |

OTHER PUBLICATIONS

Beaumont, M. et al., A Nanostructured Cellulose II Gel Consisting of Spherical Particles. ACS Sustainable Chem Eng. 2016; pp. 1-26 (27 pages).

Benavides, E.E.U., Cellulose Nanocrystals Properties and Applications in Renewable Nanocomposites. Doctoral Thesis. Graduate School of Clemson University: Chemical Engineering (2011) (197 pages).

Boussaid, et al. (2001) "Sugar recovery and fermentability of hemicellulose hydrolysates from steam-exploded softwoods containing bark," Biotechnol. Prog. 17: 887-892.

Buffiere, J., Cellulose Dissolution in Near- and Supercritical Water for Cello-Oligosaccharides Production. Master's Thesis. Aalto University School of Chemical Technology (2014) (95 pages).

Demirbas, et al. (2010) "Sub- and super-critical water depolymerization of biomass," Energy Sources, Part A: Recovery, Utilization, and Environmental Effects 32(12): 1100-1110.

DuPont, A.L., Cellulose in Lithium Chloride/N,N-dimethylacetamide, Optimization of a Dissolution Method Using Paper Substrates and Stability of the Solutions. Polymer. 2003; 44:4117-26.

Ehara, et al. (2002) "Characterization of the lignin-derived products from wood as treated in supercritical water," Journal of Wood Science 48(4): 320-325.

El Seoud, O.A. et al., Chemistry and Applications of Polysaccharide Solutions in Strong Electrolytes/Dipolar Aprotic Solvents: An Overview. Molecules. 2013; 18:1270-313.

Galkin, et al. (2005) "Subcritical and supercritical water: a universal medium for chemical reactions," Russian Chemical Reviews 7491: 21-35.

Graczyk, et al. (1990) "Explosion puling of lignocellulosic materials. Effect of steam explosion on plant raw materials and their constituents," Przelad Papierniczy, 46(12): 413-418.

Habibi, Y. et al., Cellulose Nanocrystals: Chemistry, Self-Assembly, and Applications. Chem Rev. 2010; 110(6): 3479-500.

Hennings, U. et al., Dissolution Behavior of Different Celluloses. Biomacromolecules. 2011; 12:871-9.

Jeoh (1998) "Steam Explosion Pretreatment of Cotton Gin Waste for Fuel Ethanol Produciton," Thesis submitted to the Faculty of the Virginia Polytechnic Institute and State University, Dec. 1998, pp. 1-153.

Li et al. (2014) "Preparation and characterization of cellulose nanofibers from partly mercerized cotton by mixed acid hydrolysis," Cellulose 21: 301-309.

Maache-Rezzoug, et al. (2009) "A thermomechanical pretreatment to improve enzymatic hydrolysis of wheat straw," Recents Progres en Genie des Procedes, No. 98.

Masuelli, Mark-Houwink Parameters for Aqueous-Soluble Polymers and Biopolymers at Various Temperatures. J Polymer Biopolymer Physics Chem. 2014; 2(2):37-43.

Matsunga, M. et al., Chemical Conversion of Wood by Treatment in a Semi-Batch Reactor with Subcritical Water. J Supercritical Fluids. 2008; 44:364-9.

Newman, R.H. and T.C. Davidson, Molecular Conformations at the Cellulose-Water Interface. Cellulose. 2004; 11:23-32.

Pilla, et al. (2011) Handbook of bioplastics and biocomposites engineering applications, p. 465.

Potthast, A. et al., A Novel Method for the Determination of Carbonyl Groups in Cellulosics by Fluoresence labeling. 3. Monitoring Oxidative Processes. Biomacromolecules. 2003; 4:743-9.

Potthast, A. et al., Comparison Testing of Methods for Gel Permeation Chromatography of Cellulose: Coming Closer to a Standard Protocol. Cellulose. 2015; 22(3):1591-613.

Reier, G.E., Avicel® PH Microcrystalline Cellulose, NF, Ph Eur., JP, BP. Section 11. FMC International (2000) (27 pages).

Röhrling et al., A Novel Method for the Determination of Carbonyl Groups in Cellulosics by Fluorescence Labeling. 1. Method Development. Biomacromolecules. 2002; 3:959-68.

Röhrling et al., A Novel Method for the Determination of Carbonyl Groups in Cellulosics by Fluorescence Labeling. 2. Validation and Application. Biomacromolecules. 2002; 3:969-75.

Rosnah Abdullah, "Hydrothermal decomposition of various crystalline celluloses as treated by semitflow hottcompressed Water",]ournal of Wood Science, vol. 60, pp. 278-286.

Sasaki, et al. (2000) "Dissolution and Hydrolysis of Cellulose in Subcritical and Supercritical Water," Industrial & Engineering Chemistry Research 39(8): 2883-2890.

Sasaki, et al. (2012) "Direct hydrolysis of cellulose to glucose using ultra-high temperature and pressure steam explosion," Carbohydrate Polymers 89: 298-301.

Sasaki, M. et al., Kinetics of Cellulose Conversion at 25 MPa in Sub- and Supercritical Water. Amer Inst Chem Eng. 2004; 50(1):192-202.

Sasaki, M. et al., Production of Cellulose II from Native Cellulose by Near- and Supercritical Water Solubilization. J Agric Food Chem. 2003; 51:5376-81.

Sasaki, M. et al., Rapid and Selective Conversion of Cellulose to Valuable Chemical Intermediates with Supercritical Water. Proc. 6th International Symposium on Supercritical Fluids. 2003; Tome 2:1417-22.

Savage, et al. (1995) "Reactions at supercritical conditions: applications and fundamentals," AIChE Journal 41(7): 1723-78.

Savage, et al. (1999) "Organic chemical reactions in supercritical water," Chemical Reviews (Washington, D.C.) 99(2): 603-621.

Segal, L. et al., An Empirical Method for Estimating the Degree of Crystallinity of Native Cellulose Using the X-Ray Diffractometer. Tex Res J. 1962; 29:786-94 (Abstract; 2 pages).

Terinte, N. et al., Overview on Native Cellulose and Microcrystalline Cellulose I Structure Studied by X-Ray Diffraction (WAXD): Comparison Between Measurement Techniques. Lenzinger Berichte. 2011; 89:118-31.

Tolonen, L.K. et al., Supercritical Water Treatment for Cello-Oligosaccharide Production from Microcrystalline Cellulose. Carbohydr Res. 2015; 401:16-23.

Ververis, et al. (2004) "Fiber dimensions, lignin and cellulose content of various plant materials and their suitability for paper productions," Industrial crops and products 19: 245-254.

Wang, et al. (2009) "Influence of steaming explosion time on the physic-chemical properties of cellulose from Lespedeza stalks (Lespedeza crytobotrya)," Bioresource Technology 100: 5288-5294.

Wang, et al. (2009) "Influence of steaming time during steam-explosion on the chemical composition, crystallinity and enzymatic hydrolysis of Lespedez bicolor stalks," Beijing Linye Daxue Xuebao 31(5): 121-125.

Yan Li, "Preparation and characterization of cellulose nanofibers from partly mercerized cotton by mixed acid hydrolysis", Cellulose, vol. 21 pp. 301-309.

Yu, Y. and H. Wu, Characteristics and Precipitation of Glucose Oligomers in the Fresh Liquid Products Obtained from the Hydrolysis of Cellulose in Hot-Compressed Water. Ind Eng Chem Res. 2009; 48:10682-90.

Yu, Y., Formation and Characteristics of Glucose Oligomers During the Hydrolysis of Cellulose in Hot-Compressed Water. Doctoral Thesis. Curtin University of Technology: Dept Chem Eng (2009) (192 pages).

(56) References Cited

OTHER PUBLICATIONS

Zhao, et al. (2008) "Supercritical Pretreatment and Hydrolyzation and Cellulose," Acta Chimica Sinica 66(20): 2295-2301.

Zhao, et al. (2009) "Supercritical hydrolysis of cellulose for oligosaccharide production in combined technology," Chemical Engineering Journal 150(2-3): 411-417.

Zoulikha, et al. (2009) "A thermomechanical pretreatment to improve enzymatic hydrolysis of wheat straw" Recents Progres en Genie des Procedes, No. 98.

Zuckerstatter, G. et al., The Elucidation of Cellulose Supramolecular Structure by 13C CP-MAS NMR. Lenzinger Berichte. 2009; 87:38-46.

Sasaki, M., Adschiri, T. and Arai, K. (2004), Kinetics of cellulose conversion at 25 MPa in sub- and supercritical water. AlChE J., 50: 192-202. https://doi.org/10.1002/aic.10018.

* cited by examiner

MANUFACTURE, ISOLATION, PURIFICATION, AND USES OF SMALL PARTICLE SIZE CELLULOSE PARTICLES AND COMPOSITIONS

CROSS-REFERENCE TO RELATED APPLICATIONS

This application is a continuation of U.S. application Ser. No. 16/028,359, filed Jul. 5, 2018, which claims the benefit of U.S. Provisional Patent Application No. 62/528,838 filed Jul. 5, 2017, U.S. Provisional Patent Application No. 62/587,472 filed Nov. 16, 2017, U.S. Provisional Patent Application No. 62/628,443 filed Feb. 9, 2018, and U.S. Provisional Patent Application No. 62/671,026 filed May 14, 2018, the entire disclosures of which are incorporated herein by reference in their entireties.

FIELD OF THE INVENTION

Disclosed herein are methods of manufacture, isolation, purification, and handling of cellulose particles having a small particle size. Also disclosed are uses for cellulose particles in a thickened composition, or in an emulsion or emulsifiable product, or in a suspension, or in a cosmetic or personal care formulation, or in a food product such as a leavened or leavenable food product, a meat or meat analog product, a pasta, or an ice cream. Also disclosed are uses for cellulose particles in a subterranean treatment composition (such as a drilling fluid), or in a processing or machining composition, such as a metalworking fluid, cutting fluid, stamping fluid, abrading fluid, tribological fluid, cooling fluid, or lubricating fluid. Also disclosed herein are resuspendable particles comprising cellulose.

BACKGROUND

Cellulose materials merit special consideration in the global concern over the environment and raw materials, because they are renewable, biodegradable, and are the world's most abundant natural polymer. It has been estimated that between about 1010 to about $10^{11}$ tons of cellulose are consumed globally each year in industrial applications for making textiles, paper products, plastics, food and pharmaceuticals additives, cosmetic additives, propellants, and as an affordable renewable energy source.

Lignocellulosic biomass typically contains cellulose, hemicellulose, lignin, and minerals, and in some instances minor amounts of proteins and lipids (fats, waxes, and oils). About two thirds of the dry mass of lignocellulosic materials is present as cellulose and hemicellulose with lignin making up the bulk of the remaining dry mass. There are a number of processes for converting lignocellulosic biomass into liquid streams of various sugars, extracting lignin, and/or recovering unreacted cellulose, such as in the pulp and paper industry. However, despite the widespread utility of lignocellulosic materials, the available conversion processes are complicated, capital intensive, time consuming, and require the use of harsh toxic chemicals. Therefore, there is a need for compositions containing cellulose, environmentally friendly methods for preparing them cleanly and efficiently, and applications for using them.

SUMMARY

In some embodiments, disclosed are small particle size cellulose particles, compositions comprising the particles, and methods for making and using same.

Disclosed are thickened compositions comprising: particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose; and a liquid; wherein the particles are present at a level sufficient to increase the viscosity of the composition by at least 10% compared to an otherwise identical composition without the particles; and wherein the viscosity of the formulations is determined at room temperature using a Brookfield LVT viscometer using spindle 21, at 2 rpm shear.

Also disclosed are suspensions comprising: a cellulose composition comprising particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose; and a first component suspended within the composition.

Also disclosed are suspensions comprising: a) a liquid; b) particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose; and c) a first component suspended within the liquid.

Also disclosed are emulsions or emulsifiable compositions comprising: particles comprising cellulose; wherein the particles have: at least one of (1) a $d_{75}$ of less than about 8 microns and (2) a $d_{50}$ of about 0.4 microns to about 5 microns; an aspect ratio of about 1 to about 1.5; and a non-spherical shape; and wherein at least a portion of the cellulose is type-II cellulose.

Also disclosed are emulsions or emulsifiable compositions comprising: particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

Also disclosed are cellulose compositions comprising particles and a resuspending agent: wherein the particles, when resuspended in a liquid: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose; and wherein the resuspending agent is adsorbed or bonded to at least a portion of the surface of the particles.

Also disclosed are food products comprising: particles; wherein the particles: comprise cellulose; have at least one of: (1) a $d_{75}$ of less than about 8 microns; (2) a $d_{50}$ of about 0.4 microns to about 5 microns; have an aspect ratio of about 1 to about 1.5; and have a non-spherical shape; and wherein at least a portion of the cellulose is type-II cellulose.

Also disclosed are leavened or leavenable food products comprising: particles comprising cellulose; wherein the particles have: at least one of (1) a $d_{75}$ of less than about 8 microns and (2) a $d_{50}$ of about 0.4 microns to about 5 microns; an aspect ratio of about 1 to about 1.5; and a non-spherical shape; and wherein at least a portion of the cellulose is type-II cellulose.

Also disclosed are leavened or leavenable food products comprising: particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

Also disclosed are meats or meat analog compositions comprising: particles comprising cellulose; wherein the particles have: at least one of (1) a $d_{75}$ of less than about 8 microns and (2) a $d_{50}$ of about 0.4 microns to about 5 microns; an aspect ratio of about 1 to about 1.5; and a non-spherical shape; and wherein at least a portion of the cellulose is type-II cellulose.

Also disclosed are meats or meat analog compositions comprising: particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

Also disclosed are subterranean treatment compositions, metalworking fluids, cutting fluids, stamping fluids, abrading fluids, tribological fluids, cooling fluids, or lubricating fluids comprising: (a) a fluid; and (b) particles suspended in the fluid, wherein the particles comprise cellulose, have at least one of (1) a $d_{75}$ of less than about 8 microns and (2) a $d_{50}$ of about 0.4 microns to about 5 microns, have an aspect ratio of from about 1 to about 1.5, and have a non-spherical shape, and wherein at least a portion of the cellulose is type-II cellulose.

Also disclosed are subterranean treatment compositions and machining or processing compositions, such as metalworking fluids, cutting fluids, stamping fluids, abrading fluids, tribological fluids, cooling fluids, or lubricating fluids comprising: (a) a fluid; and (b) particles suspended in the fluid, wherein the particles: comprise cellulose; have at least one of (1) a $d_{75}$ of less than about 8 microns and (2) a $d_{50}$ of about 0.4 microns to about 5 microns; have an aspect ratio of from about 1 to about 1.5; and have a non-spherical shape; and wherein at least a portion of the cellulose is type-II cellulose.

Also disclosed are personal care formulations comprising: particles; wherein the particles: comprise cellulose; have at least one of: (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

Also disclosed are methods for preparing particles comprising cellulose, comprising: (a) contacting a cellulosic substrate with a sub-critical, near-critical or supercritical fluid for a duration sufficient to form a mixture of liquid and solids, said mixture comprising gluco-oligosacharides (GOS) and particles comprising cellulose; (b) optionally, separating lignin from the mixture comprising GOS and particles comprising cellulose; (c) optionally, removing at least a portion of the liquid from the mixture comprising GOS and particles comprising cellulose to form a higher solids mixture comprising GOS and particles comprising cellulose; and (d) contacting the mixture comprising GOS and particles comprising cellulose with an organic solvent to form solid GOS and particles comprising cellulose.

Also disclosed are methods for increasing the solids content of an aqueous suspension of particles comprising cellulose, the method comprising: (a) freezing the aqueous suspension to form a frozen suspension; (b) thawing the frozen suspension to form a gradation of solids content in the suspension such that an upper portion of the suspension has a lower solids content, and a lower portion of the suspension has a higher solids content; (c) isolating at least a portion of the lower portion; and (d) optionally, repeating steps (a), (b) and (c) one or more times on the lower portion; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

Also disclosed are methods for preparing a solid sample of water-soluble glucooligosaccharides (GOS) comprising: (a) contacting a cellulosic substrate with a sub-critical, near-critical or supercritical fluid for a duration sufficient to form a mixture of liquid and solids, said liquid comprising GOS; (b) collecting at least a portion of the liquid; (c) optionally, removing at least a portion of the liquid from the liquid comprising GOS to form a higher solids liquid comprising GOS; (d) contacting the higher solids liquid comprising GOS with an organic solvent to form solid GOS; (e) separating the solid GOS from the liquid and collecting the solid GOS.

Additional advantages will be set forth in part in the description which follows, and in part will be obvious from the description, or can be learned by practice of the invention. The advantages will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying figures, which are incorporated in and constitute a part of this specification, illustrate several aspects and together with the description serve to explain the principles of the invention.

5

6

Figure 9:
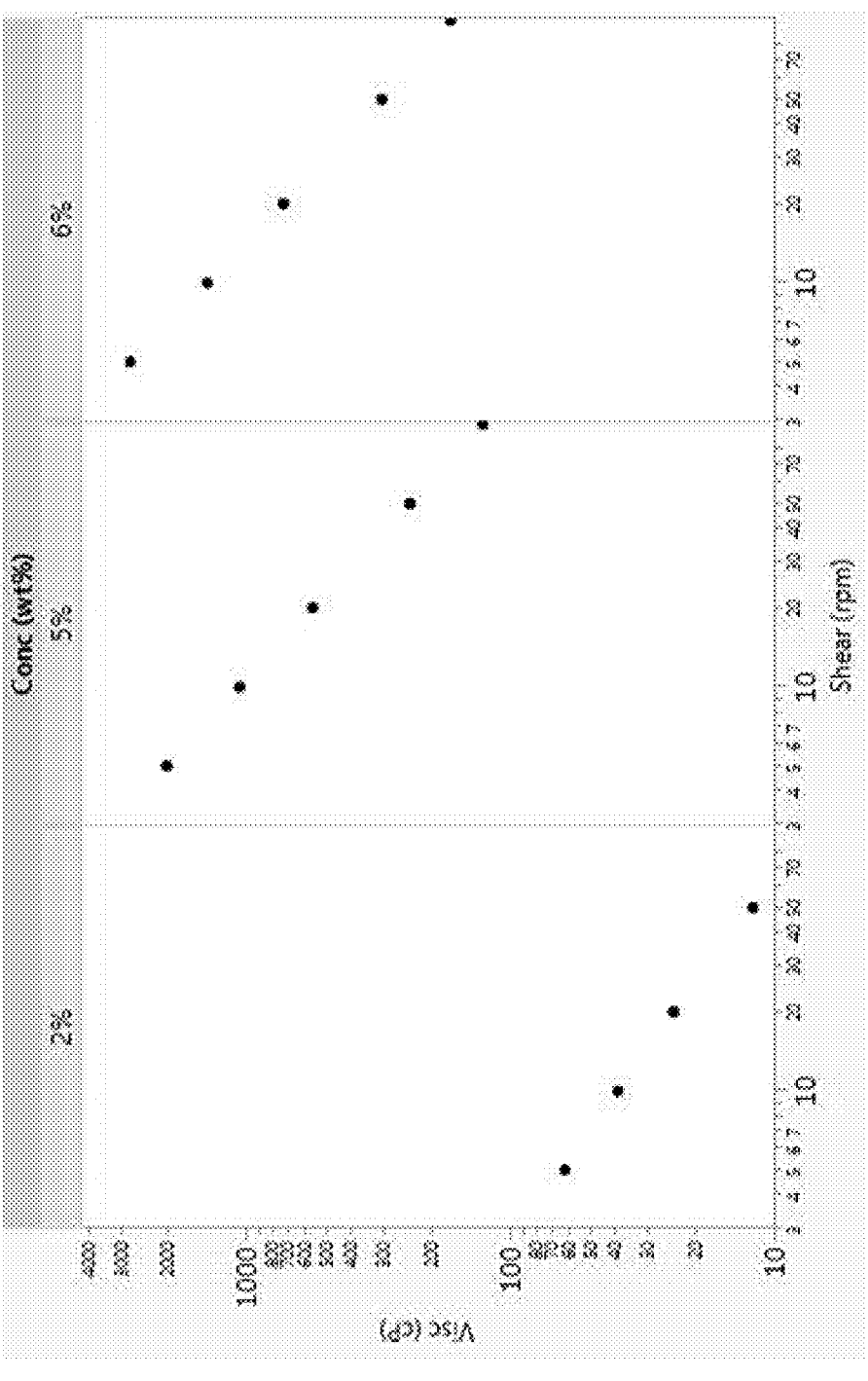

FIG. 9 shows the thixotropic behavior of aqueous suspensions of the particles comprising cellulose described herein (see Example 6).

Figure 10:
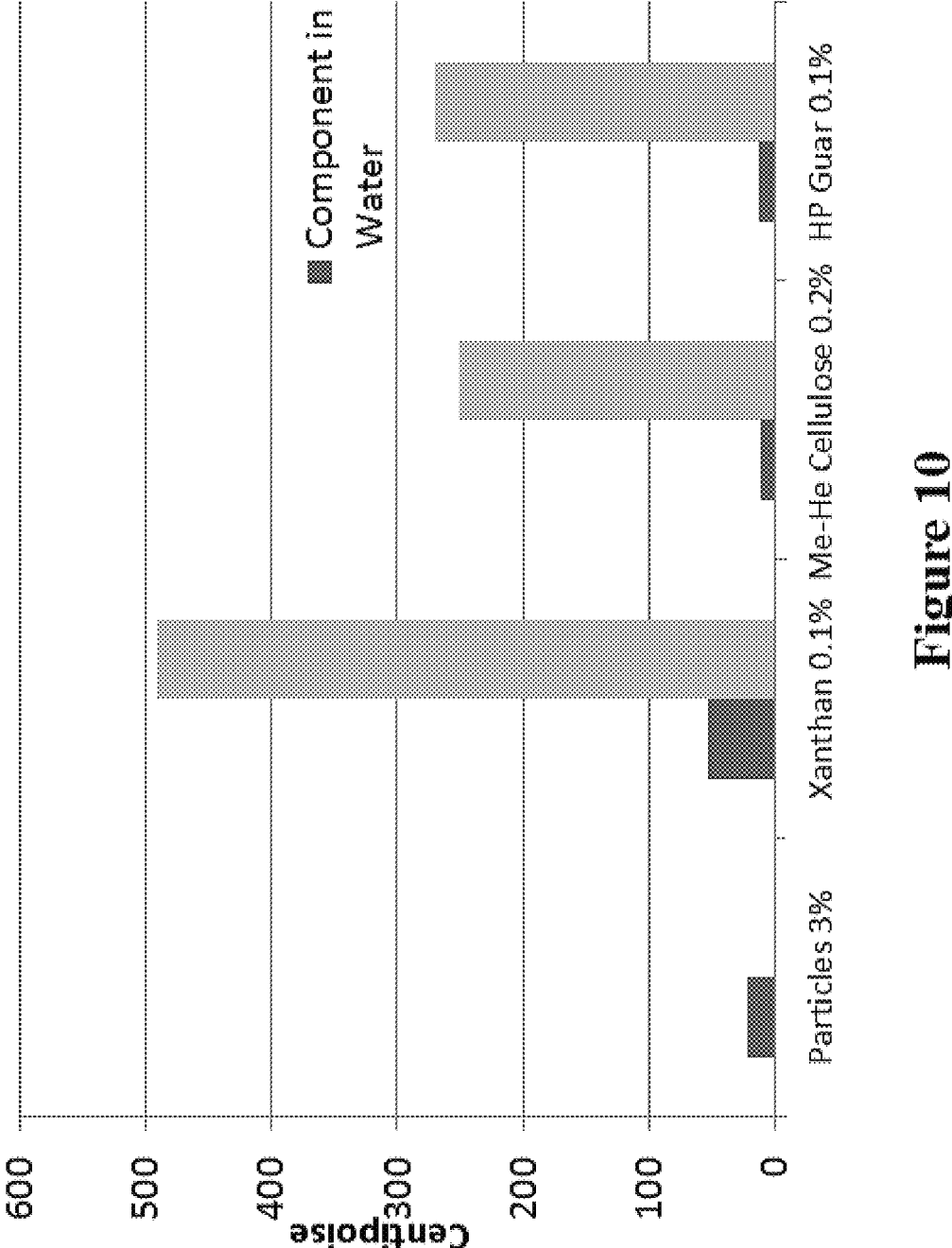

FIG. 10 shows the synergistic thickening behavior in water demonstrated by the particles comprising cellulose described herein (see Example 6).

Figure 11:
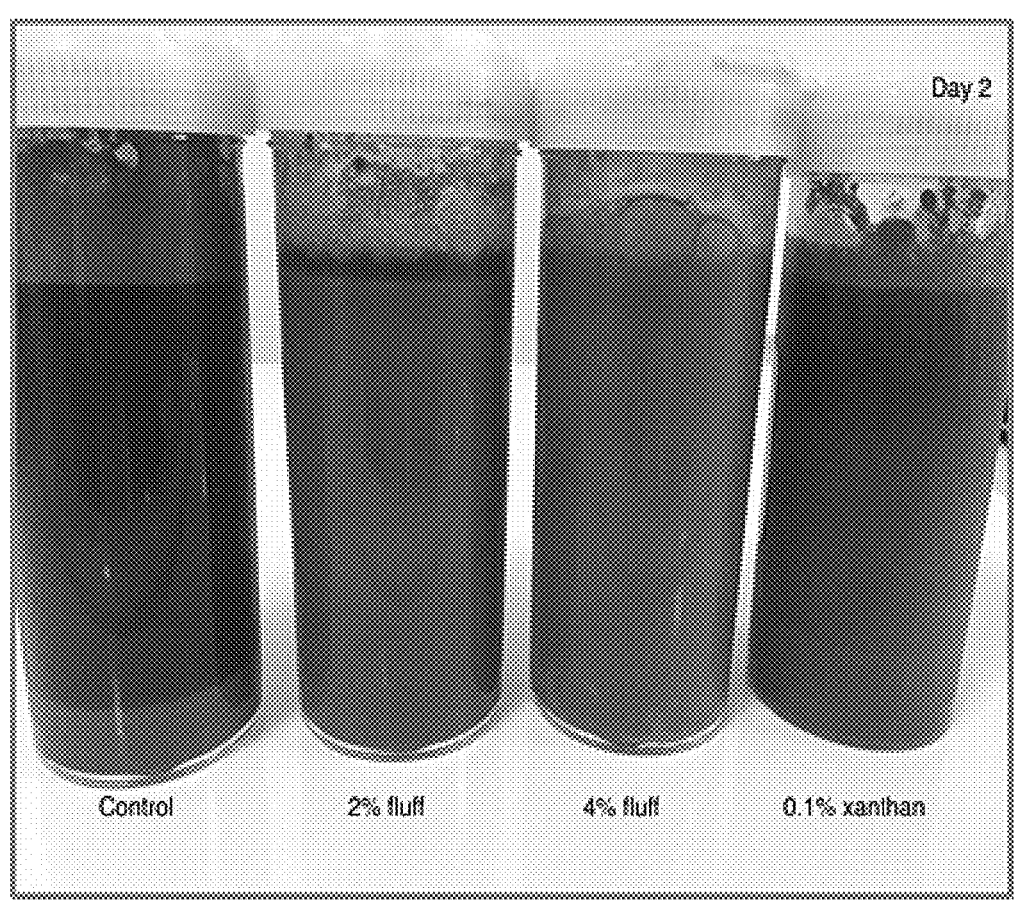

FIG. 11 shows the particles comprising cellulose described herein functioning as a stabilizing aid in stabilizing aqueous suspensions of cocoa powder (see Example 7). From the left, i) the control sample (5 g of cocoa powder suspended in 100 g of water); ii) control+2% Cellulose Particles A; iii) control+4% Cellulose Particles A; iv) control+0.1% xanthan.

Figure 12:
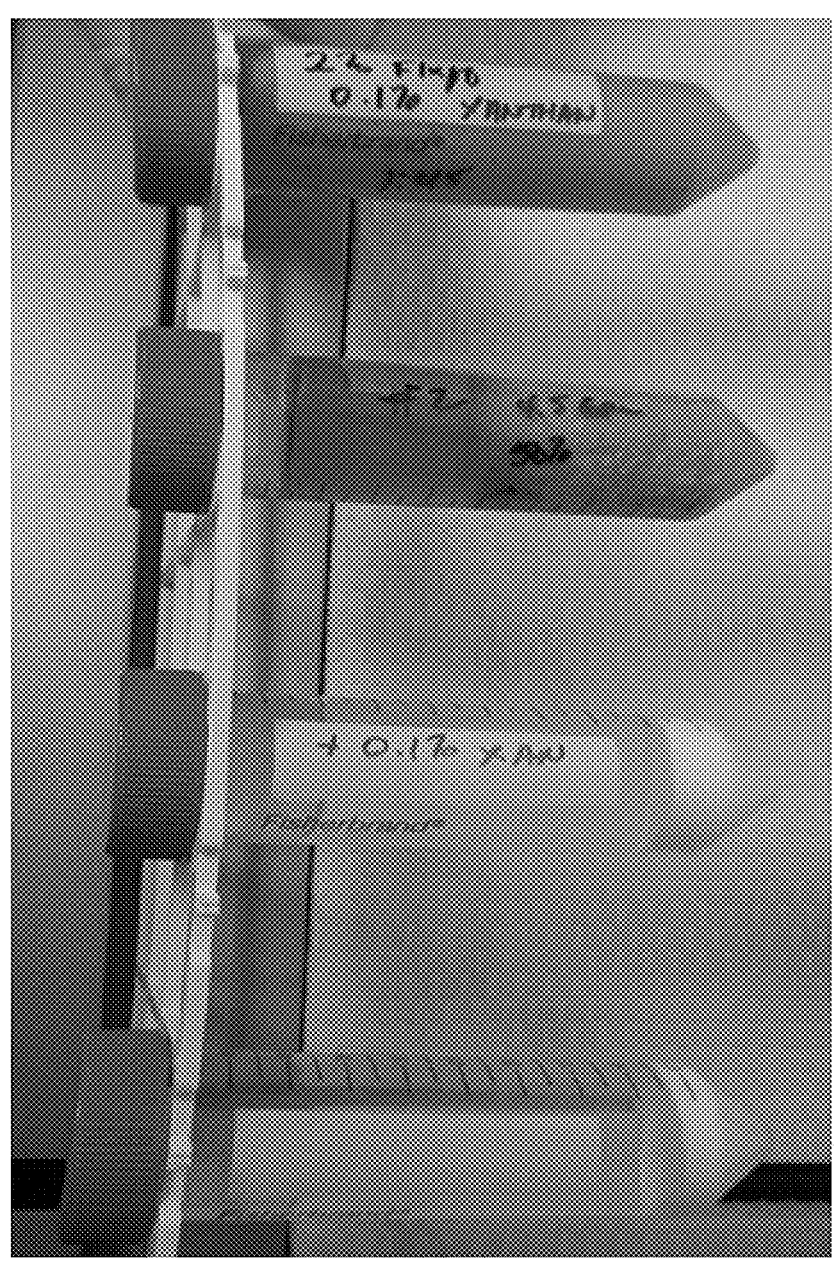

FIG. 12 shows the particles comprising cellulose described herein functioning as a stabilizing aid in stabilizing aqueous suspensions of calcium carbonate (see Example 7). From the left, i) the control sample (10 g of $CaCO_3$ suspended in 100 g of water); ii) control+0.1% xanthan; iii) control+2% Cellulose Particles A; iv) control+a combined 2% Cellulose Particles A together with 0.1% xanthan.

Figure 13:
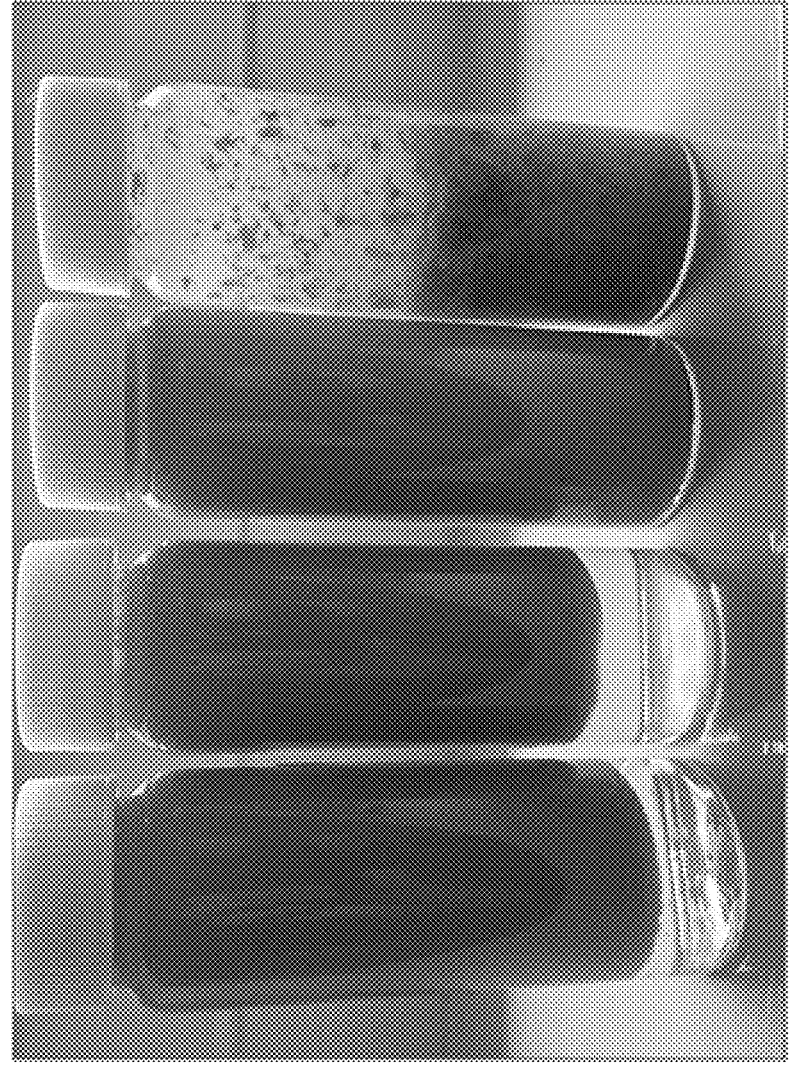

FIG. 13 shows emulsions formed using the particles comprising cellulose described herein at a 2 wt % solids level, based on total emulsion weight, for oil:water ratios of i) 10:90, ii) 20:80, iii) 50:50 and iv) 80:20 (see Example 8).

Figure 14:
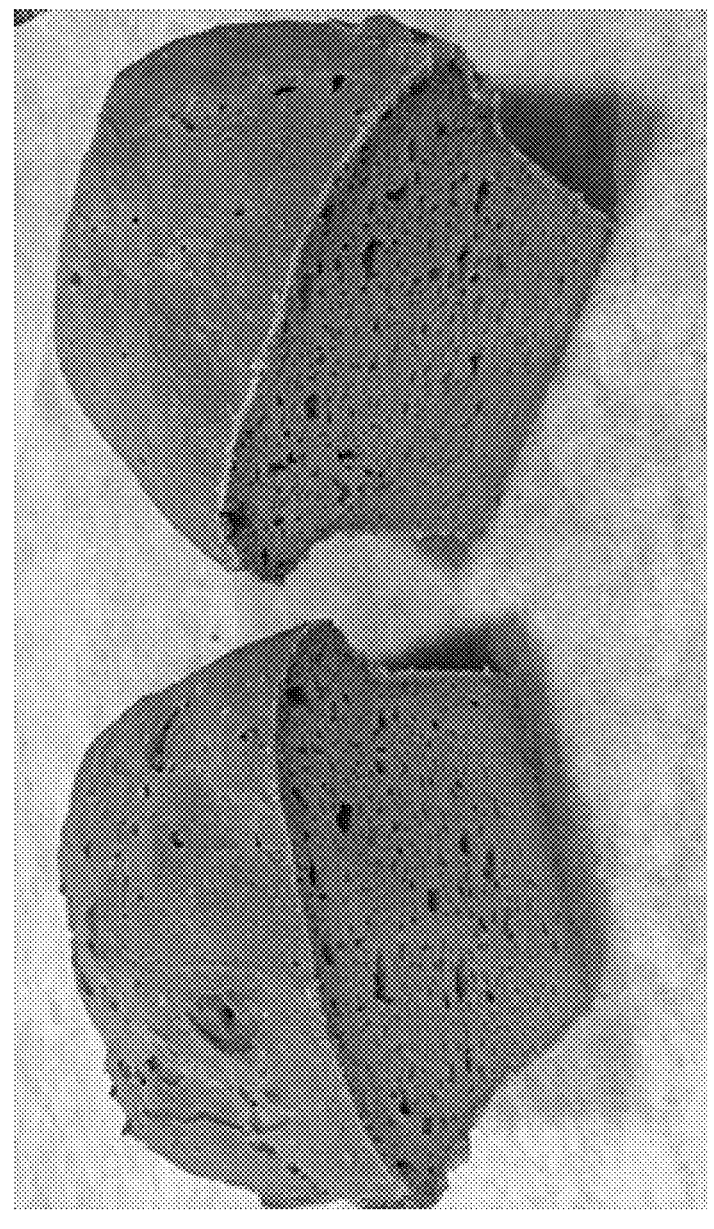

FIG. 14 shows a gluten-free bread made with the particles comprising cellulose disclosed herein, at a 5% level, replacing milk and gums that are normally included in gluten-free breads (see Example 10).

Figure 15:
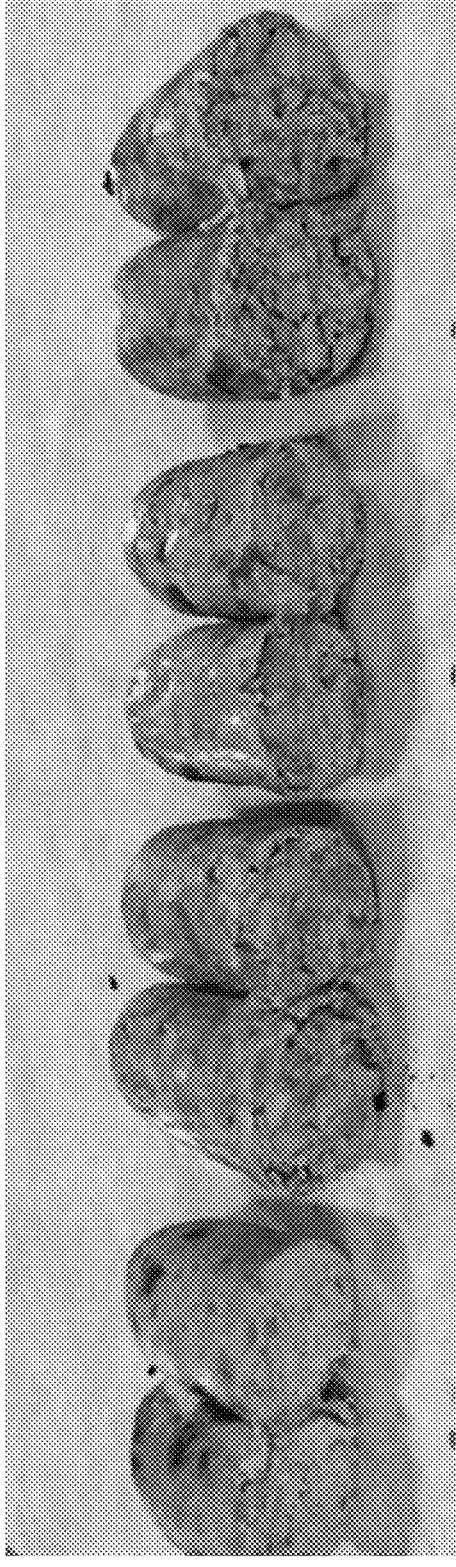

FIG. 15 shows chicken sausage made with the particles comprising cellulose disclosed herein, at a 0%, 2%, 4% and 10% levels, in order, respectively, with the lowest level (0%) on the left (see Example 11).

Figure 16A:
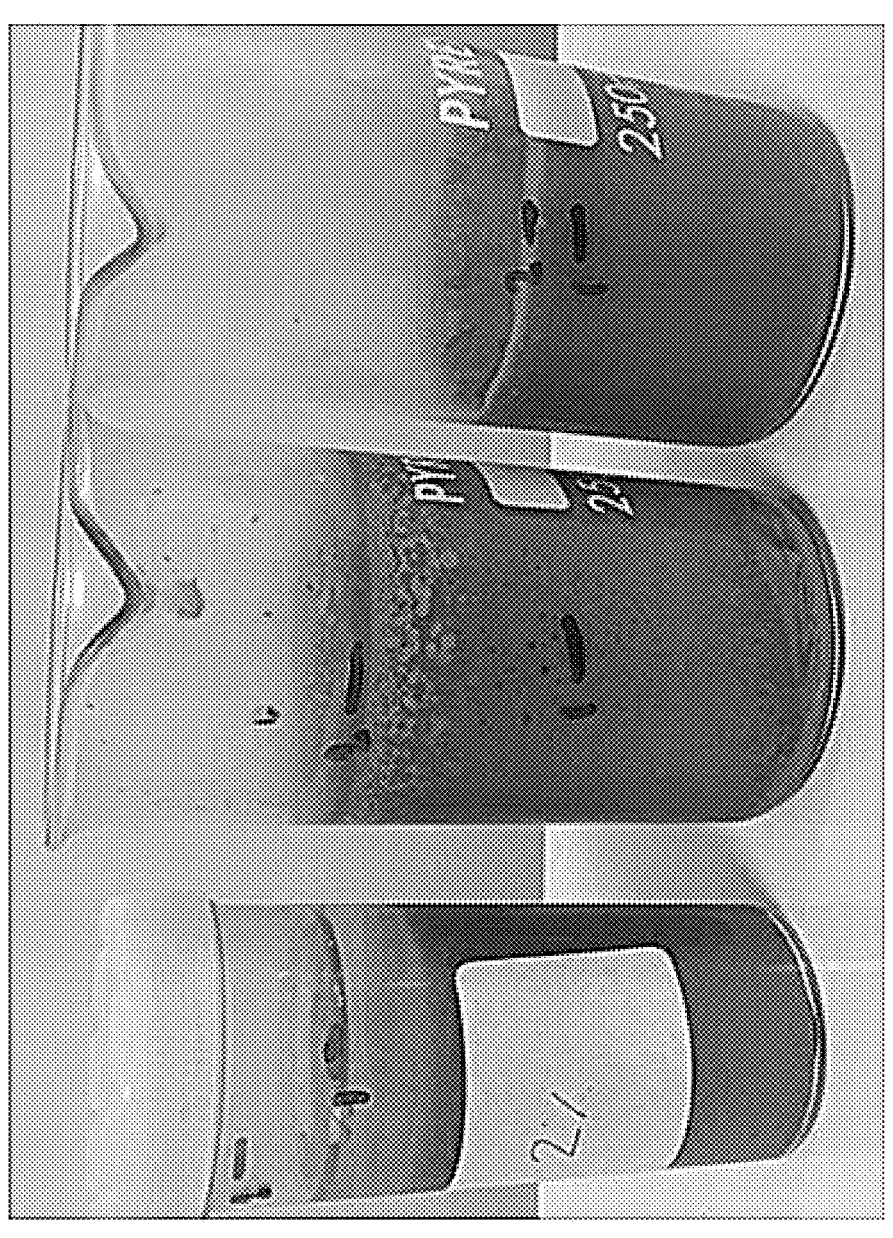
Figure 16B:
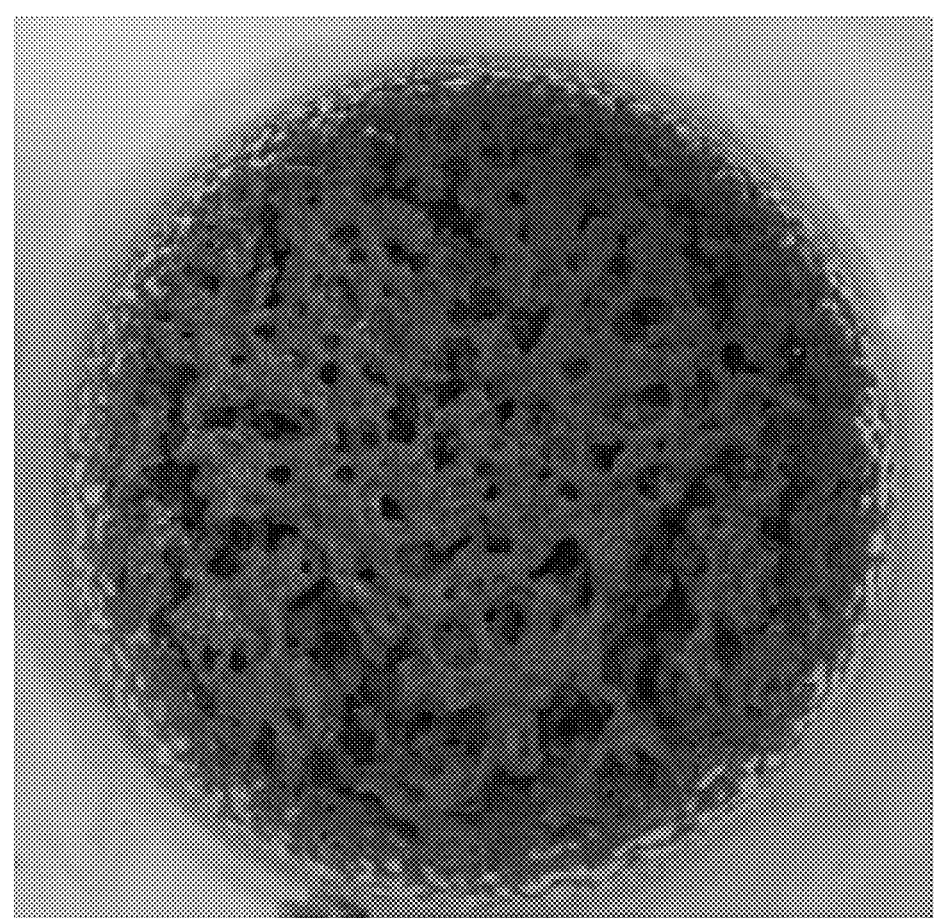

FIG. 16A and FIG. 16B show results of foams formed using particles comprising cellulose as disclosed herein, at 2%, 4%, and 8% solids content (FIG. 16A), including the stability, with some degassing, of the 4% sample after 4 days (FIG. 16B).

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such methods and reagents may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Headings are provided for convenience only and are not to be construed to limit the invention in any manner. Embodiments illustrated under any heading or in any portion of the disclosure may be combined with embodiments illustrated under the same heading or portion of the disclosure, or under any other heading or other portion of the disclosure.

While aspects of the present invention can be described and claimed in a particular statutory class, such as the composition of matter statutory class, this is for convenience only and one of skill in the art will understand that each aspect of the present invention can be described and claimed in any statutory class.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

Any combination of the elements described herein in all possible variations thereof is encompassed by the invention unless otherwise indicated herein or otherwise clearly contradicted by content.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

The use of numerical values in the various quantitative values specified in this application, unless expressly indicated otherwise, are additionally stated, in the alternative, as approximations as though the minimum and maximum values within the stated ranges were both preceded by the word "about." In this manner, slight variations from a stated value may be used to achieve substantially the same results as the stated value. Also, the disclosure of ranges is intended as a continuous range including every value between the minimum and maximum values recited as well as any ranges that may be formed by such values. For example, a disclosure that a component may be present in an amount of from 2% to 10% would include, among others from 2% to 9%, 2% to 8%, 3% to 10%, 3% to 9%, 4% to 5%, etc. Also disclosed herein are any and all ratios (and ranges of any such ratios) that may be formed by dividing a recited numeric value into any other recited numeric value. Accordingly, the skilled person will appreciate that many such ratios, ranges, and ranges of ratios may be unambiguously derived from the numerical values presented herein and in all instances such ratios, ranges, and ranges of ratios represent various aspects of the present invention.

When disclosing numerical values herein, for example, 1, 2, 3, 4, 5, 6, 7, 8, 9, 10, the following sentence may follow such numerical values: "Each of the foregoing numbers can be preceded by the term 'about,' 'at least about,' or 'less than about,' and any of the foregoing numbers can be used singly to describe an open-ended range or in combination to describe a closed-ended range." This sentence means that each of the aforementioned numbers can be used alone (e.g., 4), can be prefaced with the word "about" (e.g., about 8), prefaced with the phrase "at least about" (e.g., at least about 2), prefaced with the phrase "less than about" (e.g., less than about 7), or used in any combination with or without any of the prefatory words or phrases to define a range (e.g., 2 to 9, about 1 to 4, 8 to about 9, about 1 to about 10, and so on). Moreover, when a range is described as "about X or less" (where X is a number), this phrase is the same as a range that is a combination of "about X" and "less than about X" in the alternative. For example, "about 10 or less" is the same as "about 10, or less than about 10." Such interchangeable range descriptions are contemplated herein. Other range formats may be disclosed herein, but the difference in formats should not be construed to imply that there is a difference in substance.

As used herein, the terms "optional" or "optionally" means that the subsequently described event, condition, component, or circumstance may or may not occur, and that the description includes instances where said event, condition, component, or circumstance occurs and instances where it does not.

As used herein, the phrase "sufficient to" (e.g., "conditions sufficient to" or "sufficient for") refers to such a value or a condition that is capable of performing the function or property for which such value or condition is expressed. As will be pointed out below, the exact value or particular condition required may vary from one aspect to another, depending on recognized variables, such as the materials employed and/or the processing conditions.

The term "by weight," when used in conjunction with a component, unless specifically stated to the contrary, is based on the total weight of the formulation or composition in which the component is included. For example, if a particular element or component in a composition or article is said to be present in an amount of 8% by weight, it is understood that this percentage is in relation to a total compositional percentage of 100%. In some instances, the weight percent of a component is based on the total weight of the composition "on a dry basis," which indicates the weight of the composition without water (e.g., less than about 1%, less than about 0.5%, less than about 0.1%, less than about 0.05%, or about 0% of water by weight, based on the total weight of the composition).

As used herein, the term "substantially free of" refers to a composition having less than about 1% by weight, e.g., less than about 0.5% by weight, less than about 0.1% by weight, less than about 0.05% by weight, or less than about 0.01% by weight of the stated material, based on the total weight of the composition.

As used herein, the term "substantially" (when not used in the phrase "substantially free of"), when used in reference to a composition, refers to at least about 60% by weight, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature or component.

As used herein, the term "biomass" means a renewable energy source generally comprising carbon-based biological material derived from living or recently-living organisms. In various aspects, the biomass may serve as a "feedstock" and, as such, in appropriate context, the terms ("biomass" and "feedstock") may be used interchangeably. Suitable feedstocks include lignocellulosic feedstock, cellulosic feedstock, hemicellulosic feedstock, starch-containing feedstocks, and the like. The lignocellulosic feedstock may be from any lignocellulosic biomass, such as plants (e.g., duckweed, annual fibers, etc.), trees (softwood, e.g., fir, pine, spruce, etc.; tropical wood, e.g., balsa, iroko, teak, etc.; or hardwood, e.g., elm, oak, aspen, poplar, willow, eucalyptus, etc.), bushes, grass (e.g., miscanthus, switchgrass, rye, reed canary grass, giant reed, or sorghum), dedicated energy crops, municipal waste (e.g., municipal solid waste), and/or a by-product of an agricultural product (e.g., corn, sugarcane, sugar beets, fruits, pearl millet, grapes, rice, straw, cotton stalk). The biomass may be from a virgin source (e.g., a forest, woodland, or farm) and/or a by-product of a processed source (e.g., off-cuts, bark, and/or sawdust from a paper mill or saw mill, sugarcane bagasse, corn stover, palm oil industry residues, cotton linters, branches, leaves, roots, and/or hemp). Suitable feedstocks may also include the constituent parts of any of the aforementioned feedstocks, including, without limitation, lignin, cellulose, C6 saccharides (including C6 polymers, C6 oligosaccharides, and C6 monosaccharides), hemicellulose, C5 saccharides (including C5 polysaccharides, C5 oligosaccharides, and C5 monosaccharides), and mixtures thereof. Suitable feedstocks can also include fractionated biomass, in which at least a portion of the original components has been removed (e.g., fractionated biomass in which at least a portion, some, most, or all of originally present hemicellulose has been removed, e.g., 30, 35, 40, 45, 50, 55, 60, 65, 70, 75, 80, 85, 90, 95, or 99 wt % of the hemicellulose originally present has been removed (each of the foregoing numbers can be preceded by the word "about," "at least about," or "less than about," and any of the foregoing numbers can be used singly to describe an open-ended range or in combination to describe a close-ended range)). Suitable feedstocks can also include unfractionated biomass, in which at least a portion, some, most, or all of the hemicellulose present in the biomass has not been removed and feedstock from which the hemicellulose and the lignin have been removed (i.e., cellulose).

The feed material for the hydrolysis reaction need not be a lignocellulosic biomass, and may not be a biomass at all; any cellulose-containing feed material may be suitable for the hydrolysis process to produce the particles comprising cellulose disclosed herein including relatively pure sources of cellulose, such as, for example, microcrystalline cellulose (MCC), nanocrystalline cellulose (NCC), cotton, pulp, wood pulp, dissolving wood pulp, fresh and recycled paper, a cellulose fraction isolated from lignocellulosic biomass, and the like.

As used herein, "dry biomass" (or equivalently "bone dry biomass") refers to biomass substantially without any water (i.e., about 0% moisture content), or with only residual water remaining (i.e. no more than about 1%, no more than about 0.5%, no more than about 0.1%, no more than about 0.05%, or no more than about 0.01% moisture content). When referring to dry biomass, the biomass itself is not necessarily in a bone dry state, but rather the weight of the dry biomass is expressed as if all or substantially all of the water has been removed.

As used herein, the terms "microcrystalline cellulose" and "MCC" are used interchangeably and refer to purified, partially depolymerized cellulose prepared by hydrolysis of cellulose fibers. Cellulose fiber typically comprises cellulose microfibers comprising amorphous, paracrystalline, and crystalline regions. The hydrolysis process largely removes the amorphous fraction, destroying the fiber-like morphology of the cellulose and forming the cellulose microcrystals containing wholly or mostly crystalline regions. In various aspects, the microcrystalline cellulose may be characterized by substantially low content of inorganic impurities. Commercially available MCC includes, but is not limited to, AVICEL® products available from FMC BioPolymer, Philadelphia, PA, USA and Microcrystalline Cellulose 102 available from Blackburn Distributions, Nelson, Lancashire, UK.

As used herein, the term "nanocellulose" or "nanocrystalline cellulose" and "NCC" are used interchangeably and refer to a cellulosic material having at least one dimension in the nanometer range. Nanoparticles, including NCC, are generally considered to be in the size range of from 1-100 nm. Nanocellulose comprising cellulose fibrils may have a high aspect ratio. A fluid comprising nanocellulose may exhibit pseudo-plastic characteristics. A fluid containing nanocellulose can exhibit properties of certain gels or fluids that are viscous under normal conditions and develop a high storage modulus on standing. The nanocellulose fibrils may exhibit high surface area and bonding ability.

As used herein, "aspect ratio" refers to the ratio of the largest dimension of a particle to the smallest (e.g. length/diameter for a cylinder; length/thickness for a plate; longest axis/shortest axis for an ellipsoid).

The term "non-spherical shape," as used herein, means a shape that has an aspect ratio greater than 1 (i.e., a shape that is not spherical). For example, a non-spherical shape can have an aspect ratio of at least 1.5, 2.0, 2.5, 3.0, 3.5, 4.0, 4.5, 5.0, 5.5, 6.0, 6.5, 7.0, 7.5, 8.0, 8.5, or 9.0.

As used herein, the term "unconverted type-I cellulose" refers to a type-I cellulose that that has not been converted to a type-II cellulose when a feedstock as defined herein and having type-I cellulose is subjected to conditions sufficient to form at least some type-II cellulose. Such conditions include, for example, contacting a feedstock containing type-I cellulose with a fluid, for example a fluid comprising water, wherein the fluid (e.g., water) is subcritical, near-critical, or supercritical. Such conditions also include mercerization (alkali treatment), regeneration (solubilization followed by recrystallization), subcritical and supercritical water, ball milling of cellulose in presence of water and the like.

As used herein, "continuous" indicates a process which is uninterrupted for its duration, or interrupted, paused or suspended only momentarily relative to the duration of the process. A process is "continuous" when the starting material (e.g. biomass or biomass slurry) is fed into the apparatus without interruption or without a substantial interruption, or processing of the starting material is not done in a batch process.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. At or above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near-critical water has a temperature at or above about 300° C. and below the critical temperature of water (374.2° C.), and a pressure high enough to ensure that at least a portion of (e.g., all of) the fluid is in the liquid phase. Sub-critical water has a temperature of less than about 300° C. and a pressure high enough to ensure that at least a portion of (e.g., all of) the fluid is in the liquid phase. Sub-critical water temperature may be greater than about 250° C. and less than about 300° C., and in many instances sub-critical water has a temperature between about 250° C. and about 280° C. The term "hot compressed water" is defined herein as near-critical or sub-critical water, or at any temperature at least about 100° C. (preferably, at least about 100° C., at least about 150° C., at least about 200° C., at least about 250° C., at least about 300° C., or at least about 350° C.) but less than supercritical (e.g., less than about 374° C.), and at pressures such that at least a portion of the water (e.g., all of the water) is in a liquid state.

As used herein, a fluid which is "supercritical" (e.g., supercritical water, supercritical CO2, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g., water and ethanol, water and CO2, etc.). Thus, for example, "a mixture of sub-critical water and supercritical carbon dioxide" indicates a mixture of water and carbon dioxide at a temperature and pressure above that of the critical point for carbon dioxide but below the critical point for water, regardless of whether any supercritical phase contains water and regardless of whether the water phase contains any carbon dioxide. For example, a mixture of sub-critical water and supercritical CO2 may have a temperature of about 250° C. to about 280° C. and a pressure of at least about 225 bar.

The term "supercritical hydrolysis" refers to a hydrolysis reaction effected by one or more fluids under supercritical conditions (i.e., a supercritical fluid).

All pressures disclosed herein are gauge pressures, unless indicated otherwise or clearly contradicted by context.

As used herein, the term "degree of polymerization" (DP) is defined as the number of monomeric units in a macromolecule or polymer or oligomer. For example and without limitation, the number-average degree of polymerization is given by:

$$DP_n = X_n = \frac{M_n}{M_0}$$

where $M_n$ is the number-average molecular weight and $M_0$ is the molecular weight of the monomer unit. For cellulose, the monomer unit is the anhydroglucose unit (glucose minus the equivalent of one water molecule, 162 g/mol).

As used herein, "oligosaccharide" refers to linear or branched carbohydrate molecules of the same or different monosaccharide units joined together by glycosidic bonds having the general formula of $C_x(H_2O)_y$. Oligosaccharides may be thought of as shorter chain polysaccharides, i.e., polysaccharides simply having less monomeric residues in the polymeric chain. When an oligosaccharide contains C6 monosaccharide residues, the general formula may be represented as $(C_6H_{10}O_5)_n$, where n is about 2 to about 15 (i.e., the number of hexose monomers in the oligosaccharide). As used herein, an oligomer (e.g., cello-oligosaccharide) has a DP in the range of 2 to about 15, whereas a polymer (e.g., cellulose) has a DP of at least about 16. As used herein, the term "glucooligosaccharide" ("GOS") or "precipitated glucooligosaccharide" ("PGOS") may additionally comprise a monosaccharide as a minor component.

As used herein, "monosaccharide" refers to any of the class of sugars that cannot be hydrolyzed to give a simpler sugar. Monosaccharides typically are C5 (e.g., xylose) and C6 sugars (e.g., glucose), but may also include monosaccharides having other numbers of carbon, such as C3, C4, C7, C8, and so on. Expressed another way, monosaccharides are the simplest building blocks of oligosaccharides and polysaccharides. Monosaccharides of cellulose are predominantly C6 saccharides (e.g., glucose).

As used herein, Size-Exclusion Chromatography (SEC) and Gel Permeation Chromatography (GPC) are used interchangeably herein and refer to chromatographic separation methods in which molecules in solution are separated by their size. The separation is achieved by the differential exclusion of the sample molecules as they pass through a bed of porous particles, known as a separation column. SEC may be used to determine a substantially accurate molar mass distribution of polymer molecules. For example, the liquid fraction (an eluent) passing through the column is collected in constant volumes. As the polymer elutes through the column, molecules that are too large to penetrate the column pores are excluded from the packing pore volume and elute at earlier retention times, whereas the smaller molecules penetrate into the column pores and elute at a later time. The concentration of eluted polymers may be measured by spectroscopic techniques, such as, for example, refractive index (RI) and ultraviolet (UV). The eluent flow may also be analyzed continuously with RI, Low-Angle Laser Light Scattering (LALLS), Multi-Angle Laser Light Scattering (MALLS), UV, and/or viscosity measurements.

In various aspects, a substantial portion of the cellulose particles comprising cellulose can be solubilized when subjected to a series of steps adapted from the article: Dupont, Polymer, "Cellulose in lithium chloride/N,N-dimethylacetamide, optimization of a dissolution method using paper substrates and stability of the solutions," Vol. 44, (2003), 4117-4126, hereby incorporated by reference in its entirety. As used herein, the series of steps that enables solubilization of a substantial portion of the cellulose particles comprising cellulose, and also allows characterization by GPC, is termed the "first condition." The first condition consists of or consists essentially of the following sequential steps: (i) swelling the particles comprising cellulose twice in DI water for 1 hour each while stirring at room temperature (filter and re-suspend solids in fresh DI water after each swelling), (ii) activating the resulting solids twice in methanol for 45 minutes each at room temperature while stirring (filter and re-suspend solids in fresh methanol after each activating), (iii) activating the resulting solids in N,N-Dimethylacetamide (DMAc) (without LiCl) overnight at room temperature with stirring (followed by filtration of solids), (iv) stirring the resulting solids in 8% by weight LiCl in DMAc for 24 hours at room temperature, followed by (v) subjecting the same LiCl/DMAc mixture (without any filtration) at 2-8° C. for up to 3 days without stirring. All of the steps of the first condition are performed at ambient pressure. The weight-average molecular weight as determined by GPC typically is performed on the cellulose particles that have been solubilized according to the first condition, except the final solution of cellulose particles in 8 wt % LiCl in DMAc has been diluted to 0.8 wt % LiCl in DMAc prior to analyzing using GPC. Unless stated otherwise, all molecular weight and associated measurements (e.g., PDI, etc.) are made by GPC using a sample that has been prepared according to the "first condition."

Herein, a fluid can be in a vapor, a liquid, or a supercritical form, or any combination thereof, as will be indicated by context. A combination of a supercritical and a liquid or vapor form typically arises when a mixed fluid is employed, e.g., water and carbon dioxide. A combination of vapor and liquid forms typically arises when the temperature is above the boiling point of the liquid, but the pressure is not high enough to maintain all of the fluid in liquid form.

Herein, a "slurry" refers to a flowable or pumpable mixture of an insoluble, or partially soluble, solid with a fluid, such as, for example, suspended pieces or particles in water.

As used herein, the term "explosive decompression" (using a fluid) or "steam explosion" (in such case when the fluid is or comprises water) of biomass refers to a rapid decrease in pressure of a pressurized vessel that results in a thermomechanical process used to break down the structural integrity of the biomass aided by heat in the form of vaporized fluid or steam (thermo) and shear forces due to the expansion of the fluid or steam (mechanical). In the reaction vessel, vaporized fluid (or steam) under high pressure penetrates the biomass structure due to a pressure differential, or by convection or diffusion. With respect to water (or other fluid), the steam (or vaporized fluid) may also heat water or other fluid already present within the void spaces of the biomass (e.g., if pre-soaked or for water intrinsic to biomass), thereby forming hot water and/or steam (or other fluid) in the biomass structure. In the case of steam, the steam condenses under the high pressure, thereby "wetting" the material (in the case of hot water, the material will already be "wetted"). The "wet" material is "exploded" when the pressure within the reactor is released. Several phenomena occur at this point. First, the condensed moisture within the structure evaporates instantaneously due to the sudden decrease in pressure. The expansion of the water vapor exerts a shear force on the surrounding structure. If this shear force is high enough, the vapor will cause the mechanical breakdown of the structure.

As used herein, "comminuting" means any mechanical technique for the size reduction of a solid, such as crushing, grinding, collision milling, and the like.

As used herein, the terms "ambient temperature" and "ambient pressure" refer to normal (usually, but not necessarily, unadjusted) room temperature and room pressure. Because such conditions can vary, the term is only used to convey an approximate temperature and approximate pressure. Herein, ambient temperature is taken to mean a temperature of 20° C.+/−5° C., and ambient pressure is taken to mean an absolute pressure of 1 bar (1 atmosphere)+/−0.2 bar (0.2 atmosphere).

As used herein, the term "near ambient temperature" refers to conditions of temperature ranging from 10° C. to 30° C., and the term "near ambient pressure" refers to conditions of absolute pressure ranging from 0.6 bar to 1.4 bar (0.6 atmosphere to 1.4 atmosphere).

As used herein, the term "glass transition temperature", or Tg, refers to the temperature at or above which a glassy polymer will undergo segmental motion of the polymer chain (and transitions from the "glassy" state to a molten or rubber-like state) and as used herein refers to a measured Tg determined by differential scanning calorimetry (DSC) using a heating rate of 10° C./minute, taking the mid-point in the heat flow versus temperature transition as the Tg value.

As used herein, "C1-C5 alcohol" indicates an alcohol comprising 1 to 5 carbon atoms. Examples of C1-C5 alcohols include, but are not limited to, methanol, ethanol, n-propanol, isopropanol, n-butanol, s-butanol, t-butanol, i-butanol, n-pentanol, 2-pentanol, 3-pentanol, 2-methyl-1-butanol, 2-methyl-2-butanol, 3-methyl-1-butanol, 3-methyl-2-butanol, and 2,2-dimethyl-1-propanol. Mixtures of one or more of these alcohols may be used.

As used herein, the term "leavening" refers to the process of adding gas to a dough, batter or other food formulation before or during baking to produce a lighter, fluffier, and/or more easily chewed baked good (e.g., bread, cake, muffin, etc.). A "leavening agent" is an additive that causes the formation of gas bubble-foam, and this additive may be natural (biological) or synthetic. Examples of leavening agents include, for example, chemical(s) (e.g., baking powder, baking soda, buttermilk, acid, etc.), yeast, steam, bacteria, aeration, etc. A leavened food product, therefore, is a food product or formulation that has been prepared with the use of a leavening agent or has undergone the process of gas addition into the dough, batter or other food formulation before or during baking to produce a foodstuff. A leavenable food product refers to a food formulation or food preparation that is not leavened yet, but rather is capable of undergoing a leavening process. Examples of leavenable food products include, for example, cake mixes, muffin mixes, raw cookie dough, flour, and the like. Such leavenable food products are contemplated to be those that are packaged by a manufacturer of such leavenable food products to be prepared into a leavened food product by a third party, whether it be an individual consumer at home or an industrial bakery.

Herein, "oil/water emulsion" may refer to an oil in water emulsion or a water in oil emulsion.

Herein, "egg-free" means that the formulation contains less than about 20 ppm egg on a dry basis. For example, a formulation contains less than about 20 ppm, less than about 15 ppm, less than about 10 ppm, less than about 5 ppm, less than about 1 ppm, or 0 ppm egg on a dry basis.

Herein, "egg-substitute" or "egg-replacer" means natural or imitation products (wet or dry) that are designed, marketed or used to substitute or replace eggs in food products. Thus, in various aspects, the incorporation of such egg-substitutes or egg-replacers into a formulation can be as a replacement for all or some of the egg present in the same formulation lacking the egg-substitute or egg-replacer.

Herein, "gluten-free" means that the formulation, and the resulting food product, has less than 20 ppm gluten. This level coincides with the U.S. FDA definition of gluten-free (as well as many other countries), and complies with the labeling requirements as set forth in Federal Register Notice 78 FR 47154 published Aug. 5, 2013, hereby incorporated by reference in its entirety.

Herein, "gluten-substitute" or "gluten-replacement" means that the formulation having the particles, and the resulting food product, contains less gluten than the same formulation lacking the particles, and the resulting food product. Thus, in various aspects, the incorporation of the particles into a formulation can be as a replacement for all or some of the gluten present in the same formulation lacking the particles. For example, a formulation having the particles contains at least 1 ppm, 5 ppm, 10 ppm, 15 ppm, or 20 ppm less gluten on a dry basis than the same formulation lacking the particles.

Herein, "allergen-free" means that the formulation contains less than about 20 ppm allergen. For example, a formulation contains less than about 20 ppm, 15 ppm, 10 ppm, 5 ppm, 1 ppm, or 0 ppm allergen. Examples of allergens include, but are not limited to, eggs, gluten, milk, fish (e.g., bass, flounder, cod), crustacean shell-fish (e.g., crab, lobster, shrimp), peanuts, wheats, and soybeans.

Herein, the word "suspension" means a mixture of a liquid and at least one solid. Herein, the term "X % stable suspension" (where "X" is an individual number or a range) is used to define the stability of a suspension in terms of the apparent volume level of the solids (relative to the total volume of the suspension) 24 hours after shearing or shaking 5-10 g of the solids in 100 g of water, or a similar ratio such as 2.5-5 g of solids in 50 g or water (or any ratio of liquid to solids that allows the apparent volume to be visualized), in a centrifuge tube sufficient to uniformly distribute the solids throughout the volume of the water in the centrifuge tube, along with an amount of cellulose particles as a suspension aid, if present, as described elsewhere herein. One of skill in the art would understand the proper centrifuge tube to perform this test so as to observe the settling of the suspension, if any. As used herein, "apparent volume" means the volume that a suspension of solids appears to have as a result of the solids being suspended or at least partially suspended within a liquid. For suspensions where settling is the predominant mechanism occurring, for example, a centrifuge tube containing a suspension of solids uniformly suspended in a liquid, in which the suspension is slowly settling, the suspension will initially contain solids having an apparent volume that is 100% of the suspension volume (i.e., the "X %" is 100%)). As syneresis occurs, or as the solids settle away from the liquid, the apparent volume of the solids decreases as the volume of a liquid layer at the top of the centrifuge tube increases, such that the value of X for this suspension will be less than 100%. The values of "X" (%) can be 25, 30, 35, 40, 45, 50, 55, 60, 65, 70, 75, 80, 85, 90, 95, or 100, which are relative to the total volume of the mixture in the centrifuge tube. Each of the foregoing numbers can be preceded by the term 'about,' 'at least about,' or 'less than about,' and any of the foregoing numbers can be used singly to describe an open-ended range or in combination to describe a closed-ended range. Thus, the X % stable suspension can be expressed as any of the foregoing values, which can include individual values or ranges. For example, a suspension produced herein can be a 35-80% stable suspension, an about 50% stable suspension, an at least about 55% stable suspension, and the like. To illustrate, a 35-80% stable suspension means that the apparent volume level of suspended solids within the centrifuge tube after subjecting such suspension to the test set forth in this paragraph falls within the range of 35-80% of the total volume of the suspension in the centrifuge tube. Generally herein, a suspension that is less than about 20% stable is considered to be an unstable suspension; a suspension that is at least about 95% stable is considered to be a stable suspension (or is referred to as being "suspension stable"); and a suspension that is about 20% to less than about 95% stable is considered to be a metastable suspension. However, if desired, the suspensions herein can simply be characterized as X % stable suspensions, without any reference to whether they are stable, unstable, or metastable. The solids employed in the suspension are made up of the particles comprising cellulose described herein, if present, (and in the proportions described herein), in combination with a solid that is being suspended with or without the aid of the particles comprising cellulose.

While the X % stable suspension definition above for predominantly settling compositions will be applicable to most suspensions, there are some suspensions where the solids intended for suspension will predominantly float rather than settle, or a substantial portion will float and some will settle. In such situations, and where the X % stable suspension definition is clearly inapplicable (e.g., an apparent volume cannot be readily measured), such suspensions with floating particles will be considered unstable if, after preparing the centrifuge tube with sample as described above (i.e., 24 hours after shearing 5 g of sample in 100 g of water with an amount of cellulose particles), the amount of floating solid that can be skimmed, dried, and weighed is 10% or more by weight of the original solids content of the suspension (sample plus cellulose particles). If the amount of floating solids is less than 10% by weight of the original solids content of the suspension (samples plus cellulose particles), and the apparent volume cannot be readily measured to apply the test set forth in the preceding paragraph, then the suspension is considered stable.

Herein, a substance (e.g., particles comprising cellulose) is considered "resuspendable" in a given fluid (e.g., water) if, when a suspension of the substance is dried to a solids content of at least about 95 wt %, the dried solids, when mixed according to "mixing method A," meet the following requirements: (1) the suspension resulting from mixing method A can be sieved with a 74 μm screen such that there are less than 30 wt % of solids remaining on the screen, (2) the resulting suspension that passed through the screen is measured to have a $d_{50}$ particle size that is within about 200% of the $d_{50}$ particle size distribution of the original suspension prior to drying, and (3) the resulting suspension that passed through the screen is measured to have a $d_{75}$ particle size that is within about 100% of the $d_{75}$ particle size distribution of the original suspension prior to drying. The "mixing method A" is performed as follows: (i) add the given fluid to the dried solids to provide a suspension having a solids content of about 7 wt % based on total suspension weight; (ii) heat the suspension at 45+/−5° C. for 1 hour; and (iii) blend the suspension for 60 seconds at about 12,000 rpm.

Herein, a "resuspending agent" is an additive that enables a substance to be "resuspendable" as defined above, which substance would otherwise not meet such definition of "resuspendable" without the addition of the resuspending agent. Examples of resuspending agents include, but are not limited to, polyol compounds, polyol oligomers, polyol polymers, saccharides including "cello-oligosaccharides" (e.g., cellohexaose, cellopentaose, cellotetraose, cellotriose, and cellobiose) and "gluco-oligosaccharides," oligosaccharides, monosaccharides, sucrose, glycerol, citric acid, sodium citrate, sorbitol, maltodextrin, a sugar alcohol, xylose, glucose, and sorbitol.

Herein, "consumable" means that the composition, good, product, or the like is intended for ingestion, and is actually ingestible, by a human, animal, plant, or other organism. Such a "consumable" may be in the form of a food, medicine, supplement, nutrient composition, or other ingestible product.

Herein, the terms "particles comprising cellulose" and "cellulose particles" are used interchangeably and refer to the same thing, namely, particles that comprise cellulose. These "cellulose particles" (or "particles comprising cellulose") are referred to in various aspects described herein, and it should be understood that, when any aspect or other disclosure herein makes reference to "cellulose particles" or "particles comprising cellulose," a specific meaning is intended, namely, the cellulose particles described herein, for which there is much disclosure herein on physical and structural characteristics, as well as properties and methods of making.

As used herein, the term "thermally stable" in the context of a composition comprising a liquid and cellulose particles (e.g., in drilling muds) means that the performance benefits of the composition (e.g., viscosity) are largely preserved when pH is held constant. Thus, in various aspects, the viscosity of a thermally stable composition remains largely unaffected upon being subjected to high temperatures (e.g., greater than 300° F.). Such thermal stability has been observed even when other properties, such as the pH, of the composition have changed. For example, the following composition is considered "thermally stable" for purposes of this application: a composition comprising a liquid and cellulose particles that is hot-rolled for 18 hours at a listed temperature (e.g., 250° F.), its pH is maintained, and upon cooling and collecting low-shear rheology readings (at 3 RPM and 6 RPM data points), the viscosity change is from about 50% to about 250% of the starting viscosity readings using an OFI Model 900 Viscometer. Thermal stability measurements are exemplified by Example 15.

As used herein, the term "weighting agent" refers to high-specific gravity particulates and soluble salts used to modulate, for example, to increase, the density of a fluid (e.g., a subterranean treatment fluid). Examples of weighting agents include, but are not limited to, barite, hematite, calcium carbonate, siderite, and limonite. In various aspects, the weighting agent complies with API/ISO standards.

As used herein, the term "plastic viscosity" of "PV" refers to the resistance of a fluid (e.g., a subterranean treatment fluid) to flow. For example, with respect to drilling fluids specifically, a low plastic viscosity indicates that the fluid is capable of drilling rapidly because of the low viscosity of fluid exiting at the bit.

The term "lime" generally in the art refers to calcium oxide, however, in the context of oil drilling it may additionally include calcium hydroxide, or refer to a calcium-containing inorganic mineral in which oxides and hydroxides predominate.

As used herein, the term "fuel slurry" refers to a mixture comprising particles of coal or charcoal suspended in a liquid carrier such as, for example, water. Thus, in various aspects, a fuel slurry can consist of from about 50% to about 70% coal or charcoal particles and from about 29% to about 49% liquid carrier. The fuel slurry can further comprise a chemical, e.g., to disperse the coal or charcoal particles in the liquid or to prevent settling of the particles. A fuel slurry can be useful, for example, in power boilers, gas turbines, diesel engines, and in heating and power stations.

As used herein, the term "mining slurry" refers to a mixture comprising particles of ore or mineral (e.g., coal, iron, manganese, lead, silver, barium, aluminum, copper, tin, mercury, calcium, molybdenum, platinum, uranium, and zinc) suspended in a liquid carrier such as, for example, water. A mining slurry can be useful, for example, to facilitate transport of the ore over long distances.

As used herein, the term "cleaning slurry" or "buffering slurry" refers to a mixture comprising abrasive particles suspended in a liquid carrier such as, for example, a cleaning liquid. Examples of abrasive particles include, but are not limited to, alkali metal salts and alkaline metal salts. Examples of cleaning liquids include, but are not limited to, water, aqueous-based detergent systems comprising builder salts and/or surfactants or organic solvents, and organic solvents. A cleaning or buffering slurry can be useful, for example, to reduce mechanical and chemical finishing, to remove contaminants (e.g., greases, cutting fluids, drawing fluids, machine oils, antirust oils, carbonaceous soils, sebaceous soils, particulate matter, waxes, paraffins, used motor oil, fuel) adhered to a surface or part, and/or to clean a solid surface or part (e.g., a metal workpiece, a printed circuit board).

As used herein, the term "imitation" refers to an edible food product that imitates a naturally occurring food product. Thus, in various aspects, "imitation" refers to an edible food product that is produced from substances that do not occur naturally and/or are not inherent in the food product being imitated. For example, imitation shell-fish, e.g., imitation crab and imitation lobster, are well known. "Imitation" can also refer to a vegetarian alternative to a meat product such as, for example, a veggie burger. Additional examples of imitation food products include, but are not limited to, imitation beef, imitation chicken, imitation turkey, imitation pork, imitation lamb, imitation horse, imitation buffalo, imitation venison, imitation veal, imitation game, imitation fowl, imitation plant proteins, imitation fermented proteins, imitation fish, imitation sausage, imitation burger, imitation kebab, imitation gyro, imitation shwarma, imitation patty, imitation cake, imitation loaf, imitation nugget, imitation strip, imitation hot dog, imitation deli product, imitation bacon, imitation jerky, imitation pet food, imitation pet treat, imitation processed meat, and imitation emulsified meat.

As used herein, the term "masonry construction material" refers to any material used in building structures by laying individual units or sections of the material. Examples of masonry construction materials include, but are not limited to, brick, stone, concrete, cement, asphalt, marble, granite, limestone, glass, and clay.

As used herein, the term "occlusive agent," in the context of cosmetic and personal care products, refers to a formulation component that prevents or retards (or contributes to preventing or retarding) water leaving the skin surface. An occlusive agent can be formulated as a cream, an ointment, a lotion, or a gel, although other formulations are also envisioned. Many oils are considered to be occlusive agents. Examples of occlusive agents include, but are not limited to, petrolatum or petroleum jelly, lanolin, castor oil, jojoba oil, mineral oil, and silicones such as dimethicone.

As used herein, the term "viscosifying agent" refers to any agent that increases the viscosity of a fluid. For example, a viscosifying agent can increase the viscosity of a fluid by at least (% increase) 5, 10, 15, 20, 25, 30, 40, 50, 60, 70, 80, 90, 100, 150, 200, 250, 300, 350, 400, 500, 600, 700, 800, 900, 1000, 1500, 2000, 3000, 4000, 5000, 6000, 7000, 8000 or even greater than 8000% compared to the viscosity of the same fluid without the viscosifying agent. Examples of viscosifying agents include, but are not limited to, clays and clay derivatives, polymeric additives, diatomaceous earth, and polysaccharides such as starches. Combinations of viscosifying agents can also be used. The particular viscosifying agent used depends on a number of factors, including the viscosity desired and chemical compatibility with other fluids used in the particular application.

As used herein, the term "antibacterial agent" refers to an agent that destroys bacteria and/or suppresses their growth or their ability to reproduce. Examples of antibacterial agents include, but are not limited to, antibiotics such as neomycin, sulphates, streptomycin, novobiocin, tetracycline, chlortetracycline, oxytetracycline and salts thereof; iodine, chlorine, or an agent(s) that releases these; phenolic compounds; quaternary ammonium salts; chlorhexidene; acridenes; penicillins such as ampicillin, ampicillin trihydrate, talampicillin, amoxycillin, nafcillin, carbenicillin, dicloxacillin, cloxacillin, benzathine cloxacillin, flucloxacillin, methicillin, ticarcillin, carefecillin; and mixtures of two pencillins such as ampicillin/flucloxacillin, amoxycillin/flucloxacillin, ticarcillin/flucloxacillin; and salts and hydrates thereof, such as ampicillin trihydrate/benzathine cloxacillin.

As used herein, the term "emollient," in the context of personal care products, refers to a formulation component that is capable of softening and/or soothing the skin. An emollient can be formulated as a cream, an ointment, a lotion, or a gel, although other formulations are also envisioned. Examples of emollients include, but are not limited to, propylene glycol, propylene glycol esters (e.g., propylene glycol laurate, propylene glycol myristate, and propylene glycol linoleate) and dimethicones (e.g., dimethicone PEG-8 beeswax, dimethicone PEG-7 isostearate, and dimethicone PEG-8 phosphate).

As used herein, the term "personal care product" refers to a product used in personal hygiene and/or for beautification. Examples of personal care products include, but are not limited to, cosmetic products, beauty products, haircare products, and soaps, and other products for men, women, and children that are intended to be rubbed, poured, sprinkled, sprayed, or otherwise applied to the hair, skin, or body for cleansing, beautifying, promoting attractiveness, or alternating the appearance, texture, feel, or smell of the person to which it is applied. Personal care products can also refer to any of the foregoing that are formulated specifically for use on pets (e.g., pet shampoo).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

B. Particles

In some aspects, the cellulose particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and in which at least a portion of the cellulose is type-II cellulose.

The particles comprising cellulose disclosed herein may be prepared from the hydrolysis of biomass and other cellulose containing materials, particularly those processes utilizing near critical and supercritical fluids, such as, for example, the hydrolysis of biomass using supercritical or near-critical water as described elsewhere herein.

Particles comprising cellulose may be isolated from the mixture resulting from the hydrolysis reaction by one or more of centrifugation, cyclone separation (including hydrocyclone separation), sedimentation, elutriation, aggregation, flocculation, screening, flotation and skimming, and the like, or any combination thereof in one or more steps. Differing cellulose particle fractions are produced according to differing methods of production and isolation, as discussed further elsewhere herein.

In various aspects, disclosed is a thickened composition comprising particles comprising cellulose, a suspension comprising particles comprising cellulose, an emulsion comprising particles comprising cellulose, resuspendable particles comprising cellulose, a food product comprising particles comprising cellulose such as a leavened or leavenable food product comprising particles comprising cellulose, a meat or meat analog product comprising particles comprising cellulose, a mayonnaise, dressing, sauce, soup, butter, beverage, and the like, a personal care product comprising particles comprising cellulose, or a composition comprising fluid and particles comprising cellulose such as a subterranean treatment composition, or metalworking fluid, cutting fluid, stamping fluid, abrading fluid, tribological fluid, cooling fluid, or lubricating fluid.

In various aspects, the particles comprise cellulose in an amount of 44%, 45% 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, 99%, or 100%, based on the total weight of the particles on a dry basis. Each of the foregoing numbers can be preceded by the word "about," "at least about," or "less than about," and any of the foregoing numbers can be used singly to describe an open-ended range or in combination to describe a close-ended range. For example and without limitation, the amount of cellulose in the particles can be at least about 45% by weight, about 45% by weight to about 100% by weight, at least about 99%, or less than about 100%, by weight based on the total weight of the particles on a dry basis.

In various aspects, and as readily appreciated by one of ordinary skill in the art, the cellulose particles may comprise a number of crystalline structures. Natural cellulose, known as a type-I cellulose, can comprise Iα and Iβ structures. The amount of Iα and Iβ structures depends on the type of the natural cellulose. For example and without limitation, the cellulose produced by bacteria and algae may be enriched in Iα, while cellulose of plants consists mainly of Iβ. Type-I cellulose may be converted to a stable crystalline form of cellulose known as a type-II cellulose. The conversion of the type-I cellulose to the type-II cellulose may be achieved by different routes, for example and without limitation, by mercerization (alkali treatment), regeneration (solubilization followed by recrystallization), subcritical and supercritical water, ball milling of cellulose in presence of water and the like. The conversion may be irreversible, suggesting that the type-II cellulose is more stable than type-I cellulose. In another embodiment, additional types of the cellulose may be included. For example, and without limitation, a type-III cellulose and type-IV cellulose may be produced by various chemical treatments, such as treatment with liquid ammonia or certain amides or amines, such as ethylene diamine, or high temperature treatment in glycerol. The particles comprising cellulose herein comprise type-II cellulose, in an amount ranging up to 100% of the cellulose. In various aspects, the particles comprising cellulose herein may additionally comprise type-I cellulose.

In various aspects, the cellulose particles comprise type-I cellulose and type-II cellulose. In various aspects, the cellulose particles comprise type-II cellulose and unconverted type-I cellulose. In various aspects, the cellulose particles further comprise lignin. It should be understood that each respective component present in the cellulose particles may be present in any amount relative to the total weight percentage of the cellulose particles. For example, and without limitation, the cellulose particles can comprise type-I cellulose (e.g., unconverted type-I cellulose) or type-II cellulose in any amount. The amounts described herein can apply to the amount of type-I cellulose in the cellulose particles, the amount of type-II cellulose in the cellulose particles, or the combined amount of type-I cellulose and type-II cellulose in the cellulose particles as will be clear by context. For example, the amount of type-I cellulose, type-II cellulose, or combined type-I and type-II cellulose in the cellulose particles can be 5%, 10%, 15%, 20%, 25%, 30%, 35%, 40%, 45%, 50%, 55%, 60%, 65%, 70%, 75%, 80%, 85%, 90%, 95%, or 100% by weight, based on the total weight of the cellulose particles on a dry basis. Each of the foregoing numbers can be preceded by the word "about," "at least about," or "less than about," and any of the foregoing numbers can be used singly to describe an open-ended range or in combination to describe a close-ended range. For example, the type-I and/or type-II cellulose can be present in an amount of at least about 35% by weight, about 15% by weight to about 70% by weight, or less than about 80% by weight, based on the total weight of the cellulose particles on a dry basis.

In various aspects, there may be a type-III cellulose, a type-IV cellulose, an amorphous cellulose, or any combination thereof present in the cellulose particles. The numerical weight percent ranges disclosed herein for the type-I cellulose and/or type-II cellulose may be used to describe the amount of any of these additional cellulose types, if present, either alone or in combination with one another as will be clear by context, and weight percent values are based on the total weight of the cellulose particles (i.e., the total weight of all cellulose types, including amorphous if present, making up the cellulose particles on a dry basis).

As one of ordinary skill in the art would readily appreciate, the different crystalline phases of the cellulose may be analyzed using X-ray diffraction (XRD). The specific XRD pattern of a crystalline solid reflects the crystal structure. Using Cu Kα radiation, the XRD spectrum of the type-I cellulose show two peaks at 2θ: a primary peak around 22.5° and a secondary peak around 15.5°. The XRD spectrum of the type-II cellulose shows a primary peak at 2θ around 19.9° and a secondary peak around 12.1°.

In various aspects, at least a portion of the cellulose particles exhibits a degree of crystallinity of 70%, 72%, 74%, 76%, 78%, 80%, 82%, 84%, 86%, 88%, 90%, 92%, 94%, 96%, 98%, 99%, or 100%. Each of the foregoing numbers can be preceded by the word "about," "at least about," or "less than about," and any of the foregoing numbers can be used singly to describe an open-ended range or in combination to describe a close-ended range. For example, the crystallinity can be about at least 90%, about 86% to about 96%, or less than about 88%.

Relative amounts of type-I cellulose, type-II cellulose, and amorphous cellulose can be measured using solid-state 13C CP-MAS NMR spectroscopy or XRD. In various aspects, the cellulose particles comprise, consist of, or consist essentially of cellulose having a type-II structure, either alone or in combination with a type-I structure, an amorphous structure, or both. In other words, the cellulose in the particles can be type-II cellulose, either alone or in combination with a type-I cellulose, amorphous cellulose, or both. In various aspects, the ratio of type-I cellulose to type-II cellulose in the cellulose particles, on a dry weight basis, is about 0.5:9.5, 1:9, 1.5:9.5, 2:8, 2.5:7.5, 3:7, 3.5:6.5, 4:6, 4.5:5.5, 5:5, 5.5:4.5, 6:4, 6.5:3.5, 7:3, 7.5:2.5, 8:2, 8.5:1.5, 9:1, or 9.5:0.5. Each of the foregoing numbers can be preceded by the word "about," "at least about," or "less than about," and any of the foregoing numbers can be used singly to describe an open-ended range or in combination to describe a close-ended range.

Another way to express the amount of type-II cellulose present in the cellulose particles is the amount of type-II cellulose normalized to the amount of type-I cellulose. For example, the ratio of type-II to type-I cellulose (i.e., type-II divided by type-I) can be 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.5, 6, 6.5, 7, 7.5, 8, 8.5, 9, 9.5, or 10. Each of the foregoing numbers can be preceded by the word "about," "at least about," or "less than about," and any of the foregoing numbers can be used singly to describe an open-ended range or in combination to describe a close-ended range. Accordingly, for example, in some aspects, the ratio of type-II to type-I cellulose is about 0.2 to about 0.8, about 1 to about 2, or about 3 to about 4.

A further way to express the amount of type-II cellulose is as a percentage based on total crystalline cellulose present in the cellulose particles as measured by XRD, as would be known by one of ordinary skill in the art. For example, the amount (%) of type-II cellulose can be 5, 10, 15, 20, 25, 30, 35, 40, 45, 50, 55, 60, 65, 70, 75, 80, 85, 90, 95, or 99. Each of the foregoing numbers can be preceded by the word "about," "at least about," or "less than about," and any of the foregoing numbers can be used singly to describe an open-ended range or in combination to describe a close-ended range. In various aspects, the cellulose particles comprise cellulose, wherein the cellulose is at least 99 wt % type-II cellulose on a dry basis.

In various aspects, the cellulose particles can comprise type-I and type-II cellulose having any of the ratios herein, and the cellulose particles can further comprise amorphous cellulose. The ratio of amorphous cellulose to total amount of type-I and type-II cellulose, on a dry weight basis, can be 0.5:9.5, 1:9, 1.5:9.5, 2:8, 2.5:7.5, 3:7, 3.5:6.5, 4:6, 4.5:5.5, 5:5, 5.5:4.5, 6:4, 6.5:3.5, 7:3, 7.5:2.5, 8:2, 8.5:1.5, 9:1, or 9.5:0.5. Each of the foregoing numbers can be preceded by the word "about," "at least about," or "less than about," and any of the foregoing numbers can be used singly to describe an open-ended range or in combination to describe a close-ended range.

In various aspects, the cellulose particles can comprise cellulose having a weight-average molecular weight (Mw in g/mol) of 2200, 2400, 2600, 2800, 3000, 3200, 3400, 3500, 3600, 3800, 4000, 4200, 4400, 4500, 4600, 4800, 5000, 5200, 5400, 5500, 5600, 5800, 6000, 6200, 6400, 6500, 6600, 6800, 7000, 7200, 7400, 7500, 7600, 7800, 8000, 8500, 9000, 9500, 10000, 10500, 11000, 11500, 12000, 12500, 13000, 13500, 14000, 14500, 15000, 15500, 16000, 16500, 17000, 17500, or 18000. Each of the foregoing numbers can be preceded by the word "about," "at least about," or "less than about," and any of the foregoing numbers can be used singly to describe an open-ended range or in combination to describe a close-ended range. For example, the Mw of the cellulose particles can be at least about 4000 g/mol, about 12000 g/mol to about 15500 g/mol, about 6000 g/mol to about 12000 g/mol, about 2200 g/mol to about 9500 g/mol, or less than about 13000 g/mol, as determined on a sample of the cellulose particles that has been prepared for gel-permeation chromatography analysis according to a first condition.

The cellulose particles can have any suitable Mn. For example, the Mn (g/mol) can be 2000, 2500, 3000, 3500, 4000, 4500, 5000, 5500, 6000, 6500, 7000, 7500, or 8000. Each of the foregoing numbers can be preceded by the word "about," "at least about," or "less than about," and any of the foregoing numbers can be used singly to describe an open-ended range or in combination to describe a close-ended range. For example, the Mn of the cellulose particles can be at least about 2000 g/mol, about 3000 g/mol to about 5500 g/mol, about 3000 g/mol to about 8000 g/mol, or less than about 7000 g/mol, as determined on a sample of the cellulose particles that has been prepared for gel-permeation chromatography analysis according to a first condition.

The cellulose particles can have any suitable Mz. For example, the Mz (g/mol) can be 5000, 5500, 6000, 6500, 7000, 7500, 8000, 8500, 9000, 9500, 10000, 10500, 11000, 11500, 12000, 12500, 13000, 13500, 14000, 14500, 15000, 16000, 17000, 18000, 19000, 20000, 21000, 22000, 23000, 24000, 25000, 26000, 27000, 28000, 29000, 30000, or 40000. Each of the foregoing numbers can be preceded by the word "about," "at least about," or "less than about," and any of the foregoing numbers can be used singly to describe an open-ended range or in combination to describe a close-ended range.

In various aspects, the cellulose particles can comprise cellulose having a degree of polymerization (DPW) of 10, 12, 14, 15, 16, 18, 20, 22, 24, 25, 26, 28, 30, 32, 34, 35, 36, 38, 40, 42, 44, 45, 46, 48, 50, 55, 60, 65, 70, 75, 80, 85, 90, 95, 100, 105, 110, 115, 120, 125, 130, 135, 140, 145, 150. Each of the foregoing numbers can be preceded by the word "about," "at least about," or "less than about," and any of the foregoing numbers can be used singly to describe an open-ended range or in combination to describe a close-ended range. For example and without limitation, the DP can be at least about 16, about 20 to about 95, about 40 to about 80, or less than about 150, as determined on a sample of the cellulose particles that has been prepared for gel-permeation chromatography analysis according to a first condition. DP, as used herein (sometimes termed DPW), is calculated from MW, using the anhydroglucose molar weight of 162 g/mol.

Similarly a DPn can be calculated from the Mn for the particles comprising cellulose. In various aspects, the cellulose particles can comprise cellulose having a number average degree of polymerization (DPn) of 15, 16, 18, 20, 22, 24, 25, 26, 28, 30, 32, 34, 35, 36, 38, 40, 42, 44, 45, 46, 48, 50, 55, 60, 65, 70, 75, 80, 85, 90, 95, 100, 105, 110, 115, 120, 125, 130, 135, 140, 145, 150. Each of the foregoing numbers can be preceded by the word "about," "at least about," or "less than about," and any of the foregoing numbers can be used singly to describe an open-ended range or in combination to describe a close-ended range. For example and without limitation, the DPn can be at least about 16, about 20 to about 95, about 25 to about 40, or less than about 150, as determined on a sample of the cellulose particles that has been prepared for gel-permeation chromatography analysis according to a first condition. DPn, as used herein, is calculated from Mn, using the anhydroglucose molar weight of 162 g/mol.

The Mw, Mn, Mz, and DP reported herein for the cellulose particles are different than those same parameters measured for microcrystalline cellulose (MCC), when solubilized for GPC measurement according to the first condition. The MCC used in this comparison was Acros Organics, cellulose microcrystalline, extra pure, average particle size 90 μm, product #382310010, and this MCC should be used for comparison purposes if available. If not available, then a comparable MCC should be used for comparison. Accordingly, in various aspects, the cellulose particles herein have an Mn that is 0.05, 0.1, 0.15, 0.2, 0.25, 0.3, 0.35, 0.4, 0.45, 0.5, 0.55, 0.6, 0.65, or 0.7 times the Mn of MCC. In various aspects, the cellulose particles herein have an Mw that is 0.04, 0.02, 0.04, 0.06, 0.08, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, or 0.5 times the Mw of MCC. In various aspects, the cellulose particles herein have an Mz that is 0.01, 0.02, 0.03, 0.04, 0.05, 0.06, 0.07, 0.08, 0.09, 0.1, 0.12, 0.14, 0.15, 0.16, 0.18, 0.2, 0.22, 0.24, 0.26, 0.28, 0.3, 0.32, 0.34, or 0.36 times the Mz of MCC. In various aspects, the cellulose particles herein have DP that is 0.04, 0.02, 0.04, 0.06, 0.08, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, or 0.5 times the DP of MCC. Each of the foregoing numbers relating to the comparison of Mw, Mn, Mz and DP for MCC and cellulose particles can be preceded by "about," "at least about," or "less than about," and any of the foregoing numbers can be used singly to describe an open-ended range or in combination to describe a close-ended range. For example, the cellulose particles have an Mw that is less than about 0.5 times the Mw of MCC.

The particles comprising cellulose can have any suitable PDI (polydispersity index). For example, the PDI can be 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, or 2.8. Each of the foregoing numbers can be preceded by the word "about," "at least about," or "less than about," and any of the foregoing numbers can be used singly to describe an open-ended range or in combination to describe a close-ended range.

In various aspects, the particles comprising cellulose described herein additionally comprise lignin. In various aspects, lignin is present in an amount (weight %, dry basis) of 0, 1, 2, 3, 4, 5, 6, 7, 8, 9, 10, 11, 12, 3, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 64, 66, 68, 70, 72, 74, 76, 78, or 80. Each of the foregoing numbers can be preceded by the word "about," "at least about," or "less than about," and any of the foregoing numbers can be used singly to describe an open-ended range or in combination to describe a close-ended range. For example, lignin can be present in an amount of at least about 4% by weight, about 10% by weight to about 26% by weight, or less than about 5% by weight. In various aspects, the particles comprise less than about 1% by weight lignin, or about 0% by weight lignin, based on the weight of the particles on a dry basis.

Particle sizes are measured and reported herein using a Beckman Coulter LS 13 320 Laser Diffraction Particle Size Analyzer instrument with Universal Liquid Module attached (referred to herein as the Beckman Coulter Particle Sizer). One of ordinary skill in the art would understand how to prepare samples for particle size analysis with the Beckman Coulter Particle Sizer. While the Beckman Coulter Particle Sizer is preferred for measuring particle size, if such an instrument is not available, a different instrument known to one of ordinary skill in the art to have comparable measurement results should be employed. Samples for analysis should be prepared in a manner that enables the particles to be analyzed with the instrument. The following sample preparation is illustrative: ensure the solids suspension in the sample is homogeneous in nature before injection into the instrument and, if not homogenous, blend the suspension for ten minutes in a Waring Laboratory Variable Speed Blender before injection into the instrument. The standard software accompanying the Beckman Coulter Particle Sizer provides instructions for use of the instrument and sample preparation.

Light scattering is a commonly used technique for particle size determination for a suspension of particles in a liquid and particle sizes are generally reported herein in terms of $d(n)$. The value $d(n)$ represents the particle size at which $(n)$ percentage of the sample, ranked by volume, is smaller. For example, the quantity $d(100)$ represents the particle size at which 100% of the sample is smaller. The quantity $d(90)$ represents the particle size at which 90% of the sample is smaller. The quantity $d(50)$ represents the particle size at which 50% of the sample is smaller. The quantity $d(25)$ represents the particle size at which 25% of the sample is smaller. The quantity $d(10)$ represents the particle size at which 10% of the sample is smaller.

The particles comprising cellulose disclosed herein may be characterized according to any desired particle size distribution characteristics. Particle size distributions typically include values of $d(n)$, where $(n)$ represents a volume percentage such as 5, 10, 15, 20, 25, 30, 35, 40, 45, 50, 55, 60, 65, 70, 75, 80, 85, 90, 95, or 100, at which $(n)$ percentage of the volume is smaller.

In exemplary and non-limiting aspects, the particles comprising cellulose have a particle size distribution with a $d_{10}$ (μm) of 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0. Each of the foregoing numbers can be preceded by the word "about," "at least about," or "less than about," and any of the foregoing numbers can be used singly to describe an open-ended range or in combination to describe a close-ended range. For example, the $d_{10}$ can be at least about 0.3 μm, about 0.6 μm, about 0.4 μm to about 0.7 μm, or less than about 1.0 μm.

In various aspects, the particles comprising cellulose have a particle size distribution with a $d_{25}$ (μm) of 0.3, 0.35, 0.4, 0.45, 0.5, 0.55, 0.6, 0.65, 0.7, 0.75, 0.8, 0.85, 0.9, 0.95, or 1. Each of the foregoing numbers can be preceded by the word "about," "at least about," or "less than about," and any of the foregoing numbers can be used singly to describe an open-ended range or in combination to describe a close-ended range. For example, the $d_{25}$ can be about 0.55 μm to about 0.7 μm.

In various aspects, the particles comprising cellulose have a particle size distribution with a $d_{90}$ (μm) of 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0. Each of the foregoing numbers can be preceded by the word "about," "at least about," or "less than about," and any of the foregoing numbers can be used singly to describe an open-ended range or in combination to describe a close-ended range. For example, the $d_{50}$ can be at least about 0.5 μm, about 1.4 μm, about 0.4 μm to about 5.0 μm, about 1.0 μm to about 1.6 μm, about 0.7 to about 1.2 μm, or less than about 2.0 μm.

In various aspects, the particles comprising cellulose have a particle size distribution with a $d_{75}$ (μm) of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, or 8.0. Each of the foregoing numbers can be preceded by the word "about," "at least about," or "less than about," and any of the foregoing numbers can be used singly to describe an open-ended range or in combination to describe a close-ended range. For example, the $d_{75}$ can be at least about 0.7 μm, about 3.0 μm, about 0.8 μm to about 3.0 μm, about 0.5 μm to about 6 μm, less than about 8.0 μm, or less than about 4.0 μm.

In various aspects, the particles comprising cellulose have a particle size distribution with a $d_{90}$ (μm) of 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.5, 9.0, 9.5, or 10. Each of the foregoing numbers can be preceded by the word "about," "at least about," or "less than about," and any of the foregoing numbers can be used singly to describe an open-ended range or in combination to describe a close-ended range. For example, the $d_{90}$ can be at least about 0.8 μm, about 6.2 μm, about 1.0 μm to about 7.5 μm, about 0.5 μm to about 10 μm, or less than about 8.0 μm.

In various aspects, the particles comprising cellulose are characterized by transmission electron microscopy or scanning electron microscopy (see, e.g., FIG. 6), in which the particle shape and aspect ratios can be readily visualized and calculated. In various aspects, aspect ratios for the particles comprising cellulose can be 1.01, 1.1, 1.2, 1.3, 1.4, or 1.5. Each of the foregoing numbers can be preceded by the word "about," "at least about," or "less than about," and any of the foregoing numbers can be used singly to describe an open-ended range or in combination to describe a close-ended range. For example, the aspect ratio can be about 1.2, about 1.1 to about 1.4, or about 1.4 or less. In various aspects, the aspect ratio is not greater than 1.5. In various aspects, particle shape can be irregular, globular, or the like. In various aspects, the particle shape is not needle-like, rectangular, or the like. In various aspects, the particle shape is non-spherical.

The cellulose particles can have any suitable zeta potential. For example, in some aspects, the cellulose particles have a zeta potential (mV) of −50, −48, −46, −44, −42, −40, −38, −36, −34, −32, −30, −28, −26, −24, −22, −20, −18, −16, −14, −12, −10, −8, −6, or −2. Each of the foregoing numbers can be preceded by the word "about," "at least about," or "less than about," and any of the foregoing numbers can be used singly to describe an open-ended range or in combination to describe a close-ended range.

In various aspects, suspensions (e.g., aqueous and/or organic solvent) of the particles comprising cellulose disclosed herein can have a solids content (%) of 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25, 26, 27, 28, 28, 30, 31, 32, 33, 34, 35, 36, 37, 38, 39, 40, 41, 42, 43, 44, 45, 46, 47, 48, 49, or 50. Each of the foregoing numbers can be preceded by the word "about," "at least about," or "less than about," and any of the foregoing numbers can be used singly to describe an open-ended range or in combination to describe a close-ended range. In various aspects, the suspension has a solids content of at least about 15%, about 16% to about 20%, or less than about 40%. In various aspects, the suspension has a solids content of about 20% to about 40%.

In certain embodiments, provided is a composition comprising cellulose particles and a resuspending agent, wherein the cellulose particles, when resuspended in a liquid according to mixing method A: comprise cellulose; have a $d_{75}$ of less than about 8 microns; have an aspect ratio of about 1 to about 1.5; and have a non-spherical shape; and wherein at least a portion of the cellulose is type-II cellulose; and wherein the resuspending agent is adsorbed or bonded to at least a portion of the surface of the cellulose particles.

In various aspects, a composition is provided comprising cellulose particles comprising cellulose as disclosed herein and further comprising at least one resuspending agent. In some aspects, the at least one resuspending agent is adsorbed or bonded to at least a portion of the surface of the cellulose particles. In various aspects, suspensions of such compositions may be dried and the dried compositions can have a solids content (%) of 60, 65, 70, 75, 80, 85, 90, 90.5, 91, 91.5, 92, 92.5, 93, 93.5, 94, 94.5, 95, 95.5, 96, 96.5, 97, 97.5, 98, 98.5, 99, 99.5, or 100. Each of the foregoing numbers can be preceded by the word "about," "at least about," or "less than about," and any of the foregoing numbers can be used singly to describe an open-ended range or in combination to describe a close-ended range. In various aspects, the cellulose particles have a solids content of at least about 98.5%, about 97% to about 99%, or at least about 95%. In various aspects, the cellulose particles have a solids content of about 92% to about 93.5%. As used herein, "adsorbed" means the resuspending agent is in contact with at least a portion of the surface of the cellulose particles and, in various aspects, may be (but need not be) held to the surface through noncovalent interactions such as hydrogen bonding, van der Waals forces, or a combination thereof. As used herein, "bonded" means the resuspending agent is covalently bonded to at least a portion of the surface of the cellulose particles. In various aspects, the resuspending agent may be both adsorbed and bonded to the surface, for example, where a portion (or portions) of the agent is (are) adsorbed to the surface, and another portion (or portions) is (are) bonded to the surface.

Cellulose materials of the invention may be used for human or animal consumption. To be in compliance with the regulations of the United States Food and Drug Administration (FDA) and other governmental agencies throughout the world, the cellulose particles disclosed herein may be substantially free of hazardous impurities. In various aspects, the cellulose particles and compositions may comprise heavy metals in an amount (ppm) of 0, 0.02, 0.04, 0.06, 0.08, 0.1, 0.15, 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, or 10. Each of the foregoing numbers can be preceded by the word "about," "at least about," or "less than about," and any of the foregoing numbers can be used singly to describe an open-ended range or in combination to describe a close-ended range. For example, the heavy metals can be present in an amount of at least about 0.05 ppm, about 0.2 ppm to about 10 ppm, or less than about 4.8 ppm. Test methods in accordance with USP <231> may be used for the heavy metals determinations, hereby incorporated by reference in its entirety.

As used herein, heavy metals refer to the toxic metals. There is no standard definition assigning metals as heavy metals. Some lighter metals and metalloids are toxic and thus are termed heavy metals, while some heavy metals, such as gold, typically are not toxic. In various aspects, the heavy metals described herein include but are not limited to the group of transition metals, some metalloids, lanthanides, actinides, and any combination thereof. In other aspects, the heavy metals include but are not limited to lead, cadmium, vanadium, nickel, cobalt, mercury, chromium, arsenic, selenium, copper, manganese, iron, zinc, beryllium, aluminum, or any combination thereof. The amount of heavy metals set forth in the preceding paragraph can be used to refer to any of these metals individually, or in combination, as the context will dictate.

In various aspects, the cellulose particles can exhibit a white color or an off-white color. In various aspects, the cellulose particles can exhibit a brown color. In various aspects, the cellulose particles can exhibit a gray color. As one of ordinary skill in the art would readily appreciate, the cellulose particles are not limited to any specific color.

In various aspects, the cellulose particles may be used in various food applications. In various aspects, the food applications comprise use of the cellulose particles as a texturizer, suspension aid, emulsifier, moisture retention aid, flavor enhancer, egg-replacement (full or partial) additive, gluten replacement additive, or any combination thereof. In various aspects, the cellulose particles can act in multiple such roles.

In various aspects, the cellulose particles can exhibit a smell and/or flavor that includes smoky, vanilla, chipotle, maple, toasted marshmallow, or any combination thereof. In various aspects, the cellulose particles enhance a vanilla smell and/or flavoring separately present in a consumable. In various aspects, the cellulose particles complement well the smells and/or flavors of certain consumables, such as brownies, cookies, banana bread, desserts, chipotle mayonnaise, salad dressings, sauces (e.g., barbecue sauce), maple syrup, chocolate sauce or syrup, fruit sauce or syrup, butterscotch sauce or syrup, sweet and sour sauce, and the like. Without wishing to be bound by theory, it is believed that in aspects where the cellulose particles contain lignin in addition to cellulose, the presence of lignin, lignin hydrolysis products, lignin degradation products, or any combination thereof results in certain desirable smells and/or flavors. In various aspects, the cellulose particles do not exhibit a discernible smell and/or flavor, for example, the cellulose particles do not exhibit a smell and/or flavor such as smoky, vanilla, chipotle, or any combination thereof. For example, smells or flavors can be removed by certain solvent washes (e.g., water, ethanol, carbon dioxide, a combination thereof, or the like), or the cellulose particles inherently possess no smell or flavor as a result of employing relatively pure cellulose in the hydrolysis process, as described elsewhere herein.

It is to be understood that the characteristics and/or properties of the cellulose particles comprising cellulose described herein may be varied as described herein, and such variability in the particle characteristics (such as particle size parameters, degree of polymerization, etc.) form several aspects. Furthermore, aspects disclosed herein are combinable unless mutually exclusive. Accordingly, a new embodiment may exist corresponding to one or more changes in variables as described herein. For example, a thickened composition comprising the cellulose particles as disclosed herein may be described by different aspects representing different particles according to the variability in the particle characteristics or properties as described herein. Similarly, different aspects exist for a suspension comprising the cellulose particles comprising cellulose as disclosed herein; different aspects exist for an emulsion or emulsifiable composition comprising the cellulose particles comprising cellulose as disclosed herein; different aspects exist for a resuspendable composition comprising the cellulose particles comprising cellulose as disclosed herein; different aspects exist for a food product such as a leavened or leavenable food product comprising the cellulose particles as disclosed herein, or for a meat or meat analog product comprising the cellulose particles as disclosed herein, or for a food product such as mayonnaise, dressing, sauce, soup, butter, beverage, or the like comprising the cellulose particles as disclosed herein; different aspects exist for a personal care product comprising the cellulose particles as disclosed herein; different aspects exist for a composition comprising a fluid and cellulose particles (e.g., a subterranean treatment composition, or metalworking fluid, cutting fluid, stamping fluid, abrading fluid, tribological fluid, cooling fluid, or lubricating fluid, etc.). In some aspects, however, the same cellulose particles that are suitable for one aspect can also be suitable for a different aspect. For example, cellulose particles that are suitable for a thickened composition, a suspension, an emulsion, a resuspendable composition, a food product such as a leavened/leavenable food product, or a meat or meat analog, or a mayonnaise, dressing, sauce, soup, butter, beverage, or the like, or a personal care product, or a composition comprising a fluid (e.g., a subterranean treatment composition, or metalworking fluid, cutting fluid, stamping fluid, abrading fluid, tribological fluid, cooling fluid, or lubricating fluid, etc.), may also be suitable for one or more of a different aspect of a thickened composition, a suspension, an emulsion, a resuspendable composition, a food product such as a leavened/leavenable food product or a meat or meat analog, or a mayonnaise, dressing, sauce, soup, butter, beverage or the like, or a personal care product, or a composition comprising a fluid.

C. Methods of Making, Purifying, and Manipulating Particles

In various aspects, disclosed are methods for making the disclosed cellulose particles. Thus, in various aspects, the cellulose particles may be prepared from the hydrolysis of biomass and other cellulose containing materials, particularly those processes utilizing near critical and supercritical fluids, such as, for example, the hydrolysis of biomass using supercritical water.

The hydrolysis of biomass may be performed as a one-step or as a two-step process. In some aspects, the two-step process is sometimes preferred in order to process the more readily hydrolysable hemicellulose component separately in a first step and under milder conditions to the second step which hydrolyses the cellulose component. In some aspects, an advantage to using the two-step approach is that the hydrolysis products of hemicellulose can be processed and isolated separately without over-reacting them to degradation products resulting from the harsher conditions required to hydrolyze cellulose. Although the cellulose particles described herein may be prepared using the two-step hydrolysis process, they may also be prepared via the one-step hydrolysis process. For example, typically size-reduced biomass is contacted with a near- or supercritical fluid at the conditions described elsewhere herein without a prior step to remove at least a portion of (or all or substantially all of) the hemicellulose. Various options for temperatures, pressures, and residence times for the one-step and two-step processes are disclosed elsewhere herein.

In various aspects, the biomass or cellulose-containing feedstock is subjected to sub-, near-, or supercritical hydrolysis. In various aspects, if desired, the biomass or cellulose-containing feedstock may be subjected to size-reduction prior to sub-, near-, or supercritical hydrolysis, typically to produce average particle size, d(50), of 75, 100, 150, 200, 250, 300, 350, 400, 450, 500, 550, or 600 microns. Each of the foregoing numbers can be preceded by the word "about," "at least about," or "less than about," and any of the foregoing numbers can be used singly to describe an open-ended range or in combination to describe a close-ended range. Typically, the average particle size is less than about 500 microns. The particle size can be measured by the techniques described elsewhere herein (e.g., Beckman Coulter LS 13 320 Laser Diffraction Particle Size Analyzer). The size reduction, if desired, may be achieved by an explosive decompression, such as steam explosion, or by comminution, ball-milling or other known techniques, including any combination thereof. In various aspects, size reducing comprises exploding the cellulose-containing feedstock in the presence of ammonia. In various aspects, size reducing comprises exploding the cellulose-containing feedstock in the presence of sulfur dioxide. Size-reduction, however, may not be necessary or desired if, for example, the feedstock already has an average particle size, $d_{(50)}$, of less than about 600 micrometers. When explosive decompression is employed, the feedstock typically is in the form of chips (e.g., having a size of ¼ inch, ½ inch, ⅞ inch, etc., or any combination thereof). In the two step process, the chips may be hydrolyzed (e.g., autohydrolyzed or digested) to remove the hemicellulose, and then the resulting chips subjected to an explosive decompression process to size-reduce the chips for subsequent near or supercritical hydrolysis to hydrolyze the cellulosic portion. In the one step process, when employing the explosive decompression process, the chips may simply be subjected to explosive decompression without a prior hydrolysis process to remove hemicellulose, and then the size-reduced biomass may be subjected to near or supercritical hydrolysis.

In various aspects, the feedstock to be subjected to sub-, near-, or supercritical hydrolysis, or any other hydrolysis (e.g., enzymatic, etc.) disclosed herein (for the one-step or two-step processes), has a particle size, $d_{(50)}$, as measured by light scattering, of less than about 600 μm, or less than about 500 μm, e.g., the particle size $d_{(50)}$, (in micrometers, μm) may be 5, 10, 25, 50, 75, 100, 125, 150, 200, 250, 300, 350, 400, 450, 500, 550, 600. Each of the foregoing numbers can be preceded by the word "about," "at least about," or "less than about," and any of the foregoing numbers can be used singly to describe an open-ended range or in combination to describe a closed-ended range. For example, the particle size, $d_{(50)}$, can be about 50 μm to about 600 μm, about 50 μm to about 500 μm, about 50 μm to about 450 μm, about 25 μm to about 250 μm, or about 100 μm to about 400 μm.

Hydrolysis processes (e.g., near- or supercritical hydrolysis) to produce polysaccharides including the cellulose particles disclosed herein, as well as oligosaccharides and/or monosaccharides, in various aspects, may employ a fluid at elevated temperatures and pressures (1) to convert at least a portion of the type-I cellulose component of the feedstock to type-II cellulose, (2) to hydrolyze at least a portion of the cellulose component of the feedstock, or (3) a combination of (1) and (2). In various aspects, the feedstock, preferably size reduced as described earlier herein, is mixed with a fluid, e.g., a fluid comprising, consisting of, or consisting essentially of water, thereby forming a mixture, and the mixture is subjected to near- or supercritical hydrolysis at the conditions described elsewhere herein.

In various aspects, the solids content (%) of the mixture for hydrolysis (in the one-step or two-step processes), based on the total weight of the mixture, is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, or 40. Each of the foregoing numbers can be preceded by the word "about," "at least about," or "less than about," and any of the foregoing numbers can be used singly to describe an open-ended range or in combination to describe a closed-ended range. For example, the solids content of the mixture can be about 10 wt % to about 29 wt %, about 15 wt % to about 29 wt %, about 10 wt % to about 18 wt %, or about 24 wt % to about 27 wt %.

The fluid in the one-step or two-step processes may be any suitable fluid, including without limitation, a single component fluid or a multi-component fluid. In one aspect, the fluid is selected from the group consisting of water, carbon dioxide, sulfur dioxide, methanol, ethanol, isopropanol, propanol, butanol, pentanol, and any combination thereof. In another embodiment, the fluid comprises, consists of, or consists essentially of water. In various aspects, the fluid is a combination of water and ethanol, water and carbon dioxide, or water and sulfur dioxide. In various aspects, the feedstock stream may be brought into physical contact with the fluid. In various aspects, the feedstock stream and the fluid form a mixture that exists at specified conditions to achieve the desired conversion, hydrolysis, production of cellulose particles, or any combination thereof. In these aspects, the feedstock is in contact with the fluid at the specified conditions. In various aspects, type-I cellulose is contacted with a fluid as described herein, followed by reducing the temperature, pressure, or both, or otherwise quenching the reaction as defined elsewhere herein. Without wishing to be bound by theory, it may be possible that at least a portion of the type-I cellulose is solubilized as shorter chain cellulose polymers upon contacting with the fluid. Upon reducing the temperature, pressure, or both, or otherwise quenching, particles comprising type-II cellulose may crystallize from the solubilized cellulose. In some aspects, the resulting cellulose particles comprise both type-I and type-II cellulose.

In various aspects, including in either the one-step or two-step processes, the fluid is in a sub-critical state, near-critical state, or supercritical state prior to contacting the feedstock. In various aspects, the hydrolysis reaction is carried out under conditions sufficient to maintain a sub-critical fluid state, near-critical fluid state, or supercritical fluid state (i.e., even after contacting). In other aspects, the term "under conditions sufficient to" refers to conditions that control the state of the fluid and include, but are not limited to, pressure and temperature. In various aspects, the pressures and temperatures for the sub-critical fluid, near-critical fluid, or supercritical fluid will vary with the choice of the fluid or fluids used in the reaction. In various aspects, the fluid at conditions sufficient to maintain sub-critical fluid state, near-critical fluid state, or supercritical fluid state may be present in a single phase, or may be present in multiple phases. In one aspect, the fluid comprises hot compressed water. In another embodiment, the fluid comprises supercritical water. In a further embodiment, the reaction is carried out under conditions sufficient to maintain water in a sub-critical state or a near-critical state. In a yet further embodiment, the reaction is carried out under conditions sufficient to maintain water in a supercritical state. In various aspects, the sub-critical fluid, near-critical fluid, or super-critical fluid is substantially free of an exogenous acid (i.e., is substantially free of an acid that has been deliberately added to the contacting fluid). In various aspects, the reaction is carried out using a fluid, and is carried out under a pressure sufficient to maintain all of the fluid in liquid form or supercritical form.

In various aspects, the feedstock, which may be size reduced as described elsewhere herein, and which may be in the form of a slurry, is mixed with a fluid, e.g., a fluid comprising, consisting of, or consisting essentially of water, thereby forming a mixture, and the mixture is subjected to hydrolysis at a temperature of at least about 100° C. In various aspects, the mixture is subjected to hydrolysis for a duration sufficient to hydrolyze at least a portion of the feedstock comprising cellulose. In various aspects, the mixture has a temperature (° C.) of 100, 120, 140, 160, 180, 200, 220, 240, 250, 260, 280, 300, 320, 340, 350, 355, 360, 365, 370, 374, 380, 385, 390, 395, 400, 410, 420, 430, 440, 450, 460, 480, 500, or 575. Each of the foregoing numbers can be preceded by the word "about," "at least about," or "less than about," and any of the foregoing numbers can be used singly to describe an open-ended range or in combination to describe a closed-ended range. For example, the mixture may be subjected to hydrolysis at a temperature of from 250° C. to 374° C., such as, for example, 340° C. to 374° C., and for a duration sufficient to produce at least one $C_6$ saccha-ride; or the mixture may be subjected to hydrolysis at a temperature of from 374° C. to 500° C., such as, for example, 375° C. to 430° C., or greater than 500° C., for a duration sufficient to dissolve at least a portion of the feedstock cellulose. In some such aspects, the mixture is substantially free of exogenous acid. In some such aspects, the mixture is substantially free of $C_1$-$C_5$ alcohols. Option-ally, for each embodiment, one or more preheating steps may also be employed. The temperatures for the one-step and the two-step processes can be formed from any of the tempera-tures disclosed in this paragraph, though typically the first step of the two-step process is performed at temperatures of 100° C. to about 350° C., and the second step is typically performed at temperatures of about 300° C. to about 500° C. When one step is employed, the temperature is typically about 300° C. to about 500° C.

In various aspects, the fluid that is contacted with the feedstock has a temperature (° C.) of 100, 120, 140, 160, 180, 200, 220, 240, 250, 260, 280, 300, 320, 340, 350, 355, 360, 365, 374, 380, 385, 390, 395, 400, 410, 420, 430, 440, 450, 460, 470, 480, 490, 500, 550, or 575. Each of the foregoing numbers can be preceded by the word "about," "at least about," or "less than about," and any of the foregoing numbers can be used singly to describe an open-ended range or in combination to describe a closed-ended range. Typi-cally, the temperatures of the fluid used for the one-step and the two-step processes can be formed from any of the temperatures disclosed in this paragraph, though typically the fluid in the first step of the two-step process has a temperature of about 100° C. to about 350° C., and the fluid in the second step typically has a temperature of about 350° C. to about 450° C. When one step is employed, the fluid typically has a temperature of about 350° C. to about 500° C.

In aspects where the mixture is subjected to sub-, near-, or supercritical hydrolysis, the hydrolysis is conducted at a pressure (bar) of 1, 5, 10, 20, 30, 40, 50, 60, 70, 80, 90, 100, 110, 120, 130, 140, 150, 160, 170, 180, 190, 200, 210, 220, 221, 225, 230, 250, 275, 300, 325, 350, 375, 400, 425, 450, 475, 500, 525, 550, 575, 600, 625, 650, 675, 700, 725, 750, 775, or 800. Each of the foregoing numbers can be preceded by the word "about," "at least about," or "less than about," and any of the foregoing numbers can be used singly to describe an open-ended range or in combination to describe a closed-ended range. For example, the pressure can be about 221 bar to about 800 bar, about 230 bar to about 500 bar, about 325 bar to about 750 bar, or about 275 bar to about 350 bar. In various aspects, the pressure may be greater than 800 bar. In various aspects, the pressure is sufficient to maintain at least a portion or all of the fluid in liquid or supercritical form. The pressure is not particularly limited provided that the fluid or mixture of the hydrolysis is in the desired form (e.g., liquid, liquid/vapor, or supercritical). The pressures in this paragraph can apply to the conditions of the one-step or the two-step processes, or to the pressure of the fluid that is contacted with the mixture.

In various aspects, where the mixture is subjected to near- or supercritical hydrolysis, the duration (seconds) of the hydrolysis is 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or 20. Each of the foregoing numbers can be preceded by the word "about," "at least about," or "less than about," and any of the foregoing numbers can be used singly to describe an open-ended range or in combination to describe a closed-ended range. In various aspects, where the mixture is subjected to subcritical hydrolysis, the duration (minutes) of the hydro-lysis is 0.5, 1, 1.5, 2, 2.5, 3, 3.5, 4, 5, 10, 20, 30, 40, 50, 60, 80, 100, 120, 140, 160, 180, 200, 220, 240, 260, 280, or 300. Each of the foregoing numbers can be preceded by the word "about," "at least about," or "less than about," and any of the foregoing numbers can be used singly to describe an open-ended range or in combination to describe a closed-ended range. The residence times in this paragraph can apply to the conditions of the one-step or the two-step processes. The residence times for the near- or supercritical hydrolysis is typically for the second step of the two step process, or for the one step process. The residence times for the subcritical process are typically for the first step of the two step process.

In various aspects, the mixture comprising the cellulose-containing feedstock that is subject to hydrolysis is substan-tially free of $C_1$-$C_5$ alcohol. In various aspects, the mixture is substantially free of exogenous acid. Optionally, for each embodiment, one or more preheating steps may also be employed prior to the hydrolysis. In other aspects, the mixture comprises any $C_1$-$C_5$ alcohol (as disclosed else-where herein), an exogenous acid, or any combination thereof. The mixture in this paragraph can be the mixture for either step of the two step process, or for the one step process.

In various aspects, and as readily understood by one of ordinary skill in the art, the methods described herein may be performed in any reactor known in the art that is capable of withstanding the methods' conditions. For example, and without limitation, the reactor may comprise one vessel. In various aspects, the reactor may comprise more than one vessel. In various aspects, the vessels may be connected to allow the reactant to flow against the flow of the fluid it contacts (i.e., countercurrent flow). In other aspects, the vessels may be connected to allow the mixture to flow in parallel with the flow of the fluid it contacts (i.e., co-current flow). The reactor comprises any possible configurations known in the art and it also may allow in situ separation of solids and liquid. In various aspects, the separation comprises filter press, centrifugation, gravity separation, cyclone, or similar, or any combination thereof, in one or more steps.

In various aspects, the hydrolysis reaction for either step of the two step process, or for the one step process, may be quenched, via one or more steps comprising one or more of flash cooling, a cool water quench, a heat exchange, or similar. Such quenching, for example, may comprise cooling to a temperature (° C.) of 20, 25, 30, 40, 50, 60, 70, 80, 90, 100, 110, 120, 130, 140, 150, 160, 170, 180, 190, 200, 210, 220, 230, 240, 250, 260, 270, 280, 290, or 300. Each of the foregoing numbers can be preceded by the word "about," "at least about," or "less than about," and any of the foregoing numbers can be used singly to describe an open-ended range or in combination to describe a close-ended range. For example, the temperature can be at least about 90° C., about 30° C. to about 180° C., or less than about 250° C.

In another embodiment, the quenching may comprise changing (e.g. reducing) the pressure to a pressure (bar) of 1, 5, 10, 15, 20, 25, 30, 35, 40, 45, 50, 55, 60, 65, 70, 75, 80, 85, 90, 95, or 100. Each of the foregoing numbers can be preceded by the word "about," "at least about," or "less than about," and any of the foregoing numbers can be used singly to describe an open-ended range or in combination to describe a close-ended range. For example, the pressure can be changed to a pressure of at least about 10 bar, about 15 bar to about 60 bar, or less than about 40 bar.

In various aspects, the hydrolysis process products produced by the methods described herein (e.g., the one step or two step processes) further comprise lignin. In one aspect, the method further comprises separating at least a portion of the lignin from the cellulose particles using one or more of centrifugation, cyclone separation (including hydrocyclone separation), sedimentation, elutriation, aggregation, flocculation, screening, flotation and skimming, and the like, or any combination thereof, in one or more steps. In another embodiment, the method comprises separating at least a portion of the lignin from the cellulose particles using a hydrocyclone. In another embodiment, at least a portion of the lignin is removed in an underflow of the hydrocyclone. In yet another embodiment, at least a portion of the cellulose particles is removed in an overflow of the hydrocyclone.

Without wishing to be bound by theory, it is believed that the setting rate of particles in gravitational or centrifugal force fields is proportional to the difference between particle and liquid densities. Thus, the denser particles are generally removed in the underflow of a hydrocyclone and the less dense particles are generally removed in the overflow. In order to remove denser particles (e.g., cellulosic oligomers) in the overflow stream, those particles need to be made much smaller than the less dense lignin type particles. A rapid quench of a solution of supersaturated dissolved cellulose oligomers produces desirably small particle sizes. In this way, the denser particles can be made smaller than the less dense particles, and the denser particles can then be removed in the overflow of the hydrocyclone. As a result, the finer cellulosic oligomer particles can be separated from the lignin particles prior to filtration (e.g., using a filter press) to avoid problems encountered when attempting to filter fine particles (e.g., slow filtration, and the tendency of the small particles to become entrapped in the lignin-rich filter cake, which can avoid a yield loss).

In one aspect the yield (wt %, dry basis) of the recovered cellulose particles, based on the amount of cellulose in the reactant, can be 5, 7, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, or 99. Each of the foregoing numbers can be preceded by the word "about," "at least about," or "less than about," and any of the foregoing numbers can be used singly to describe an open-ended range or in combination to describe a close-ended range. The yield can be any value bounded by the foregoing endpoints, or can be an open-ended range. For example, the yield can be at least about 10%, about 20% to about 66%, or less than about 82%.

In various aspects, the cellulose particles comprise a type-I cellulose (e.g., unconverted type-I cellulose) and type-II cellulose; in various aspects the cellulose particles comprise type-II cellulose and do not comprise type-I cellulose. In various aspects, the cellulose particles comprise amorphous cellulose.

In various aspects, the hydrolysis of the cellulosic feedstock also produces at least one of a monosaccharide and an oligosaccharide. In various aspects, a one step process is employed and both hemicellulose and cellulose are hydrolysed to produce at least one of a monosaccharide and an oligosaccharide. In certain such aspects, the monosaccharide comprises a saccharide selected from the group consisting of a $C_5$ monosaccharide, a $C_6$ monosaccharide, and a combination thereof. In certain such aspects, the oligosaccharide comprises a saccharide selected from the group consisting of a $C_5$ oligosaccharide, a $C_6$ oligosaccharide, and a combination thereof. $C_5$ saccharides include xylose, arabinose, lyxose, ribose, xylulose, or combinations thereof. $C_6$ saccharides include glucose, mannose, galactose, cello-oligosaccharides, or combinations thereof. In various aspects, the $C_6$ saccharide is a $C_6$ monosaccharide, and the $C_6$ monosaccharide is at least one sugar selected from the group consisting of glucose, mannose, galactose, fructose, and combinations thereof. In various aspects, said $C_6$ saccharide is glucose. In various aspects, the $C_5$ saccharide is a $C_5$ monosaccharide, and the $C_5$ monosaccharide is at least one sugar selected from the group consisting of xylose, arabinose, lyxose, ribose, xylulose, or combinations thereof. In various aspects, said $C_5$ monosaccharide is xylose.

In various aspects, the $C_6$ saccharide is a $C_6$ oligosaccharide, and the $C_6$ oligosaccharide has a degree of polymerization of about 2 to about 15. For example, the $C_6$ oligosaccharide has a degree of polymerization of 2, 3, 4, 5, 6, 7, 8, 9, 10, 11, 12, 13, 14, 15. Each of the foregoing numbers can be preceded by the word "about," "at least about," or "less than about," and any of the foregoing numbers can be used singly to describe an open-ended range or in combination to describe a closed-ended range. For example, the $C_6$ oligosaccharide can have a degree of polymerization of about 3 to about 5, about 10 to about 15, or about 2 to about 7. $C_6$ oligosaccharides are often referred to as cello-oligosaccharides or gluco-oligosaccharides (GOS). Lower molecular weight GOS may be soluble in water or aqueous solvents.

In various aspects, the methods disclosed herein, including the hydrolysis (e.g., near- or supercritical hydrolysis) and collection of $C_6$ saccharides, are run continuously, although, in other aspects, they may be run as batch or semi-batch processes.

In various aspects, a liquid fraction formed by the hydrolysis methods described herein comprises a soluble glucose monomer, soluble glucose oligomer, soluble xylose, or any combination thereof. Typically, this liquid fraction is formed from near or supercritical hydrolysis. In various aspects, the "solubility" is relative to water or aqueous solvents (as the case may be) at ambient conditions. For example, in various aspects, the hydrolysis reaction produces at least one cello-saccharide selected from a group consisting of one or more of cellohexaose, cellopentaose, celloteraose, cellotriose, cellobiose, and any combination thereof. In various aspects, the hydrolysis products comprise glucose. These lower DP cello-saccharides are generally soluble in water at ambient conditions.

In various aspects, the method further comprises purifying at least one of the $C_5$ or $C_6$ saccharides. Suitable purification methods include chromatography and the like. In various aspects, the method further comprises purifying or partially purifying at least one of the $C_6$ oligosaccharides or some fraction of mixed oligosaccharides and/or low molecular weight polysaccharides, as discussed below. For example, one method of at least partial purification comprises isolating the aqueous GOS solution and, optionally, removing at least a portion of the aqueous solvent of the solution (e.g., by evaporation) to produce a solids content of about 50-90%, followed by addition of an organic solvent, preferably an alcohol, such as, for example, ethanol (or, alternatively or additionally, methanol, isopropanol, n-propanol, butanol, acetone, or acetonitrile) in order to precipitate solvent-insoluble oligomers, referred to herein as precipitated GOS (also called "PGOS"). Mixtures of solvents may be suitable, including the use of denatured solvents (such as, the commercial grade of ethanol comprising about 90% ethanol, 5% methanol and 5% isopropanol). The PGOS solids may be easily isolated by any suitable solid/liquid separation technique, such as, for example, filtering.

The PGOS solids (or a solution of PGOS, or a solution of GOS prior to the precipitation to make PGOS described herein) may be useful as a resuspending agent for the cellulose particles herein, or may be useful as a resuspending agent for any other suitable particle. Suitable particles include silica, cellulose (e.g., MCC, NCC, etc.), inorganic particles, and organic particles, as well as any components intended for resuspendable compositions, such as "dry paint formulations" sometimes referred to as "paint in a bag" and spray dried formulations that may suffer from agglomeration. Examples of inorganic or organic particles include pigment particles. To make a particle resuspendable, the PGOS can be dissolved in solution, and the cellulose particles added to this solution. The solution of PGOS plus particles may then be dried to the desired extent (e.g., at least 80, 85, 90, 95, 99, or 100 wt % solids). Without wishing to be bound by theory, the dissolved PGOS may adsorb and/or bond to the particle surface and act as a buffer between other particles, thereby allowing the cellulose particles to dry to a substantial extent without agglomerating, or at least the dissolved PGOS allows the cellulose particles to be resuspendable (i.e., any agglomerating that occurs is substantially reversible). Similarly, a GOS solution (prior to precipitation to make PGOS) which is filtered from the mixture after a hydrolysis process described herein can be used as is, or concentrated, and then particles can be added to this GOS solution. The GOS solution plus particles can then be dried to a desired extent (as noted above) to form resuspendable particles.

The PGOS solids may also be useful in various other applications, including as standards for GPC, probiotics, and so forth.

The PGOS solids may have a small residual color, which can be removed, for example, by re-dissolving in water or an aqueous solution (using any of the solvents or combinations thereof listed in the preceding paragraph) and passing the solution through a chromatography column (or alternatively, by bleaching with hydrogen peroxide, or by extraction with acetone).

Once isolated wet, the white PGOS solid may darken over time while drying in air. This may occur whether the PGOS has been isolated from GOS formed from the hydrolysis of lignocellulosic biomass, or even from GOS formed from hydrolysis of commercially obtained (white) MCC. The darkening may be avoided by one or more of (1) drying the solids immediately at elevated temperatures (e.g., between 50-105° C.), and/or (2) drying the material under an inert atmosphere such as nitrogen. In either case, spreading the solids to provide a larger surface area is beneficial. Once dry, the solids are stable to discoloration at room temperature, but higher temperatures (e.g., above 70° C.) should be avoided, since, once dry, the dry solids darken at higher temperatures, especially at extended periods of time. Further purification may be achieved by dissolving PGOS in a solvent (described above) and passing the solution through a chromatography column.

In one aspect, disclosed are methods for preparing a solid sample of water-soluble glucooligosaccharides (GOS) comprising: (a) contacting a cellulosic substrate with a sub-critical, near-critical or supercritical fluid (e.g., water) for a duration sufficient to form a mixture of liquid and solids, said liquid comprising GOS; (b) collecting at least a portion of the liquid; (c) optionally, removing at least a portion of the liquid from the liquid comprising GOS to form a higher solids mixture comprising GOS; (d) contacting the higher solids mixture comprising GOS with an organic solvent to form solid GOS; and (e) separating the solid GOS from the mixture and collecting the solid GOS. In a further aspect, the method further comprises: (0 drying the solids at a temperature greater than 50° C. or drying the solids under an inert atmosphere or both.

In various aspects, the yield of PGOS is at least 30% of theoretical yield. In various aspects, the yield (%) of PGOS is 30, 35, 40, 45, 50, 55, 60, 65, 70, 75, 80, 85, 90, 95, or 99% of theoretical yield. Each of the foregoing numbers can be preceded by the word "about," "at least about," or "less than about," and any of the foregoing numbers can be used singly to describe an open-ended range or in combination to describe a closed-ended range. For example, in various aspects, the yield of the PGOS is at least about 70% of theoretical yield, or at least about 85% of theoretical yield. The percent yield, as used herein, may refer to the total yield of all PGOS, or to the percent yield of any specific DP range of PGOS disclosed elsewhere herein, or any combination of these specific DP ranges of PGOS.

Figure 1:
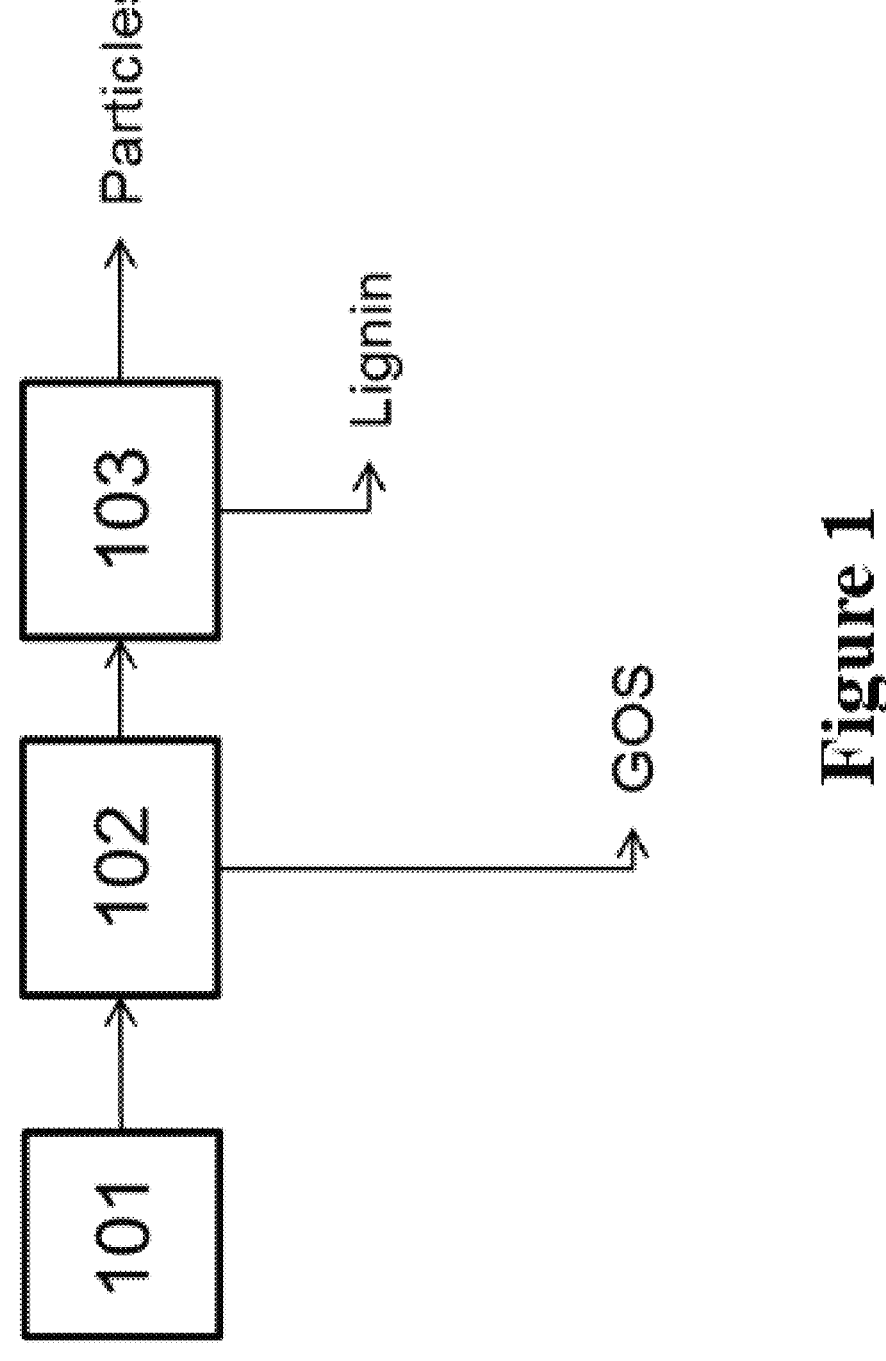
FIG. 1 shows a simplified diagram of a process to make the particles comprising cellulose described herein.

The particles comprising cellulose disclosed herein may be formed and isolated in a one step or two-step hydrolysis process as follows and as outlined in (FIGS. 1 and 2) (and described elsewhere herein): in an optional first step, often referred to as hemi-hydrolysis, an aqueous slurry of size-reduced biomass is subjected to a temperature of about 150-250° C. for a period of about 1-120 minutes under a pressure sufficient to keep all of the fluid in liquid form (generally less than about 50 bar). Alternatively, the optional first step may be performed as a digester/steam explosion process, as described in the Examples and elsewhere herein. In either case, the resulting mixture of solids and liquids is separated (e.g., by filtration), the solids re-slurried with water, and the slurry subjected to sub-critical, near-critical or supercritical hydrolysis, such as, for example, a temperature of about 340-450° C. for a period of less than about 10 sec under a pressure sufficient to keep the fluid in liquid or supercritical form (but, in any case, generally less than about 250 bar). The one-step process may be performed by using a slurry of the size-reduced biomass or cellulose-containing feedstock (without prior removal of hemicellulose) and subjecting the size-reduced feedstock to near or supercritical hydrolysis. FIG. 1 illustrates this process in simplified form: Hydrolysis of the biomass or cellulose-containing feedstock occurs in the hydrolysis reactor (101), from which the resulting mixture from the hydrolysis reaction, comprising a first liquid fraction and a first solid fraction, is cooled via one or more cooling steps, of which one or more may be flash, water quench, heat exchange or similar, before passing to a solid/liquid separation apparatus (102), such as a filter press or a pressurized filter, where the solids and liquid may be separated, for example by filtration, to separate the first liquid fraction (predominantly gluco-oligosaccharides, GOS, in aqueous solution) from the first solids fraction (predominantly lignin and cellulosic polysaccharide solids). If desired, the lignin and cellulosic solids from the first solids fraction may be separated in a separation apparatus (103) using any suitable separation technique, such as, for example, one or more hydrocyclones and/or centrifuges. If the GOS is the only intended product, then the solid/solid separation step (103) is not necessary. The cellulose particles are recovered as the hydrocyclone overs in the form of a slurry or suspension, which may be further dewatered by centrifugation to produce a stable suspension of cellulose particles typically having a solids content of about 16-25% and a $d_{50}$ of about 0.5-2 μm (as measured by the Beckman Coulter Particle Sizer described elsewhere herein).

Removal of water by heating or rotary evaporation or spray drying or freeze drying results in agglomeration of the cellulose particles and a much higher average particle size (e.g., $d_{50}$ of at least 20 μm). The agglomerated dry solids are not readily resuspended in water. However, a higher solids content suspension may be achieved without agglomeration of the cellulose particles by subjecting the suspension to one or more freeze-thaw cycles. A first freeze of a freeze-thaw cycle has the effect of loosely associating the solids, such that the corresponding thaw results in a partially separated suspension, from which the excess water at the upper surface can be readily removed (e.g., by pipette, or by decanting). The resulting suspension has a solids content of about 25-30%. Repeated freeze-thaw cycles allow the solids level of the cellulose suspension to increase to 40% solids or more.

Accordingly, in one aspect, disclosed are methods for increasing the solids content of an aqueous suspension of the particles comprising cellulose as described herein comprising: a) freezing the aqueous suspension to form a frozen suspension; b) thawing the frozen suspension to form a gradation of solids content in the suspension such that an upper portion of the suspension has a lower solids content, and a lower portion of the suspension has a higher solids content; c) isolating at least a portion of the lower portion; and d) optionally, repeating steps (a), (b) and (c) one or more times on the lower portion; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

Figure 2:
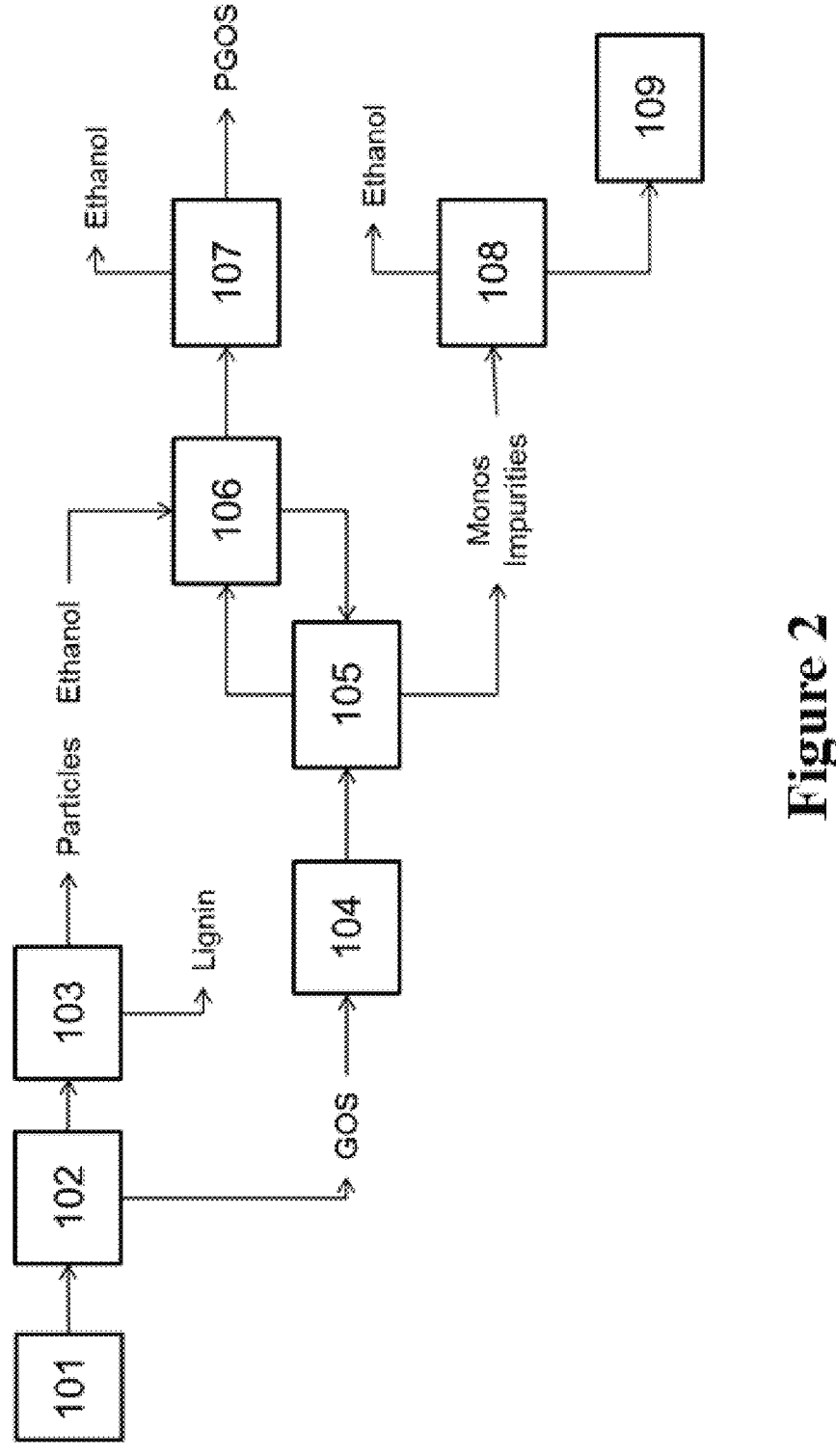
FIG. 2 shows a simplified diagram of a manufacturing process to make the particles comprising cellulose described herein.

In the above process (FIG. 1), the liquid filtrate (first liquid fraction) from filtration of the resulting mixture from the hydrolysis reaction contains predominantly an aqueous GOS solution, which, optionally, may be purified or at least partially purified as discussed elsewhere herein. FIG. 2 illustrates a process that includes the steps shown in FIG. 1, and additionally illustrates purification of the components of the liquid fraction. For example, the liquid filtrate (predominantly gluco-oligosaccharides, GOS, in aqueous solution)

may be concentrated for example, to 50-90% solids in an evaporator (104), followed by washing/re-suspending with ethanol (or another suitable solvent) in a wash tank (105), in order to precipitate the PGOS, which can then be separated, and optionally washed, in a suitable solid/liquid separation apparatus (106), such as a filtration apparatus. Ethanol can be stripped from the PGOS solids in a drying chamber (107) and the clean ethanol recovered, which also leaves the precipitated glucooligosaccharides (PGOS) solids for collection. Various impurities and products do not precipitate upon addition of ethanol and these can be isolated from the filtrate and collected, if desired. For example, the filtrate can pass to a distillation column (108) and the ethanol can be distilled off and recovered, and the monosaccharides and disaccharides can be isolated and collected, if desired, for example, by evaporating the aqueous filtrate or running the aqueous filtrate through a separation system (109), such as, for example, a chromatography column or membrane.

In one aspect, the particles comprising cellulose formed by the methods described herein are separated from the first liquid fraction, the first solid fraction, or a combination thereof by any suitable technique or combination of techniques, which may include, e.g., filter press, centrifugation, gravity separation, cyclone, or similar, in one or more steps, as described elsewhere herein. In various aspects, optionally the method further comprises washing the collected particles comprising cellulose with a solvent to form a liquid wash fraction and a washed solid fraction. In various aspects, the solvent is selected from water, a C1-C5 alcohol, dioxane, aqueous dioxane, aqueous alkaline solution, aqueous alkaline dioxane, and any combination thereof. In one aspect, the aqueous dioxane solution can comprise any ratio of dioxane to water. For example, the aqueous dioxane solution comprises about 4% of water in dioxane by volume, based on the total volume of the solution. In one aspect, the aqueous alkaline solution comprises a solution of sodium hydroxide (NaOH) in water, a solution of potassium hydroxide (KOH) in water, a solution of lithium hydroxide (LiOH) in water, or any combination thereof. The amount of alkaline compound in the aqueous alkaline solution is not particularly limited, but typically may be about 1% by weight. In various aspects, an aqueous alkaline dioxane solution comprises about 4% of water in dioxane by volume, based on the total volume of the solution, and about 1% hydroxide (e.g., NaOH, LiOH, and/or KOH) by weight, based on the total weight of the solution. In various aspects, the aqueous alkaline solution is any concentration sufficient to wash the collected particles comprising cellulose without significantly altering the chemical and physical properties of the cellulose particles.

Figure 3:
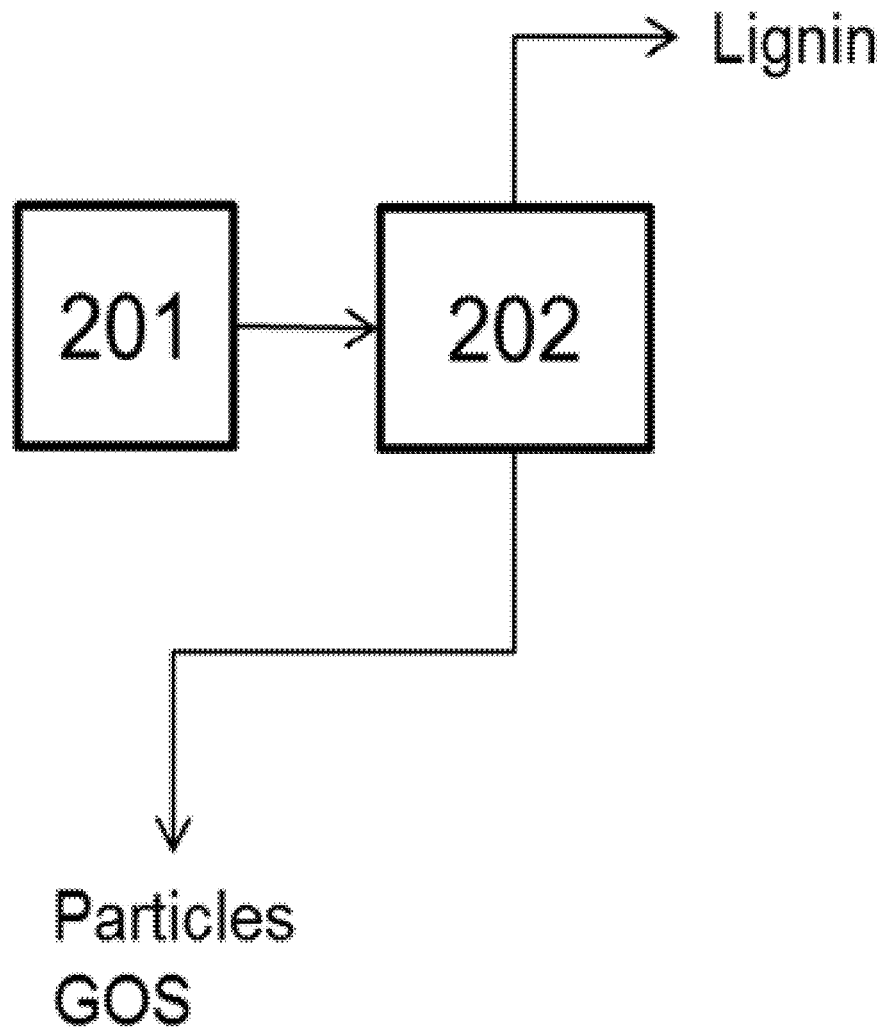
FIG. 3 shows a simplified diagram of an alternative process to make the particles comprising cellulose described herein.
Figure 4:
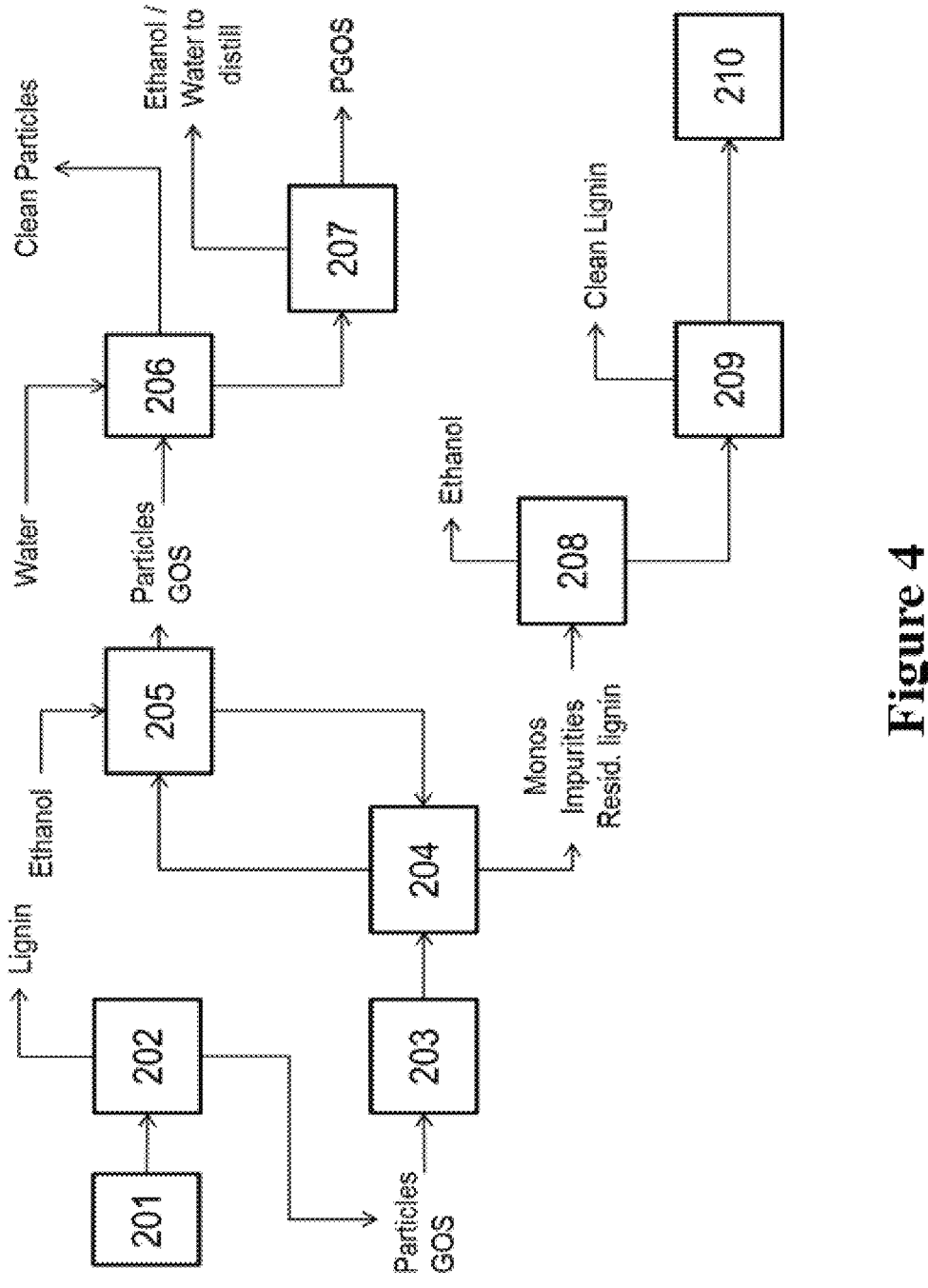
FIG. 4 shows a simplified diagram of an alternative manufacturing process to make the particles comprising cellulose described herein.

In another embodiment (see FIGS. 3 and 4), hydrolysis of the biomass or cellulose-containing feedstock occurs in the hydrolysis reactor (201), from which the resulting mixture from the hydrolysis reaction (the one-step process, or step two of the two-step process) comprising a first liquid fraction and a first solid fraction is processed directly in a separation vessel (or vessels) (202), for example, in one or more hydrocyclones or one or more centrifuges, or a combination thereof, without performing a prior separation step by filtration. A separation using hydrocyclones and/or centrifuges can separate the lignin in one stream from the combined GOS and cellulose particles in another stream (FIG. 3). FIG. 4 illustrates a process that includes the steps shown in FIG. 3, and additionally illustrates purification of the GOS and particles comprising cellulose, as well as other products. In one aspect, the combined aqueous mixture of GOS and cellulose particles are isolated together by simply evaporating or heating to dryness in the evaporator (203).

Although a dried sample of the particles comprising cellulose (where GOS was filtered off) is not resuspendable in water, it was unexpectedly found that the combination of the GOS and the particles comprising cellulose can be dried and then re-suspended in water without suffering from agglomeration of the cellulose particles. Without wishing to be bound by theory, it is believed the GOS adsorbs to the surface of the cellulose particles, providing a protective layer or partial layer that prevents the cellulose particles from agglomerating on drying. However, the combined GOS and cellulose particles stream may additionally contain small particle size lignin and other impurities and it may be preferable to remove the impurities, especially since this stream can undergo a purification in one convenient step, as described below (and elsewhere herein). In particular, the combined GOS/particles comprising cellulose/impurities stream is first concentrated in the evaporator (203), for example, by evaporating some liquid or by drying to remove a portion of the liquid, for example, to 50-90% solids, followed by washing/re-suspending with ethanol in the wash tank (204) in order to precipitate the PGOS along with the cellulose particles, which can then be separated, and optionally washed, with ethanol in a suitable solid/liquid separation apparatus (205), such as a filtration apparatus. The filtrate contains lignin in solution, along with some monosaccharides (and disaccharides), some residual impurities, and water and ethanol (or other suitable solvent). All of these components may be recovered. For example, the ethanol can be distilled off in a distillation column (208) to recover clean ethanol, and simultaneously precipitate the small particle size lignin, which may then be easily collected at the solid/liquid separation apparatus (209), for example, the lignin may be filtered off and the clean lignin collected as the solid on the filter. The monosaccharides (and disaccharides) can be isolated and collected by running the aqueous filtrate through a separation system (210), such as, for example, a chromatography column or membrane. The PGOS along with the particles comprising cellulose can be collected from solid/liquid separation apparatus (205) as a combined solid product, discussed herein below. Alternatively, these two components can be collected separately: the particles comprising cellulose, which are water insoluble at ambient conditions, can be isolated from the surface-adsorbed water soluble PGOS components by water dissolution in a separation apparatus (206), which allows the dissolved PGOS to be recovered as an aqueous solution. Examples include ultrafiltration, dilution and centrifugation, and the like. The water and residual ethanol can be removed (e.g., distilled or evaporated off) from the aqueous PGOS solution in a drying chamber (207) leaving a solid PGOS sample. The solid cellulose particles can be recovered as a stable suspension or as a filter cake that can be resuspended to form a stable suspension, and such suspensions have particles having a $d_{50}$ of 0.5-2 μm (as measured by the Beckman Coulter Particle Sizer). This method avoids the difficult filtration step of the resulting mixture from hydrolysis, incorporates an ethanol wash step that effectively separates the ethanol-insoluble oligo- and poly-saccharides from the residual ethanol-soluble lignin, low molecular weight saccharides (DP 1-2) and other impurities, and provides a cleaner lignin product and a cleaner PGOS, as well as the purified cellulose particles. If desired, the cellulose composition which contains adsorbed PGOS can be collected without a water wash (such that the PGOS remains adsorbed onto the cellulose). This combined product has been cleansed of the small lignin particles and other impurities by the earlier step of washing/re-suspending with ethanol.

In one aspect, disclosed are methods for preparing the particles comprising cellulose disclosed herein comprising: (a) contacting a cellulosic substrate with a sub-critical, near-critical or supercritical fluid for a duration sufficient to form a mixture of liquid and solids, said mixture comprising gluco-oligosacharides (GOS) and particles comprising cellulose; (b) optionally, separating lignin from the mixture comprising GOS and particles comprising cellulose; (c) optionally, removing at least a portion of the liquid from the mixture comprising GOS and particles comprising cellulose to form a higher solids mixture comprising GOS and particles comprising cellulose; and (d) contacting the mixture comprising GOS and particles comprising cellulose with an organic solvent to form solid GOS and particles comprising cellulose.

In a further aspect, the method further comprises: isolating the solid GOS and particles comprising cellulose as solids from the liquid. In a still further aspect, the method further comprises: contacting the solid GOS and particles comprising cellulose with water to dissolve the GOS. In yet a further aspect, the method further comprises: separating the solid particles comprising cellulose from the liquid, and collecting the particles comprising cellulose; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

D. Resuspendable Particles

As discussed above, a dried sample of the particles comprising cellulose (where GOS has been filtered off) is not typically resuspendable in water without extremely high shear, but the combination of the GOS adsorbed on the cellulose particles can be dried and then readily resuspended in water. Since resuspendability in water is an attractive feature for most end-users, and dry particles are easier and cheaper to ship than suspended particles, this makes the alternative process shown in FIG. 4 even more advantageous, since the combined product is easily isolated in the same ethanol precipitation step.

Accordingly, in one aspect, disclosed are methods for preparing a dry solid sample of the particles comprising cellulose described herein, wherein the dry solids are resuspendable (e.g., in water or an aqueous solution), the method comprising: a) contacting a cellulosic substrate with a sub-critical, near-critical or supercritical fluid for a duration sufficient to form a mixture of liquid and solids, said mixture comprising gluco-oligosacharides (GOS) and particles comprising cellulose; b) optionally, separating lignin from the mixture comprising GOS and particles comprising cellulose (c) optionally, removing at least a portion of the liquid from the mixture comprising GOS and particles comprising cellulose to form a higher solids mixture comprising GOS and particles comprising cellulose; d) contacting the higher solids mixture comprising GOS and particles comprising cellulose with an organic solvent to form solid GOS and particles comprising cellulose; (e) isolating the solid GOS and particles comprising cellulose as solids from the liquid and allowing to dry together; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

In one aspect, disclosed are resuspendable cellulose compositions comprising cellulose particles and a resuspending agent, wherein the cellulose particles, when resuspended in a liquid according to mixing method A: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; wherein at least a portion of the cellulose is type-II cellulose; and wherein the resuspending agent is adsorbed or bonded to at least a portion of the surface of the cellulose particles.

In various aspects, the resuspending agent is one or more polyol compound, one or more polyol oligomer or one or more polyol polymer, or any combination thereof.

In various aspects, the resuspending agent comprises at least one saccharide. In various aspects, the at least one saccharide is a "cello-oligosaccharide" or "gluco-oligosaccharide". The terms "cello-oligosaccharide" and "gluco-oligosaccharide" are used interchangeably herein. In various aspects, the at least one cello-oligosaccharide comprises at least one compound selected from the group consisting of cellohexaose, cellopentaose, cellotetraose, cellotriose, cellobiose, or any combination thereof. In various aspects, the composition comprises at least two, three, four, five, six, or seven cello-oligosaccharides. In various aspects where more than one cello-oligosaccharide is present, it should be understood that each respective cello-oligosaccharide may be present in any desired amount relative to the total weight percentage of the cello-oligosaccharides (i.e., the amounts set forth in the discussion below are applicable to each saccharide, e.g., cello-oligosaccharide, individually or in combination, as the context will dictate).

In various aspects, the resuspending agent comprises one or more oligosaccharide, one or more monosaccharide, sucrose, glycerol, citric acid, sodium citrate, sorbitol, maltodextrin, a sugar alcohol, xylose, or any combination thereof. In various aspects, the resuspending agent comprises glucose or sucrose. In various aspects, the resuspending agent comprises sorbitol.

In various aspects, the resuspending agent comprises one or more glucooligosaccharide (GOS or PGOS). In various aspects, the resuspending agent consists essentially of monosaccharides and oligosaccharides.

In one aspect, the resuspendable composition of particles comprising cellulose is easier and cheaper to ship than suspended particles (comprising a significant amount of liquid), and the dry particles can be resuspended at a later time. In various aspects, the composition is in a dry form having a solids content of at least about 80, 85, 90, 95, or 99 wt % solids. Conversely, in various aspects, the composition is in a dry form comprising less than about 20, 15, 10, 5, or 1 wt % water.

Any suitable amount of resuspending agent can be employed. In various aspects, the amount of resuspending agent is 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 105, 110, 120, 125, 130, 135, 140, 145, 150, 160, 170, 180, 190, or 200 wt %, on a dry basis based on the total amount of solids of resuspending agent and particles comprising cellulose. Each of the foregoing numbers can be preceded by the word "about," "at least about," or "less than about," and any of the foregoing numbers can be used singly to describe an open-ended range or in combination to describe a close-ended range. The maximum amount of resuspending agent is not particularly limited. For example, in some applications, a relatively large amount of resuspending agent may be desirable in embodiments where the resuspending agent is desirable in the application. For example, when the resuspending agent is sucrose, and the application is a food, a relatively large amount (e.g., at least about 50 wt %) of sucrose may be employed, since the sucrose not only aids in resuspending the cellulose particles, but also imparts a desirable sweet flavor to the food. In this way, various combinations of particles and resuspending agent can be prepared which are intended for various end use applications where the presence of the resuspending agent is desired and beneficial. Such combinations are useful to reduce the amount of, for example, sucrose, that needs to be added from an external source since an amount of, for example, sucrose, already comes from the resuspendable particles comprising cellulose.

Advantageously, the dried resuspendable composition of particles comprising cellulose is resuspendable in water while retaining its characteristics, such as a $d_{75}$ of less than about 8 microns and a $d_{50}$ of about 0.4 microns to about 5 microns. The dried resuspendable composition of particles comprising cellulose is resuspendable in water so that the composition is in the form of a suspension comprising water. In an embodiment, the suspension has a solids content of at least about 5 wt %, such as, for example, 15-25 wt %, or 40-50 wt %. The dried composition of particles comprising cellulose, after resuspension as set forth herein, has been found to maintain its utility in many of the applications and utilities described herein (e.g., breads, muffins and mayonnaise) and would be expected to maintain its application and utility in all applications and utilities described herein.

The feed material for the hydrolysis reaction need not be a lignocellulosic biomass, and may not necessarily be a biomass at all; any cellulose-containing feed material may be suitable for the hydrolysis process to produce the particles comprising cellulose disclosed herein, such as, for example, MCC, nanocrystalline cellulose (NCC), cotton, wood pulp, dissolving wood pulp, and the like. In various aspects, the feed material is microcrystalline cellulose (MCC), which is available commercially, for example, from Blackburn Distributions, Nelson, Lancashire, UK, with a broad particle size distribution with $d_{(50)}$ of 35 μm (as measured by the Beckman Coulter Particle Size Analyzer). For cleaner feedstocks comprising primarily cellulose, a one-step hydrolysis (sub-critical, or near critical, or super-critical hydrolysis) may be more appropriate as described elsewhere herein. For example, the MCC may be mixed with water to form a slurry, and subjected to a temperature of about 350-450° C. for a period of less than about 10 sec under a pressure sufficient to keep all, or at least a portion of, the fluid in liquid or supercritical form (generally less than about 250 bar). The resulting mixture is cooled to a temperature of less than about 100° C. via one or more cooling steps, of which one or more may be flash, water quench, heat exchange or similar, screened through a 74 μm (200 mesh) screen, and then centrifuged to separate the liquid (predominantly gluco-oligosaccharides, GOS) from the solids (cellulosic polysaccharide solids). As described elsewhere herein, the cellulose particles may be isolated.

The particles comprising cellulose disclosed herein are intermediate in particle size to the two most common commercial types of cellulose particles: nanocrystalline cellulose (NCC) and microcrystalline cellulose (MCC). Nanoparticles, including NCC, are generally considered to be in the size range of from 1-100 nm. There is a growing concern that some materials, which themselves are not very harmful, could be toxic if they are inhaled in the form of nanoparticles. It has been reported that inhaled nanoparticles can reach the bloodstream and may reach other target sites such as the liver, heart, brain, or blood cells. The pulmonary injury and inflammation resulting from the inhalation of nanosize urban particulate matter appears to be due to the oxidative stress that these particles cause in the cells. Accordingly, nanoparticles of many types are viewed with caution in some application areas because of the potential for inhalation or absorption in the human body. On the other hand, MCC may be provided at a particle size, typically centered at about 50 µm, 100 µm or 200 µm, that fails to provide the same properties and benefits of smaller particle size cellulose particles. It is thought that the cellulose particles and compositions disclosed herein, typically having a $d_{50}$ of about 0.4-5.0 µm, provide the advantages of small particle size while avoiding the negative health effects of the 1-100 nm materials.

E. Thickeners

The cellulose particles disclosed herein can exist as a stable suspension in water (or other suitable liquid or liquid mixture) and also can provide favorable rheological properties, such as thixotropy, which is usually considered to be desirable in coatings applications, such as architectural and industrial paints (it allows relatively facile brush, roller, or spray application of the paint, without the paint running or dripping from the applied surface). Furthermore, the cellulose particles exhibit an unusual synergistic thickening behavior, which may be advantageously employed to reduce overall thickener levels in some formulations (see, e.g., Example 6).

In various aspects, the particles comprising cellulose described herein are present in a thickened composition or formulation in an amount (weight %, dry solids of particles comprising cellulose based on the total weight of the thickened composition or formulation) of 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0. Each of the foregoing numbers can be preceded by the word "about," "at least about," or "less than about," and any of the foregoing numbers can be used singly to describe an open-ended range or in combination to describe a close-ended range. For example, the cellulose particles disclosed herein can be present in a thickened composition or formulation in an amount of at least about 0.5% by weight, about 1% by weight to about 4% by weight, or less than about 5% by weight. In various aspects, the cellulose particles comprise about 15% to about 25%) by weight of lignin (or other range as described elsewhere herein), based on the weight of the cellulose particles on a dry basis. In various aspects, the cellulose particles comprise less than 1%, or about 0%, by weight of lignin, based on the weight of the cellulose particles on a dry basis.

In one aspect, disclosed are thickened compositions comprising cellulose particles, wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose; and a liquid; wherein the cellulose particles are present at a level sufficient to increase the viscosity of the composition by at least 10% compared to an otherwise identical composition without the cellulose particles; and wherein the viscosity of the formulations is determined at room temperature using a Brookfield LVT viscometer using spindle 21, at 2 rpm shear.

In various aspects, the cellulose particles are present at a level sufficient to increase the viscosity of the composition (in %) by at least 10, 20, 30, 40, 50, 60, 70, 80, 90, 100, 110, 120, 130, 140, 150, 175, 200, 225, 250, 275, 300, 325, 350, 375, 400, 475, 500, 550, 600, 650, 700, 750, 800, 850, 900, 950, 1000, 1100, 1200, 1300, 1400, 1500, 1700, 1900, 2000, 2200, 2400, 2600, 2800, 3000, 3250, 3500, 3750, 4000, 4250, 4500, 4750, 5000, 5250, 5500, 5750, 6000, 6250, 6500, 6750, 7000, 7500, or 8000% compared to the viscosity of an otherwise identical composition without the cellulose particles. Each of the foregoing numbers can be preceded by the word "about," "at least about," or "less than about," and any of the foregoing numbers can be used singly to describe an open-ended range or in combination to describe a close-ended range.

In various aspects, the composition further comprises one or more additional thickeners, such that the resulting viscosity is greater than the sum of the viscosity of the otherwise identical composition with the cellulose composition and the viscosity of the otherwise identical composition with the one or more additional thickeners. Suitable additional thickeners include starch (e.g., arrowroot, cornstarch, katakuri starch, potato starch, sago, tapioca, and derivatives thereof), vegetable gum (e.g., alginin, guar gum, locust bean gum, xanthan gum, and derivatives thereof, such as hydroxypropyl guar), proteins (e.g., collagen, egg whites, gelatin, cassein, and derivatives thereof), modified castor oil, organosilicones (silicone resins, dimethicones), saccharides and polysaccharides (pectin, agar, carrageenan, pullulan, konjac, and alginate), polyurethanes (such as HEUR thickeners: hydrophobically modified ethylene oxide based urethane thickeners), acrylic polymers (e.g., polyacrylic acid, polymethacrylic acid, and copolymers of acrylic acid or methacrylic acid with acrylic monomers such as alkyl acrylate, alkyl alkylacrylate, for example, methyl acrylate, methylmethacrylate, etc. (where "alkyl" is any C1-C5 group)), latex polymers, styrene/butadiene, polyvinyl alcohol, clay (e.g., attapulgite, bentonite, montmorillonite), modified cellulose (methylhydroxyethyl cellulose, carboxymethyl cellulose, hydroxymethyl cellulose, hydroxypropyl methyl cellulose), polyethylene glycol, petroleum jelly, wax, silica (e.g., fumed silica, colloidal silica, hydrated silica), or any combination thereof.

In various aspects, the thickened composition further comprises other formulation ingredients, or a combination of ingredients, depending on the use of the thickened composition. For example, in various aspects, the thickened composition further comprises pigment particles, filler or extender particles, polymer particles, or a combination thereof, and/or other formulation ingredients. In various aspects, the thickened composition is a paint, coating, ink, adhesive or sealant. In various aspects, the thickened composition may be a personal care product, for example, health and beauty or cosmetic product, such as, for example, a lotion, cream, ointment, serum, shampoo, conditioner, hairspray, hair gel, deodorant, facial or body wash, facial or body scrub, exfoliant, emollient, moisturizer, soap, foundation make up, BB cream, CC cream, eye cream, sunscreen, anti-acne serum or cream or lotion, cellular serum or cream or lotion, facial or body mask, blush, eyeshadow, mascara, lipstick or lip balm, or clay, kaolin or mud suspension.

In various aspects, the thickened composition is a sunscreen containing a light absorbing compound, a light scattering compound, or a combination thereof. The light absorbing or light scattering compound can be, e.g., an oxide particle (e.g., zinc oxide, titanium oxide), a polymer particle (such as hollow sphere pigment, comprising polystyrene, or acrylic or styrene-acrylic copolymers), an organic compound (p-aminobenzoic acid, octyldimethyl p-aminobenzoic acid, phenylbenzimidazole sulfonic acid, cinoxate, dioxybenzone, oxybenzone, homosalate, menthyl anthranilate, octocrylene, octyl methoxycinnamate, octyl salicylate, sulisobenzone, trolamine salicylate, avobenzone, ecamsule, 4-methylbenzylidene, bisoctrizole, bemotrizinol, tris-biphenyl triazine, bisimidazylate, drometrizole trisiloxane, sodium dihydroxyl dimethoxy disulfobenzopenone, octyl triazone, diethylamino hydroxybenzoyl hexyl benzoate, iscotrizinol, dimethico-diethylbenzalmalonate, amiloxate), or any combination thereof. For some uses, the higher viscosity of the thickened composition is desirable to avoid any running of the product either during application of the product to the surface or running of the product from the applied surface. In various aspects, the sunscreen may be more aptly characterized as a suspension when the sunscreen contains a suspended particle, such as an inorganic particle or polymer particle, or as an emulsion.

In various aspects, the thickened composition may be a cleaning fluid, such as, for example, dishwashing detergent, laundry detergent, liquid fabric conditioner, no-splash bleach, toilet bowl cleaner, or drain cleaner, or industrial detergents or cleaning fluids. Higher viscosity is desirable in these thickened cleaning compositions so that, for example, the cleaning product does not run straight off the surface (e.g., in a toilet bowl), but clings long enough for some adsorption and cleaning effect to occur. In some cases, it is also helpful to have a higher viscosity to minimize splashing of the liquid composition, especially for types of cleaning fluids comprising harsh chemicals that may be skin or eye or respiratory irritants (such as, e.g., sodium hypochlorite in household bleach). In various aspects, such as in drain cleaners, the higher viscosity is desirable to allow the thickened composition to remain cohesive (i.e., stay together) and to sink when added to water to allow the composition to reach and act on the drain clog.

In various aspects, the thickened composition may be an edible composition, such as, for example, a beverage, smoothie, shake, syrup, soup, broth, sauce, marinade, dressing, gravy, pie filling, condiment, pudding, or pet food or treat. The higher viscosity for some food products often relates to texture and mouth-feel, but convenience of handling is another factor.

F. Suspensions

In one aspect, disclosed are suspensions comprising: a cellulose composition comprising particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose; and a first component suspended within the composition.

In one aspect, disclosed are suspensions comprising: a) a liquid; b) particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose; and c) a first component suspended within the liquid.

The particles comprising cellulose disclosed herein provide stabilization to solid particles in suspension (e.g., aqueous suspension; see, e.g., Example 7). In various aspects, the suspension is a stable suspension. For solid particles that do not dissolve in solution (e.g., aqueous solution), and do not form a stable or metastable suspension (or an X % stable suspension as discussed elsewhere herein), but instead, over a shorter or longer time period, settle on the bottom of the container (e.g., calcium carbonate), or even float to the surface (e.g., cocoa powder and cinnamon both settle out and has some portion rise to the surface), the particles comprising cellulose disclosed herein function as a suspension aid and allow the formation of homogeneous stable or metastable suspensions. In certain end uses, even temporary stabilization of solid particles in a suspension may be beneficial. For example, a solid may need to only be temporarily suspended (e.g., on the order of minutes) to, for example, enable pumping. In various aspects, the particles comprising cellulose disclosed herein function as a suspension aid and allow the formation of metastable suspensions, such as, for example a 50-95% stable suspension. The mechanism of stabilization is not known, although, without wishing to be bound by theory, in some case the particles comprising cellulose may provide improved rheology (e.g., higher viscosity) which may contribute to the stabilization of a first component solid in suspension. In various aspects, the suspension comprising the cellulose composition comprising particles is sufficiently thickened to enable the first component to be in a stable suspension in the composition. In some aspects, the formation of an emulsion facilitates suspension of a solid.

The particles comprising cellulose disclosed herein provide stabilization of a first component in a composition. The first component can be a solid within the composition. The first component typically is insoluble, or at least partially insoluble, in the composition at ambient conditions at the concentration that the first component is intended to be employed in the compositions. For example, the first component can be a plurality of pigment particles (e.g., titanium dioxide, red iron oxide, yellow iron oxide, black iron oxide, umber, cobalt violet, ultramarine, cadmium green, chrome green, cadmium orange, red ochre, yellow ochre, carbon black, barium sulfate, and the like, or any combination thereof), filler/extender particles (e.g., calcium carbonate, mica, wollastonite, amorphous silica, and the like, or any combination thereof), polymer particles (e.g., polyethylene, polypropylene, polystyrene, Kevlar™, and the like, or any combination thereof), inorganic particles (e.g., silica, alumina, titania, iron oxide, zinc oxide, magnesium silicate, clay, calcium carbonate, or the like, or any combination thereof), ore or mineral particles (e.g., iron ore, bauxite, hematite, calcium phosphate), coal dust or charcoal particles, dirt particles, rock cuttings, cocoa particles, an active pharmaceutical ingredient, an excipient, an exfoliant, a fiber, or any combination thereof. Specific non-limiting examples of first components and the compositions containing them include use in various industrial uses, including stabilization of solids such as: pigment particles, filler/extender particles or polymer particles in paints, coatings, caulks, sealants or adhesives; inorganic particles in cement or concrete; dirt particles or rock cuttings in drilling mud or drilling fluid; ore or mineral particles in a mining slurry; coal dust or charcoal particles in a fuel slurry; solid particles (such as molybdenum disulfide or a fluoropolymer) in a solid lubricant or grease; and oxide particles in a cleaning or buffing slurry or polish (such as a car detailing cleaner, or a chemical mechanical planarization slurry). Specific non-limiting examples of first components and the compositions containing them include use in various pharmaceutical, or personal care or beauty products, and health products, including stabilization of solids such as: an excipient or an active pharmaceutical ingredient in a medicine or supplement; polymer particles or inorganic particles or oxide particles (e.g., hollow sphere pigment, titanium dioxide or zinc oxide) in a lotion, sunscreen, BB cream, CC cream; pigment particles or inorganic particles in a make-up foundation, blush, eye shadow, mascara, facial or body mask, or clay/kaolin/mud suspension; exfoliant particles (e.g., the polymer particles or inorganic particles as disclosed herein, or any combination thereof) in a skin care product or scrub; inorganic or polymer particles in a soap; and inorganic or polymer particles in a toothpaste. Specific non-limiting examples of first components and the compositions containing them include use in various food or beverage products, including stabilization of solids such as: cocoa, malt, or artificially or naturally flavored particles (including herbs and spices) in a milk, hot or cold beverage, syrup, dressing, marinade, soup, or sauce; fruit, vegetable, fiber or protein particles in a beverage, smoothie, or shake, and pet food or pet treat.

In various aspects, the particles comprising cellulose described herein are present in a liquid suspension of at least partially insoluble particles in an amount (weight %, dry solids of particles comprising cellulose based on the total weight of the suspension) of 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0. Each of the foregoing numbers can be preceded by the word "about," "at least about," or "less than about," and any of the foregoing numbers can be used singly to describe an open-ended range or in combination to describe a close-ended range. For example, the cellulose particles disclosed herein can be present in the suspension in an amount of at least about 0.5% by weight, about 1% by weight to about 4% by weight, or less than about 5% by weight. In various aspects, the cellulose particles comprise about 15% to about 25% by weight of lignin, based on the weight of the cellulose particles on a dry basis. In various aspects, the cellulose particles comprise less than 1%, or about 0%, by weight of lignin, based on the weight of the cellulose particles on a dry basis.

In various aspects, the suspension may be an edible composition, such as, for example, a beverage, smoothie, shake, syrup, soup, broth, sauce, marinade, dressing, gravy, pie filling, condiment, pudding, or pet food or treat. The higher viscosity for some food products often relates to texture and mouth-feel, but convenience of handling is another factor.

G. Emulsions

The cellulose particles disclosed herein can stabilize oil/water emulsions, for example, Pickering emulsions. Various aspects are discussed in the Examples (see, e.g., Example 8).

Thus, in one aspect, disclosed are emulsions or emulsifiable compositions comprising: particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

In various aspects, the emulsion or emulsifiable composition is an emulsion, and the emulsion comprises: a first fluid and a second fluid; wherein the first fluid is at least partially immiscible with the second fluid.

In a further aspect, the first fluid comprises an oil and the second fluid comprises water. Suitable liquids that are immiscible with water include olive oil, canola oil, vegetable oil, coconut oil, peanut oil, corn oil, palm oil, palm kernel oil, or any combination thereof. In various aspects, the emulsion or emulsifiable composition is an egg-free composition.

In a further aspect, the emulsion is a non-food related emulsion. For example, an emulsion can be used to formulate a personal care product (e.g., acne gels). In a further example, an emulsion can be used as an industrial formulation (e.g., paint).

In a further aspect, the second fluid comprises an oil and the second fluid comprises vinegar.

Accordingly, the cellulose particles and compositions may find use in any applications for which formulations comprising two at least partially immiscible liquids (e.g., a hydrophobic liquid and a hydrophilic liquid) are useful, particularly oil/water emulsions. Accordingly, in various aspects, the emulsion is, or is a component of, a mayonnaise, a salad dressing, a sandwich spread, vegetable spread, vegetable shortening, a vinaigrette, a condiment, a cheese, a yogurt, an ice cream, a sauce, a butter, a nut butter, a margarine, a cream, a milk, a gravy, a coffee beverage, chocolate, or a sauce comprising oil/water emulsions (such as, e.g., pasta sauces, BBQ sauces, hot sauces, hollandaise, béarnaise, etc.), as well as baked goods that utilize an oil/water emulsion in the pre-baked formulation. In various aspects, the emulsion is, or is a component of, a fruit-butter, -sauce, -jelly, -jam, -chutney, -custard, -marinade, or -soup. In some embodiments, the emulsion comprising the cellulose particles is, or is a component of, pet food or pet treats.

In various aspects, the particles comprising cellulose described herein are present in emulsions in an amount (weight % of particles comprising cellulose based on the total weight of the emulsion formulation) of 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0. Each of the foregoing numbers can be preceded by the word "about," "at least about," or "less than about," and any of the foregoing numbers can be used singly to describe an open-ended range or in combination to describe a close-ended range. For example, the cellulose particles disclosed herein can be present in the emulsion formulation in an amount of at least about 0.5% by weight, about 1% by weight to about 4% by weight, or less than about 10% by weight. In various aspects, the cellulose particles comprise about 15% to about 25% by weight of lignin, based on the weight of the cellulose particles on a dry basis. In various aspects, the cellulose particles comprise less than 1%, or about 0%, by weight of lignin, based on the weight of the cellulose particles on a dry basis.

In various aspects, the particles comprising cellulose described herein are present in emulsifiable compositions, for example in pre-mix formulations wherein the emulsifiable composition or formulation is, or is a component of, a mayonnaise mix, a salad dressing mix, a sandwich spread mix, vegetable spread mix, a vinaigrette mix, a milk mix, a gravy mix, or a coffee beverage mix, or a sauce mix (e.g. pasta sauce, BBQ sauce, hot sauce and the like). In various aspects, the emulsifiable composition is in a powder form, a granular form, a paste, or a concentrate. Such mixes are contemplated to be those that are packaged by a manufacturer of mixes to be prepared into a vinaigrette, mayonnaise, dressing, etc., by a third party, whether it be an individual consumer at home, an industrial producer, or a restaurant, caterer, or other food preparer of such vinaigrettes, mayonnaises, pet food (e.g., a "gravy" that forms when you pour water over the dry food), etc.

In various aspects, the particles comprising cellulose described herein are present in emulsifiable compositions in an amount (weight % of particles comprising cellulose based on the total weight of the emulsifiable composition or formulation) of 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15, 16, 17, 18, 19, 20, 22, 24, 26, 28, 30, 32, 34, 36, 38, or 40. Each of the foregoing numbers can be preceded by the word "about," "at least about," or "less than about," and any of the foregoing numbers can be used singly to describe an open-ended range or in combination to describe a close-ended range. For example, the cellulose particles disclosed herein can be present in the emulsifiable composition or formulation in an amount of at least about 0.5% by weight, about 1% by weight to about 4% by weight, or less than about 10% by weight. In various aspects, the cellulose particles comprise about 15% to about 25% by weight of lignin, based on the weight of the cellulose particles on a dry basis. In various aspects, the cellulose particles comprise less than 1%, or about 0%, by weight of lignin, based on the weight of the cellulose particles on a dry basis.

Furthermore, the cellulose particles disclosed herein may find use in stabilizing emulsions, or a component of the emulsion, in any application for which at least partially immiscible liquids are used together in a composition, particularly oil/water emulsions, and may be used in the same amounts as disclosed above concerning compositions and formulations comprising two immiscible liquids. Such applications include, for example, pharmaceuticals (the active ingredient may be a liquid that is immiscible in water, but more conveniently delivered in aqueous carrier formulation); personal care or health and beauty products such as a cosmetic product (e.g., foundation make up, a lipstick or lip balm, a mascara, blush, eyeshadow), a skin-care product, such as creams (e.g., hand, face, and/or body creams and moisturizers/emollients, bb cream, cc cream, eye cream, anti-acne serum or cream, cellular serum or cream), lotions or ointments (e.g., dermatological lotions or ointments, such as, e.g., anti-acne lotion or cellular lotion), sunscreen products, or a hair care product (such as hair conditioners, shampoo, hair gel, hairspray, or hair dye), or a toothpaste, teeth whitener, or fluoride composition; agricultural products, such as, for example, delivery vehicles for pesticides, insecticides, biocides, fungicides, herbicides and fertilizers; waterborne coatings wherein the hydrophobic polymer is stabilized in emulsion form (e.g., which has been formed via inversion by addition of water into the resin), such as, for example, waterborne alkyd resin, polyester resin, epoxy resin, acrylic resin, polyurethane, fluoropolymer, wax emulsion, etc.); industrial chemical additives, such as, for example, silicone defoamers, biocides and colorants used in formulations like paints, coatings, sealants, caulks and inks;

drilling fluids, for example as used in oil wells. In various aspects, the emulsion is, or is a component of, a subterranean treatment composition (such as a drilling fluid), or is created in situ when such composition or drilling fluid is used in treating or drilling; or a metalworking fluid or a component of a metalworking fluid, or is created in situ when a metalworking fluid is used in metalworking; or a cutting fluid, stamping fluid, abrading fluid, tribological fluid, cooling fluid, or lubricating fluid, or component thereof, or is created in situ when such fluids are used in cutting, stamping, abrading, tribological modification, cooling, or lubricating, respectively. In various aspects, the emulsion is, or is a component of, a leather care product or shoe polish. The cellulose particles disclosed herein may also find use (and at the same amounts disclosed above) in any formulation that functions at least in part by stabilizing an immiscible liquid in a carrier liquid, even temporarily, such as, for example, laundry detergents, dishwasher fluids or solids, dry-cleaning formulations, industrial detergents, etc. Accordingly, in various aspects, the emulsion is, or is a component of a cleaning agent, dishwasher fluid, dishwasher paste, laundry detergent, laundry paste, liquid fabric conditioner, no-splash bleach, toilet bowl cleaner or drain cleaner, a dry-cleaning cleaning formulation, or industrial cleaning fluids and detergents.

In various aspects, the emulsion may be an edible composition, such as, for example, a beverage, smoothie, shake, syrup, soup, broth, sauce, marinade, dressing, gravy, pie filling, condiment, pudding, or pet food or treat. The higher viscosity for some food products often relates to texture and mouth-feel, but convenience of handling is another factor.

H. Food Products

In various aspects, disclosed are food products comprising: particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

Cooked or baked goods that utilize an oil/water emulsion in the pre-baked formulation include leavened or leavenable food products, such as breads, cakes, sponge puddings and various baked goods, which may include, for example, muffins, brownies, pasta, etc.

Many cooked or baked goods include egg in the formulation; the egg yolk provides lecithin, which acts as an emulsifier. As described herein, the particles comprising cellulose and compositions thereof are also able to stabilize oil/water emulsions (Example 8), and our studies show that the cellulose particles can function as an egg-replacement additive in many instances where oil/water emulsions are used (see, e.g., Examples 9-11). The egg white coagulates as it cooks that provides structure to baked goods. The cellulose particles help provide this structural integrity, cohesive strength and elasticity to cakes, breads, and other baked goods.

Thus, in one aspect, disclosed are leavened or leavenable food products comprising: particles comprising cellulose; wherein the cellulose particles have: at least one of (1) a $d_{75}$ of less than about 8 microns and (2) a $d_{50}$ of about 0.4 microns to about 5 microns; an aspect ratio of about 1 to about 1.5; and a non-spherical shape; and wherein at least a portion of the cellulose is type-II cellulose.

In one aspect, disclosed are leavened or leavenable food products comprising: particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

In various aspects, the leavened or leavenable food product is a leavened food product, and the leavened food product is a bagel, a muffin, a scone, a bread, a pizza base, a cracker, a pastry, a pie, a cake, a shortcake, a cupcake, a pancake, a waffle, a sponge pudding, a Yorkshire pudding, a doughnut, a bun, a brownie, a blondie, a biscuit, a cookie, a pasta, a noodle, pet food, or pet treats.

In various aspects, the particles comprising cellulose described herein are present in a cooked or baked food product, such as a leavened food product, including bagel, muffin, scone, bread, pizza base, cracker, pastry, pie, cake, shortcake, cupcake, pancake, waffle, sponge pudding, York-shire pudding, doughnut, bun, brownie, blondie, biscuit, cookie, pasta, noodle, a pet food or pet treat, or the like, in an amount (weight %, dry solids of particles based on the total weight of the cooked or baked food product on a dry basis) of 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0. Each of the foregoing numbers can be preceded by the word "about," "at least about," or "less than about," and any of the foregoing numbers can be used singly to describe an open-ended range or in combination to describe a close-ended range. For example, the cellulose particles disclosed herein can be present in the cooked or baked food product in an amount of at least about 0.5% by weight, about 1% by weight to about 4% by weight, or less than about 5% by weight based on the total weight of the cooked or baked food product on a dry basis. In various aspects, the cellulose particles comprise about 15% to about 25% by weight of lignin, based on the weight of the cellulose particles on a dry basis. In various aspects, the cellulose particles comprise less than 1%, or about 0%, by weight of lignin, based on the weight of the cellulose particles on a dry basis.

In various aspects, the leavened or leavenable food product is a leavenable food product, and the leavenable food product is a bagel mix, a muffin mix, a scone mix, a bread mix, a pizza base mix, a cracker mix, a pastry mix, a pie mix, a cake mix, a shortcake mix, a cupcake mix, a pancake mix, a waffle mix, a sponge pudding mix, a Yorkshire pudding mix, a doughnut mix, a bun mix, a brownie mix, a blondie mix, a biscuit mix, a cookie mix, a pasta mix, a noodle mix, a flour composition, or a dough thereof.

In various aspects, the particles comprising cellulose described herein are present in an uncooked food formulation, such as a leavenable food product, cookie dough, bread dough, pizza base dough, bun dough, doughnut dough, pasta dough, or a batter or dry or partially dry mix for a bagel, muffin, scone, bread, pizza base, cracker, pastry, pie, cake, shortcake, cupcake, pancake, waffle, sponge pudding, York-shire pudding, doughnut, bun, brownie, blondie, biscuit, cookie, pasta, noodle, or the like in an amount (weight %, dry solids of particles comprising cellulose based on the total weight on a dry basis of the pre-cooked or uncooked formulation) of 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15, 16, 17, 18, 19, 20, 22, 24, 26, 28, 30, 32, 34, 36, 38, or 40. Each of the foregoing numbers can be preceded by the word "about," "at least about," or "less than about," and any of the foregoing numbers can be used singly to describe an open-ended range or in combination to describe a close-ended range. For example, the cellulose particles disclosed herein can be present in the pre-cooked or uncooked food formulation in an amount of at least about 0.5% by weight, about 1% by weight to about 4% by weight, or less than about 10% by weight, based on total weight of the pre-cooked or uncooked food formulation on a dry basis. In various aspects, the cellulose particles comprise about 15% to about 25% by weight of lignin, based on the weight of the cellulose particles on a dry basis. In various aspects, the cellulose particles comprise less than 1%, or about 0%, by weight of lignin, based on the weight of the cellulose particles on a dry basis.

Furthermore, the cellulose particles also stabilize gas bubbles-foam in compositions and provide structure, cohe-sive strength and elasticity in leavened breads, baked goods, and pasta. Such properties are often provided by gluten from the flour in these baked goods; accordingly, as shown herein (see, e.g., Example 10-11), the cellulose particles and com-positions are also able to support structure development in gluten-free compositions, and so may find utility in replac-ing gluten in these systems (not necessarily a direct 1:1 by weight replacement), thereby allowing formulation of glu-ten-free baked goods. Since a subset of the population has an allergy to eggs, and another subset of the population (over-lapping or not) has an allergy to gluten, baked goods that are both egg-free and gluten-free are sometimes referred to as allergen-free. Advantageously, if viewed in this way, the cellulose particles and compositions may find utility in the formulation and production of egg-free, gluten-free, or aller-gen-free foodstuffs, such as egg-free, gluten-free, or aller-gen-free bread, muffins, cakes, brownies, pasta, etc. In addition, there is a strong and growing market trend to eat "gluten-free" and/or "vegan," which can be satisfied by utilizing the cellulose particles.

In various aspects, the leavened or leavenable food prod-uct comprising the cellulose particles disclosed herein is egg-free. In various aspects, the leavened or leavenable food product comprising the cellulose particles disclosed herein is gluten-free. In various aspects, the leavened or leavenable food product comprising the cellulose particles disclosed herein is egg-free and gluten-free. In various aspects, the leavened or leavenable food product comprising the cellu-lose particles disclosed herein is allergen-free.

In various aspects, a food product containing the cellulose particles may comprise an allergen in an amount (ppm) of 2000, 1750, 1500, 1250, 1000, 900, 800, 700, 600, 500, 400, 300, 200, 150, 100, 50, 20, or 10. Each of the foregoing numbers can be preceded by the word "about," "at least about," or "less than about," and any of the foregoing numbers can be used singly to describe an open-ended range or in combination to describe a close-ended range. The allergen can be any allergen, including egg, gluten, soy, or a nut, or a combination thereof. The allergen amounts herein can also refer to the total level of such allergen(s) in the product. For example, the product may comprise an allergen such as egg in an amount of less than 20 ppm; and/or may comprise an allergen such as gluten in an amount of less than 20 ppm. The product may comprise a total level of allergens in an amount of less than 20 ppm.

The cellulose particles disclosed herein also find use as an ingredient in ice cream. Ice cream requires the co-stabiliza-tion of ice crystals, air bubbles and fat droplets from the cream, together with an aqueous sugar solution. Ice cream thus contains all three states of matter simultaneously, and is both a foam and an oil in water emulsion. As disclosed herein, the cellulose particles can stabilize air bubbles and also stabilize oil in water emulsions. Ice cream prepared using the cellulose particles disclosed herein does not require any unnatural emulsifiers often found in commercial ice cream, or egg component as found in some custard-based ice creams. It was found by comparison to the equivalent ice cream without cellulose particles that the cellulose stabilized ice cream melted more slowly than a conventional ice cream. This has importance for the end-user, for example, as the ice cream is being eaten from a cone, so that it does not drip on one's clothes. It also has importance during transportation outside of a refrigerated truck, either from the point of manufacture to the store, or from the store to the consumer household. Any melting that occurs at those times affects the ice crystal size and the preferred (small) ice crystal size cannot be recovered simply by re-freezing at the point of destination. The creamy quality of the ice cream is irreversibly and negatively impacted by such melting. In another example/embodiment, the amount of fats (in the form of oils or butter) can be reduced in many leavened and leavenable products when adding cellulose particles, which in turn reduces the calorie content of the baked good. Such fats are added, in part, to provide moisture to the baked good and to prevent it from becoming too dry while and after baking. The cellulose particles described herein have a high moisture content, which is generally maintained during baking, obviating the need of the fats for this purpose.

Thus, also provided is an ice cream comprising particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

As described above and in other studies, compositions containing the cellulose particles have been found to support stable air-in-water foams. Typically, in order to form a stable foam, a surfactant such as lecithin, mono-glycerides or proteins, must be present to reduce the interfacial tension between the air phase and the aqueous phase. Without wishing to be bound by theory, the cellulose particles seem to provide the surfactant to reduce the interfacial tension in these compositions where air bubbles and foams are being stabilized. This property has proven to be beneficial in leavened and leavenable food products by stabilizing the air bubbles in the food product (such as breads, muffins, etc.) as disclosed herein, and in stabilizing the air bubble foams in ice cream as disclosed herein. Such air bubble stabilizing properties could also be of utility in other food products such as marshmallows, whipped cream, meringue, and the like, as well as food products that incorporate the foregoing or are "whipped" in order to create a lighter a lighter texture and/or different mouth-feel (e.g., mousse, whipped jello or pudding desserts and yogurts), and in other non-food products such as personal care products such as hair care, lotion, soap and make-up "mousse" or "whipped" products.

Another use for the cellulose particles disclosed herein in the context of food products is to provide a lower calorie content food. A hazelnut spread (or peanut butter, or nut butter generally) can be provided at a similar viscosity, texture and taste, but with a lower caloric intake if made with the cellulose particles described herein. Nut butters are generally high in calories (high fat/oil content), although relatively healthy in the context of a high calorie food. The cellulose particles disclosed herein can support oil/water emulsions, and therefore allow the addition of water into the recipe. Despite an overall dilution due to addition of water, the texture, mouth-feel and taste can be maintained since the cellulose particles additionally have a thickening effect and support spatial structure within the mixture. Further, doughs comprising the cellulose particles that are fried in oils and fats (e.g., deep frying doughnuts) have a lower calorie content in comparison to similar products without cellulose particles cooked in a similar fashion. Without wishing to be bound by theory, the high moisture content of the cellulose particles and the moisture retaining property of the cellulose particles is believed to repel the fats as opposed to other doughs without the cellulose particles that absorb the fats. Accordingly, it is possible to both reduce the caloric intake (substituting water for nut butter content including fats/oils), while at the same time reducing cost (for the same reason).

Thus, also provided is a nut butter (such as, e.g., a peanut butter or a hazelnut spread, etc.) comprising particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

I. Meat Food Products

The cellulose particles disclosed herein can be used as an additive in meat products. In various aspects, the cellulose particles can be used in meat products as a fat replacement, a moisture retention aid, a texture enhancer, a mouth-feel enhancer, or any combination thereof. Without wishing to be bound by theory, the cellulose particles can be used as a fat replacement, since it appears the cellulose particles provide a moisture retention function within the meat product that aids in maintaining the expected texture and mouth-feel that consumers have come to expect in these products (see, e.g., Example 12D). Accordingly, these cellulose particles find use in such products as fat-free, fat-reduced, and/or moisture reduced meat products, such as sausages, burgers, hot dogs, jerkies, pet food and pet treats, etc., which may contain any known type of meat, such as poultry (chicken, turkey, Cornish game hen, etc.), beef, pork, lamb, rabbit, venison, buffalo, etc., or any combination thereof and vegetarian alternatives to traditional meat products (e.g., "veggie" burgers, sausages, nuggets, etc.).

In one aspect, disclosed are meats or meat analog compositions comprising: particles comprising cellulose; wherein the cellulose particles have: at least one of (1) a $d_{75}$ of less than about 8 microns and (2) a $d_{50}$ of about 0.4 microns to about 5 microns; an aspect ratio of about 1 to about 1.5; and a non-spherical shape; and wherein at least a portion of the cellulose is type-II cellulose.

In one aspect, disclosed are meats or meat analog compositions comprising: particles; wherein the particles: comprise cellulose; have at least one of (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

In various aspects, the meat or meat analog composition further comprises beef, chicken, turkey, pork, lamb, rabbit, venison, game, buffalo, horse, plant proteins, fermented proteins, shell-fish (e.g., scallops, crab, lobster, etc.), fish, imitations of the foregoing, or combinations thereof. The meat or meat analog composition may further comprise plant proteins, such as, for example, peas, chick peas, beans, lentils, legumes, mushrooms, soy, peanut, rapeseed meal, grains (e.g., quinoa), and the like and combinations thereof. The meat or meat analog composition may further comprise fermented proteins, such as, for example, tofu or Quorn.

In various aspects, the meat or meat analog composition is in the form of a sausage, a burger, a kebab, a gyro, a shwarma, a patty, a cake, a loaf, a nugget, a strip, a hot dog, a deli product, a jerky, a pet food, a pet treat, a processed meat, an emulsified meat, or combinations thereof, or imitations thereof, and wherein the meat or meat analog composition is made with beef, chicken, turkey, pork, lamb, horse, buffalo, venison, veal, game, fowl, plant proteins, fermented proteins, shell-fish, fish, or combinations thereof, or imitations thereof.

A number of meat products deliberately include a lower grade or cut meat component specifically to incorporate a higher fat content (or simply add fat). Although this provides a lower cost component, another primary reason is actually to add a moisturizing component, and flavorable texture, positive mouth-feel, and/or flavors to enhance the taste. For example, some chicken products use rib meat blended with chicken breast meat in order to give an improved texture and mouth-feel compared to the 100% chicken breast meat. However, many consumers are looking for healthier alternatives that remove or replace the fat content, and thus would prefer the 100% breast meat or similar white meat portions if it could be made somewhat juicier and easier to chew. The cellulose particles disclosed herein, therefore, may also find use in this type of meat product, as a fat replacement additive, a moisture retention additive, a texture enhancing additive, a mouth-feel enhancing additive, or any combination thereof, since, for example (and without wishing to be bound by theory) they provide a moisture retention function within the meat product that aids in maintaining the expected texture and mouthfeel that consumers have come to expect in these products. Such meat products may take the form of, for example, a nugget, burger, loaf, deli product, cake, gyro, shwarma, strip, patty, bacon, jerky, hot dog, pet food, pet treat, and other processed or imitation meats.

In various aspects, the cellulose particles disclosed herein may also find use in other types of meat products (i.e., meat products made of other cuts of meat). Such cuts of meat include, but are not limited to, beef and pork cuts where the cut of meat does not have the fat content (or marbling) that provides the texture, moisture, and mouth-feel of other cuts of meat while still having a "healthier" or "cheaper" benefit (e.g., pork chops, rib eye, roast).

In various aspects, the particles comprising cellulose described herein are present in a meat product (described above), an imitation meat or a meat analog (such as vegetarian or vegan products comprising tofu, tempeh, seitan, beans, legumes, grain, or a combination thereof, in a form mimicking burgers, hot dogs, nuggets, etc.) in an amount (weight % of particles based on the total weight of the meat product in its uncooked form) of 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0. Each of the foregoing numbers can be preceded by the word "about," "at least about," or "less than about," and any of the foregoing numbers can be used singly to describe an open-ended range or in combination to describe a close-ended range. For example, the cellulose particles disclosed herein can be present in the meat product or meat analog in an amount of at least about 0.5% by weight, about 1% by weight to about 4% by weight, or less than about 5% by weight. In various aspects, the cellulose particles comprise about 15% to about 25% by weight of lignin, based on the weight of the cellulose particles on a dry basis. In various aspects, the cellulose particles comprise less than 1%, or about 0%, by weight of lignin, based on the weight of the cellulose particles on a dry basis.

J. Oil and Drilling Applications

In further aspects, disclosed are compositions comprising: (a) a liquid; and (b) cellulose particles suspended in the liquid, wherein the particles: comprise cellulose; have at least one of (1) a $d_{75}$ of less than about 8 microns and (2) a $d_{50}$ of about 0.4 microns to about 5 microns have an aspect ratio of from about 1 to about 1.5; and have a non-spherical shape; and wherein at least a portion of the cellulose is type-II cellulose. Such compositions are useful, for example, as subterranean treatment compositions, such as drilling fluids (or "drilling muds"), fracturing fluids, well control fluids, well kill fluids, well cementing fluids, acid fracturing fluids, acid diverting fluids, stimulation fluids, sand control fluids, completion fluids, wellbore consolidation fluids, remediation treatment fluids, spacer fluids, frac-packing fluids, water conformance fluids, gravel packing fluids, and mixtures thereof. Other non-limiting uses for such compositions include as machining or processing compositions, such as, for example, metalworking fluids, cutting fluids, stamping fluids, abrading fluids, tribological fluids, cooling fluids, or lubricating fluids, or components thereof.

In various aspects, the composition comprising a liquid and cellulose particles is thermally stable. For example, the composition is stable at a temperature (° F.) of 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, or 475. Each of the foregoing numbers can be preceded by the term "about," "at least about," or "less than about," and any of the foregoing numbers can be used singly to describe an open-ended range or in combination to describe a closed-ended range. Thus, without wishing to be bound by theory, in various aspects the performance benefits of the composition (e.g., the rheology and viscosity) remain largely unaffected by increases in temperature.

In various aspects, the composition comprising the cellulose particles and a liquid is stable in a variety of saline environments. For example, the viscosity of the composition in an environment having a salinity of greater than about 100 g/L, 150 g/L, 200 g/L, 250 g/L, 300 g/L, 350 g/L, 400 g/L or 450 g/L is approximately equal to the viscosity of the composition in an environment having a salinity of about 90 g/L, 80 g/L, 70 g/L, 60 g/L, 50 g/L, 40 g/L, 30 g/L, 20 g/L, or 10 g/L. Each of the foregoing numbers can be preceded by the term "about," "at least about," or "less than about," and any of the foregoing numbers can be used singly to describe an open-ended range or in combination to describe a closed-ended range.

At times it is necessary to emulsify acids with hydrocarbons to improve the acid effectiveness in subterranean treatments. Such fluids, or a composition comprising a liquid and cellulose particles, can have a pH of −1, −0.5, 0, 0.5, 1, 1.5, 2, 2.5, or 3. Each of the foregoing numbers can be preceded by the term "about," "at least about," or "less than about," and any of the foregoing numbers can be used singly to describe an open-ended range or in combination to describe a closed-ended range.

Alternatively, the fluids, or a composition comprising a liquid and cellulose particles, can have a pH of 8, 8.5, 9, 9.5, 10, 10.5, 11, 11.5, or 12. Each of the foregoing numbers can be preceded by the term "about," "at least about," or "less than about," and any of the foregoing numbers can be used singly to describe an open-ended range or in combination to describe a closed-ended range.

In a further aspect, the composition comprising a liquid and cellulose particles further comprises a viscosifying agent. In a still further aspect, the viscosifying agent is an inorganic viscosifying agent. Examples of inorganic viscosifying agents include, but are not limited to, bentonite, laponite, a hectorite, a mixed metal hydroxide, a mixed metal oxide, and mixtures thereof. In yet a further aspect, the viscosifying agent is an organic viscosifying agent. Examples of organic viscosifying agents include, but are not limited to, xantham gum, diutan, carboxymethyl cellulose, guar gum, carboxymethylstarch, welan gum, hydroxyethyl-cellulose, a polysaccharide oligomer and mixtures thereof. The viscosifying agent can be present in an amount (wt %) of 0.001, 0.01, 0.1, 0.5, 1.0, 5, or 10. Each of the foregoing numbers can be preceded by the term "about," "at least about," or "less than about," and any of the foregoing numbers can be used singly to describe an open-ended range or in combination to describe a closed-ended range.

In various aspects, the composition has a viscosity at least 10% greater than the sum of the viscosity of an otherwise identical composition with the cellulose particles and the viscosity of an otherwise identical composition with the viscosifying agent.

In a further aspect, the composition further comprises a thermal stabilizing agent. Examples of thermal stabilizing agents include, but are not limited to, magnesium oxide, monoethanolamine, citric acid, diethanolamine, glyoxal, a formate solution, and mixtures thereof. The thermal stabilizing agent can be present in an amount (wt %, based on total weight of the composition) of 0.1, 0.5, 1, 1.5, 2, 2.5, 3, 3.5, 4, 4.5, 5, 5.5, 6, 6.5, 7, 7.5, 8, 8.5, 9, 9.5, or 10. Each of the foregoing numbers can be preceded by the term "about," "at least about," or "less than about," and any of the foregoing numbers can be used singly to describe an open-ended range or in combination to describe a closed-ended range.

In various aspects, the composition further comprises an additive. Examples of additives include, but are not limited to, fly ash, volcano ash, silica compounds, fluid loss control additives, emulsifying agents, latex, dispersants, accelerators, retarders, clays, lubricants, lime, salt, mica, sand, fibers, formation containing agents, fumed silica, bentonite, microspheres, carbonates, barite, hematite, epoxy resins, curing agents, crosslinkers, biocides, surfactants, activators, stabilizers, breakers, and mixtures thereof. Additional examples of additives include, but are not limited to, corrosion inhibitors, extreme pressure additives, anti-mist agents, emulsifying agents, alkanolamines, biocides, stabilizers, dispersants, defoamers, colourants, dyes, odourants, chlorinated compounds, sulphurized compounds, fragrances, weighting agents, and mixtures thereof. The additive can be present in an amount of (wt %, based on total weight of the composition) 0.1, 0.5, 1, 2, 3, 4, 5, 6, 7, 8, 9, 10, 12, 14, 16, 18, 20, 25, 30, 35, 40, 45, 50, 55, or 60. Each of the foregoing numbers can be preceded by the term "about," "at least about," or "less than about," and any of the foregoing numbers can be used singly to describe an open-ended range or in combination to describe a closed-ended range.

In a further aspect, the composition is substantially free of an antibacterial agent. Thus, in various aspects, the composition comprises (wt %, based on total weight of the composition) 1, 0.5, 0.25, 0.1, 0.05, 0.01, or 0.00 of an antibacterial agent. Each of the foregoing numbers can be preceded by the term "about," "at least about," or "less than about," and any of the foregoing numbers can be used singly to describe an open-ended range or in combination to describe a closed-ended range.

In various aspects, the composition is a subterranean treatment composition. Examples of subterranean treatment compositions include, but are not limited to, drilling fluids (or "drilling muds"), fracturing fluids, well control fluids, well kill fluids, well cementing fluids, acid fracturing fluids, acid diverting fluids, stimulation fluids, sand control fluids, completion fluids, wellbore consolidation fluids, remediation treatment fluids, spacer fluids, frac-packing fluids, water conformance fluids, gravel packing fluids, and mixtures thereof. In a further aspect, the composition is a drilling fluid. In a further aspect, the composition is a metal working fluid. In a further aspect, the composition is a cutting fluid. In a further aspect, the composition is a stamping fluid. In a further aspect, the composition is an abrading fluid. In a further aspect, the composition is a tribological fluid. In a further aspect, the composition is a cooling fluid. In a further aspect, the composition is a lubricating fluid.

A non-exclusive list of several exemplary compositions is illustrated in Table i. below.

TABLE i

| Composition Type | Liquid | Cellulose Particles | Fluid Loss Reducer | Weighting Agent | Other |
|---|---|---|---|---|---|
| Water- based Fluid[1] | Water (305 lbs/barrel) | 22 lbs/barrel (dry basis) | Carboxymethyl starch (4 lbs/barrel) | Barite (90 lbs/barrel) | Lubricant (4 lbs/barrel) |
| Brine-based Fluid[2] | Brine (374 lbs/barrel) | 22 lbs/barrel (dry basis) | Carboxymethyl starch (4 lbs/barrel) | Barite (15 lbs/barrel) | Lubricant (4 lbs/barrel) |
| Non-Aqueous Fluid[3] | Brine (26 lbs/barrel) and diesel (208 lbs/barrel) | 7 lbs/barrel (dry basis) | 5 lbs/barrel | Barite (235 lbs/barrel) | Organoclay (8 lbs/barrel); primary emulsifier (5 lbs/barrel); secondary emulsifier (3 lbs/barrel) Lime (1 lbs/barrel) |
| Emulsified Acid | 37% HCl solution | 5 lbs/barrel (dry basis) | | | |

TABLE i-continued

| Composition Type | Liquid | Cellulose Particles | Fluid Loss Reducer | Weighting Agent | Other |
|---|---|---|---|---|---|
| | (217 lbs/barrel) and mineral oil (137 lbs/barrel) | | | | |

[1] Assume drilling in a low temperature (i.e., less than 250° F.) well near a fresh water source with minimal concerns about interaction with the underlying geology. May use 10 lb per gallon liquid.
[2] Assume drilling in a low temp. well similar to 1 above, but without fresh water around. Rather, the only available liquid in the location is 20% $CaCl_2$, 10% NaCl brine. Also, assume there is some concern for shale stability in the formation below. May use 10 lb per gallon liquid.
[3] Assume drilling deeper, at a higher temperature, and with more demanding shale. Here, a higher weight is recommended, e.g., 12 lbs per gallon. Also, assume a high oil to water ratio, e.g., 85% oil and 15% of 25% $CaCl_2$ brine (both 85% and 15% are % by mass of the liquid phase).

In various aspects, a disclosed composition comprises a liquid (in addition to the cellulose particles). Examples of liquids include water, oil, and mixtures thereof In a further aspect, the liquid comprises a weighting agent. Examples of weighting agents include, but are not limited to, barite, hematite, calcium carbonate, ilmenite, manganese tetroxide, and mixtures thereof.

Compositions used for drilling fluids typically have specific densities depending on the properties of the well being drilled. Typically, the densities are higher than the density of pure water (i.e., higher than 1000 g/L at 1 atm and 4° C.). To obtain the desired density, the composition can be turned into a "slurry" by adding insoluble heavier solids; however, as insoluble solids are added to the fluid, the drilling properties of the slurry may degrade, most notably the plastic viscosity (PV). Instead of adding insoluble weighting solids, cheap, soluble components can be added to obtain some benefit while maintaining more desirable values for plastic viscosity. However, in some aspects, it may be desirable to employ insoluble weighting solids. In some aspects, it may be desirable to employ both soluble and insoluble weighting components. Exemplary densities are shown in Table ii below. Other brines can approach 2500 g/L at 1 atm.

TABLE ii

| Liquid | Density (g/L) at 1 atm |
|---|---|
| Water | 1000 |
| NaCl saturated brine | 1199 |
| $CaCl_2$ saturated brine | 1435 |

Typically, a balance is struck between the cost of solute and the possible drilling rate. As the desired liquid density increases, it becomes easier to add particles of a weighting agent instead of adding less common dissolving salts. However, heavy brines can also be used when insoluble solids cannot be (or should not be) used such as, for example, right before drilling into the actual petroleum formation, since the formation may be negatively impacted if the pores were plugged by small weighting particles.

Thus, in various aspects, the liquid has a density (g/L) of 720, 740, 760, 780, 800, 820, 840, 860, 880, 900, 920, 940, 960, 980, 1000, 1050, 1100, 1150, 1200, 1250, 1300, 1350, 1400, 1450, 1500, 1550, 1600, 1650, 1700, 1750, 1800, 1850, 1900, 1950, or 2000. Each of the foregoing numbers can be preceded by the term "about," "at least about," or "less than about," and any of the foregoing numbers can be used singly to describe an open-ended range or in combination to describe a closed-ended range.

In a further aspect, the liquid has a density approximately equal to the density of water at a pressure of about 1 atm and 4° C. (i.e. approximately 1000 g/L). In a still further aspect, the liquid has a density greater than the density of water. For example, the liquid has a density (%) that is 10, 20, 30, 40, 50, 60, 70, 80, 90, or 100% greater than the density of water. Each of the foregoing numbers can be preceded by the term "about," "at least about," or "less than about," and any of the foregoing numbers can be used singly to describe an open-ended range or in combination to describe a closed-ended range. In yet a further aspect, the liquid has a density that is more than 80% greater than the density of water. Notably, a composition comprising the cellulose particles will not be impacted by the use of density agents, etc.; rather, such a composition will work as expected alongside these additives.

In a further aspect, the liquid is present in an amount (wt % based on total weight of the composition) of 20, 25, 30, 35, 40, 45, 50, 55, 60, 65, 70, 75, 80, 85, 90, 95, or 99. Each of the foregoing numbers can be preceded by the term "about," "at least about," or "less than about," and any of the foregoing numbers can be used singly to describe an open-ended range or in combination to describe a closed-ended range.

In a further aspect, the liquid comprises, consists of, or consists essentially of water. In some aspects, the liquid is water. Water-based fluids are generally cheaper than non-aqueous fluids, although water-based fluids typically require more monitoring during drilling, as they have more inherent flaws than non-aqueous fluids. A true "water" fluid would require nearly pure water. Since transporting water to the drilling site may be a challenge or may be expensive, it is common to use locally sourced water, which in many cases comes from water wells or even sea water. This often results in a salt- and/or mineral-containing solution, although when freshwater is available, it can also be used.

Thus, in various aspects, the liquid (e.g., water) further comprises a salt. For example, the liquid can further comprise a salt in an amount (wt %, based on total weight of the liquid) 1, 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 75, or 80 wt %. Each of the foregoing numbers can be preceded by the term "about," "at least about," or "less than about," and any of the foregoing numbers can be used singly to describe an open-ended range or in combination to describe a closed-ended range. In some aspects, the water further comprises greater than 80 wt % salt.

The salt can contain, for example, a Group I, a Group II, or a Group XVII element, or any combination thereof. In a further aspect, the salt is selected from a sodium salt, a calcium salt, a zinc salt, a potassium salt, a magnesium salt, an acetate salt, and a formate salt and a mixture thereof. Examples of salts include NaCl, CaCl2, CaBr2, ZnCl2, ZnBr2, KCl, KBr, NaBr Na(OC(O)CH₃), Na(OC(O)H), K(OC(O)CH₃), K(OC(O)H), and Cs(OC(O)H), and mixtures thereof.

In a still further aspect, the liquid (e.g., water) is saturated with salt (i.e., the liquid is a brine). Due to the high osmotic pressures associated with brines, they are less likely to "give-up" water to rock as the drilling takes place. Briefly, rocks will swell if they can absorb water from the drilling fluid. By maintaining a proper (high) osmotic pressure in the drilling fluid, there is less likelihood of swelling the rock formation towards the drill pipe and causing the pipe to get stuck. Additionally, brines inherently depress the freezing point of water, so there are use cases where brines make it easier to drill in near-freezing temperatures because they will not freeze while on the surface.

In a further aspect, the liquid comprises, consists of, or consists essentially of oil. In some aspects, the liquid is oil. Examples of oils include, but are not limited to, hydrocarbon oils, silicones, and hydrosilicone oils. Non-aqueous fluids are more expensive and can potentially have a higher negative impact on the environment, but also have fewer inherent use issues (can be used with a "set it and forget it" mentality) and are more forgiving while drilling. For example, non-aqueous fluids have a high thermal stability, improved lubricating properties (compared to aqueous fluids), and will not "water-wet" the rocks as the well is being drilled. This can be advantageous in certain types of rock (e.g., shale) because this stabilizes the operation similar to the situation with brines described above, but via a different mechanism. Without wishing to be bound by theory, it is hypothesized that the oil physically coats the rock and prevents water from reaching it. Unfortunately, non-aqueous fluids can have trouble with lower temperatures because they "gel" and may be difficult to pour or get to flow (similar to diesel problems in cold environments).

In various aspects, the liquid (e.g., oil) further comprises lime. For example, the liquid (e.g., oil) can further comprise lime in an amount (wt % based on total weight of the liquid and lime) of 1, 2, 3, 4, 5, 6, 7, 8, 9, 10, 11, 12, 13, 14, 15. Each of the foregoing numbers can be preceded by the term "about," "at least about," or "less than about," and any of the foregoing numbers can be used singly to describe an open-ended range or in combination to describe a closed-ended range. Limes naturally drive the pH high. In some instances, lime can be added to help make calcium soaps, which serve as a common emulsifying agent in non-aqueous fluids.

In a further aspect, the liquid is a mixture of water and oil. In a still further aspect, the water further comprises a salt (in any amount disclosed hereinabove). In yet a further aspect, the water is saturated with salt (i.e., a brine). In an even further aspect, water is present in an amount (wt % based on total weight of the fluid) of 1, 2, 4, 6, 8, 10, 12, 14, 16, 18, 20, 22, 24, 25, 30, 35, 40, or 45, and the oil is present in an amount (wt % based on total weight of the liquid) of 55, 60, 65, 70, 75, 76, 78, 80, 82, 84, 86, 88, 90, 92, 94, 95, 96, 97, 98, or 99. Each of the foregoing numbers can be preceded by the term 'about,' at least about,' or 'less than about,' and any of the foregoing numbers can be used singly to describe an open-ended range or in combination to describe a closed-ended range. For example, in some aspects, the water is present in any amount of from 1 wt % to 45 wt % and the oil is present in any amount of from 55 wt % to 95 wt %, all of which are based on total weight of the liquid.

In an even further aspect, water is present in an amount (wt % based on total weight of the composition) of 1, 2, 4, 6, 8, 10, 12, 14, 16, 18, 20, 22, 24, or 25, and the oil is present in an amount (wt % based on total weight of the composition) of 75, 76, 78, 80, 82, 84, 86, 88, 90, 92, 94, 95, 96, 97, 98, or 99. Each of the foregoing numbers can be preceded by the term 'about,' at least about,' or 'less than about,' and any of the foregoing numbers can be used singly to describe an open-ended range or in combination to describe a closed-ended range. For example, in some aspects, the water is present in any amount of from 1 wt % to 25 wt % and the oil is present in any amount of from 75 wt % to 95 wt %, all of which are based on total weight of the composition.

In various aspects, the cellulose particles in the disclosed compositions (e.g., drilling fluids, stamping fluids, etc.) that comprise cellulose particles and a liquid are the same cellulose particles described elsewhere herein.

In the composition comprising cellulose particles and a liquid, the cellulose particles typically are present in the composition in an amount (wt %, based on total weight of the composition) of 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, or 30. Each of the foregoing numbers can be preceded by the term 'about,' at least about,' or 'less than about,' and any of the foregoing numbers can be used singly to describe an open-ended range or in combination to describe a closed-ended range.

In various aspects, the cellulose particles are present in the composition (also comprising a liquid) at a level sufficient to improve various properties of the compositions compared to an otherwise identical composition without the cellulose particles. For example, the cellulose particles can be present at a level sufficient to improve the viscosity, the thermal stability, the emulsifying properties, or any combination thereof in the presence of typical ingredients used in such fluids, such as salt/brine, weighting agents, and alkaline and acidic pH adjustments.

For example, in various aspects, the cellulose particles are present at a level sufficient to increase the viscosity of the composition by X % compared to the viscosity of an otherwise identical composition without the cellulose particles, in which X is 10, 20, 30, 40, 50, 60, 70, 80, 90, 100, 120, 150, 200, 250, 300, 350, 400, 500, 600, 700, 800, 900, 1000, 1500, 2000, 3000, 4000, 5000, 6000, 7000, or 8000. Each of the foregoing numbers can be preceded by the term "about," "at least about," or "less than about," and any of the foregoing numbers can be used singly to describe an open-ended range or in combination to describe a closed-ended range.

In one aspect, disclosed are methods for making compositions comprising a liquid and particles comprising cellulose. In one aspect, disclosed are methods for making a composition, the method comprising combining: (a) a liquid; and (b) particles comprising cellulose, wherein the particles have at least one of (1) a $d_{75}$ of less than about 8 microns and (2) a $d_{50}$ of about 0.4 microns to about 5 microns, have an aspect ratio of from about 1 to about 1.5, and have a non-spherical shape, and wherein at least a portion of the cellulose is type-II cellulose, thereby forming the composition.

In one aspect, disclosed are methods for making compositions comprising a liquid and particles comprising cellulose. In one aspect, disclosed are methods for making a composition, the method comprising combining: (a) a liquid; and (b) particles; wherein the particles: comprise cellulose; have at least one of (1) a $d_{75}$ of less than about 8 microns and (2) a $d_{50}$ of about 0.4 microns to about 5 microns; have an aspect ratio of from about 1 to about 1.5; and have a non-spherical shape; and wherein at least a portion of the cellulose is type-II cellulose, thereby forming the composition.

In a further aspect, the composition comprising a liquid and cellulose particles is prepared in situ as when, for example, a drilling fluid is used in drilling. For example, the cellulose particles (either dried or in a fluid) are mixed with a liquid on site and immediately used in the particular application (e.g., drilling mud or fluid), as opposed to the composition comprising a liquid and cellulose particles being prepared off-site and then transported on-site. Such in situ mixing includes using the cellulose particles described herein as an additive to an existing composition (whether or not such existing composition has already been used for its intended purpose, such as a drilling fluid used in drilling a well) that then creates the composition comprising a liquid and cellulose particles described herein. In some aspects, however, the composition comprising a liquid and cellulose particles is prepared off-site and transported on-site.

In various aspects, the disclosed compositions comprising cellulose particles and a liquid are useful as subterranean treatment compositions. A subterranean treatment composition may be used in a subterranean formation in a variety of ways. For example, a subterranean treatment composition may be used to drill a borehole in a subterranean formation, to stimulate a well bore in a subterranean formation, or to clean up a well bore in a subterranean formation, as well as for numerous other purposes.

In various aspects, the composition comprising cellulose particles and a liquid is selected from a drilling fluid, a fracturing fluid, a well control fluid, a well kill fluid, a well cementing fluid, an acid fracturing fluid, an acid diverting fluid, a stimulation fluid, a sand control fluid, a completion fluid, a wellbore consolidation fluid, a remediation treatment fluid, a spacer fluid, a frac-packing fluid, a water conformance fluid, and a gravel packing fluid, or a combination thereof.

In various aspects, the subterranean treatment composition is a drilling fluid. A drilling fluid is commonly used in connection with drilling a well bore in a subterranean formation. Drilling fluids can be used, inter alia, to cool the drill bit, lubricate the rotating drill pipe to prevent it from sticking to the walls of the well bore, prevent blowouts by serving as a hydrostatic head to counteract the sudden entrance into the well bore of high pressure formation fluids, and to remove drill cuttings from the well bore.

In various aspects, the subterranean treatment composition is a fracturing fluid. A fracturing fluid is typically injected into a well to create fractures and to expand the surface area of a reservoir so as to enhance oil and gas recovery. These induced fractures create a pathway used by operators to recover oil or natural gas from the subterranean formation.

A slurry of cellulose particles (described elsewhere herein) typically is a viscous, shear-thinning material that displays increased viscosity as temperature increases. Without wishing to be bound by theory, an ideal drilling fluid provides a relatively high viscosity at rest (i.e., low or zero-shear) and a low viscosity under flow (i.e., high-shear). A high viscosity in the low-shear region provides a drilling fluid with the ability to maintain drill cuttings in suspension and deliver them from the bottom of the well to the solids control equipment at the drilling site. Low viscosity in the high-shear region dictates the speed with which the fluid can be pumped through the drill bit—higher flow rates lead to higher drilling rates, which reduce the time to drill and in turn reduces the cost to drill and leads to improved economics. The cellulose particles demonstrate the low plastic viscosity desired in an ideal drilling fluid.

A further challenge for drilling fluid rheology is the ability of the fluid to thicken to a gel at zero-shear (i.e., no flow) but then easily break from a gel to a flowing fluid again once the fluid needs to be pumped. Without wishing to be bound by theory, an ideal drilling fluid will quickly gel once pumping stops and will hold drilled solids in suspension, but when pumping resumes, an ideal fluid will have very little overpressure required to resume pumping, as too much required overpressure can fracture the hole being drilled. This behavior is referred to as "low, flat gels," which indicates a low energy to overcome, and the behavior doesn't change with time (i.e., the buildup behavior is "flat"). The rheology of drilling fluids is typically represented using the Bingham Plastic model and an ideal drilling fluid will have a low plastic viscosity and a manageable yield point. Compositions comprising cellulose particles and a liquid as described herein can provide this desirable rheology profile.

In various aspects, compositions comprising cellulose particles and a liquid can further comprise a viscosifying agent. Such cellulose particles can be combined with a viscosifying agent to later be combined with a liquid for the various uses described herein. In a further aspect, such a combination can result in a synergistic effect, such as synergistic thickening, as discussed earlier herein. For example, a synergistic effect can be achieved by combining cellulose particles with an inorganic viscosifying agent including, but not limited to, bentonite, laponite, synthetic hectorites, natural hectorites, mixed metal hydroxides, and mixed metal oxides. Alternatively, a synergistic effect can be achieved by combining small particle size cellulose particles with organic viscosifying agents including, but not limited to, xanthan gum, diutan, carboxymethyl starch, carboxymethyl cellulose, guar gum, and polysaccharide oligomers. This unique property allows the viscosity profile of the composition to be tuned based on the location of drilling.

Water-based drilling fluids have been formulated with a host of bio-derived materials including, but not limited to, guar gum, xanthan gum, and diutan, as well as starches, celluloses, and modifications thereof. These bio-derived materials share a common drawback in that they thermally degrade in drilling fluids at greater than 300° F. Typically, a drilling well is considered to have a "high temperature" when the temperature in the range of 285° F.-350° F. and above. On some occasions, drilling wells can reach up to 450° F., while higher temperatures are not unheard of. Thermal extenders can be applied to increase the temperature limitation slightly. Thus, a drilling fluid with an inherent thermal stability above 300° F. is desirable because it could prevent the need to use a non-aqueous (or "invert-emulsion") drilling fluid, which is typically more thermally stable than a water-based drilling fluid but more expensive and could have a greater negative impact on the environment.

The cellulose particles described herein have survived submersion in supercritical water by design. Moreover, such particles have a highly crystalline structure. Thus, in various aspects, compositions comprising cellulose particles are thermally stable as defined elsewhere herein. For example, the compositions comprising small particle size cellulose particles can be thermally stable at a temperature of at least about 375° F. (e.g., greater than: 375° F., 400° F., 425° F., 450° F., 475° F., or 500° F.). In various aspects, compositions comprising cellulose particles are more thermally stable than compositions comprising alternative bio-polymers. Additionally, the thermal stability of a disclosed composition can be further improved by addition of a thermal stabilizing agent such as, for example, magnesium oxide (MgO), monoethanolamine (MEA), citric acid, formate solutions ($Na^+$, $K^+$, $Cs^+$), and combinations thereof.

While commonly available viscosifying agents are negatively impacted by microorganisms naturally present in the environment, the $\beta$ ($1\rightarrow4$)-glycosidic bonds present in cellulose particles are far more stable. Although some microbes can break cellulose bonds, these microbes are less frequently encountered in the proper conditions in the natural environment to impact the effectiveness of cellulose, thus the timespan for digestion of cellulose is far longer than other common viscosifying agents. Without wishing to be bound by theory, the cellulose particles are bacteriostatic in that bacteria neither grow nor die when subjected to the cellulose particles. Additionally, the presence of a small amount of lignin in the material may confer additional benefit over cellulose-only materials such as microcrystalline cellulose in that antimicrobial treatment may not be needed as the fluid would retain its useful characteristics even in the face of microbial contamination. Thus, without wishing to be bound by theory, a cellulose particle based-fluid can allow for re-use/re-cycling opportunities for non-aqueous or water-based fluids due to the long-term stability of the material (an opportunity that, until this disclosure, had been reserved primarily for non-aqueous fluids).

Saline environments are encountered at different times and places in the process of exploring for oil and gas. A water-based drilling fluid will typically utilize water sourced locally to the drilling location as the basis for the fluid. By using locally-available water, it is possible to reduce shipping costs for the supplies related to the drilling fluid makeup. This water is sometimes low in dissolved minerals; however, it is typically contaminated with salts of one type or another in concentrations ranging from ppm to near-saturation. In some cases, salts are added as an inexpensive way to increase the weight of the drilling fluid due to requirements of the well drilling operation. The variable water chemistries can have profound impacts on the additives in the drilling fluid. The cellulose particle-based compositions demonstrate improved rheological performance compared to alternative technologies using a variety of monovalent and divalent brine solutions. Thus, in various aspects, the cellulose particle-based compositions remain substantially unaffected by the presence of dissolved minerals. As a variety of dissolved salts, salt deposits, and brine layers can be encountered while drilling, this is an extremely beneficial property.

In oil and gas operations, there are common activities that involve pH adjustment of fluids in order to modify fluid properties temporarily or permanently to achieve specific goals, and the processes of acidifying and alkalizing are well established. For Example, this is encountered when preparing a well for production—drilling crews typically dissolve calcium carbonate contaminants with HCl to remove the "scale" from the wellbore, thus making it easier for hydrocarbons to exit the underground chambers and make their way to the surface. Another example would be continuous alkali addition to drilling fluids to maintain a buffer against acidic inflows encountered during drilling. For most commonly available viscosifying agents, it is not possible to modify the viscosity or the viscosifying agent simply by changing the pH. Moreover, many inexpensive inorganic viscosifiers, such as bentonite, irreversibly damage (via pore plugging) the production formation if used for drilling the "pay-zone", and pH variation cannot be used to free the pores and remove the bentonite. This precludes their use except in portions of the well that don't include the hydrocarbon bearing areas. In contrast, when using small particle size cellulose particles, the viscosifying properties of the particles can be modified by simply changing the pH of the mixture and the particles can be dissolved by further pH manipulation. Thus, in various aspects, small particle size cellulose particles are a non-damaging viscosifier. Furthermore, in addition to using small particle size cellulose particles with a liquid in a drilling composition, a more concentrated "pill" or thick, slurry of small particle size cellulose particles can be pumped into a well for specific well operations, and then dissolved using pH adjustment following the operation.

In addition to beneficial rheological properties, cellulose particles also function as a useful emulsifier. Without wishing to be bound by theory, the salinity tolerance and thermal resistance of the cellulose particles permit its use as an emulsifier for non-aqueous/invert-emulsion drilling fluids. Because the cellulose particles function as a Pickering emulsion stabilizer rather than as a traditional surfactant, micellar, or lamellar emulsifier, emulsions formed with the disclosed particles can offer many advantages in various applications (e.g., challenging thermal environments, unique chemistries, etc.). In addition to emulsification of non-aqueous fluids, the other characteristics detailed herein are also fully expected in non-aqueous fluids. Thus, the Pickering-emulsification properties of the cellulose particles allows its use as a unique emulsifier and/or thickener for acid-treatments used in oil and gas operations for dissolving rock in the hydrocarbon bearing zones of an oil and gas well. The cellulose particles may also act as a suspension aid and/or thickener.

In various aspects, the disclosed compositions comprising a liquid and cellulose particles are useful as a wellbore strengthening material (WSM). During the drilling process, it is common to encounter various geological formations that have differentiating fragility. When drilling these formations, care must be exercised regarding fluid selection & makeup to ensure that the wellbore is not damaged to the point where drilling operations are affected. A common method to improve the drilling opportunity in these scenarios is the addition of so-called wellbore strengthening materials (WSMs). These additives, true to their name, can strengthen the wellbore via a multitude of different interactions (primarily physical, chemical, thermal, and mechanical) with the wellbore. In various aspects, due to the size of the cellulose particles, the cellulose particles can move into locations where typical WSMs may be precluded. This unique sizing enables users to provide additional strength where current materials are unsuited. Moreover, testing for wellbore strengthening is prohibitively expensive, but particle size data and electron microscopy data for small particle size cellulose particles may enable a user to accurately predict the outcome of adding the material as a WSM.

Without wishing to be bound by theory, other oil and gas related uses for the cellulose particles are also envisioned including, but not limited to, in formulations used for fracturing (where the solids carrying capacity of the composition comprising the cellulose particles has been shown to synergize with guar gum), in completion fluids (whereby the non-reservoir damaging characteristics of the cellulose particles can be utilized), and in cementing operations (where the cellulose particles impart improved properties, e.g., curing, strength, pumpability, and allowability, to concrete and/or asphalt mixtures).

In various aspects, the disclosed compositions comprising a liquid and cellulose particles are useful as metal working compositions. Metal working compositions are commonly used in grinding, milling, machining, polishing and cutting to cool and/or lubricate, for example, metal workpieces, rock, stone, concrete, roads, and asphalt, as in, for example, countertops, flooring, sculpture, roads, and sidewalks. Specifically, metal working compositions reduce the heat and friction between the cutting tool and the workpiece, and help prevent burning and smoking. Without wishing to be bound by theory, metal working compositions can also help to improve the quality of the workpiece by continuously removing the fines, chips, and swarfs (i.e., the small pieces of metal removed from a workpiece by the cutting tool) from the tool being used and the surface of the workpiece. It is understood that the beneficial properties of the disclosed metal working compositions include, inter alia, the properties disclosed in relation to subterranean treatment compositions.

In various aspects, the disclosed compositions comprising cellulose particles and a liquid are useful as cutting compositions. Cutting compositions are used in metal machining for a variety of reasons including, inter alia, to improve tool life, to reduce workpiece thermal deformation, to improve surface finish, and to flush away chips from the cutting zones. Specifically, cutting compositions prevent friction at the interface between a tool's cutting edge and the metal by cooling and lubricating the interface. It is understood that the beneficial properties of the disclosed cutting compositions include, inter alia, the properties disclosed in relation to subterranean treatment compositions.

In various aspects, the disclosed compositions comprising cellulose particles and a liquid are useful as stamping compositions. Stamping compositions are typically used to provide lubrication and cooling in metal cutting (in a method like a cookie cutter through dough, or a hole puncher through paper), bending, stretching, and shaping operations. It is understood that the beneficial properties of the disclosed stamping compositions include, inter alia, the properties disclosed in relation to subterranean treatment compositions.

In one aspect, disclosed are methods for treating subterranean formations, the methods comprising introducing a disclosed composition into the subterranean formation. In one aspect, disclosed are methods for treating a subterranean formation, the method comprising introducing particles comprising cellulose into the subterranean formation, wherein the particles have any of the particle characteristics disclosed elsewhere herein, for example, the particles have: at least one of (1) a $d_{75}$ of less than about 8 microns and (2) a $d_{50}$ of from about 0.4 microns to about 5 microns; have an aspect ratio of from about 1 to about 1.5; and have a non-spherical shape; and wherein at least a portion of the cellulose is type-II cellulose.

In various aspects, the method further comprises introducing a liquid into the subterranean formation. Thus, the liquid and the cellulose particles need not be pre-mixed prior to introduction into a subterranean formation.

In various aspects, the method further comprises subsequently introducing more of the liquid into the subterranean formation. Thus, additional liquid can be added into the formation after a disclosed composition comprising cellulose particles has already been introduced into the formation. This may be desirable, for example, to tune the properties of the composition as detailed herein above.

In a further aspect, the cellulose particles and the liquid are introduced simultaneously. In a still further aspect, the cellulose particles and the liquid are introduced sequentially.

Environments of extreme pressure, high temperature, continuous high speed, and/or contamination can create strenuous demands on a system, whether during metalworking operations, plastics operations, or masonry operations, although other similarly operating environments are also envisioned. Under such circumstances, lubrication of a component of the system is often required, or cooling of a component of the system is often required. Thus, in various aspects, a disclosed composition can be used to lubricate or cool a component of the system, e.g., a metal, a plastic, or a masonry construction material.

In one aspect, disclosed are methods of lubricating a substrate, the method comprising applying to the substrate a composition disclosed herein comprising a liquid and cellulose particles, wherein the substrate is selected from a metal, a plastic, and a masonry construction material.

In a further aspect, the substrate is a plastic.

In a further aspect, the substrate is a masonry construction material. Examples of masonry construction materials include, but are not limited to, concrete, cement, asphalt, brick, and mixtures thereof.

In a further aspect, the substrate is a metal.

In a further aspect, the metal is formed as a prefabricated article.

Examples of prefabricated articles include, but are not limited to, tools, machine parts, pipes, tubes, beams, coins, badges, pins, jewelry, sheets, brackets, screws, nails, pistons, and rods.

In various aspects, the method further comprises one or more of polishing the substrate, honing the substrate, cutting the substrate, drilling the substrate, grinding the substrate, milling the substrate, or use of a lathe on the substrate.

In one aspect, disclosed are methods of cooling a substrate, the method comprising applying to the substrate a disclosed composition comprising a liquid and cellulose particles, wherein the substrate is selected from a metal, a plastic, and a masonry construction material.

In a further aspect, the substrate is a plastic.

In a further aspect, the substrate is a masonry construction material. Examples of masonry construction materials include, but are not limited to, concrete, cement, asphalt, brick, and mixtures thereof.

In a further aspect, the substrate is a metal.

In a further aspect, the metal is formed as a prefabricated article.

Examples of prefabricated articles include, but are not limited to, tools, machine parts, pipes, tubes, beams, coins, badges, pins, jewelry, sheets, brackets, screws, nails, pistons, and rods.

In various aspects, the method further comprises one or more of polishing the substrate, honing the substrate, cutting the substrate, drilling the substrate, grinding the substrate, milling the substrate, or use of a lathe on the substrate.

K. Personal Care and Cosmetic Products

Additionally, in various aspects, the cellulose particles can be used, either alone or in combination with other components (e.g., in the form of the various other types of compositions described herein, such as a thickened composition, suspension, emulsion, and the like), as a personal care or cosmetic product. The cellulose particles themselves can provide an exfoliating, softening, or other desirable property (such as a feeling of rejuvenation) to a composition containing them (e.g., as a suspension of the cellulose particles in water, or as a suspension comprising the cellulose particles) when such a composition is applied to the skin (e.g., face, hands, feet, arms, legs, or any other skin on the body of a human or animal). In embodiments where the particles comprising cellulose further comprise lignin, or where lignin is present in the composition containing the particles comprising cellulose, the lignin also may provide (in conjunction with the cellulose particles) an exfoliating, softening, or other desirable property (such as a feeling of rejuvenation) to a composition containing such components.

In some embodiments, disclosed is a personal care formulation comprising: particles; wherein the particles: comprise cellulose; have at least one of: (1) a $d_{75}$ of less than about 8 microns and (2) a $d_{50}$ of about 0.4 microns to about 5 microns; have an aspect ratio of about 1 to about 1.5; and have a non-spherical shape; and wherein at least a portion of the cellulose is type-II cellulose.

Some compositions may be a combination of those described herein. In particular, a composition may technically be an emulsion, but it may also have suspended particles (e.g., particles other than the cellulose particles described herein). Similarly, a thickened composition may also be an emulsion and/or a suspension. As one of ordinary skill in the art would understand, the cellulose particles herein need not be used only in compositions that are strictly considered to be emulsions, suspensions, or thickened compositions, etc., but rather the cellulose particles can be used in compositions that may have characteristics of any combination of these types of compositions (e.g., the composition may overlap to be considered a member of more than one category of composition type).

An example of such compositions, where the particles comprising cellulose may function in one or more capacity as described above, is a personal care formulation (e.g., a beauty formulation, cosmetic formulation, a skin care formulation, etc.). The cellulose particles may function, for example, as an exfoliant, a texturizer, or both. The cellulose particles, when functioning as an exfoliant, a texturizer, or both, may be present in a composition that is an emulsion, a suspension, a thickened composition, (or any other composition or type of composition described herein), or any combination thereof. In some embodiments, the cellulose particles may be used directly (e.g., alone or minimally formulated), or used in a formulation comprising other ingredients (i.e., contain more ingredients than a minimally formulated composition), as an exfoliant. The cellulose particles may also function (e.g., alone, minimally formulated, or more than minimally formulated) as texturizers. Accordingly, alone, minimally formulated, or more than minimally formulated, the cellulose particles may function both as an exfoliant and as a texturizer. In such a capacity, the cellulose particles may be present at any use level, including 100% of the solids (weight of solid particles based on total formulation solids). For example, in personal care formulations (e.g., beauty formulations, cosmetic formulations, skin care formulations, and so on), such as a facial scrub formulation, body scrub formulation, or lotion, the cellulose particles described herein are present in the personal care formulation (weight % of dry solids of particles based on the total weight of the formulation) in an amount of 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10, 10.5, 11, 11.5, 12, 12.5, 13, 13.5, 14, 14.5, 15, 16, 17, 18, 19, 20, 22, 24, 26, 28, 30, 32, 34, 36, 38, 40, 42, 44, 46, 48 or 50. Each of the foregoing numbers can be preceded by the word "about," "at least about," or "less than about," and any of the foregoing numbers can be used singly to describe an open-ended range or in combination to describe a close-ended range. For example, the cellulose particles disclosed herein can be present in the formulation in an amount of at least about 0.5% by weight, about 1% by weight to about 4% by weight, or less than about 10% by weight. In a minimally formulated formulation, the cellulose particles disclosed herein can be present in the formulation in an amount of at least about 10% by weight, about 12% by weight to about 18% by weight, or less than about 20% by weight. In the case of a high solids personal care product, such as an exfoliating bar or pumice stone substitute, the cellulose particles described herein are present in the high solids personal care product (weight % of dry solids of particles based on the total weight of the product) in an amount of 50, 60, 70, 80, 90, 95, or 97. Each of the foregoing numbers can be preceded by the word "about," "at least about," or "less than about," and any of the foregoing numbers can be used singly to describe an open-ended range or in combination to describe a close-ended range. For example, the cellulose particles disclosed herein can be present in the high solids product in an amount of at least about 50% by weight, about 50% by weight to about 90% by weight, at least 95% by weight, or less than about 97% by weight. In some embodiments of the personal care formulations and of the high solids personal care product, the cellulose particles comprise about 15% to about 25% by weight of lignin, based on the weight of the cellulose particles on a dry basis. In some embodiments, the cellulose particles comprise less than 1%, or about 0%, by weight of lignin, based on the weight of the cellulose particles on a dry basis. As used in this context, "minimally formulated" means that the formulation contains the cellulose particles and a minimal amount of other ingredients that are necessary to produce a formulation satisfactory for its intended use (e.g., as a body scrub, a facial scrub, a skin lotion, etc.). See also Example 14 for examples of minimally formulated formulations.

Personal care formulations may comprise additional ingredients in order to provide a different balance of properties. For example, personal care formulations may comprise one or more additional thickener in order to optimize a formulation viscosity or texture. In such cases, the particles comprising cellulose may function as synergistic thickeners by providing a synergistic effect over and above that of the sum of the effect of the thickener(s) and the particles comprising cellulose. In such formulations, the particles comprising cellulose may be present at levels described elsewhere herein, and the one or more additional thickener may be present at the levels normally associated with the specific thickener (suitable thickeners are described elsewhere herein and may be used for personal care formulations). For example, xanthan gum can be present in an amount of (weight % based on the total weight of the formulation) 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.5, 3, 3.5, 4, or 5. Each of the foregoing numbers can be preceded by the word "about," "at least about," or "less than about," and any of the foregoing numbers can be used singly to describe an open-ended range or in combination to describe a close-ended range. For example, xanthan gum can be present in the formulation in an amount of at least about 0.05% by weight, about 0.1% by weight to about 0.5% by weight, or less than about 1% by weight. Examples of other thickeners used in personal care products include, but are not limited to, polyacrylates, polyacrylamides, and ammonium acryloyldimethyltaurate/vinyl pyrrolidone copolymer.

Personal care formulations (e.g., beauty formulations, cosmetic formulations, body scrub formulations, facial scrub formulations, skin care formulations, hair care formulations, etc.) may additionally comprise other ingredients, including, for example, moisturizers, humectants, which can attract and bind water to improve hydration at the skin or hair surface, occlusive agents (such as oils), which may prevent or retard water leaving the skin or hair surface, emollients, which may create a smooth skin look or feel by filling in cracks or spaces in the skin, chemical peel agents (such as, e.g., glycolic acid, alpha hydroxyl acid, or salicylic acid, which are believed to generate an immune response that may help promote the growth of new skin cells for a rejuvenated skin, chemically exfoliate the skin and unclog pores, and inhibit growth of bacteria that causes acne), antioxidants, and a formulation biocide (e.g., one or more of caprylyl glycol, phenoxyethanol, hexylene glycol, or a food-grade biocide such as a sodium benzoate/potassium sorbate/glycerin combination). Notably, some ingredients can function in one or more of the roles described above (e.g., an ingredient may be both an occlusive agent and an emollient), and therefore an attempt to categorize the ingredients should not be construed as limiting any ingredient to a particular function; such categorization is made merely to aid an ordinarily skilled person to understand the disclosure. Oils can be very effective for certain functions or purposes, but in some circumstances may not be desirable in skin care or hair care formulations, including body scrubs and facial scrubs, because the target formulation is intended to be water-based or "oil free," or the formulations may require additional emulsifiers in order to fully disperse the oil(s) in aqueous formulations. The emulsifiers in some circumstances may impart a greasy feel to the formulation, which may be undesirable for some end uses. Moreover, some view formulation emulsifiers as potential skin irritants (one school of thought posits that the formulation emulsifiers aid in removal of natural lipids in the skin and hair when rinsed with water). Examples of emulsifiers that typically have been used in personal care formulations include fatty acids, such as stearic acid and palmitic acid, fatty alcohols such as stearyl alcohol and cetyl alcohol, fatty acid esters such as glyceryl monostearate and glycol mono- or di-stearate, as well as sodium stearyl glutamate, potassium cetyl phosphate and hydrogenated palm glycerides. Such species may be present in traditional personal care formulations at levels as high as 5-10% (weight % based on the total weight of the formulation). The particles comprising cellulose described herein can act as emulsifiers for oils, which renders the addition of emulsifiers to be unnecessary or undesirable. In addition to convenience and cost advantages, the removal of the emulsifiers may also provide a lighter, less greasy feel to the composition, and also the emulsifier-free formulation may be both greener and milder to the skin. In any event, the above-described other ingredient(s), either alone or in any combination, can be present in the personal care formulation in an amount of (weight % of the other ingredient(s), individually or in combination, based on the total weight of the formulation) 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5.0, 5.5, 6, 6.5, 7.0, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 64, 66, 68, 70, 72, 74, 76, 76, 78, or 80. Each of the foregoing numbers can be preceded by the word "about," "at least about," or "less than about," and any of the foregoing numbers can be used singly to describe an open-ended range or in combination to describe a close-ended range. These numbers can be used to describe any ingredient alone, or any combination of two or more ingredients. For example, oils can be present in the formulation in an amount of at least about 5% by weight, about 10% by weight to about 20% by weight, or less than about 30% by weight.

The personal care formulations can include suitable occlusive agents, humectants, emollients, or any combination thereof. Suitable occlusive agents include, for example, petrolatum, lanolin, mineral oil, silicones, dimethicone, argan oil, caprylic capric triglyceride, squalane, coconut oil, shea butter, or any combination thereof. Suitable humectants include, for example, propylene glycol, trehalose, glycerin, urea, hyaluronates, hyaluronic acid, pyrrolidonecarboxylate, or any combination thereof. Suitable emollients include, for example, fatty acid esters (octanoates such as octyl octanoate; laurates such as isoamyl laurate; adipates such as diisopropyl adipate; palmitates such as ethylhexyl palmitate), an oil, squalane, sesame oil, argan oil, algae extract, grape seed oil, caprylic capric triglyceride, cetyl stearate, glycerin, 1,3-butylene glycol, or any combination thereof. As noted earlier, some ingredients can function in one or more of the roles described above (e.g., an ingredient may be both an occlusive agent and an emollient). As used in the context of the other ingredients listed above, the term "moisturizer" is a category that includes an emollient, an occlusive agent, a humectant, or any combination thereof.

Suitable antioxidants for the personal care formulations include any of those known in the art, such as ascorbic acid. The particles comprising cellulose may additionally comprise lignin as described elsewhere herein. This lignin may also function as an antioxidant, which may render the addition of a separate antioxidant unnecessary, or it may work synergistically with an added antioxidant.

Personal care formulations, e.g., scrub formulations or skin care formulations, may additionally comprise other exfoliant materials. The particles of cellulose provide a fine abrasive exfoliant (also known as a polish) because the cellulose particles are small, having a $d_{50}$ of about 0.4 microns to about 5 microns as measured by the Beckman Coulter Particle Sizer. It may be advantageous to additionally include an additional exfoliant, such as, one that has a similar $d_{50}$ particle size, a smaller $d_{50}$ particle size, a larger $d_{50}$ particle size, or any combination thereof. A suitable additional exfoliant can be a microbead (e.g., polymeric), a nanobead, microcrystalline cellulose, nanocellulose; crushed sea shells, nut shells, and other hard organic matter; appropriately sized table sugar or salt crystals; or any known exfoliant. The additional exfoliant can be present in an amount of (weight % based on the total weight of the formulation) 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0. Each of the foregoing numbers can be preceded by the word "about," "at least about," or "less than about," and any of the foregoing numbers can be used singly to describe an open-ended range or in combination to describe a close-ended range. For example, the additional exfoliant can be present in the formulation in an amount of at least about 0.5% by weight, about 1% by weight to about 4% by weight, or less than about 5% by weight. For formulations comprising an additional exfoliant, or, indeed, any solid particulate added to the formulation, the particles comprising cellulose may additionally function to help in stabilizing such suspended solid particles.

In some embodiments, a personal care formulation comprises cellulose particles and an occlusive agent. In some embodiments, a personal care formulation comprises cellulose particles and squalane. In some embodiments, a personal care formulation comprises cellulose particles, squalane, and a biocide. In some embodiments, a personal care formulation comprises cellulose particles, squalane, and a thickener. In some embodiments, a personal care formulation comprises cellulose particles, squalane, and xanthan gum. In some embodiments, a personal care formulation comprises cellulose particles, squalane, xanthan gum, and a biocide. The amounts of these components can be any suitable amount as described elsewhere herein. For example, in some embodiments, a personal care formulation comprises cellulose particles (about 90 wt % to about 98 wt %, added as a 15-30% solids suspension) and squalane (about 0.5 wt % to about 5 wt %) in the indicated amounts. For example, in some embodiments, a personal care formulation comprises cellulose particles (about 90 wt % to about 98 wt %, added as a 15-30% solids suspension), squalane (about 0.5 wt % to about 5 wt %), and xanthan gum (about 0.05 wt % to about 0.6 wt %).

The cellulose particles disclosed herein can find utility in many personal care products, for example, health and beauty or cosmetic products, such as, for example, a lotion, cream, ointment, serum, shampoo, conditioner, hair moisturizer, hairspray, hair gel, deodorant, facial or body wash, facial or body scrub, exfoliant, emollient, moisturizer, soap, foundation make up, BB cream, CC cream, eye cream, sunscreen, anti-acne serum or cream or lotion, cellular serum or cream or lotion, facial or body mask, blush, eyeshadow, mascara, lipstick or lip balm, or clay, kaolin or mud suspension. Depending on the product type, the use of the cellulose particles disclosed herein in a personal care product may present one or more of the following non-limiting beneficial properties: ability to remove undesirable chemicals such as emulsifiers from the formulation, resulting in a greener and milder product (less irritant chemicals); a less oily or greasy feel to the product (described as a "lighter" or "airy" composition) resulting from removal of emulsifiers and better incorporation of oils and other occlusive agents; reduced quantities of viscosifying agents, since the cellulose particles act as a thickener, and additionally show a synergistic thickening effect with other thickeners; a mattifying and/or line filling effect for the skin, since the small particle size facilitates access to and filling of uneven skin and wrinkles; and a rejuvenating sensation for the skin, since the small particles act as a non-irritating exfoliant. Moreover, the cellulose particles may facilitate the delivery of either suspended solid- or immiscible liquid-active ingredients to the skin, since the cellulose particles are able to stabilize solids in suspension and emulsions comprised of immiscible liquids.

L. Exemplary Aspects

As discussed earlier herein, variability in the particle characteristics (such as particle size parameters, degree of polymerization, etc.) form several aspects.

Exemplary uses of the disclosed cellulose particles include, but are not limited to, in resuspendable cellulose compositions, thickened compositions, suspensions, and emulsifiable compositions. Additional exemplary uses of the disclosed cellulose particles include, but are not limited to, as leavenable food products and meat or meat analog compositions. Still other exemplary uses of the disclosed cellulose particles include, but are not limited to, subterranean treatment compositions, metal working compositions, cutting compositions, and stamping compositions.

Aspect 1: A thickened composition comprising:
particles;
    wherein the particles:
        comprise cellulose;
        have at least one of:
            (1) a $d_{75}$ of less than about 8 microns;
            (2) a $d_{50}$ of about 0.5 microns to about 5 microns;
        have an aspect ratio of about 1 to about 1.5; and have a non-spherical shape; and
        wherein at least a portion of the cellulose is type-II cellulose; and
a liquid;
wherein the particles are present at a level sufficient to increase the viscosity of the composition by at least 10% compared to an otherwise identical composition without the particles; and
wherein the viscosity of the formulations is determined at room temperature using a Brookfield LVT viscometer using spindle 21, at 2 rpm shear.

Aspect 2: The thickened composition of aspect 1, wherein the particles comprising cellulose are present at a level of at least 0.5 wt % of particles based on the total weight of thickened composition.

Aspect 3: The thickened composition of aspect 1 or 2, wherein the particles comprising cellulose are present at a level of from 0.5-15.0 wt % of particles based on the total weight of thickened composition.

Aspect 4: The thickened composition of any one of aspects 1-3, further comprising one or more additional thickeners, and wherein the resulting viscosity is at least 10% greater than the sum of the viscosity of the otherwise identical composition with the cellulose composition and the viscosity of the otherwise identical composition with the one or more additional thickeners.

Aspect 5: The thickened composition of any one of aspects 1-4, wherein the composition further comprises pigment particles, filler or extender particles, polymer particles, or a combination thereof, Aspect 6: The thickened composition of any one of aspects 1-5, wherein the composition is a paint, coating, ink, adhesive or sealant.

Aspect 7: The thickened composition of any one of aspects 1-6, wherein the composition is an edible composition.

Aspect 8: The thickened composition of any one of aspects 1-7, wherein the composition is a beverage, shake, soup, broth, sauce, dressing, gravy, pie filling, condiments, ice cream, yogurt or pudding.

Aspect 9: The thickened composition of any one of aspects 1-8, wherein the composition is a health and beauty or cosmetic product.

Aspect 10: The thickened composition of any one of aspects 1-9, wherein the health and beauty or cosmetic product is a lotion, cream, ointment, serum, shampoo, conditioner, hairspray, hair gel, deodorant, facial or body wash, facial or body scrub, exfoliant, emollient, moisturizer, liquid soap, foundation make up, bb cream, cc cream, eye cream, sunscreen, anti-acne serum or cream or lotion, cellular serum or cream or lotion, facial or body mask, blush, eyeshadow, mascara, lipstick or lip balm, or clay, kaolin or mud suspension.

Aspect 11: The thickened composition of any one of aspects 1-10, wherein the thickened composition is a sunscreen containing a light absorbing compound, a light scattering compound, or a combination thereof.

Aspect 12: The thickened composition of any one of aspects 1-11, wherein the composition is a cleaning fluid.

Aspect 13: The thickened composition of any one of aspects 1-12, wherein the cleaning fluid is a dishwashing detergent, laundry detergent, liquid fabric conditioner, no-splash bleach, toilet bowl cleaner, drain cleaner, or industrial detergent or cleaning fluid.

Aspect 14: A method for making the thickened composition of aspect 1, the method comprising combining:
(a) a liquid or liquid-based composition; and
(b) particles;
    wherein the particles:
        comprise cellulose;
        have at least one of:
            (1) a $d_{75}$ of less than about 8 microns;
            (2) a $d_{50}$ of from about 0.5 microns to about 5.0 microns;
        have an aspect ratio of from about 1 to about 1.5; and
        have a non-spherical shape; and
        wherein at least a portion of the cellulose is type-II cellulose;
thereby forming the composition.

Aspect 15: A suspension comprising:
(a) a liquid;
(b) particles;
    wherein the particles:
        comprise cellulose;
        have at least one of:
            (1) a $d_{75}$ of less than about 8 microns;
            (2) a $d_{50}$ of about 0.5 microns to about 5 microns;
        have an aspect ratio of about 1 to about 1.5; and
        have a non-spherical shape; and
        wherein at least a portion of the cellulose is type-II cellulose; and
(c) a first component suspended within the liquid.

Aspect 16: The suspension of aspect 15, wherein the suspension is a stable suspension.

Aspect 17: The suspension of aspect 15 or 16, wherein the suspension is a metastable suspension.

Aspect 18: The suspension of any one of aspects 15-17, wherein the suspension is a 50-95% stable suspension.

Aspect 19: The suspension of any one of aspects 15-18, wherein the suspension is sufficiently thickened by the particles to enable the first component to be in a stable suspension in the composition.

Aspect 20: The suspension of any one of aspects 15-19, wherein the first component is at least partially insoluble in the composition at ambient conditions.

Aspect 21: The suspension of any one of aspects 15-20, wherein the particles are present at a level of at least 0.5 wt % of particles based on the total weight of the suspension.

Aspect 22: The suspension of any one of aspects 15-21, wherein the particles are present at a level of from 0.5-35.0 wt % of particles based on the total weight of the suspension or wherein the particles are present at a level of from 0.5-15.0 wt % of particles based on the total weight of the suspension.

Aspect 23: The suspension of any one of aspects 15-22, wherein the first component is a plurality of one or more of pigment particles, filler or extender particles, or polymer particles, and the suspension is a paint, coating, ink, caulk, sealant or adhesive.

Aspect 24: The suspension of any one of aspects 15-23, wherein the first component is a plurality of inorganic particles and the suspension is cement or concrete.

Aspect 25: The suspension of any one of aspects 15-24, wherein the first component is a plurality of dirt particles or rock cuttings and the suspension is drilling mud or drilling fluid.

Aspect 26: The suspension of any one of aspects 15-25, wherein the first component is a plurality of ore or mineral particles and the suspension is a mining slurry or wherein the first component is a plurality of metal fines, chips, and/or swarfs and the suspension is a metal working composition.

Aspect 27: The suspension of any one of aspects 15-26, wherein the first component is a plurality of charcoal particles or coal dust and the suspension is a fuel slurry.

Aspect 28: The suspension of any one of aspects 15-27, wherein the first component is a plurality of solid particles in a solid lubricant or grease.

Aspect 29: The suspension of any one of aspects 15-28, wherein the first component is a plurality of inorganic particles or polymer particles and the suspension is toothpaste.

Aspect 30: The suspension of any one of aspects 15-29, wherein the first component is a plurality of inorganic particles or polymer particles and the suspension is soap.

Aspect 31: The suspension of any one of aspects 15-30, wherein the first component is an excipient or an active pharmaceutical ingredient and the suspension is a liquid medicine, a liquid medicine encapsulated in a pill, an externally delivered medicine, a medicine to be injected, or supplement.

Aspect 32: The suspension of any one of aspects 15-31, wherein the first component is or comprises a plurality of fruit, vegetable, fiber, or protein particles, or combinations or imitations thereof, and the suspension is a beverage, a smoothie, or a shake.

Aspect 33: The suspension of any one of aspects 15-32, wherein the first component is a plurality of cocoa particles, malt particles, or artificially or naturally flavored particles, herbs or spices or combinations or imitations thereof, and the suspension is a milk, a hot beverage, a cold beverage, a syrup, a dressing, a marinade, a soup or a sauce.

Aspect 34: The suspension of any one of aspects 15-33, wherein the first component is a plurality of pigment particles or inorganic particles and the suspension is a make-up foundation, a blush, an eye shadow, a mascara, a BB cream, a CC cream, an eye cream, a sunscreen, a deodorant, a facial or body wash, a facial or body scrub, an exfoliant, a facial or body mask, a lipstick or lip balm, a clay suspension, a kaolin suspension, or a mud suspension.

Aspect 35: The suspension of any one of aspects 15-34, wherein the first component is a plurality of exfoliant particles and the suspension is a skin care product or scrub.

Aspect 36: The suspension of any one of aspects 15-35, wherein the first component is a plurality of inorganic particles, oxide particles, or polymer particles and the suspension is a lotion or sunscreen.

Aspect 37: The suspension of any one of aspects 15-36, wherein the first component is a plurality of oxide particles and the suspension is a cleaning or buffing slurry or polish.

Aspect 38: The suspension of any one of aspects 15-37, wherein the cleaning slurry is a chemical mechanical planarization slurry.

Aspect 39: A method for making the suspension of aspect 15, the method comprising combining, optionally with stirring or otherwise mixing:

(a) a liquid;

(b) particles;

wherein the particles:

comprise cellulose;

have at least one of:

(1) a $d_{75}$ of less than about 8 microns;

(2) a $d_{50}$ of from about 0.5 microns to about 5.0 microns;

have an aspect ratio of from about 1 to about 1.5; and have a non-spherical shape; and wherein at least a portion of the cellulose is type-II cellulose; and (c) a first component suspended within the liquid;
thereby forming the composition.

Aspect 40: An emulsion or emulsifiable composition comprising:

particles comprising cellulose;

wherein the particles:

have at least one of:

(1) a $d_{75}$ of less than about 8 microns;

(2) a $d_{50}$ of about 0.5 microns to about 5 microns;

have an aspect ratio of about 1 to about 1.5; and have a non-spherical shape; and wherein at least a portion of the cellulose is type-II cellulose.

Aspect 41: The emulsion or emulsifiable composition of aspect 40, wherein the emulsion or emulsifiable composition is an emulsion, and the emulsion comprises:

a first fluid and a second fluid;

wherein the first fluid is at least partially immiscible with the second fluid.

Aspect 42: The emulsion of aspect 40 or 41, wherein the first fluid comprises an oil and the second fluid comprises water.

Aspect 43: The emulsion or emulsifiable composition of any one of aspects 40-42, wherein the particles comprising cellulose are present at a level of at least 0.5 wt % of particles based on the total weight of the emulsion.

Aspect 44: The emulsion or emulsifiable composition of any one of aspects 40-43, wherein the particles comprising cellulose are present at a level of from 0.5-15.0 wt % of particles based on the total weight of the emulsion.

Aspect 45: The emulsion of any one of aspects 40-44, wherein the emulsion is, or is a component of, a mayonnaise, a salad dressing, a marinade, an aioli, a sandwich spread, a vegetable spread, a vegetable shortening, a vinaigrette, a condiment, a topping, a cheese, a yogurt, an ice cream, a butter, a margarine, a cream, a milk, a gravy, a fruit butter, a nut butter, a coffee beverage, a chocolate beverage, an imitation flavored beverage, a syrup, a soup or a sauce.

Aspect 46: The emulsion or emulsifiable composition of any one of aspects 40-45, wherein the emulsion or emulsifiable composition is an emulsifiable composition, and wherein the emulsifiable composition is, or is a component of, a mayonnaise mix, a salad dressing mix, a marinade mix, a sandwich spread mix, vegetable spread mix, a vinaigrette mix, a milk or creamer mix, a gravy mix, or a coffee beverage mix, a chocolate beverage mix, an imitation flavored beverage mix, a syrup mix, or a sauce mix.

Aspect 47: The emulsifiable composition of any one of aspects 40-46, wherein the emulsifiable composition is in a powder form, a granular form, a paste, or a concentrate.

Aspect 48: The emulsion or emulsifiable composition of any one of aspects 40-47, wherein the emulsion or emulsifiable composition is egg-free or is egg-free and free of egg-substitutes and egg-replacers.

Aspect 49: The emulsion of any one of aspects 40-48, wherein the emulsion is, or is a component of, a fruit-butter, -sauce, -jelly, -jam, -chutney, -custard, -marinade, or -soup.

Aspect 50: The emulsion of any one of aspects 40-49, wherein the emulsion is, or is a component of, a cleaning agent, dishwasher fluid, dishwasher paste, laundry detergent, laundry paste, or a dry-cleaning formulation.

Aspect 51: The emulsion of any one of aspects 40-50, wherein the emulsion is, or is a component of, a pharmaceutically-acceptable emulsion comprising at least one active pharmaceutical ingredient.

Aspect 52: The emulsion of any one of aspects 40-51, wherein the pharmaceutically-acceptable emulsion is, or is a component of, benzoyl peroxide topical emulsion.

Aspect 53: The emulsion of any one of aspects 40-52, wherein the at least one active pharmaceutical ingredient is benzoyl peroxide, alpha hydroxyl acid, salicylic acid or glycolic acid or a combination thereof.

Aspect 54: The emulsion or emulsifiable composition of any one of aspects 40-53, wherein the emulsion or emulsifiable composition is, or is a component of, an emulsifiable composition, and wherein the emulsifiable composition is a pharmaceutically-acceptable emulsifiable composition.

Aspect 55: The pharmaceutically-acceptable emulsifiable composition of any one of aspects 40-54, further comprising at least one active pharmaceutical ingredient.

Aspect 56: The pharmaceutically-acceptable emulsifiable composition of any one of aspects 40-55, wherein the composition is in a powder form, a granular form, a paste, or a concentrate.

Aspect 57: The emulsion of any one of aspects 40-56, wherein the emulsion is, or is a component of, a paint, coating, sealant, caulk, or ink formulation.

Aspect 58: The emulsion of any one of aspects 40-57, wherein the emulsion is a defoamer or biocide or colorant in a paint, coating, sealant, caulk, or ink formulation.

Aspect 59: The emulsion of any one of aspects 40-58, wherein the first fluid comprises water and the second fluid comprises an alkyd resin, polyester resin, epoxy resin, acrylic resin, polyurethane, or fluoropolymer, or wax.

Aspect 60: The emulsion of any one of aspects 40-59, wherein the emulsion is, or is a component of, a personal care or health and beauty product.

Aspect 61: The emulsion of any one of aspects 40-60, wherein the personal care or health and beauty product is a cosmetic product, or a skin-care product, or a hair care product, or pet care product.

Aspect 62: The emulsion of any one of aspects 40-61, wherein the cosmetic product, or skin-care product, or hair care product is a lotion, cream, serum, ointment, shampoo, conditioner, hairspray, hair gel, deodorant, facial or body wash, facial or body scrub, exfoliant, emollient, moisturizer, liquid soap, foundation make up, bb cream, cc cream, eye cream, sunscreen, anti-acne serum or cream or lotion, cellular serum or cream or lotion, facial or body mask, blush, eyeshadow, mascara, or clay, kaolin or mud suspension, hand cream or lotion, face cream or lotion, body cream or lotion, lipstick, or lip balm.

Aspect 63: The emulsion of any one of aspects 40-62, wherein the emulsion is, or is a component of, a fertilizer, or a pesticide, insecticide, biocide, or herbicide.

Aspect 64: The emulsion of any one of aspects 40-63, wherein the emulsion is, or is a component of, a drilling fluid, or is created in situ when a drilling fluid is used in drilling; or a metalworking fluid or a component of a metalworking fluid, or is created in situ when a metalworking fluid is used in metalworking.

Aspect 65: The emulsion of any one of aspects 40-64, wherein the emulsion is, or is a component of, a leather care product or shoe polish.

Aspect 66: A method for making the emulsion of aspect 40, the method comprising combining, optionally with stirring or otherwise mixing:

(a) a first liquid component;

(b) a second liquid component, at least partially immiscible in the first liquid component;

(c) particles;

wherein the particles:

comprise cellulose;

have at least one of:

(1) a $d_{75}$ of less than about 8 microns;

(2) a $d_{50}$ of from about 0.5 microns to about 5.0 microns;

have an aspect ratio of from about 1 to about 1.5; and have a non-spherical shape; and wherein at least a portion of the cellulose is type-II cellulose; and thereby forming emulsion.

Aspect 67: A food product comprising:

particles;

wherein the particles:

comprise cellulose have at least one of:

(1) a $d_{75}$ of less than about 8 microns;

(2) a $d_{50}$ of about 0.5 microns to about 5 microns;

have an aspect ratio of about 1 to about 1.5; and have a non-spherical shape; and wherein at least a portion of the cellulose is type-II cellulose.

Aspect 67: A leavened or leavenable food product comprising:

particles;

wherein the particles:

comprise cellulose;

have at least one of:

(1) a $d_{75}$ of less than about 8 microns;

(2) a $d_{50}$ of about 0.5 microns to about 5 microns;

have an aspect ratio of about 1 to about 1.5; and have a non-spherical shape; and wherein at least a portion of the cellulose is type-II cellulose.

Aspect 68: The food product of aspect 67, wherein the food product is a leavened or leavenable food product.

Aspect 69. The food product of aspect 67, wherein the particles are present at a level of at least 0.5 wt % of particles based on the total weight of the food product on a dry basis.

Aspect 70: The food product of aspect 67 or 68, wherein the particles are present at a level of from 0.5-15.0 wt % of particles based on the total weight of the food product on a dry basis.

Aspect 71: The food product of any one of aspects 67-70, wherein the food product is a leavened food product selected from a bagel, a muffin, a scone, a bread, a pizza base, a cracker, a pastry, a pie, a cake, a shortcake, a cupcake, a pancake, a waffle, a sponge pudding, a Yorkshire pudding, a doughnut, a bun, a brownie, a blondie, a biscuit, a cookie, a pasta, and a noodle.

Aspect 72: The food product of any one of aspects 67-70, wherein the food product is a leavenable food product selected from a bagel mix, a muffin mix, a scone mix, a bread mix, a pizza base mix, a cracker mix, a pastry mix, a pie mix, a cake mix, a shortcake mix, a cupcake mix, a pancake mix, a waffle mix, a sponge pudding mix, a Yorkshire pudding mix, a doughnut mix, a bun mix, a brownie mix, a blondie mix, a biscuit mix, a cookie mix, a pasta mix, a noodle mix, and a flour composition, or a dough thereof.

Aspect 73: The food product of any one of aspects 67-72, wherein the food product is egg-free or is egg-free and free of egg-substitutes and egg-replacers.

Aspect 74: The leavened or leavenable food product of any one of aspects 67-73, wherein the leavened or leavenable food product is gluten-free.

Aspect 75: The food product of any one of aspects 67-74, wherein the food product is egg-free and gluten-free.

Aspect 76: The food product of any one of aspects 67-75, wherein the food product is allergen-free.

Aspect 77: The food product of aspect 67, wherein the food product is a meat or meat analog composition.

Aspect 78: A meat or meat analog composition comprising:

particles;

wherein the particles:

comprise cellulose;

have at least one of:

(1) a $d_{75}$ of less than about 8 microns;

(2) a $d_{50}$ of about 0.5 microns to about 5 microns;

have an aspect ratio of about 1 to about 1.5; and have a non-spherical shape; and wherein at least a portion of the cellulose is type-II cellulose.

Aspect 79: The meat or meat analog composition of aspect 78, wherein the particles are present at a level of at least 0.5 wt % of particles based on the total weight of the meat or meat analog composition.

Aspect 80: The meat or meat analog composition of aspect 78 or 79, wherein the particles are present at a level of from 0.5-15.0 wt % of particles based on the total weight of the meat or meat analog composition.

Aspect 81: The meat or meat analog composition of any one of aspects 77-79, further comprising beef, chicken, turkey, pork, lamb, horse, buffalo, venison, veal, game, fowl, plant proteins, fermented proteins, shell-fish, fish, or combinations thereof, or imitations thereof.

Aspect 81: The meat or meat analog composition of any one of aspects 77-81, wherein the meat or meat analog composition is in the form of a sausage, a burger, a kebab, a gyro, a shwarma, a patty, a cake, a loaf, a nugget, a strip, a hot dog, a deli product, a jerky, a pet food, a pet treat, a processed meat, an emulsified meat, or combinations thereof, or imitations thereof, and wherein the meat or meat analog composition is made with beef, chicken, turkey, pork, lamb, horse, buffalo, venison, veal, game, fowl, plant proteins, fermented proteins, shell-fish, fish, or combinations thereof, or imitations thereof.

Aspect 82: A cellulose composition comprising particles and a resuspending agent:

wherein the particles, when resuspended in a liquid:

comprise cellulose;

have at least one of:

(1) a $d_{75}$ of less than about 8 microns;

(2) a $d_{50}$ of about 0.5 microns to about 5 microns;

have an aspect ratio of about 1 to about 1.5; and have a non-spherical shape; and wherein at least a portion of the cellulose is type-II cellulose; and wherein the resuspending agent is adsorbed or bonded to at least a portion of the surface of the particles.

Aspect 83: The cellulose composition of aspect 82, wherein the resuspending agent is one or more polyol compound, one or more polyol oligomer or one or more polyol polymer, or any combination thereof.

Aspect 84: The cellulose composition of aspect 82 or 83, wherein the resuspending agent comprises one or more oligosaccharide, one or more monosaccharide, sucrose, glycerol, citric acid, sorbitol, maltodextrin, a sugar alcohol, or any combination thereof.

Aspect 85: The cellulose composition of any one of aspects 82-84, wherein the resuspending agent comprises a gluco-oligosaccharide.

Aspect 86: The cellulose composition of any one of aspects 82-85, wherein the resuspending agent comprises precipitated gluco-oligosaccharide.

Aspect 87: The cellulose composition of any one of aspects 82-86, wherein the resuspending agent comprises glucose or sucrose.

Aspect 88: The cellulose composition of any one of aspects 82-87 wherein the resuspending agent comprises sorbitol.

Aspect 89: The cellulose composition of any one of aspects 82-88, wherein the composition is in a dry form comprising less than about 20 wt % water.

Aspect 90: The cellulose composition of any one of aspects 82-89, wherein the composition in a dry form is resuspendable in water while retaining the $d_{75}$ of less than about 8 microns and the $d_{50}$ of about 0.5 microns to about 5 microns.

Aspect 91: The cellulose composition of any one of aspects 82-90, wherein the composition is in the form of a suspension comprising water.

Aspect 92: The cellulose composition of any one of aspects 82-91, wherein the suspension has a solids content of at least about 5 wt %.

Aspect 93: The cellulose composition of any one of aspects 82-92, wherein the resuspending agent consists essentially of monosaccharides and oligosaccharides.

Aspect 94, The cellulose composition of any one of aspects 82-93, wherein the composition is in a dry form having a solids content of at least about 90 wt % solids.

Aspect 95: A subterranean treatment composition, or metalworking fluid, cutting fluid, stamping fluid, abrading fluid, tribological fluid, cooling fluid, or lubricating fluid comprising:
(a) a liquid; and
(b) particles suspended in the liquid, wherein the particles:
comprise cellulose;
have at least one of:
(1) a $d_{75}$ of less than about 8 microns;
(2) a $d_{50}$ of from about 0.5 microns to about 5.0 microns;
have an aspect ratio of from about 1 to about 1.5; and
have a non-spherical shape; and
wherein at least a portion of the cellulose is type-II cellulose.

Aspect 96: The composition of aspect 95, wherein the liquid comprises a weighting agent.

Aspect 97: The composition of aspect 96, wherein the weighting agent is selected from barite, hematite, calcium carbonate, ilmenite, and manganese tetroxide and a mixture thereof.

Aspect 98: The composition of any one of aspects 95-97, wherein the liquid has a density of at least about 720 g/L at a pressure of about 1 atm.

Aspect 99: The composition of any one of aspects 95-98, wherein the liquid has a density of greater than about 1000 g/L.

Aspect 100: The composition of any one of aspects 95-99, wherein the liquid is selected from water, one or more oil, and mixtures thereof.

Aspect 101: The composition of any one of aspects 95-100, wherein the liquid is water.

Aspect 102: The composition of any one of aspects 95-101, wherein the water further comprises a salt.

Aspect 103: The composition of any one of aspects 95-102, wherein the salt is selected from a sodium salt, a calcium salt, a zinc salt, a potassium salt, a magnesium salt, a cesium salt, an acetate salt, and a formate salt and a mixture thereof.

Aspect 104: The composition of any one of aspects 95-102, wherein the salt is selected from NaCl, $CaCl_2$, $CaBr_2$, $ZnCl_2$, $ZnBr_2$, KCl, $Na(OC(O)CH_3)$, $Na(OC(O)H)$, $K(OC(O)CH_3)$, $K(OC(O)H)$, and $Cs(OC(O)H)$ and a mixture thereof.

Aspect 105: The composition of any one of aspects 95-100, wherein the liquid is an oil.

Aspect 106: The composition of any one of aspects 95-100 and 105, wherein the oil is a hydrocarbon oil or a hydrosilicone oil.

Aspect 107: The composition of any one of aspects 95-100, 105, and 106, wherein the oil further comprises lime.

Aspect 108: The composition of any one of aspects 95-100, wherein the liquid is a mixture of water and an oil.

Aspect 109: The composition of aspect 108, wherein the water comprises a salt.

Aspect 110: The composition of any one of aspects 108 and 109, wherein water is present in the liquid in an amount of from about 5 wt % to about 25 wt %, and wherein the oil is present in the liquid in an amount of from about 75 wt % to about 95 wt %.

Aspect 111: The composition of any one of aspects 108-110, wherein water is present in the liquid in an amount of from about 10 wt % to about 20 wt %, wherein the oil is present in the liquid in an amount of about 80 wt % to about 90 wt %, and wherein the water comprises a salt.

Aspect 112: The composition of any one of aspects 95-111, wherein the liquid is present in an amount of from about 25 wt % to about 99 wt % based on the total weight of the composition.

Aspect 113: The composition of any one of aspects 95-112, wherein the particles are present at a level of at least about 0.5 wt % of particles, based on the total weight of the composition.

Aspect 114: The composition of any one of aspects 95-113, wherein the particles are present at a level of from about 0.5 wt % to about 35 wt % of particles, based on the total weight of the composition.

Aspect 115: The composition of any one of aspects 95-114, wherein the particles are present at a level sufficient to increase the viscosity of the composition by at least 10% compared to an otherwise identical composition without the particles.

Aspect 116: The composition of any one of aspects 95-115, wherein the composition is thermally stable at a temperature of at least about 300° F.

Aspect 117: The composition of any one of aspects 95-116, wherein the composition is thermally stable at a temperature of greater than 300° F.

Aspect 118: The composition of any one of aspects 95-117, wherein the composition is thermally stable at a temperature of greater than 330° F.

Aspect 119: The composition of any one of aspects 95-118, wherein the composition is thermally stable at a temperature of greater than 350° F.

Aspect 120: The composition of any one of aspects 95-119, wherein the composition has a viscosity, and wherein the viscosity in an environment having of a salinity of greater than about 0.5 g/L is approximately equal to the viscosity in an environment having a salinity of about 0.5 g/L or less.

Aspect 121: The composition of any one of aspects 95-120, wherein the composition has a pH of about 1.5 or less.

Aspect 122: The composition of any one of aspects 95-121, wherein the composition has a pH of from about 8.5 to about 11.

Aspect 123: The composition of any one of aspects 95-122, wherein the composition has a pH of from about 8.5 to about 10.

Aspect 124: The composition of any one of aspects 95-123, wherein the composition is prepared in situ when a drilling fluid is used in drilling.

Aspect 125: The composition of any one of aspects 95-124, further comprising a viscosifying agent.

Aspect 126: The composition of aspect 125, wherein the composition has a viscosity at least 10% greater than the sum of the viscosity of an otherwise identical composition with the particles and the viscosity of an otherwise identical composition with the viscosifying agent.

Aspect 127: The composition of aspects 125 or 126, wherein the viscosifying agent is an inorganic viscosifying agent.

Aspect 128: The composition of aspect 127, wherein the inorganic viscosifying agent is selected from bentonite, laponite, a hectorite, a mixed metal hydroxide, and a mixed metal oxide, and a mixture thereof.

Aspect 129: The composition of aspect 125 or 126, wherein the viscosifying agent is an organic viscosifying agent.

Aspect 130: The composition of aspect 129, wherein the organic viscosifying agent is selected from xantham gum, diutan, carboxymethyl cellulose, guar gum, carboxymethylstarch, welan gum, hydroxyethylcellulose, and a polysaccharide oligomer and a mixture thereof.

Aspect 131: The composition of any one of aspects 95-130, further comprising a thermal stabilizing agent.

Aspect 132: The composition of aspect 131, wherein the thermal stabilizing agent is selected from magnesium oxide, monoethanolamine, citric acid, diethanolamine, glyoxal, and a formate solution, and a mixture thereof.

Aspect 133: The composition of any one of aspects 95-132, further comprising fly ash, a silica compound, a fluid loss control additive, an emulsifying agent, latex, a dispersant, an accelerator, a retarder, a clay, a lubricant, lime, a salt, mica, sand, a fiber, a formation containing agent, fumed silica, bentonite, a microsphere, a carbonate, barite, hematite, an epoxy resin, a curing agent, a crosslinker, a biocide, a surfactant, an activator, a stabilizer, or a breaker, or a combination thereof.

Aspect 134: The composition of any one of aspects 95-133, wherein the composition is substantially free of an antibacterial agent.

Aspect 135: The composition of any one of aspects 95-134, further comprising a corrosion inhibitor, an extreme pressure additive, an anti-mist agent, an emulsifying agent, an alkanolamine, a biocide, a stabilizer, a dispersant, a defoamer, a colourant, a dye, an odourant, a chlorinated compound, a sulphurized compound, or a fragrance, or a combination thereof.

Aspect 136: The composition of any one of aspects 95-135, wherein the composition is a subterranean treatment composition.

Aspect 137: The composition of aspect 136, wherein the subterranean treatment composition is selected from a drilling fluid, a fracturing fluid, a well control fluid, a well kill fluid, a well cementing fluid, an acid fracturing fluid, an acid diverting fluid, a stimulation fluid, a sand control fluid, a completion fluid, a wellbore consolidation fluid, a remediation treatment fluid, a spacer fluid, a frac-packing fluid, a water conformance fluid, and a gravel packing fluid and a mixture thereof.

Aspect 138: The composition of any one of aspects 95-135, wherein the composition is a machining/processing composition.

Aspect 139: The composition of aspect 138, wherein the machining/processing composition is selected from a metalworking fluid, cutting fluid, stamping fluid, abrading fluid, tribological fluid, cooling fluid, and lubricating fluid, or a mixture thereof.

Aspect 140: The composition of any one of aspects 95-137, wherein the composition is a cutting fluid, or wherein the composition is a drilling fluid, or wherein the composition is a metal working fluid.

Aspect 141: The composition of any one of aspects 95-137, wherein the composition is a stamping fluid.

Aspect 142: The composition of any one of aspects 95-137, wherein the composition is an abrading fluid.

Aspect 143: The composition of aspect 94, wherein the composition is a tribological fluid.

Aspect 144: The composition of any one of aspects 95-137, wherein the composition is a cooling fluid.

Aspect 145: The composition of any one of aspects 95-137, wherein the composition is a lubricating fluid.

Aspect 146: A method for making the composition of any one of aspects 95-145, the method comprising combining:
(a) a liquid; and
(b) particles,
  wherein the particles:
    comprise cellulose;
    have at least one of:
      (1) a $d_{75}$ of less than about 8 microns;
      (2) a $d_{50}$ of from about 0.5 microns to about 5.0 microns;
    have an aspect ratio of from about 1 to about 1.5; and
    have a non-spherical shape; and
  wherein at least a portion of the cellulose is type-II cellulose,
thereby forming the composition.

Aspect 147: A method for treating a subterranean formation, the method comprising introducing the composition of any one of aspects 95-137 into the subterranean formation.

Aspect 148: The method of aspect 147, further comprising subsequently introducing more of the liquid into the subterranean formation.

Aspect 149: The method of aspect 147 or 148, wherein the composition is selected from a drilling fluid, a fracturing fluid, a well control fluid, a well kill fluid, a well cementing fluid, an acid fracturing fluid, an acid diverting fluid, a stimulation fluid, a sand control fluid, a completion fluid, a wellbore consolidation fluid, a remediation treatment fluid, a spacer fluid, a frac-packing fluid, a water conformance fluid, and a gravel packing fluid, or a combination thereof.

Aspect 150: A method of lubricating a substrate, the method comprising applying the composition of any one of aspects 95-135 to the substrate, wherein the substrate is selected from a natural rock, a metal, a plastic, and a masonry construction material.

Aspect 151: The method of aspect 150, wherein the substrate is a plastic.

Aspect 152: The method of aspect 150, wherein the substrate is a masonry construction material.

Aspect 153: The method of aspect 150 or 152, wherein the masonry construction material is selected from concrete, cement, asphalt, brick, and a mixture thereof.

Aspect 154: The method of aspect 150, wherein the substrate is a metal.

Aspect 155: The method of aspect 150 or 154, wherein the metal is formed as a prefabricated article.

Aspect 156: The method of aspect 155, wherein the prefabricated article is selected from a tool, a machine part, a pipe, a tube, a beam, a coin, a sheet, a bracket, a screw, a nail, a piston, and a rod.

Aspect 157: The method of any one of aspects 150-156, wherein the method further comprises one or more of polishing the substrate, honing the substrate, cutting the substrate, stamping the substrate, drilling the substrate, grinding or abrading the substrate, milling the substrate, or use of a lathe on the substrate.

Aspect 158: A method of cooling a substrate, the method comprising applying the composition of any one of aspects 95-135 to the substrate, wherein the substrate is selected from a natural rock, a metal, a plastic, and a masonry construction material.

Aspect 159: The method of aspect 158, wherein the substrate is a plastic.

Aspect 160: The method of aspect 158, wherein the substrate is a masonry construction material.

Aspect 161: The method of aspect 158 or 160, wherein the masonry construction material is selected from concrete, cement, asphalt, brick, and a mixture thereof.

Aspect 162: The method of aspect 158, wherein the substrate is a metal.

Aspect 163: The method of aspect 158 or 162, wherein the metal is formed as a prefabricated article.

Aspect 164: The method of aspect 163, wherein the prefabricated article is selected from a tool, a machine part, a pipe, a tube, a beam, a coin, a sheet, a bracket, a screw, a nail, a piston, and a rod.

Aspect 165: The method of any one of aspects 158-164, wherein the method further comprises one or more of polishing the substrate, honing the substrate, cutting the substrate, stamping the substrate, drilling the substrate, grinding or abrading the substrate, milling the substrate, or use of a lathe on the substrate.

Aspect 166: A method for treating a subterranean formation, the method comprising introducing particles into the subterranean formation,
  wherein the particles:
    comprise cellulose;
    have at least one of:
      (1) a $d_{75}$ of less than about 8 microns;
      (2) a $d_{50}$ of from about 0.5 microns to about 5.0 microns;
    have an aspect ratio of from about 1 to about 1.5; and
    have a non-spherical shape; and
    wherein at least a portion of the cellulose is type-II cellulose.

Aspect 167: The method of aspect 166, further comprising introducing a liquid into the subterranean formation.

Aspect 168: The method of aspect 167, wherein the particles and the liquid are introduced simultaneously.

Aspect 169: The method of aspect 167, wherein the particles and the liquid are introduced sequentially.

Aspect 170: The method of any one of aspects 167-169, further comprising subsequently introducing more of the liquid into the subterranean formation.

Aspect 171: A personal care formulation comprising:
  particles;
    wherein the particles:
      comprise cellulose;
      have at least one of:
        (1) a $d_{75}$ of less than about 8 microns;
        (2) a $d_{50}$ of about 0.5 microns to about 5 microns;
      have an aspect ratio of about 1 to about 1.5; and
      have a non-spherical shape; and
      wherein at least a portion of the cellulose is type-II cellulose; and
    wherein the personal care formulation modifies the appearance or feel of a substrate.

Aspect 172: The personal care formulation of aspect 171, wherein the particles are present at a level of at least about 0.5 wt % of particles based on the total weight of personal care formulation.

Aspect 173: The personal care formulation of aspect 171 or 172, wherein the cellulose particles are present at a level of from about 0.5 to about 40.0 wt % of particles based on the total weight of personal care formulation.

Aspect 174: The personal care formulation of any one of aspects 171-173, further comprising one or more additional thickeners, and wherein the resulting viscosity is at least 10% greater than the sum of the viscosity of the otherwise identical composition with the cellulose composition and the viscosity of the otherwise identical composition with the one or more additional thickeners.

Aspect 175: The personal care formulation of any one of aspects 171-174, wherein the composition further comprises solid particles.

Aspect 176: The personal care formulation of any one of aspects 171-175, wherein the personal care formulation further comprises pigment particles, filler or extender particles, polymer particles, beads or a combination thereof.

Aspect 177: The personal care formulation of any one of aspects 171-176 wherein the personal care formulation further comprises one or more occlusive agent.

Aspect 178: The personal care formulation of aspect 177, wherein the one or more occlusive agent comprises one or more oil.

Aspect 179: The personal care formulation of aspect 177, wherein the one or more occlusive agent comprises squalane.

Aspect 180: The personal care formulation of any one of aspects 171-179, wherein the personal care formulation further comprises an emollient.

Aspect 181: The personal care formulation of aspect 180, wherein the emollient comprises squalane.

Aspect 182: The personal care formulation of any one of aspects 171-181, wherein the personal care formulation is a lotion, a cream, a serum, an ointment, a shampoo, a conditioner, a hairspray, a hair gel, a deodorant, a facial or body wash, a facial or body scrub, an exfoliant, an emollient, a moisturizer, a liquid soap, a bar soap, a foundation make-up, a BB cream, a CC cream, an eye cream, a sunscreen, an anti-acne serum or cream or lotion, a cellular serum or cream or lotion, a facial or body mask, a blush, an eyeshadow, a mascara, a lipstick, a lip balm, or a clay suspension, a kaolin suspension, or a mud suspension.

Aspect 183: The personal care formulation of any one of aspects 171-182, wherein the personal care formulation is a skin care formulation.

Aspect 184: The personal care formulation of any one of aspects 171-183, wherein the personal care formulation is a body scrub or a facial scrub formulation.

Aspect 185: The personal care formulation of any one of aspects 171-183, wherein the personal care formulation is a sunscreen formulation.

Aspect 186: The personal care formulation of any one of aspects 171-185 wherein the personal care formulation is a bb cream, a cc cream, or an eye cream formulation.

Aspect 187: The personal care formulation of any one of aspects 171-186, wherein the personal care formulation is an anti-acne serum or cellular serum formulation.

Aspect 188: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles have a $d_{75}$ of less than about 6 microns.

Aspect 189: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles have a $d_{75}$ of about 0.5 microns to about 6 micron.

Aspect 190: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles have a $d_{50}$ of about 0.6 microns to about 2.0 microns.

Aspect 191: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles have a $d_{10}$ of about 0.4 microns to about 0.8 microns.

Aspect 192: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles have a $d_{90}$ of about 1 microns to about 12 microns.

Aspect 193: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles have a $d_{90}$ of about 1 microns to about 8 microns.

Aspect 194: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles further comprise lignin.

Aspect 195: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles comprise:

at least about 70 wt % cellulose, and at least about 5 wt % lignin.

Aspect 196: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles further comprise less than 1% lignin.

Aspect 197: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles have a globular shape.

Aspect 198: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein at least a portion of the cellulose is type-I cellulose.

Aspect 199: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the ratio of type-II to type-I cellulose is at least about 0.2.

Aspect 200: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the cellulose has a degree of polymerization, $DP_w$, of about 16 to about 120.

Aspect 201: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the cellulose has a degree of polymerization, $DP_w$, of about 35 to about 60.

Aspect 202: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the particles have a zeta potential of about −2 to about −50 mV.

Aspect 203: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, further comprising a resuspending agent.

Aspect 204: The thickened composition, or the suspension, or the emulsion or the emulsifiable composition, or the leavened or leavenable food product, or the meat, meat analog or imitation meat product, or the resuspendable cellulose composition, or the personal care product, or the subterranean treatment composition, or metalworking fluid, cutting fluid, stamping fluid, abrading fluid, tribological fluid, cooling fluid, or lubricating fluid of any one of the preceding aspects, wherein the resuspending agent comprises an oligosaccharide, a monosaccharide, sucrose, glycerol, citric acid, sorbitol, maltodextrin, a polyol, a sugar alcohol, or any combination thereof.

Aspect 205: A food-grade egg replacement comprising the composition of any one of the preceding aspects.

Aspect 206: A method for preparing particles comprising cellulose, comprising:
   (a) contacting a cellulosic substrate with a sub-critical, near-critical or supercritical fluid for a duration sufficient to form a mixture of liquid and solids, said mixture comprising gluco-oligosacharides (GOS) and particles comprising cellulose;
   (b) optionally, separating lignin from the mixture comprising GOS and particles comprising cellulose;
   (c) optionally, removing at least a portion of the liquid from the mixture comprising GOS and particles comprising cellulose to form a higher solids mixture comprising GOS and particles comprising cellulose; and
   (d) contacting the mixture comprising GOS and particles comprising cellulose with an organic solvent to form solid GOS and particles comprising cellulose.

Aspect 207: The method of aspect 206, further comprising isolating the solid GOS and particles comprising cellulose as solids from the liquid.

Aspect 208: The method of aspect 207, further comprising contacting the solid GOS and particles comprising cellulose with water to dissolve the GOS.

Aspect 209: The method of aspect 208, further comprising separating the solid particles comprising cellulose from the liquid, and collecting the particles comprising cellulose;
   wherein the particles:
      comprise cellulose;
      have at least one of:
         (1) a $d_{75}$ of less than about 8 microns;
         (2) a $d_{50}$ of about 0.5 microns to about 5 microns;
      have an aspect ratio of about 1 to about 1.5; and
      have a non-spherical shape; and
      wherein at least a portion of the cellulose is type-II cellulose.

Aspect 210: The method of any one of aspects 206-209, wherein the organic solvent is an alcohol.

Aspect 211: The method of any one of aspect 206-210, wherein the organic solvent is ethanol.

Aspect 212: A method for increasing the solids content of an aqueous suspension of particles comprising cellulose, the method comprising:
   (a) freezing the aqueous suspension to form a frozen suspension;
   (b) thawing the frozen suspension to form a gradation of solids content in the suspension such that an upper portion of the suspension has a lower solids content, and a lower portion of the suspension has a higher solids content;
   (c) isolating at least a portion of the lower portion; and
   (d) optionally, repeating steps (a), (b) and (c) one or more times on the lower portion;
   wherein the particles:
      comprise cellulose;
      have at least one of:
         (1) a $d_{75}$ of less than about 8 microns;
         (2) a $d_{50}$ of about 0.5 microns to about 5 microns;
      have an aspect ratio of about 1 to about 1.5; and
      have a non-spherical shape; and
   wherein at least a portion of the cellulose is type-II cellulose.

Aspect 213: A method for preparing a solid sample of water-soluble glucooligosaccharides (GOS) comprising:
   (a) contacting a cellulosic substrate with a sub-critical, near-critical or supercritical fluid for a duration sufficient to form a mixture of liquid and solids, said liquid comprising GOS;
   (b) collecting at least a portion of the liquid;
   (c) optionally, removing at least a portion of the liquid from the liquid comprising GOS to form a higher solids liquid comprising GOS;
   (d) contacting the higher solids liquid comprising GOS with an organic solvent to form solid GOS;
   (e) separating the solid GOS from the liquid and collecting the solid GOS.

Aspect 214: The method of aspect 213, wherein the organic solvent is an alcohol.

Aspect 215: The method of aspects 213 or 214, wherein the organic solvent is ethanol.

Aspect 216: The method of any one of aspects 213-215, further comprising drying the solids at a temperature greater than 50° C. or drying the solids under an inert atmosphere or both.

Aspect 217: The method of aspect 206, or aspect 212, or aspect 213, wherein the particles are as defined in any of the preceding aspects.

Aspect 218: A combination of any two or more of the preceding aspects.

Aspect 219: A foam comprising:

particles;

wherein the particles:

comprise cellulose;

have at least one of:

(1) a $d_{75}$ of less than about 8 microns;

(2) a $d_{50}$ of about 0.5 microns to about 5 microns;

have an aspect ratio of about 1 to about 1.5; and have a non-spherical shape; and wherein at least a portion of the cellulose is type-II cellulose; and wherein the foam is incorporated into a composition to provide structure to such composition.

Aspect 220: The foam of aspect 219, wherein the particles are present at a level of at least about 0.5 wt % of particles based on the total weight of the structure composition.

Aspect 221: The foam of aspects 219 or 220, wherein the particles are present at a level of from about 0.5 to about 40.0 wt % of particles based on the total weight of structure composition.

Aspect 222: The foam of any one of aspects 219-221, further comprising one or more additional thickeners, and wherein the resulting viscosity is at least 10% greater than the sum of the viscosity of the otherwise identical composition with the structure composition and the viscosity of the otherwise identical composition with the one or more additional thickeners.

Aspect 223: The foam of any one of aspects 219-222, wherein the composition further comprises solid particles.

Aspect 224: The foam of any one of aspects 219-223, wherein the structure composition further comprises personal care ingredients such as conditioners, moisturizers, emollients, occlusive agents, soaps, detergents, exfoliants, pigment particles, filler or extender particles, polymer particles, beads or a combination thereof.

Aspect 225: The foam of any one of aspects 219-224, wherein the structured composition is a cream, an ointment, a shampoo, a conditioner, a mousse hair treatment, a facial or body wash, an exfoliant, an emollient, a moisturizer, a liquid soap, a foundation make-up, a BB cream, a CC cream, an eye cream, a sunscreen, an anti-acne serum cream, a cellular cream, a facial or body mask, a blush, an eyeshadow, a lipstick, a lip balm.

Aspect 226: The foam of any one of aspects 219-223, wherein the structured composition is a food product that is a leavened food product selected from a bagel, a muffin, a scone, a bread, a pizza base, a cracker, a pastry, a pie, a cake, a shortcake, a cupcake, a pancake, a waffle, a sponge pudding, a Yorkshire pudding, a doughnut, a bun, a brownie, a blondie, a biscuit, a cookie, a pasta, and a noodle.

Aspect 227: The foam of any one of aspects 219-223, wherein the structured composition is a food product that is a leavenable food product selected from a bagel mix, a muffin mix, a scone mix, a bread mix, a pizza base mix, a cracker mix, a pastry mix, a pie mix, a cake mix, a shortcake mix, a cupcake mix, a pancake mix, a waffle mix, a sponge pudding mix, a Yorkshire pudding mix, a doughnut mix, a bun mix, a brownie mix, a blondie mix, a biscuit mix, a cookie mix, a pasta mix, a noodle mix, and a flour composition, or a dough thereof.

Aspect 228: The foam of any one of aspects 219-223 or 226-227, wherein the structured composition is a food product that is egg-free or is egg-free and free of egg-substitutes and egg-replacers.

Aspect 229: The foam of any one of aspects 219-223 or 226-228, wherein the structured composition is a food product that is gluten-free.

Aspect 230: The foam of any one of aspects 219-223 or 226-229, wherein the structured composition is a food product that is egg-free and gluten-free.

Aspect 231: The foam of any one of aspects 219-223 or 226-230, wherein the structured composition is a food product that is allergen-free.

Aspect 232: The foam of any one of aspects 219-223 or 226-231, wherein the structured composition is a marshmallow, ice cream, sherbert, frozen yogurt, whipped cream, meringue, mousse, whipped gelatin, whipped pudding, whipped yogurt.

Aspect 233: The foam of any one of aspects 219-223 or 226-232, wherein the structured composition is an ice cream or sherbert or frozen yogurt that melts slower than ice cream, or sherbert or frozen yogurt that is not made with particles comprising small size cellulose.

Aspect 234: A food product comprising particles, wherein the particles:

comprise cellulose;

have at least one of:

(1) a $d_{75}$ of less than about 8 microns;

(2) a $d_{50}$ of about 0.4 microns to about 5 microns;

have an aspect ratio of about 1 to about 1.5; and have a non-spherical shape; and wherein at least a portion of the cellulose is type-II cellulose, and wherein the food product is or comprises an emulsion selected from a mayonnaise, an aioli, a salad dressing, a marinade, a sandwich spread, a vegetable spread, a vegetable shortening, a vinaigrette, a condiment, a topping, a cheese, a yogurt, an ice cream, a pudding, a custard, a filling, a puree, a butter, a margarine, a cream, a milk, a soup, a gravy, a fruit butter, a nut butter, a coffee beverage, a chocolate beverage, an imitation flavored beverage, a syrup, a soup, and a sauce.

Aspect 235: A method of lubricating and/or cooling a substrate, the method comprising applying a subterranean treatment composition or a machining/processing composition to the substrate, the composition comprising:

(a) a fluid; and (b) particles suspended in the fluid, wherein the particles:

comprise cellulose;

have at least one of:

(1) a $d_{75}$ of less than about 8 microns;

(2) a $d_{50}$ of from about 0.4 microns to about 5.0 microns;

have an aspect ratio of from about 1 to about 1.5; and have a non-spherical shape; and wherein at least a portion of the cellulose is type-II cellulose, and wherein the substrate is selected from a natural rock, a metal, a plastic, and a masonry construction material.

Aspect 236: The method of aspect 235, wherein the method further comprises one or more of polishing the substrate, honing the substrate, cutting the substrate, stamping the substrate, drilling the substrate, grinding or abrading the substrate, milling the substrate, or using of a lathe on the substrate.

Aspect 237: The emulsion of any one of aspects 40-44, wherein the emulsion is, or is a component of, a barb-b-que sauce or a tomato sauce.

Aspect 238: The food product of any one of aspects 67-70, wherein the food product is bread.

Aspect 239: The food product of any one of aspects 67-70, wherein the food product is gluten-free bread.

Aspect 240: The food product of any one of aspects 67-70, wherein the food product is bread that is egg-free or egg-free and free of egg-substitutes and egg-replacers.

Aspect 241: The food product of any one of aspects 67-70, wherein the food product is gluten-free and egg-free bread.

Aspect 242: The food product of any one of aspects 67-70, wherein the food product is a brownie.

Aspect 243: The food product of any one of aspects 67-70, wherein the food product is a gluten-free brownie.

Aspect 244: The food product of any one of aspects 67-70, wherein the food product is a brownie that is egg-free or egg-free and free of egg-substitutes and egg-replacers.

Aspect 245: The food product of any one of aspects 67-70, wherein the food product is a gluten-free and egg-free brownie.

Aspect 246: The food product of any one of aspects 67-70, wherein the food product is a muffin.

Aspect 247: The food product of any one of aspects 67-70, wherein the food product is gluten-free muffin.

Aspect 248: The food product of any one of aspects 67-70, wherein the food product is a muffin that is egg-free or egg-free and free of egg-substitutes and egg-replacers.

Aspect 249: The food product of any one of aspects 67-70, wherein the food product is gluten-free and egg-free muffin.

Aspect 250: The food product of any one of aspects 67-70, wherein the food product is a pasta or noodle.

Aspect 251: The food product of any one of aspects 67-70, wherein the food product is gluten-free pasta or noodle.

Aspect 252: The food product of any one of aspects 67-70, wherein the food product is pasta or noodle that is egg-free or egg-free and free of egg-substitutes and egg-replacers.

Aspect 253: The food product of any one of aspects 67-70, wherein the food product is gluten-free and egg-free pasta or noodle.

Aspect 254: The meat or meat analog composition of any one of aspects 77-81, wherein the meat or meat analog composition is a sausage.

Aspect 255: The meat or meat analog composition of any one of aspects 77-81, wherein the meat or meat analog composition is a chicken sausage.

Aspect 256: The food product of any one of aspects of 1-4, 14-22, 39-44, 66-67, 219-223, wherein the food product is ice cream, gelato, sherbert, frozen yogurt, frozen milk or frozen custard.

Aspect 256: The food product of any one of aspects of 1-4, 14-22, 39-44, 66-67, 219-223, wherein the food product is ice cream.

Various aspects of the compositions, methods, and products disclosed herein are set forth in the claims, and any combination of these claims (or portions thereof) may be made to define an embodiment.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

M. Examples

The following examples are put forth so as to provide those of ordinary skill in the art with a complete disclosure and description of how the compositions and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

Example 1: Preparation of the Cellulose Particles

Figure 5:
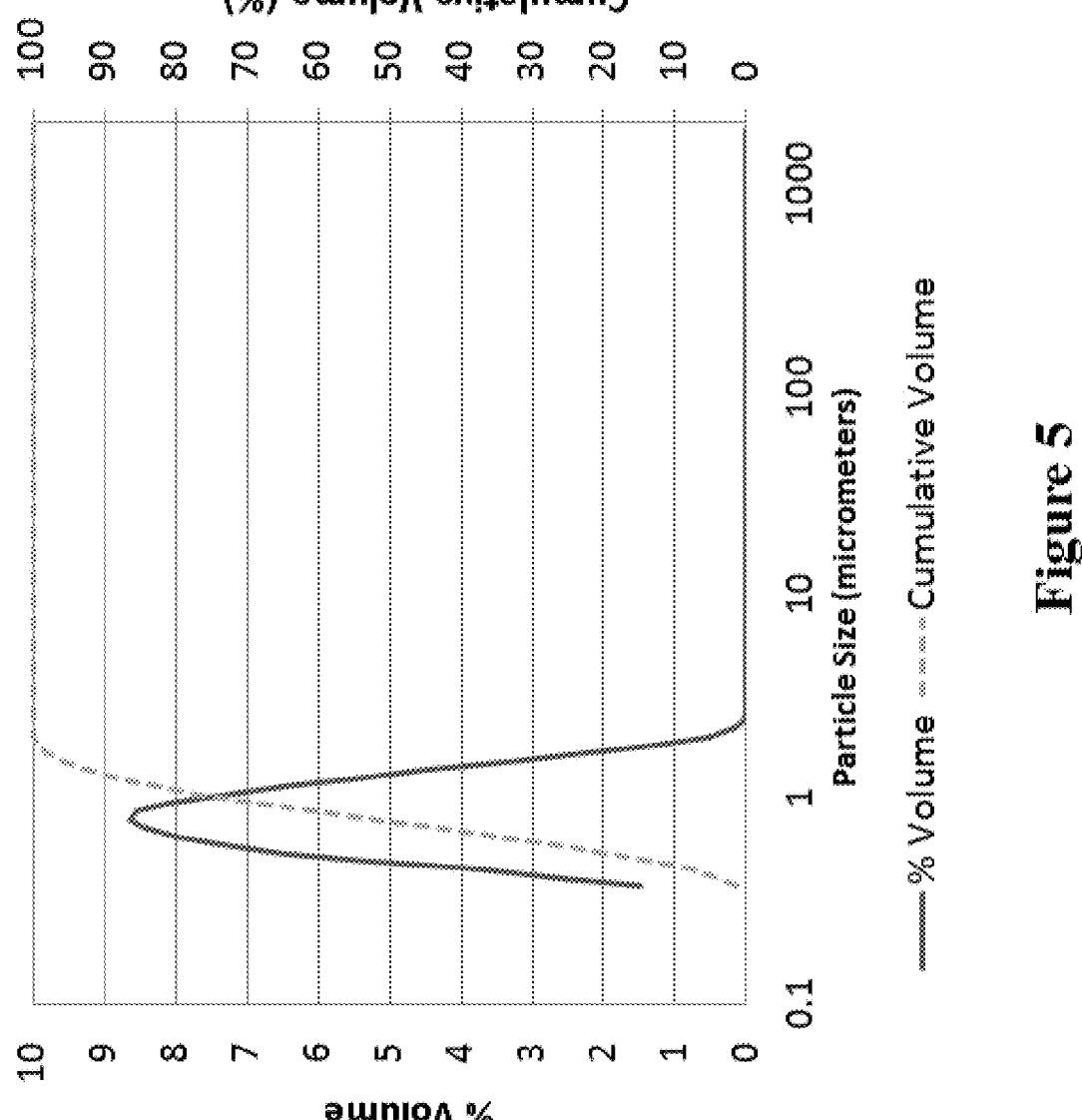
FIG. 5 shows a particle size distribution of a sample of the particles comprising cellulose described herein.
Figure 6:
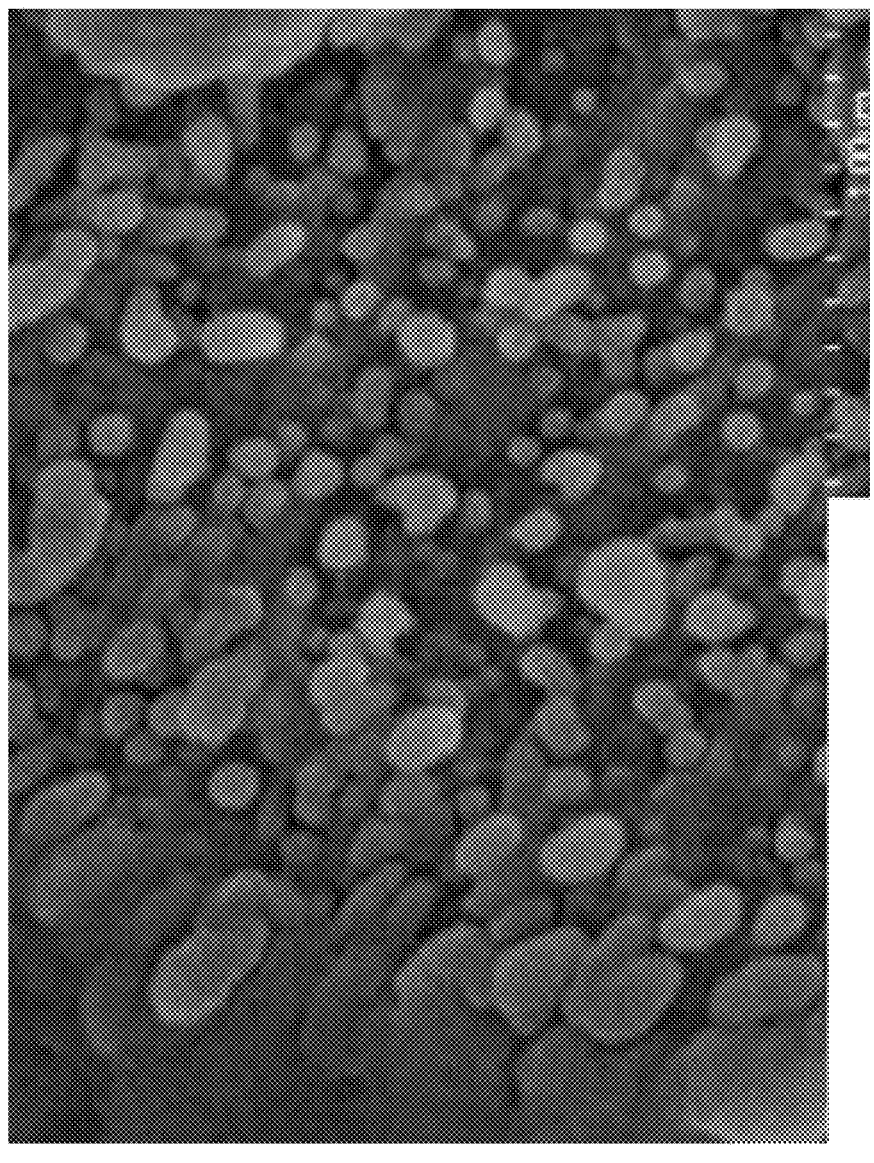
FIG. 6 shows an environmental scanning electron microscopy image of a sample of the particles comprising cellulose described herein, acquired at a temperature of −90° C.

In this example, the cellulose particles were formed from biomass using a two-step process. The first step produced a digested steam exploded (DSE) biomass. An aqueous slurry of size-reduced biomass was subjected to digestion in a horizontal screw digester at a temperature of about 180-205° C. for a period of about 20-30 minutes under a pressure sufficient to keep all of the fluid in liquid form (generally less than about 20 bar). The product from digestion was run through a steam mixing screw and horizontal screw digester, this time at a temperature of about 190-240° C. and at a pressure of less than about 35 bar for about 5-30 minutes. The biomass was discharged through a blow line, causing the pressure to rapidly drop and the biomass to explode into smaller particles (steam explosion). The DSE material was used as the feed to a supercritical hydrolysis reactor for the second step. In that reactor, an aqueous slurry of DSE biomass was subjected to a temperature of about 350-420° C. for a period of less than about 10 sec under a pressure sufficient to keep the fluid in liquid or supercritical form (generally less than about 250 bar). The resulting mixture from hydrolysis was cooled via a series of cooling steps to a temperature of about 60-100° C. and then filtered to separate the liquid (predominantly gluco-oligosaccharides, GOS) from the solids (predominantly lignin and cellulosic polysaccharide solids). The lignin and cellulosic polysaccharide solids were separated and the particles comprising cellulose were recovered as a slurry or suspension, which was further dewatered to produce a stable suspension having a maximum solids content of about 16-25% and a median average particle size of about 1.0 μm ($d_{(50)}$ of about 1 μm as measured by the Beckman Coulter Particle Sizer). FIGS. 1 and 2 show an outline of the process to prepare the cellulose particles. The following particle size data was obtained for the cellulose particles obtained from four separate preparations (Table 1), and FIG. 5 shows the % volume of particles (and also the % cumulative volume of particles) plotted against particle size (in μm) for a representative sample (Sample A). FIG. 6 shows AFM micrograph images of the cellulose particles at 1 wt % dilution (left hand image) and 0.1 wt %) dilution (right hand image).

Table 1 shows the particle size distribution for cellulose particles obtained from lignocellulosic biomass.

TABLE 1

| | Particle Size Distribution (μm) | | | | | | |
|---|---|---|---|---|---|---|---|
| | $d_{(10)}$ | $d_{(25)}$ | $d_{(50)}$ | $d_{(75)}$ | $d_{(90)}$ | Mean | Median |
| Sample A Particle Size (μm) | 0.55 | 0.71 | 0.99 | 1.38 | 1.92 | 1.2 | 0.99 |
| Sample B Particle Size (μm) | 0.52 | 0.64 | 0.85 | 1.13 | 1.44 | 0.92 | 0.85 |
| Sample C Particle Size (μm) | 0.52 | 0.66 | 0.91 | 1.33 | 2.27 | 1.2 | 0.91 |
| Sample D Particle Size (μm) | 0.52 | 0.66 | 0.96 | 3.55 | 6.71 | 2.64 | 0.96 |

Removal of water, for example, by heating or rotary evaporation, resulted in agglomeration of the particles and a much higher average particle size. However, it was found that higher solids content could be achieved without agglomeration of the particles by subjecting the suspension to one or more freeze-thaw cycles. A first freeze of a freeze-thaw cycle had the effect of loosely associating the solids, such that the corresponding thaw resulted in a partially separated suspension, from which the excess water at the upper surface can be readily removed (e.g., by pipette, or by decanting). The resulting suspension had about 28% solids. Repeated freeze-thaw cycles allowed the solids level of the suspension to increase to as high as 40% solids.

Example 2: Preparation of Precipitated Gluco-Oligosaccharides (PGOS)

This example details the preparation of a sample of precipitated gluco-oligosaccharides (PGOS). The GOS fraction from Example 1, if desired, may be further purified or partially purified in a separate step or series of steps. The GOS solution was partially evaporated to concentrate the solution (to 50-90% solids), and then washed/re-suspended with ethanol (or methanol, or isopropanol, or butanol, or acetone, or any combination thereof), which precipitated, as a white solid, a mixture of precipitated GOS oligomers (PGOS). The PGOS solids may have a small residual color, which can be substantially removed, for example, by re-dissolving in water or other suitable solvent and passing the solution through a chromatography column (or alternatively, by bleaching with hydrogen peroxide, or by extraction with acetone). The dark brown liquid portion (containing, e.g., monosaccharides, soluble lignin, and other impurities) can be removed and purified separately if desired, for example by passing the liquid through a chromatography column.

Once isolated wet, the white PGOS solid darkened over time while drying in air. It was found that the following procedures, either alone or in combination, help to avoid the darkening of the white PGOS solids: (1) drying the solids immediately at elevated temperatures (e.g., between 50-105° C.), and/or (2) drying the material under an inert atmosphere such as nitrogen. In either case, spreading the solids to provide a larger surface area is also beneficial. Once dry, the solids are stable to discoloration at room temperature, but, once dry, higher temperatures should be avoided, since the dry solids darken at higher temperatures (e.g., above 70° C.). Further purification may be achieved by passing a solution of the PGOS solids through a chromatography column.

If discoloration occurs, the solids can be re-suspended in water or an aqueous solvent (e.g., at about 50% solids) and then re-precipitated with ethanol (and/or methanol-acetone), which, upon filtering, regenerates the white solid PGOS. Alternatively, the addition of hydrogen peroxide in an ethanol slurry of the white solid PGOS also has the effect of removing the color from the solids.

Figure 7:
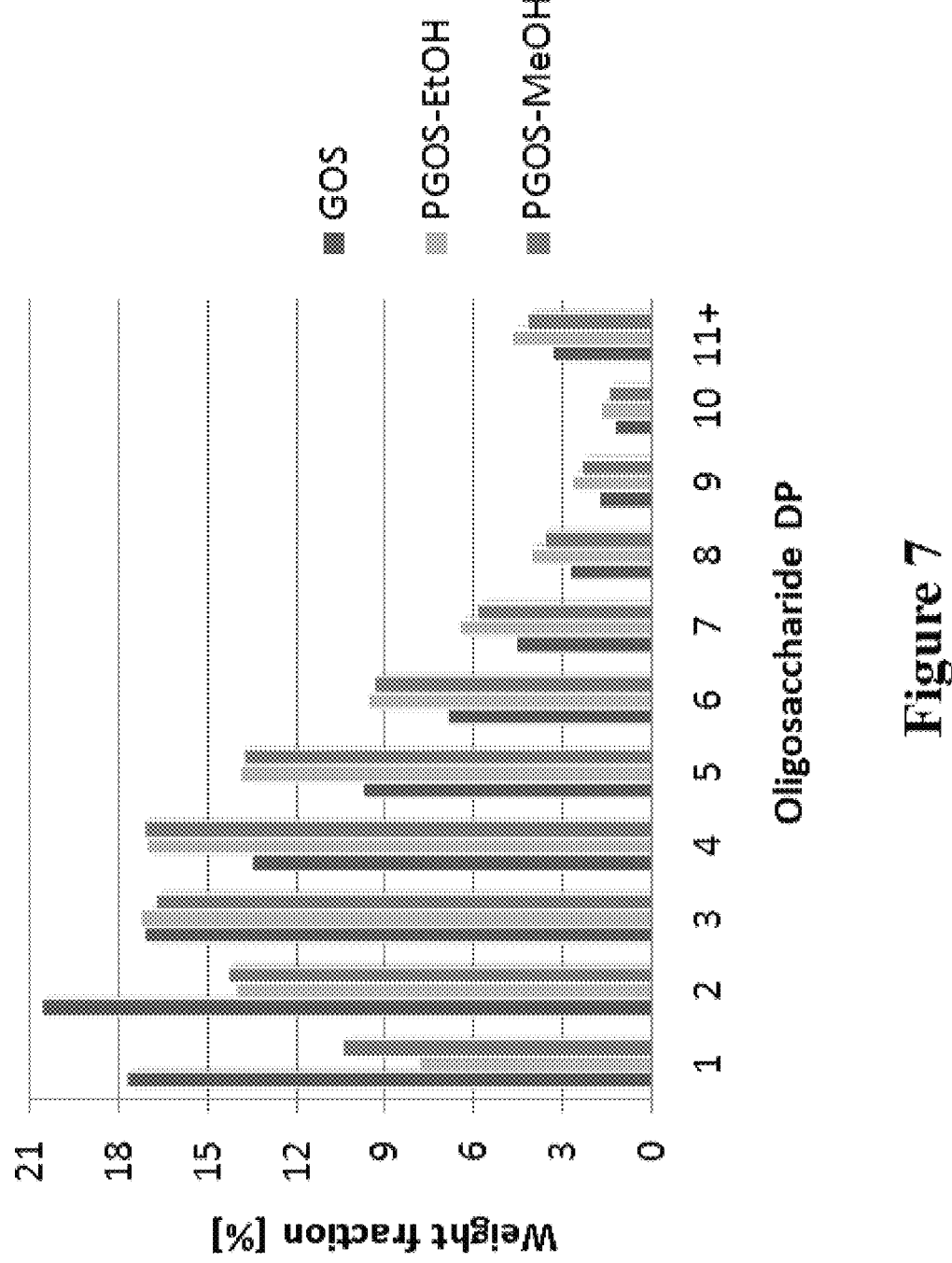
FIG. 7 shows a comparison of the molecular mass distribution for i) the water-soluble gluco-oligosaccharides (GOS) produced in a representative hydrolysis reaction and the precipitated GOS (PGOS) derived therefrom following precipitation with ii) ethanol; and iii) methanol (see Example 2).

The relative content of the various oligosaccharides in the GOS can be determined by known methods using Gel Permeation Chromatography (GPC). A typical distribution of GOS oligomers is shown in FIG. 7 and compared to that obtained for the PGOS formed by precipitation of GOS using ethanol.

Example 3: Consolidated Preparation of the Cellulose Particles

This example outlines an alternative method to process and isolate the cellulose particles (see FIG. 4). The cellulose particles were formed from biomass using a two-step hydrolysis process. The first step produced a digested steam exploded (DSE) biomass. An aqueous slurry of size-reduced biomass was subjected to digestion in a horizontal screw digester at a temperature of about 180-205° C. for a period of about 20-30 minutes under a pressure sufficient to keep all of the fluid in liquid form (generally less than about 20 bar). The product from digestion was run through a steam mixing screw and horizontal screw digester, this time at a temperature of about 190-240° C. and at a pressure of less than about 35 bar for about 5-30 minutes. The biomass was discharged through a blow line, causing the pressure to rapidly drop and the biomass to explode into smaller particles (steam explosion). The DSE material was used as the feed to a supercritical hydrolysis reactor for the second step. In that reactor, an aqueous slurry of DSE biomass was subjected to a temperature of about 350-400° C. for a period of less than about 10 sec under a pressure sufficient to keep the fluid in liquid or supercritical form (e.g. 221-250 bar). The resulting mixture was cooled to a temperature of 60-100° C. via a series of cooling steps, and the lignin was separated from a composition comprising the gluco-oligosaccharides (GOS), cellulosic polysaccharides, and water. The lignin may be processed further if desired.

The composition comprising GOS, cellulosic polysaccharides, and water may also carry some small lignin particles and other impurities, and so the saccharides were further purified and isolated together in the following series of steps. The suspension was concentrated with mild heat (e.g., to 60-90% solids) and then washed/re-suspended with ethanol or aqueous ethanol, which precipitates, as a solid, the higher molecular weight GOS oligomers and a portion of the lower molecular weight GOS oligomers (collectively PGOS) along with the (already) solid cellulosic polysaccharides while dissolving all or a portion of the solid lignin particles and mono- and di-saccharides. Without wishing to be bound by theory, it is believed that the PGOS oligomers precipitate onto the surface of the solid cellulosic polysaccharides. The liquid portion (comprising a portion of the monosaccharides and disaccharides, dissolved lignin and other impurities) was filtered from the cellulosic solids, and a substantial portion of the ethanol was removed (e.g., distilled or evaporated off) in order to precipitate the lignin component, which was filtered from the remaining liquid component (mostly water) to isolate a clean lignin product on the filter. The monosaccharides may be purified by passing the liquid through a chromatography column.

The resulting cellulose composition with PGOS adsorbed to the surface of at least a portion of the cellulose contained therein can be dried (e.g., <5 wt % water). If desired, this dried composition can then be resuspended in a liquid, and the original particle size distribution substantially reproduced (see Example 5). This phenomenon of substantially reproducing the original particle size distribution is not observed if the cellulose composition is not dried in the presence of GOS or another resuspending agent (as described elsewhere herein); rather, the cellulose particles will agglomerate and a much larger particle size distribution will be formed.

If desired, the cellulosic solids, which are water insoluble, can be isolated from the surface-adsorbed water soluble PGOS components by a water wash and filtration, which allows the aqueous solution of PGOS to pass through the filter. The water and residual ethanol were removed (e.g., evaporation, distillation, etc.) from the PGOS solution, leaving a solid PGOS sample. The clean cellulose particles were isolated on the filter as a stable suspension having a $d_{(50)}$ of about 1 μm as measured by the Beckman Coulter Particle Sizer, and with a lower lignin content than the 16-20 wt %) suspension described in Example 1.

Compared to Example 1, this ethanol precipitation method avoids a difficult filtration step (e.g., filtration of the GOS stream from the cellulose/lignin mixture obtained from supercritical hydrolysis), incorporates an ethanol wash step that effectively separates the ethanol-insoluble oligo- and poly-saccharides from the residual ethanol-soluble lignin, low molecular weight saccharides (DP 1-2) and other impurities, and provides a clean lignin product and cleaner PGOS, as well as the purified cellulose particles which may be isolated with or without PGOS adhered to the surface (which combined PGOS/cellulose composition may be dried, if desired, to form a resuspendable cellulose composition).

Example 4: Alternative Route to the Cellulose Particles

In this example, the cellulose particles were formed from microcrystalline cellulose (MCC) using a one-step process. The MCC (obtained from Blackburn Distributions, Nelson, Lancashire, UK), having a broad particle size distribution and $d_{50}$ of about 35 μm (as measured by the Beckman Coulter Particle Size Analyzer), was mixed with water to form a slurry, which was subjected to a temperature of about 350-420° C. for a period of less than about 10 sec under a pressure sufficient to keep the fluid in liquid or supercritical form (generally less than about 250 bar). The resulting mixture was cooled to a temperature of less than about 100° C. via a cooling step, screened through a 74 μm (200 mesh) screen, and then centrifuged to separate the liquid (predominantly gluco-oligosaccharides, GOS) from the solids (cellulosic polysaccharide solids). The cellulose particles were isolated as a stable suspension (16-25% solids). Table 2 shows the particle size distributions obtained for several preparations of this type using MCC as the starting material.

TABLE 2

| | Particle Size Distribution (μm) | | | | | | |
|---|---|---|---|---|---|---|---|
| | $d_{(10)}$ | $d_{(25)}$ | $d_{(50)}$ | $d_{(75)}$ | $d_{(90)}$ | Mean | Median |
| Sample A Particle Size (μm) | 0.51 | 0.62 | 0.83 | 1.20 | 4.33 | 1.5 | 0.83 |

TABLE 2-continued

| | Particle Size Distribution (μm) | | | | | | |
|---|---|---|---|---|---|---|---|
| | $d_{(10)}$ | $d_{(25)}$ | $d_{(50)}$ | $d_{(75)}$ | $d_{(90)}$ | Mean | Median |
| Sample B Particle Size (μm) | 0.52 | 0.66 | 0.93 | 2.64 | 5.96 | 2.3 | 0.93 |
| Sample C Particle Size (μm) | 0.51 | 0.63 | 0.85 | 1.24 | 4.23 | 1.6 | 0.85 |
| Sample D Particle Size (μm) | 0.57 | 0.76 | 1.17 | 2.44 | 5.81 | 2.8 | 1.17 |

Alternatively, the resulting mixture can be dried without first separating the GOS solution, thereby providing a cellulose composition with GOS adsorbed to at least a portion of the surface of the cellulose. This cellulose (co-dried with GOS) is resuspendable in water, and the original particle size distribution substantially reproduced (see Example 5). The routes described in this example provide cellulose particles and compositions that are free of or substantially free of lignin, which may be desirable for certain applications.

Example 5: Resuspendability of the Cellulose Particles

As outlined above (Examples 1, 3 and 4), the cellulose particles are isolated in the form of a stable suspension, where the cellulose suspension, upon centrifugation, has a maximum solids content of about 16-25% and a $d_{50}$ particle size of about 0.8-1.0 μm. Removal of water (e.g., by heating or rotary evaporation) caused agglomeration of the particles, resulting in a much higher $d_{50}$ particle size, and results in dry flakes of the cellulose that do not form a stable suspension in water. Accordingly, drying the cellulose particles in the above-stated manners, which would be desirable from a shipping standpoint, is problematic from a technical standpoint, because the recipient cannot formulate the component into an aqueous formulation having the same properties of the pre-dried cellulose particles (e.g., particle size distribution). This example explores the phenomenon further and provides methods to circumvent the problem.

Unexpectedly, in repeat preparations of the cellulose particles by the method of Example 4, it was found that, if the mixture produced from the near critical or supercritical hydrolysis of MCC without filtration is screened to remove unreacted MCC particles (>74 μm), and then the mixture evaporated to dryness, the solids are substantially resuspendable to achieve substantially the same particle size distribution that is present prior to drying (Table 3). The other component present in this mixture, likely adsorbed to the surface of the cellulose particles, is the water-soluble gluco-oligosaccharides (GOS). Table 3 shows the particle size distribution for the cellulose particles obtained wet (i.e. before drying) from the process of Example 4 (supercritical hydrolysis of MCC), compared to those obtained then dried and then resuspended.

TABLE 3

| | Particle Size Distribution (μm) | | | | | | |
|---|---|---|---|---|---|---|---|
| | $d_{(10)}$ | $d_{(25)}$ | $d_{(50)}$ | $d_{(75)}$ | $d_{(90)}$ | Mean | Median |
| Particles Before Drying | 0.52 | 0.66 | 0.94 | 2.2 | 5.1 | 1.9 | 0.94 |

TABLE 3-continued

| | Particle Size Distribution (µm) | | | | | | |
|---|---|---|---|---|---|---|---|
| | $d_{(10)}$ | $d_{(25)}$ | $d_{(50)}$ | $d_{(75)}$ | $d_{(90)}$ | Mean | Median |
| Particles After Re-Suspension | 0.52 | 0.66 | 0.93 | 2.6 | 6.0 | 2.3 | 0.93 |

The data show substantially the same particle size distribution was re-generated when the cellulose suspension was dried down in the presence of the reaction mixture resulting from the hydrolysis of MCC and then re-suspended in water.

To confirm the observation, the addition of gluco-oligosaccharides (GOS) or the addition of PGOS (from Example 2) to a wet slurry of either the cellulose particles from Example 1 or the cellulose particles from Example 4 in each case produced a mixture that could be oven dried to a powder which could be resuspended in water by mild heating (at 45° C.) for 1 hour followed by stirring (low shear, 12,000 rpm) for 30 sec. A control experiment confirmed that without the addition of the GOS or PGOS, the cellulose particles agglomerated to form large particles that settled out of the water very quickly.

Similarly, a mixture of the cellulose particles and GOS, as obtained from the hydrolysis reaction in Example 4, was re-suspended with water, then filtered through a filter press and washed through with water so that the GOS solution was removed, and the cellulose particles remained on the filter. The filter cake was re-suspended with water and the GOS solution was added back while still wet and then heated to dryness. The powder mixture of the cellulose particles and GOS was readily resuspended in water using the same mild heat and stirring as described above. Without the added back GOS, the cellulose particles from the filter, after heating to dryness, were not resuspendable.

The water-soluble additives shown in Table 4 were separately tested to see if the additive prevented agglomeration of the cellulose particles and enabled the resuspension of the solids after substantially drying the composition. The cellulose particles employed in this example were the solids isolated after supercritical hydrolysis of MCC, followed by filtration to remove GOS, forming a mixture in water to remove any residual GOS, and then addition of water to provide a 50.0 g sample of a 7% solids mixture of the cellulose particles. The cellulose mixture was first sieved through a 74 µm (200 mesh) screen before adding the soluble additive. The additive was then added, and the mixture was oven dried overnight at 55° C. Water was added back (without any attempt at size reduction prior to rehydration), heated for 1 hour at 45° C., and blended for 30 sec at medium speed (12,000 rpm). The new mixture was passed through a 74 µm screen, and the grit fraction was determined gravimetrically. Since the material had originally passed through a 74 µm screen prior to drying, any material captured on the 74 µm screen on the second pass after forming a mixture in water would result from non-resuspendable agglomerated particles (greater than 74 µm). The amount of non-resuspendable material is recorded in Table 4 as a percentage of the amount of the solids in the original 7% sample. Accordingly, a low percentage of starting material caught on the screen corresponds to a successful resuspension of the cellulose composition.

Table 4 shows the resuspendability of the cellulose particles according to this method.

TABLE 4

| Additive | Weight of Screened Material (g) | % of Solid Non-Resuspended |
|---|---|---|
| None | 2.10 | 60 |
| Sodium Chloride (1:1) | 2.01 | 57 |
| PGOS (1:1) | 0.20 | 6 |
| PGOS (1:2.3) | 0.84 | 24 |
| Sorbitol (1:2.3) | 0.014 | 0.4 |
| Maltodextrin (1:1) | 0.42 | 12 |
| Sucrose (1:2.3) | 0.091 | 2.6 |
| Whey Protein (1:1) | (Not filtered) | (>60) |

Various polyols (e.g., sugars and/or sugar alcohols) are able to aid in the resuspension of the cellulose particles if present when the cellulose is dried completely. When the same sucrose blend was freeze dried instead of oven dried, there was no need to heat or mix in order to resuspend the cellulose particles, with practically no grit on the screen after filtering. Similarly, in a separate experiment from that in Table 4, freeze drying with glycerol (in an amount of 50% on total solids) produces a paste that also enables the re-suspension in water to regenerate the cellulose particles in aqueous suspension. However, addition of any of these additives after the particles are dried is ineffective for aiding resuspension.

A further experiment tested to see if monomeric glucose could also act as a resuspending agent after substantially drying the cellulose particles and to see whether substantially the same particle size distribution could be re-generated. The cellulose particles employed in this example were the solids isolated after supercritical hydrolysis of MCC, followed by filtration to remove GOS, forming a mixture in water to screen the solids of any residual MCC (by passing through a 74 µm screen) and washing the solids of any residual GOS, and then addition of water to provide a 50.0 g sample of a 7% solids suspension of the cellulose particles. The particle size distribution (Beckman Coulter Particle Sizer) was recorded for this 7% cellulose composition suspension before adding the glucose. The glucose was added (1:1 ratio glucose to cellulose particles, based on the combined weight of the particles and glucose on a dry basis) with stirring, and the mixture was then oven dried overnight at 55° C. Water was added back (without any attempt at size reduction prior to rehydration), heated for 1 hour at 45° C., and blended for 30 sec at medium speed (12,000 rpm). The particle size distribution for the re-suspended cellulose composition (Beckman Coulter Particle Sizer) was recorded again to see whether substantially the same particle size distribution could be re-generated. Table 5, below, shows the particle size parameters for the cellulose particles before glucose addition (and before being substantially dried), and after glucose addition followed by drying and then followed by re-suspension in water.

TABLE 5

| | Particle Size Distribution (µm) | | | | | | |
|---|---|---|---|---|---|---|---|
| Particles | $d_{(10)}$ | $d_{(25)}$ | $d_{(50)}$ | $d_{(75)}$ | $d_{(90)}$ | Mean | Median |
| Particles Before Drying | 0.52 | 0.66 | 0.97 | 3.6 | 6.7 | 2.6 | 1.0 |
| Particles After Re-Suspension | 0.53 | 0.68 | 1.01 | 3.6 | 7.2 | 2.8 | 1.0 |

The data show substantially the same particle size distribution was re-generated when the cellulose suspension was dried down in the presence of glucose and then re-suspended in water.

The model system (above) isolated the particles comprising cellulose on a filter while still wet (solids content around 15-20 wt %) and then added glucose prior to drying the sample. Precipitation of PGOS as a solid in the presence of solid particles comprising cellulose, and then filtering, also is possible. In particular, a lignocellulosic biomass was subjected to supercritical hydrolysis yielding the particles comprising cellulose, along with GOS, monosaccharides (and disaccharides), lignin components and other minor water-soluble impurities. The mixture was centrifuged to remove a substantial portion of the lignin components, and then water was evaporated from the remaining mixture, until a 7% solids mixture resulted. A particle size distribution was determined for the resulting particles comprising cellulose. Further water was evaporated from the remaining mixture, until a 13% solids mixture resulted. Ethanol was then added, which caused precipitation of the majority of the water-soluble GOS, (as PGOS) as described in Example 2, likely onto the particles comprising cellulose. The resulting white solids in water/ethanol was stirred and then filtered to remove the liquid component, and washed through the filter with ethanol. This wash removed the water and soluble saccharide components (monosaccharides and some disaccharides), as well as any small particle lignin that survived the centrifuge separation, and the water soluble impurities from the hydrolysis reaction. The alcohol-wet solids were collected and dried overnight in a 55° C. oven until dry. The dried solids were then resuspended in water using mixing method A (the PGOS is water soluble), and sampled for a particle size distribution determination. The results are shown below in Table 6.

TABLE 6

| | Particle Size Distribution (μm) | | | | | | |
| | $d_{(10)}$ | $d_{(25)}$ | $d_{(50)}$ | $d_{(75)}$ | $d_{(90)}$ | Mean | Median |
|---|---|---|---|---|---|---|---|
| Particles Before Ethanol Addition | 0.58 | 0.78 | 1.18 | 2.0 | 3.5 | 1.6 | 1.2 |
| Particles After Re-Suspension | 0.59 | 0.83 | 1.39 | 3.2 | 9.8 | 4.2 | 1.4 |

The data show substantially the same particle size distribution was re-generated when PGOS was precipitated in the presence of the particles comprising cellulose, the solids filtered, and then dried down before being re-suspended in water.

Further experiments were performed to determine whether the precipitation step is essential. In particular, a lignocellulosic biomass was subjected to supercritical hydrolysis yielding the particles comprising cellulose, along with GOS, monosaccharides, lignin components and other minor water-soluble impurities. A particle size distribution was determined for the particles comprising cellulose. Without any centrifuge step, water was evaporated from the mixture until the solids were dry. The dried solids were then resuspended in water using mixing method A, and sampled for a particle size distribution determination. The results are shown below in Table 7.

TABLE 7

| | Particle Size Distribution (μm) | | | | | | |
| | $d_{(10)}$ | $d_{(25)}$ | $d_{(50)}$ | $d_{(75)}$ | $d_{(90)}$ | Mean | Median |
|---|---|---|---|---|---|---|---|
| Particles Before Drying | 0.58 | 0.78 | 1.18 | 2.0 | 3.5 | 1.6 | 1.2 |
| Particles After Re-Suspension | 1.6 | 6.0 | 13.3 | 23.4 | 36.9 | 17.8 | 13.3 |

The original particle size distribution was not regenerated. Precipitation of the glucooligosaccharides (as PGOS) onto the cellulose particles is far more effective than attempting to dry down the whole in situ reaction mixture (without isolating the particles) as the resuspending agent.

Particles comprising cellulose that are resuspendable typically can be resuspended by blending at 12,000 rpm a 4-8 wt % mixture of the particles in water at a temperature of about 45° C. for 30-60 sec. Specifically, particles were prepared via supercritical hydrolysis of a cellulosic feedstock (as discussed elsewhere herein), followed by filtration, followed by reslurrying with water, followed by isolation of the particles (still wet) with a $d_{50}$ of around 1 μm. The cellulose particles (solids content of about 4.2 wt %) were then subjected to a freeze-thaw cycle to obtain a 15 wt % solids suspension, in which some larger particles settled out. These solids were then diluted to 4 wt % with water and subjected to 30 sec of blending at the conditions noted in this paragraph to result in Sample A (see Table 8 below). As can be seen in Table 8, the $d_{50}$ particle size for Sample A is still quite large at 6.5 μm. Additional blending for 30 sec was sufficient to return the $d_{50}$ to about 1 μm, and the $d_{10}$ and $d_{90}$ values are also within acceptable limits (Sample B in Table 8). An additional 30 sec blending (90 sec total) did nothing to further reduce particle size distribution (Sample C). The weak agglomeration resulting from freeze-thaw cycles can be broken up by extending the blending time for an additional 30 seconds. The particles size reduction from this approach is limited to that of the primary particles present before the weak agglomeration occurred.

TABLE 8

| | $d_{10}$ (μm) | $d_{50}$ (μm) | $d_{90}$ (μm) |
|---|---|---|---|
| Sample A (30 sec) | 0.7 | 6.5 | 60 |
| Sample B (60 sec) | 0.59 | 1.2 | 5.8 |
| Samples C (90 sec) | 0.58 | 1.2 | 5.8 |

Example 6: Stability and Properties of Aqueous Suspensions

The stability of the cellulose particles in aqueous suspensions was compared to that of commercially available cellulose products widely used in the food industry: (1) HERBACEL™, which is a fruit fiber, and (2) Micro Crystalline Cellulose (MCC), particle size $d_{50}$ (as measured by the Beckman Coulter Particle Sizer) of about 35 μm obtained from Blackburn Distributions, UK. In each case (in duplicate), 1.0 g of solid cellulose material was placed in a centrifuge tube and 40 ml of water was added and stirred for 5 minutes, then allowed to equilibrate for 1 hour. In the case of the cellulose particles disclosed herein, 1.0 g of solids was introduced as 6.25 g of 16% solids suspension, diluted to 40 ml of water. The tubes were centrifuged at 1,000 rpm (slow)

Figure 8:
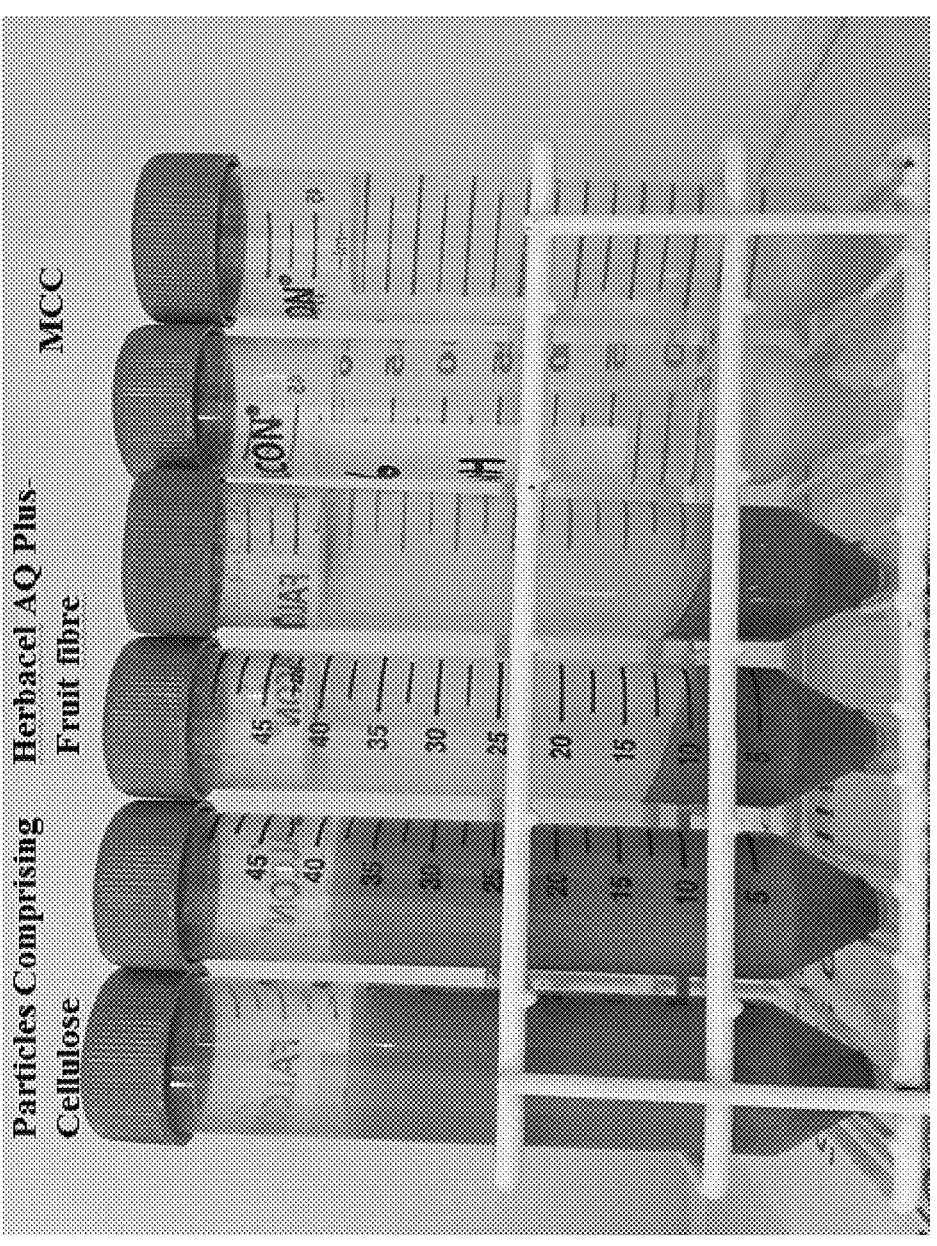
FIG. 8 shows (in each case: 1.0 g of solid cellulose material in 40 ml of water in duplicate): i) a stable aqueous suspension of the particles comprising cellulose described herein; ii) HERBACEL™ AQ Plus (a fruit fiber); and iii) Micro Crystalline Cellulose (MCC), particle size $d_{50}$ (as measured by the Beckman Coulter Particle Sizer) of about 35 μm, obtained from Blackburn Distributions, UK (see Example 6).

103                                                                                                    104 for 10 minutes. After being centrifuged, the MCC settled out completely, the HERBACEL™ swelled a little and held some of the water but mostly settled out, whereas the present cellulose particles remained in suspension, and, even after centrifuging at increased speed and duration, did not settle (over a period of at least 2 weeks), FIG. 8. The small particle size cellulose particles form a very stable suspension in water in marked contrast to MCC and HERBACEL.

Aqueous suspensions of the cellulose particles were found to exhibit Non-Newtonian viscosity behavior (generally, a Newtonian fluid is a fluid whose viscosity does not change with the rate of flow). Specifically, the aqueous suspensions of the cellulose particles are thixotropic, meaning they are shear thinning (thixotropy is a time-dependent shear thinning property; certain gels or fluids that are thick, or viscous, under static conditions will flow (or become thin, or less viscous) over time when shaken, agitated, sheared or otherwise stressed). See FIG. 9, which shows (for concentrations of cellulose particles in water of 2 wt %, 5 wt % and 6 wt %) an approximate 10-fold drop in viscosity upon an increase of about 10-fold in shear (i.e. shear thinning). Separately, the addition of the cellulose particles to a polymer latex (about 30% solids) was observed to impart the desired thixotropic behavior, which is a useful property for latex paints (e.g., it allows relatively facile brush application of the paint, without the paint running or dripping from the applied surface). Furthermore, increasing the cellulose content increased the thixotropic ratio (the thixotropic ratio is the viscosity at 2 rpm divided by the viscosity at 20 rpm). It was also noted that adjusting the pH (which is also important for paint and coatings applications), for example in increments from pH=3 to pH=11, does change the viscosity slightly, but does not have a significant effect on the thixotropic behavior.

The cellulose particles also exhibit synergistic thickening. FIG. 10 shows blends of the cellulose particles (2 wt %) in water with, separately, 0.1% xanthan gum, 0.2%) methylhydroxyethyl cellulose, and 0.1% hydroxypropyl guar (percentages are solids of component based on total water content). Each component individually, provided minimal viscosity enhancement at the levels studied; however, the blends provided a 4-10 fold increase in the viscosity compared to the individual materials at the same levels. The same comparison was made using 3 wt % cellulose particles (combined with the same levels—0.1%, 0.2% and 0.1%—of the other three components), and the same trends were observed except each blend viscosity was a further 2-fold higher than those observed for the corresponding 2 wt % blends.

Example 7: Suspension Aid

The ability of the cellulose particles to stabilize insoluble solid particles in aqueous suspension was assessed for two different types of solids: cocoa powder and calcium carbonate. Attempts to suspend cocoa powder utilized 5.0 g of cocoa powder in a total aqueous mixture of 100 g. Cocoa typically fails to maintain a homogeneous suspension in water, with hydrophobic components floating to the top and some heavier powder elements sinking as a precipitate. Samples were simply shaken (order of addition: water, then suspension aid, then cocoa) in a 120 ml plastic container to produce a homogeneous mixture and left to settle for 24 hours in a refrigerator (8° C.). Table 9 (below) shows the formulation ingredients for the cocoa suspensions.

TABLE 9

|  | Control | Cellulose Particles A (2%) | Cellulose Particles A (4%) | Xanthan |
|---|---|---|---|---|
| Water | 100 g | 89.5 | 79.0 | 100 g |
| Cellulose Particles A (16% solids) | — | 12.5 g | 25 g | — |
| Xanthan | — | — | — | 0.1 g |
| Cocoa | 5 g | 5 g | 5 g | 5 g |

The addition of 12.5 g of 16% suspension of cellulose particles corresponds to 2.0 g solids and 10.5 g of water.

The addition of 25 g of 16% suspension of cellulose particles corresponds to 4.0 g solids and 21 g of water.

The results are shown in FIG. 11. As expected, the control sample containing only cocoa powder and water failed to suspend the cocoa solids, with solids both rising to the surface and precipitating to the bottom. Xanthan is typically used at a 0.1% level, and, although it performed better than the control, it also failed to suspend the cocoa since it had accumulated a layer of cocoa at the surface after 24 hours. The cellulose particles disclosed herein almost stabilize the suspension at a 2% level (a minor layer appearing at the surface after 24 hours), but the 4% level of Cellulose Particles A appears to have been successful as a stabilizing aid, maintaining a homogeneous mixture at the 24 hour timeframe (with virtually no precipitate or floating layer). Similar results were obtained in experiments to stabilize a chocolate milk of milk, water and cocoa.

A similar experiment was performed in testing the Cellulose Particles A in stabilizing suspensions of calcium carbonate ($CaCC_3$), a common mineral filler in paints and coatings, except that the $CaCO_3$ was present at 10 g in 100 g of water. Along with i) the control sample (10 g of $CaCO_3$ suspended in 100 g of water), the prospective suspension aids were: ii) 0.1% xanthan, iii) 2% Cellulose Particles A, and iv) a combination of 2% Cellulose Particles A with 0.1% xanthan. The results are shown in FIG. 12. i) $CaCO_3$ precipitated completely from water within 10 minutes in the control sample; ii) 0.1% xanthan failed to prevent separation of the $CaCO_3$ which had precipitated within an hour; iii) addition of 2% Cellulose Particles A produced a meta-stable suspension which, after 24 hours, showed separation at about halfway down the sample tube, i.e., a 50% stable suspension (compared to complete separation which would leave the precipitate in a volume of less than 20% of the contents at the bottom of the tube); and iv) the combined 2% Cellulose Particles A+0.1% xanthan resulted in a 100% stable suspension (homogeneously mixed suspension maintained after 24 hours, and apparently stable indefinitely in this case). Later, a second control sample was added: a combination of 2% commercial MCC with 0.1% xanthan. Significantly, the second control sample completely precipitated within 3 hours. The cellulose particles disclosed herein can function as a suspension aid, and are far superior to commercial MCC in this application.

Example 8: Stable Emulsions

The ability of the cellulose particles to stabilize emulsions was assessed as follows. Various oil and water mixtures, each mixture totaling 100 g, were prepared where the cellulose was present in an amount of about 2 wt % solids based on the total oil and water mixture weight. Specifically, 12.5 g of a 16 wt % suspension ("cellulose suspension")

contains 2.0 g of solids (including cellulose and possible solid impurities) and 10.5 g of water (12.5 g×0.16=2.0 g). In 100 g total of emulsion, this corresponds to a cellulose particle content of 2.0% cellulose particles by weight of oil/water mixture. Table 10 below shows the quantities of oil, cellulose suspension, and added water employed in each sample.

TABLE 10

| Sample | Oil (g) | Cellulose Suspension (g) | Added Water (g) | TOTAL (g) |
|---|---|---|---|---|
| 1 | 10 | 12.5 | 77.5 | 100 |
| 2 | 20 | 12.5 | 67.5 | 100 |
| 3 | 50 | 12.5 | 37.5 | 100 |
| 4 | 80 | 12.5 | 7.5 | 100 |

100 g samples (as in Table 10) were prepared in 250 ml glass beakers and mixed for 5 minutes at 6000 rpm. Samples were made in duplicate and left in glass sample containers. FIG. 13 shows emulsions formed using the proportions shown in Table 10. The 50% oil emulsion was the most stable, while the 10% and 20% oil samples both developed creaming (where the droplets rise to the top of the emulsion due to buoyancy). The 80% emulsion was unstable and split, forming sediment. Separately, a drop test revealed that all the emulsions are oil in water emulsions (the oil is suspended within the continuous water phase). Common oil in water emulsions include, for example, mayonnaise, vinaigrette, and espresso crema (and others described elsewhere herein). A quick proof of concept was achieved by preparing balsamic vinegar dressing (a minimally formulated vinaigrette comprising oil, balsamic vinegar and seasonings). It was found that a control balsamic vinegar emulsion preparation separated after just one hour, whereas the same emulsion formulation with the addition of the cellulose particles (2.0 g of cellulose particles on a dry solids basis present in a total of 100 g of balsamic vinegar emulsion—i.e. 2.0% cellulose solids by weight of oil/vinegar emulsion) was still stable more than 2 weeks later. It is surprising that the small particle size cellulose particles stabilize emulsions since cellulose, especially MCC, typically fails to act as an emulsifier.

egg yolk acts as the emulsifier to help stabilize the oil and vinegar based formulation). There is a desire in the food industry to reduce or remove egg from many formulations, including mayonnaise, to provide a product free of some allergens, to provide low cholesterol diet options, as a cost reduction adjustment, to prepare a vegan food product, or to promote animal welfare.

Four types of cellulose composition (as summarized in Table 11 below) were studied in the standard mayonnaise formulation prepared as follows: Two whole eggs were broken into a stick blender, a tablespoon of mustard was added, followed by a pinch of salt and 2 tablespoons of white vinegar. About 100 ml oil (from a total quantity of 500 ml oil) was immediately added to the mixture and the blender turned on for about 10 seconds. The blender was opened, another portion of the oil (~100 ml) was added, with further mixing. This was repeated two or three more times with the remainder of the oil until the mayonnaise had the required consistency. (In the event the mayonnaise becomes too thick to turn around, it can be thinned by the addition of a little lemon juice, or water or vinegar).

The procedure for the egg-free mayonnaise was the same except simply replacing the weight of egg, gram-for-gram, with the weight content of cellulose particles (in each case, added as a 16% solids suspension). [1 egg contents taken as 60.0 g; 2 eggs used, therefore 120.0 g of 16% suspension in egg-free recipe=19.2 g cellulose solids and 100.8 g water added with it. 2 tablespoons of vinegar corresponds to 30.0 g vinegar, therefore total water/vinegar/oil=100.8 water+ 30.0 g vinegar+500.0 g oil=630.8 g water/vinegar/oil. 19.2 g cellulose solids on 630.8 g water/vinegar/oil=19.2/ 630.8=3.0% cellulose solids added based on weight of water/vinegar/oil contents in the emulsion]. Not shown in Table 11, a similarly formulated egg-free chipotle sandwich spread was also prepared using the same cellulose composition 1 listed below (3.0 wt % cellulose solids based on water/vinegar/oil contents in the emulsion). Both the egg-free mayonnaise and this chipotle mayonnaise were stable (upon visual inspection, the emulsion is not observed to break for more than >2 weeks).

Table 11 shows the characteristics of the various samples of cellulose particles formulated in the egg-free mayonnaise recipe.

TABLE 11

| Cellulose | Cellulose Source[1] | % Lignin Content | Particle Size $d_{50}$ (µm) | Mean Average Particle Size (µm) | Particle Size $d_{75}$ (µm) | Emulsion Stability |
|---|---|---|---|---|---|---|
| Control (Egg) | — | 0% | — | — | — | Stable |
| Cellulose Particles 1 | SH of Lignocellulosic Biomass | ~20% | 0.9 | 1.2 | 1.3 | Stable |
| Cellulose Particles 2 | SH of MCC | 0% | 0.8 | 1.5 | 1.2 | Stable |
| Comparative Cellulose 3 | SH of MCC | 0% | 2.9 | 8.5 | 10.8 | Unstable |
| Comparative Cellulose 4 | Commercial MCC | 0% | 35 | 48 | 68 | Unstable |

Example 9: Egg-Free or Egg-Reduced Mayonnaise/Dressings

Traditional mayonnaise is stabilized in an emulsion form by the presence of egg (the phospholipid lecithin present in In Table 11, Cellulose Particles 1 were prepared by supercritical hydrolysis (SH) of the source material according to Example 1. Cellulose Particles 2 were prepared by supercritical hydrolysis of the source material according to Example 4. Comparative Cellulose 3 was prepared by supercritical hydrolysis of the source material according to Example 4 except that the resulting mixture from hydrolysis was not passed through a 74 μm screen. Comparative Cellulose 4 employed commercial MCC formulated as a 16% solids suspension.

The cellulose particles functioned successfully as an egg replacement ingredient, producing a stable emulsion in an egg-free mayonnaise. The cellulose particles can be added directly as the 16% solids suspension, which allows a direct gram-for-gram replacement (one non-limiting theory is that this direct replacement is possible because the solids and water content of the added suspension is similar to the solids and water content of the egg being replaced—the eggs are approximately 23% solids and 77% water, whereas the suspension is approximately 16% solids and 84% water).

It is significant to note that a cellulose sample (Comparative Cellulose 3, Table 11) having a significant fraction of a larger particle size (as shown, e.g., by the $D_{50}$ and especially the $d_{75}$ particle sizes) fails to produce a stable emulsion in the same egg-free mayonnaise formulation. Without wishing to be bound by theory, it is believed that the small size cellulose may be able to adsorb onto at the oil-water (vinegar) interface forming a boundary aiding the suspension of the two phases (a so-called "Pickering" emulsion), whereas the large particle size fraction is unable to form an emulsion or a stable Pickering emulsion, and therefore fails to stabilize the emulsion in the egg-free mayonnaise formulation.

Other emulsified products also have been prepared successfully, such as sauces comprising a fat or oil component, for example, barbeque sauce and pasta sauce. Such sauces were prepared using cellulose particles from Sample A (Table 1) in place of traditionally used starch, gum and/or lecithin. In the case of pasta sauce, the sauce was prepared using cellulose particles from Sample A in place of soy lecithin (which is often present as an emulsifier); and in BBQ sauce, cellulose particles from Sample A replaced modified food starch, which serves the dual purpose of moisture control and thickener, with both properties unaffected, as well as preserving stability (e.g., stability to syneresis) and freeze-thaw stability.

Example 10: Egg-Free, Fat-Free and/or Gluten-Free Muffins, Brownies, Cakes

As described above for emulsions (e.g., mayonnaise), there is a desire across many baked goods product lines to reduce or remove egg or gluten or fat, or dairy products, or combinations thereof, from many formulations, including muffins, brownies, cakes, or other leavened food products, either to provide an allergen-free product, a perceived healthier product, or simply as a cost reduction adjustment. In all of these products, however, there is a delicate balance of end properties required in order for any potential substitute to gain acceptance. Currently, simply removing any or all of these ingredients produces an unsatisfactory product in terms of texture, taste, mouth-feel, or other property. The small particle size cellulose particles (Cellulose Particles 1 and Cellulose Particles 2) as well as the Comparative Cellulose 3, referred to in Table 11 above, were studied in the standard muffin formulation prepared as follows (and using quantities outlined in Table 12, below): The oven was heated to 200° C. (or 180° C. with fan). Two muffin trays were lined with paper muffin baking cups. The eggs were beaten lightly with a handheld electric mixer in a large bowl for 1 min. The oil and milk were added with additional mixing until just combined, and the sugar was then added and whisked until it produced a smooth batter. The flour and salt (and baking powder if used) were sifted in and then mixed until just smooth, taking care not to over-mix the batter as this makes the muffins tough. The muffin cases were filled two-thirds full and baked for 20-25 mins, until they had risen, were firm to the touch, and a skewer inserted in the middle came out clean. The muffins were left in the tin to cool for a few mins and then transferred to a wire rack to cool completely.

TABLE 12

| Ingredient | Control (A) | Egg Free Control (B) | Egg Free with Cellulose Compos. (C) | Gluten Free Control (D) | Gluten Free with Cellulose Compos. (E) | Fat Free with Cellulose Compos. (F) |
|---|---|---|---|---|---|---|
| Eggs | 2 eggs | — | — | 2 eggs | 2 eggs | 2 eggs |
| Cellulose Particles (16 wt %) | — | — | 125 ml[2] | — | 200 ml[2] | 125 ml[2] |
| Water | — | 105 ml | — | — | — | — |
| Vegetable Oil | 125 ml | 125 ml | 125 ml | 125 ml | 125 ml | — |
| Semi-Skimmed Milk | 250 ml | 250 ml | 250 ml | 250 ml | 80 ml | — |
| Skimmed Milk | — | — | — | — | — | 250 ml |
| Caster Sugar | 200 g | 200 g | 200 g | 200 g | 200 g | 200 g |
| Plain Flour | 400 g | 400 g | 400 g | — | — | 400 g |
| Gluten Free Flour | — | — | — | 400 g | 400 g | — |

TABLE 12-continued

| Ingredient | Control (A) | Egg Free Control (B) | Egg Free with Cellulose Compos. (C) | Gluten Free Control (D) | Gluten Free with Cellulose Compos. (E) | Fat Free with Cellulose Compos. (F) |
|---|---|---|---|---|---|---|
| Baking Powder | 3 tsp | 3 tsp | 3 tsp | 3 tsp | 3 tsp | 3 tsp |
| Salt | 1 tsp[1] | 1 tsp | 1 tsp | 1 tsp | 1 tsp | 1 tsp |

[1] 1 tsp = about 5.5 g;

[2] C) 125 ml of 16% suspension of cellulose = 20.0 g of cellulose particles and 105 g water; 20.0 g of cellulose corresponds to 20/480 = 4.2% cellulose based on oil/water, and 20/1102 = 1.8% cellulose based on total formulation. E) 200 ml of 16% suspension of cellulose = 32.0 g of cellulose particles and 168 g water; 32.0 g of cellulose corresponds to 32/373 = 8.6% cellulose based on oil/water, and 32/1115 = 2.8% cellulose based on total formulation. F) 125 ml of 16% suspension of cellulose = 20.0 g of cellulose particles and 105 g water; 20.0 g of cellulose corresponds to 20/355 = 5.6% cellulose based on oil/water, and 20/1097 = 1.8% cellulose based on total formulation.

The recipes were originally formulated (and followed herein) using a quantity of wet 16% solids suspension of cellulose particles that was based on (approximately equivalent to) the quantity of egg being replaced in the control formulation (because the cellulose suspension and the eggs have similar % solids—see Example 8). It was later found that halving the quantity of cellulose suspension in the recipe was more effective in these muffin recipes.

Muffins were made for each of the recipes detailed above, and separate muffin batches were prepared using each of Cellulose Particles 1, Cellulose Particles 2, and Comparative Cellulose 3 for each muffin type indicating cellulose as an ingredient. For each muffin recipe, Cellulose Particles 1 was easily incorporated into the formulations, Cellulose Particles 2 was incorporated but not as readily as Cellulose Particles 1; and Comparative Cellulose 3 was only incorporated with difficulty (required a higher shear mixer). Muffins containing Cellulose Comp. 1 have a slightly richer brown color due to the presence of some lignin in the product.

As well as qualitative assessments such as look, feel, mouth-feel, and taste, the muffins were also assessed using a Texture Analyzer (which measures a resistive force upon compression on the top of the muffin as a function of time), and a C-Cell (which provides an area and depth contour of pores (cells) in the cell structure when the muffins are cut open).

The C-Cell analysis of the muffins showed that the gluten-free muffin with cellulose particles (E) and the egg-free muffin with the cellulose particles (C) had a very similar cell structure to that of the egg-containing control (A). The fat-free muffin containing cellulose (F) rose well during baking and, from the exterior, visually appeared to be comparable to the control muffin (A). However C-Cell analysis also highlighted a much more open cell structure with large deep holes for this fat-free muffin with cellulose (F). Some tweaking would be required to optimize the formulation for use of the cellulose particles in a fat-free muffin. (Fat-free brownies containing the cellulose composition were successfully prepared having superior rise and surface structure as well as comparable cell texture and taste to that of the control brownie formulation, which used a commercial MCC product).

The Texture Analyzer confirmed what was qualitatively evident: the failed-control egg-free muffin (no cellulose particles, B) was the least firm of the muffins, failing to spring back after compression; whereas the failed-control gluten-free muffin (no cellulose particles, D) showed a different shape force curve to all of the other samples, as it crumbled on compression. All of the cellulose particle-containing muffins, and particularly the gluten-free muffin containing the cellulose particles, were firmer than the control muffin. It was found that the firmness could be easily controlled by altering the level of addition of the cellulose particles (higher levels were firmer, lower levels resulted in lower firmness).

The muffins comprising the small particle size cellulose particles, including both the gluten-free muffin with cellulose and the egg-free muffin with cellulose, appeared to provide all of the pre-requisite properties for an acceptable muffin recipe. However, identically formulated and baked muffins comprising the Comparative Cellulose 3 (described in Example 8, Table 11) were also prepared, but the Comparative Cellulose 3 was incorporated into the formulation only with difficulty, and these muffins failed to rise properly during baking. It is thought that the larger particle size of Comparative Cellulose 3 fails to stabilize the formulation sufficiently prior to and during baking, resulting in insufficient expansion and poor cell structure in the muffin crumb. And, following the trend (difficulty of incorporating the respective suspension of particles into the batter), generally, muffins made using the "white" cellulose particles prepared from MCC (Cellulose Particles 2) did not produce as good a crumb structure and texture as muffins made using the "brown" cellulose particles (Cellulose Particles 1 that contain about 20% lignin) prepared from a lignocellulosic feedstock. An attempt to "add back" a quantity of lignin into the suspension of the white MCC-derived particles equivalent to the amount of lignin present in the "brown" cellulose particles did result in an improvement in the crumb structure and texture of the resulting muffins compared to the white particles without lignin; however, the "brown" cellulose particles performed better than both the "reconstituted" particles (prepared from MCC with added back lignin) and the "white" cellulose particles prepared from MCC. It would appear that lignin offers a secondary benefit independent of the cellulose.

The formulations were robust enough to incorporate a number of different ingredient variables, successfully incorporating the cellulose composition into chocolate muffins, whole wheat, bran, molasses, brown sugar, vanilla, raisin, blueberry, and gluten-free chocolate muffins. As an unexpected benefit, an experienced panel of taste-testers discerned enhanced vanilla flavoring for the muffins prepared using cellulose particles comprising lignin (compared to identically formulated muffins prepared using cellulose particles containing no lignin) when minimal vanilla flavoring was included in the recipe.

In traditional muffins, the egg yolk provides lecithin, which acts as an emulsifier helping to mix the oil throughout the mixture; and the white of the egg coagulates as it cooks, which provides structure to the cake. The results indicate that the small particle size cellulose particles can help with both emulsification and structural integrity in muffins. Accordingly, the small particle size cellulose particles have potential as both a gluten-replacement and/or egg-replacement ingredient. Indeed, allergen-free (both gluten-free and egg-free) cellulose-containing muffins were successfully prepared with the small particle size Cellulose Particles 1 and Cellulose Particles 2, and with comparable and near-comparable properties (respectively) to the control muffins.

Example 11: Gluten-Free and Allergen-Free Bread

Although gluten-free flours exist, the objective of providing a universally accepted gluten-free bread has remained elusive, at least in part because the gluten component does actually have a functional role in both the bread making process and the finished product, generally adding a familiar texture, chewiness, moisture, and elasticity to the bread.

A gluten-free bread comprising the cellulose particles disclosed herein was prepared as follows using the formulation in Table 13:

TABLE 13

| Ingredient | Supplier | Code | Weight (g) | Percent of Formulation | Baker's Percentage[2] |
|---|---|---|---|---|---|
| Stage 1 | | | | | |
| Whole Grain Gluten-Free Flour[1] | Bay State Milling | 91205 | 375.0 | 41.7 | 62.5 |
| Sugar, granulated | C&H | Superfine | 35.0 | 3.9 | 5.8 |
| Salt | Morton | Culinex 999 | 4.5 | 0.5 | 0.75 |
| Instant Active Yeast | Fleischmann's | | 5.5 | 0.6 | 0.9 |
| Stage 2 | | | | | |
| Water | | | 300.0 | 33.3 | — |
| Cellulose Particles A (16%)[3] | | | 50.0 | 5.5 | 8.3 |
| Egg | | | 70.0 | 7.8 | 11.7 |
| Canola Oil | Wesson | | 60.0 | 6.7 | 10.0 |
| Totals | | | 900.0 | 100.0 | 100.0 |

[1]Gluten-free flour has brown rice flour, rice starch, potato starch, xanthan gum and locust bean gum. An exemplary formulation used a blend of two gluten-free flours (blend ratio was $2/3$ brown rice flour to $1/3$ white rice flour);
[2]No water;
[3]Cellulose Particles A are present at a level of 5.5% of wet suspension based on the total weight of formulation. Since the cellulose particles are 16% solids in the suspension, the particles are present at a level of 0.9% solids based on the total weight of formulation.

The procedure to prepare the gluten-free bread was as follows: Add Stage One ingredients to 5 Qt. Hobart Mixer Bowl fitted with paddle. Mix for one minute until homogeneous. Add Stage Two ingredients to mixer. Mix 3 minutes on low speed, Scrape bowl and paddle as necessary. Spray 9"×5" loaf pan with cooking spray. Empty batter from Hobart bowl into bread pan. Proof bread at 90° F./75% Relative Humidity, for about 1 hour, or until batter reaches ¼" above the pan. Bake in 350° F. oven for 55 minutes. This should produce some oven spring and a nice golden crust. Allow bread to cool before slicing. Gluten Free Bread formulations typically have milk or whey, higher egg content (than regular bread), and gums, such as locust bean or xanthan, in addition to the gums and starches in the flour preparation. In the absence of gums, gluten free bread usually fails to stabilize the air bubble, and the bread suffers from lack of lift (no oven spring). The above formulation (Table 13) for gluten-free bread comprising the cellulose particles disclosed herein has no dairy (no milk or whey), considerably less egg, and only a small amount of gums (only those from the pre-mixed gluten-free flour), and this formulation produces a very good gluten-free bread with good oven spring and a moist texture which slices easily without crumbling (FIG. 14). A control bread, identically formulated but without the addition of cellulose particles suffered from lack of lift (no oven spring). Further experiments eliminated egg from the gluten-free recipe and thus produced an allergen-free, vegan bread as well (gluten-free, egg-free, and dairy-free) using the cellulose particles as both an egg-replacement and gluten-replacement additive. A further advantage anticipated for baked goods, and especially bread, is that the cellulose particles should perform as anti-staling agents; in this regard, the moisture retention properties should additionally have the effect of slowing the baked goods from drying out over time.

Generally, a number of baked goods have been made using various gluten-free flour mixes in conjunction with the cellulose particles disclosed herein, and similar results have been obtained.

Example 12a: Egg-Free and Allergen-Free Pasta

Although complicated pasta recipes do exist, a pasta recipe in its simplest form can be very basic indeed, consisting essentially of flour and egg(s). Most recipes additionally incorporate a small amount of regular table salt, and, optionally, a small amount of water simply to adjust the consistency of the pasta dough. It was found that the cellulose particles described herein can be used as an egg-replacement ingredient in pasta recipes as well.

Compared to a normal basic pasta recipe that consisted of 1 cup flour, 1 egg, and $2/3$ cup of water, the current pasta recipe simply used 1 cup all-purpose flour and 1 cup of the chilled aqueous suspension of cellulose particles (16% solids of cellulose particles in water).

Preparation of the pasta was as follows:

1) 1 cup all-purpose flour (approx. 120 g) and 1 cup of the chilled aqueous gel of cellulose particles (16% solids of cellulose particles in water; approx. 20 g of cellulose particles and 105 g of water) were blended with a small spatula on a flat surface until well incorporated. It was noted that the cellulose particles seem to bind with the flour more completely than egg. The resulting dough ball was kneaded by hand for 3 minutes, rolled in flour, wrapped in plastic, and refrigerated for 3 hours. Other than the use of cellulose particles in place of egg, this is the same procedure normally used by the practitioner for making pasta.

2) After chilling, the dough ball was pressed by hand into a "pancake" of about ¼ inch thickness. Both sides of the dough were floured and the sheet was separated into two halves. The pasta sheeter attachment on a KitchenAid was used to roll out the 2 sheets of pasta into thinner pressed sheets about 3/32 inch thick (setting 4 of 8) and 8 inches long. The dough was rolled, folded, and re-rolled three times. Then, using the cutter attachments, one sheet of the dough was used to make spaghetti and the other sheet was used for fettucine. The noodles were well-formed and did not tend to stick together as is often the case with homemade pasta.

3) The pasta was allowed to rest for 30 minutes, and then the noodles were boiled for 7 minutes in a pasta pot. The noodles were 'free' and did not have a tendency to clump. Salt (1 Tbsp, equivalent to approx. 17 g) was added to the water, but no olive oil.

4) After cooking, the pasta was drained and placed into a bowl with a splash of olive oil and mixed.

5) The pasta was observed to be perfectly al dente, with a mild taste and excellent mouth-feel. There was no pastiness or gritty residue. The pasta was delicious and appetizing.

For traditional pasta, any leftover pasta that is refrigerated often forms a clump and the individual noodles tend to be difficult to separate after refrigeration. However, with the pasta comprised of cellulose particles, this was not a problem. After overnight refrigeration the individual noodles were readily pulled out of the leftovers container without breakage. The leftover pasta was reheated in a bowl without adding anything. The pasta was observed to have the same taste and mouth-feel on the second day as the first. It also appears that the cellulose particles help the pasta retain moisture and shape even after cooking, refrigeration, and reheating.

No attempt was made to prepare gluten free pasta (allergen-free pasta), although following the same procedure, simply replacing all-purpose flour with a gluten free flour, should present no additional difficulties and would be expected to readily produce an egg-free and gluten-free (allergen-free) pasta.

Example 12B: Low Calorie Nut Butter

This Example demonstrates the use of the cellulose particles disclosed herein to produce a lower calorie nut butter or spread, such as a peanut butter or hazelnut spread. Table 14a shows formulations used to make hazelnut spread:

TABLE 14A

| | Formulation 1 | | Formulation 2 | |
|---|---|---|---|---|
| Ingredient | g | % wt | g | % wt |
| Roasted Hazelnuts | 175 | 50 | 156 | 50.2 |
| Vegetable Oil | 2 | 0.6 | 1.8 | 0.6 |
| Cocoa | 18 | 5.1 | 11 | 3.5 |
| Cellulose Particles (16% solids) | 80 | 22.9 | 72 | 23.2 |

TABLE 14A-continued

| | Formulation 1 | | Formulation 2 | |
|---|---|---|---|---|
| Ingredient | g | % wt | g | % wt |
| Sugar | 75 | 21.4 | 70 | 22.5 |
| Total | 350 | 100 | 310.8 | 100 |

Roasted hazelnuts were homogenized using a hand held Hamilton Beach blender. A plastic sheet was used to cover the mixing bowl in such a way as to allow access and mobility to the blender, yet prevent splashing of the hazelnut paste. Since the hazelnuts contained significant skin content and since the blending did not produce a uniform particle size, the oily paste was passed through a 140 mesh screen. A smooth, uniform hazelnut cream was produced.

Cocoa, vegetable oil and sugar were added to the hazelnut cream and mixed thoroughly. For better results, the sugar and cocoa should be passed through an 80 mesh screen before use. The mixture of hazelnut and other ingredients was added slowly to an aqueous suspension of cellulose particles (16% solids, by weight) while blending with the same hand held blender. The final product was a smooth hazelnut spread.

The cellulose particles disclosed herein can support oil/water emulsions, and therefore allow the addition of water into the recipe. Despite an overall dilution due to addition of water compared to conventional recipes, the texture, mouth-feel and taste can be maintained since the particles additionally have a thickening effect and support spatial structure within the mixture. Accordingly, it is possible to both reduce the caloric intake (substituting water for nut butter content including fats/oils), while at the same time reducing cost (for the same reason). That is, the conventional recipe would require a higher oil content and would contain no water.

Example 12C: Slow Melting Ice Cream

This Example demonstrates the use of the cellulose particles disclosed herein to produce an ice cream with an exceptionally creamy and smooth mouthfeel and a slow melting profile. Ice cream requires the co-stabilization of ice crystals, air bubble and fat droplets from the cream, together with an aqueous sugar solution. Ice cream thus contains all three states of matter simultaneously, and is both foam and an oil in water emulsion. As disclosed herein, the cellulose particles can stabilize air bubble and also stabilize oil in water emulsions. Table 14b outlines the ice cream formulation:

TABLE 14B

| Ingredient | g |
|---|---|
| Cellulose Particles (16% solids) | 280 |
| Cream | 304 |
| Skim Milk Powder | 14 |
| Sugar | 102 |
| Total | 700 |

The ingredients were blended using a Kitchen Aid Artisan power blender at low speed. The aqueous suspension of cellulose particles (15% solids, by weight) was placed in the mixer first and the other ingredients were added. The total mixture (base) was placed in a 4° C. fridge for 24 hours before the freezing process.

The freezing was performed using a Cuisineart 2 gallon ice cream maker. The base was added slowly over a period of 15 minutes while churning continuously. It was found by comparison to the equivalent ice cream without cellulose particles that the cellulose stabilized ice cream melted more slowly (than a conventional ice cream), typically taking an additional 20 minutes to melt.

Example 12D: Fat Replacement and Moisture Retention Aid in Meat Products

A number of meat products deliberately include a lower grade (or cut) meat component specifically to incorporate a higher fat content (or simply add fat). Although this provides a lower cost component, another primary reason is actually to add a moisturizing component, and to add a favorable texture and mouth-feel. Added flavors may also enhance the taste. However, consumers are looking for healthier alternatives (such as, lower saturated fats in the diet), including removing or replacing the fat content in meat products. The cellulose particles disclosed herein can be used as an additive in meat products, such as a fat replacement additive, a moisture retention additive, a texture enhancing additive, a mouth-feel enhancing additive, or any combination, since, for example (and without wishing to be bound by theory) they provide a moisture retention function within the meat product that aids in maintaining the expected texture and mouth-feel that consumers have come to expect in these products. Accordingly, these cellulose particles find use in such products as fat free and/or fat reduced chicken sausage. Fat reduced chicken sausage was prepared as follows:

The chicken sausage prepared was a fat-free sausage using chicken breast meat only, along with onion, apple and spices and cellulose particles from Sample A, Table 1 (at 0%, 2%, 4% and 10% levels (wt %) of solid particles based on the total pre-cooked formulation weight). The control chicken sausage (i.e., 0% cellulose particles from Sample A, Table 1) was dry and crumbly, and generally not very appealing, whereas the particles comprising cellulose imparted improved juiciness (moisture retention) and color to the cooked products (containing 2%, 4% and 10% of cellulose particles), and these chicken sausage products were viewed very favorably by a group of experienced food tasters (see FIG. 15, levels shown in order, with lowest level of cellulose particles, 0%, on the left).

Other chicken products use rib meat blended with chicken breast meat in order to give an improved texture and mouth-feel compared to the 100% chicken breast meat. However, many consumers would prefer the 100% breast meat if it could be made somewhat juicier and easier to chew. It is anticipated that the cellulose particles disclosed herein would also find use in this type of product, as a moisture retention aid, and replacing the rib meat.

The cellulose particles disclosed herein also provided benefits to hot dog compositions, initially acting as an emulsifier and binder, and also as a moisture retention additive. It is expected that the cellulose particles would also function as a (partial) fat replacement additive since the observed moisture retention properties should maintain mouth-feel and juiciness even as fat content is reduced.

Example 12E: Foams

Compositions containing the cellulose particles disclosed herein have been found to support stable air-in-water foams. Typically, in order to form a stable foam, a surfactant such as lecithin, mono-glycerides or proteins, must be present to reduce the interfacial tension between the air phase and the aqueous phase. Without wishing to be bound by theory, the cellulose particles seem to provide the surfactant necessary to reduce the interfacial tension. In this example, samples were made in the proportions shown in Table 14c and then subjected to a handheld whisk just below the surface of each sample for 1 minute. Foams were formed in the samples with 2%, 4% and 8% cellulose particles. The sample with 4% cellulose particles solids content nearly doubled in size with foam formation, which was stable (but for some degassing as shown in FIG. 16B) after 4 days. See FIG. 16A which illustrates the foam results, wherein the black mark with a "1" on each beaker indicates the level of the sample composition before whisking and the black mark with a "2" on each beaker indicates the level of the sample composition directly after whisking. The 2% sample did produce a foam that disappeared within a couple of hours. The 8% sample achieved some increase in volume which was very stable.

TABLE 14C

| Sample | Cellulose Suspension (g) | Water in Cellulose Suspension (ml) | Added Water (ml) |
|---|---|---|---|
| 16% | 100 | 84 | 0 |
| 8% | 50 | 42 | 50 |
| 4% | 25 | 21 | 75 |
| 2% | 12.5 | 10.5 | 87.5 |
| 1% | 6.25 | 5.25 | 93.75 |

Example 13: Compositions Comprising Cellulose Particles and a Liquid

Example 13a. Rheological Performance

Cellulose particles were added to water at a 21 pound per barrel (PPB or #/bbl) concentration of cellulose particles in water, and blended with a commercial milkshake mixer for 30 minutes. If necessary, a de-foaming agent was applied. The sample was allowed to sit briefly until the foam had dissipated upon visual inspection. The API (American Petroleum Institute) rheology testing protocol was followed and data generated via an OFI Model 900 Viscometer. The temperature set point was set to 120° F. and the sample temperature was given adequate time to equilibrate. Readings were collected at the following settings, with adequate time between readings to allow the sample to equilibrate: 600 RPM, 300 RPM, 6 RPM, and 3 RPM (600 RPM measures at the very high shear end of the spectrum and 300 RPM is high shear, simulating the drill bit shear; and 6 RPM and 3 RPM are low shear, simulating a move of the drill pipe, for example, being lifted out of the well bore). Following these readings, the "gels" program was run and automated sequence performed for the 10 second and 10 minute gel readings. The latter gives an indication of the force to start turning, to see how much torque would be needed when the drill is first started up. Measuring at 10 seconds and again at 10 minutes gives an indication of whether the drilling fluid is setting up (becoming a viscous gel). If the 10 second and 10 minute reading are similar, this at least indicates the fluid is not setting up immediately. The rheological performance for a 21 pound per barrel (PPB or #/bbl) concentration of cellulose particles in water is illustrated in Table 15 below.

TABLE 15

| Obtained Values: | |
| --- | --- |
| OFI Model 900 Test Setting | Example Value: |
| 600 RPM | 11 |
| 300 RPM | 9 |
| 6 RPM | 8 |
| 3 RPM | 8 |
| Gels after 10 sec | 8 |
| Gels after 10 min | 10 |
| Calculated Values: | |
| Plastic Viscosity (PV) | Subtract 300 RPM value from 600 RPM value: 2 |
| Yield Point (YP) | Subtract PV from 300 RPM value: 7 |
| Low Shear Yield Point (LSYP) | Multiply 3 RPM value by 2 and subtract 6 RPM value: 8 |

Example 13B: Combined Use with a Viscosifying Agent

Testing was commenced to measure synergies with other commonly available viscosifying agents. The test battery demonstrated viscosity performance improvements with inorganic viscosifying agents (i.e., bentonite, laponite, synthetic hectorites, natural hectorites, mixed metal hydroxides, and mixed metal oxides) and organic viscosifying agents (i.e., xanthan gum, diutan, carboxymethyl starch, carboxymethyl cellulose, guar gum, and polysaccharide oligomers.

Briefly, particles comprising cellulose were mixed with sodium chloride brine at varying concentrations, shown in the table heading below. Rheological profiles are listed below in Table 16, demonstrating the low plastic viscosity and high "low-end" rheology.

TABLE 16

| RHEOLOGY @ 120° F. | 33.3 #/bbl | 30.0 #/bbl | 27.0 #/bbl | 24.4 #/bbl |
| --- | --- | --- | --- | --- |
| 600 RPM | 30 | 19 | 15 | 12 |
| 300 RPM | 28 | 17 | 13 | 10 |
| PV | 2 | 2 | 2 | 2 |
| YP | 26 | 15 | 11 | 8 |
| GELS | 23/24 | 14/12 | 11/8 | 7/6 |
| 6 RPM | 24 | 15 | 11 | 6 |
| 3 RPM | 24 | 15 | 11 | 6 |
| LSYP | 24 | 15 | 11 | 6 |

See Table 15 above for the "low-flat" gels. The gels at 10 seconds and 10 minutes are nearly identical and are nearly the same as the 6 and 3 RPM values. The low shear numbers are all considered to be acceptable (preferably up above 5, and are good up to about 10, although numbers of 10 and higher are not problematic as the fluid can simply be diluted if too viscous). The data shows that the cellulose particles can provide appropriate rheology across a range of cellulose particle concentrations and in a high salinity environment.

Additionally, particles comprising cellulose were added at approximately 24 #/bbl loading level to a sodium chloride brine (26% NaCl) and aged overnight at 300° F. (Table 17). The rheology on the left is representative (BHR is before hot rolling; and AHR is after hot rolling). The above sample was mixed with 1 #/bbl guar gum (organic viscosifier) and the rheology in column 4 was obtained. For comparison, 1 #/bbl guar gum was added to sodium chloride brine solution alone (column 5) and the rheology on the right side was obtained. The latter shows that guar gum alone may not be suitable as a rheology modifier in this application, because the low shear viscosity is too low. Addition of the cellulose particles (24 #/bbl) shows a significantly improved rheology, column 4 in Table 17 (below).

TABLE 17

| | 26% NaCl Fluid (BHR) | 26% NaCl Fluid (AHR) | AHR Fluid + 1 PPB Guar | 1 PPB Guar-Only Fluid |
| --- | --- | --- | --- | --- |
| 600 | 12 | 12 | 58 | 17 |
| 300 | 10 | 9 | 42 | 11 |
| PV | 2 | 3 | 16 | 6 |
| YP | 8 | 6 | 26 | 5 |
| Gels | 7/6 | 8/13 | 10/18 | 0/0 |
| 6 | 6 | 5 | 12 | 0.6 |
| 3 | 6 | 5 | 11 | 0.5 |
| LSYP | 6 | 5 | 10 | 0.4 |

BHR performed at 120° F. after mixing.
AHR performed at 120° F. after aging 18 hrs/300° F. then mixing.

In addition, particles comprising cellulose at 2% and 3% were measured in direct comparison to other organic polymers, as well as measuring the combined effect of the organic polymer thickeners added together with the small particle size cellulose particle solutions. The results were presented earlier under "Thickeners" in Example 6 and FIG. 10. The cellulose particles exhibit synergistic thickening. FIG. 10 shows blends of the cellulose particles (2 wt %) in water with, separately, 0.1% xanthan gum, 0.2%) methyl-hydroxyethyl cellulose, and 0.1% hydroxypropyl guar (percentages are solids of component based on total water content). Each component individually, provided minimal viscosity enhancement at the levels studied; however, the blends provided a 4-10 fold increase in the viscosity compared to the individual materials at the same levels. The same comparison was made using 3 wt % cellulose particles (combined with the same levels—0.1%, 0.2% and 0.1%—of the other three components), and the same trends were observed except each blend viscosity was a further 2-fold higher than those observed for the corresponding 2 wt % blends.

As shown in Table 18 below, small particle size cellulose particle were also directly compared to inorganic viscosifiers, and to the combination of the two.

TABLE 18

| Rheology at 120° F. | 7.8 PPB Small Particle Size Cellulose | 15 PPB Prehydrated Bentonite | 7.8 PPB Small Particle Size Cellulose + 15 PPB Prehydrated Bentonite |
| --- | --- | --- | --- |
| 600 RPM | ND | 25 | 42 |
| 300 RPM | ND | 19 | 36 |
| PV | ND | 6 | 6 |
| YP | ND | 13 | 30 |
| Gels | ND | 9/15 | 25/35 |
| 6 RPM | ND | 8 | 26 |
| 3 RPM | ND | 8 | 26 |
| LSYP | ND | 8 | 26 |

*ND for non-detect or too-low for accurate measurement

It can be seen that at 7.8 parts per barrel of cellulose particles, the viscosity is too low to detect (column 2). However, in combination with the prehydrated bentonite (inorganic viscosifier), there is a drastic increase (column 4) compared to the sum of the two viscosifiers individually (columns 2 and 3).

Example 13C: Thermal Stability

Particles comprising cellulose were formulated and tested as detailed above. Next, a 500 mL OFI testing equipment aging cell was filled with the sample to approximately 70% full (350 mL). The cell was closed and nitrogen pressurized to approximately 200 psig. Next, an OFI 4 Roller Oven was pre-heated to the required temperature. The cell was installed into the roller oven such that it could roll on the rollers. The start time was recorded. After the prescribed aging time, the cell was removed and the end time was recorded. The sample was allowed to air cool until ambient temperature was reached. The sample cell was depressurized and sample contents transferred back into the commercial milkshake mixing cup. The pH was then adjusted back to the starting point, as needed. Notably, pH control of the lab samples is essential for accurate readings. Finally, the steps detailed above were performed again and the rheology was re-measured at ambient pH. A sample undergoing these steps is "stable" if the rheology readings at 3 RPM and 6 RPM are between 50% and 250% of the starting readings.

The effectiveness of non-thermally-extended examples at 350° F. is shown in Table 19 below. Without wishing to be bound by theory, the data demonstrate that positive viscosity results in a concentrated brine environment. The data show that the fluid does not break down under high temperature conditions (350 F, 18 hours).

TABLE 19

| | Fresh H$_2$O | | 26% NaCl Brine | | 25% CaCl$_2$ Brine | |
|---|---|---|---|---|---|---|
| | BHR | AHR | BHR | AHR | BHR | AHR |
| 600 | 11 | 19 | 14 | 28 | 15 | 34 |
| 300 | 9 | 16 | 12 | 24 | 13 | 29 |
| PV | 2 | 3 | 2 | 4 | 2 | 5 |
| YP | 7 | 13 | 10 | 20 | 11 | 24 |
| Gels | 8/6 | 11/8 | 8/9 | 13/14 | 9/11 | 16/16 |
| 6 | 8 | 10 | 9 | 15 | 8 | 17 |
| 3 | 8 | 10 | 9 | 15 | 8 | 17 |
| LSYP | 8 | 10 | 9 | 15 | 8 | 17 |

BHR performed at 120° F. after mixing.
AHR performed at 120° F. after aging 18 hrs/350° F. then mixing, no pH adjustment.
*no thermal extender present.

An improvement in rheology is noted after thermally treating the material—this stands in stark contrast to competing bio-polymers which lose their viscosifying functionality after rolling at these conditions.

Example 13D: Combined Use with a Thermal Extender

In addition to the base material, particles comprising cellulose can be improved in much the same way as common drilling additives, by using commonly available thermal stabilizing agents, including magnesium oxide (MgO), monoethanolamine (MEA), citric acid, and formate solutions (Na$^+$, K$^+$, Cs$^+$).

The effectiveness of non-thermally-extended examples at 350° F. is shown in Table 20 below. Without wishing to be bound by theory, the data demonstrate that HTHP (high temperature, high pressure) fluid loss reducer shows chloride ion susceptibility, while viscosity performance is retained.

TABLE 20

| | Fresh H$_2$O | | 26% NaCl Brine | | 25% CaCl$_2$ Brine | |
|---|---|---|---|---|---|---|
| | BHR | AHR | BHR | AHR | BHR | AHR |
| 600 | 58 | 60 | 49 | 40 | 44 | 40 |
| 300 | 41 | 38 | 33 | 24 | 28 | 26 |
| PV | 17 | 22 | 16 | 16 | 16 | 14 |
| YP | 24 | 16 | 17 | 8 | 12 | 12 |
| Gels | 11/17 | 6/8 | 12/19 | 6/8 | 10/17 | 9/14 |
| 6 | 15 | 7 | 11 | 4 | 8 | 9 |
| 3 | 14 | 7 | 11 | 4 | 8 | 9 |
| LSYP | 13 | 7 | 11 | 4 | 8 | 9 |
| API | 10 mL | 11 mL | — | *30 mL | — | *35 mL |
| Filtrate | 2 mm | 1 mm | | 5 mm | | 5 mm |
| HPHT | — | 32 mL | — | — | — | — |
| (300° F./ | | 2 mL spurt | | | | |
| 500 psi) | | | | | | |

BHR performed at 120° F. after mixing.

AHR performed at 120° F. after aging 18 hrs/350° F. then mixing, no pH adjustment.

*no thermal extender present.

Example 13E: Salinity

To determine the effect of different salinities on the composition, the cellulose particles were added to different salt solutions (via the mixing method detailed above), as well as to fresh water, until the desired rheological behavior was observed. Following the original rheological testing, the samples were heat aged at 350° F. for 18 hrs and rheological behavior was again observed (see Table 19 above). The promising rheological improvements were maintained in each of the brine samples tested. Currently, data has been gathered for NaCl, KCl, and CaCl$_2$ solutions. Given the monovalent and divalent nature of the aforementioned brines, it is expected that any ionic salt solution should produce similar results. Thus, without wishing to be bound by theory, the cellulose particles are unaffected by any encountered dissolved minerals.

Example 13F: Effect of pH Levels

A set of samples were prepared at varying pH levels (pH of 8.2, 10.5, and 11.2) using the aforementioned methods (see Table 21 below). The samples were then aged as detailed above (350 F, 18 hours) and the viscosity was measured (at 120 F). During the heat aging the pH drifts lower. Following measurements, the pH of each sample was then modified (to 11.5) and viscosity measured again (at 120 F). These results indicate that the viscosifying properties of the cellulose particles can be modified as necessary by simply changing the pH of the mixture.

TABLE 21

| | pH of 8.2 (BHR) | | | pH of 10.5 (BHR) | | | pH of 11.2 (BHR) | | |
|---|---|---|---|---|---|---|---|---|---|
| | BHR | AHR | AHR @ pH = 11.5 | BHR | AHR | AHR @ pH = 11.5 | BHR | AHR | AHR @ pH = 11.5 |
| 600 | 11 | 19 | 24 | 14 | 28 | 19 | 15 | 34 | 18 |
| 300 | 9 | 16 | 21 | 12 | 24 | 16 | 13 | 29 | 15 |
| PV | 2 | 3 | 3 | 2 | 4 | 3 | 2 | 5 | 3 |
| YP | 7 | 13 | 18 | 10 | 20 | 13 | 11 | 24 | 12 |
| Gels | 8/6 | 11/8 | 14/12 | 8/9 | 13/14 | 11/8 | 9/11 | 16/16 | 8/7 |
| 6 | 8 | 10 | 14 | 9 | 15 | 10 | 8 | 17 | 9 |
| 3 | 8 | 10 | 14 | 9 | 15 | 10 | 8 | 17 | 9 |
| LSYP | 8 | 10 | 14 | 9 | 15 | 10 | 8 | 17 | 9 |

BHR performed at 120° F. after mixing.
AHR performed at 120° F. after aging 18 hrs/350° F. then mixing, no pH adjustment.

The data show that the rheology profile can be largely re-established by pH modification after the heat aging.

Example 13G: Emulsification

A quick test was performed using ice-melting rock salt brine (a mixture of NaCl, CaCl$_2$, and MgCl$_2$), the cellulose particles, bentonite, and diesel in a formulation with about 30 vol % brine and about 70 vol % diesel. The mixture was emulsified with a kitchen immersion blender and left to sit overnight. No settling became visible until close to 2 weeks of sitting at ambient temperature. Based on these results, the cellulose particles are likely a valuable emulsifying agent for non-aqueous fluids (e.g., oil-based fluids).

A quick acid-emulsion test was also performed, using 37% HCl solution and mineral oil, with and without small particle cellulose added as an emulsifying agent. To 40 mL of 37% HCl solution was added 40 mL of mineral oil (and no cellulose particles). The mixture was thoroughly agitated at 1800 RPM using a bench-top lab stirrer for approximately 1 minute. The sample was left to settle for 5 minutes on the bench-top. Following the 5 minute time, the sample was visually inspected and was observed to have separated into a mineral oil layer and an HCl solution layer, indicating a fast-settling emulsion. A similar sample was prepared with 40 mL of 37% HCl solution with another 40 mL of mineral oil again being added. To this sample was also added 7 mL of cellulose particle slurry (15% solid suspension of particles. This sample was again agitated at 1800 RPM for approximately 1 minute and then the agitator was removed. The sample was visually inspected after 1 hour and then 2.5 hrs with no visible separation of layers and then daily thereafter, again with no visible separation until day 4 when an approximately 5 mL layer was seen forming at the bottom of the container. The cellulose particles were able to stabilize the acid-emulsion over three days, and one would expect the cellulose particles to be effective in stabilizing oil/water emulsions in the acid environments often encountered in oil and gas operations.

Additionally, 240 mL of 25% CaCl2 brine was blended in a milkshake mixer with 160 mL of diesel, then poured into a beaker. Oil and water separation was readily apparent. The mixture was added back into the milkshake mixer and 50 g of wet particles comprising cellulose (6 PPB) were added to the mixture and stirred vigorously for 5 minutes. The mixture was again poured into a beaker and allowed to separate. After 1 hr, no separation was observed. After 5 hrs, a visible, but yet unquantifiable separation existed, and after 24 hrs, 20% separation was observed. Without wishing to be bound by theory, it is expected that higher concentrations will lead to a nearly "un-separable" emulsion.

Example 13H: Lubrication

Data was generated for oil and gas applications using a lubricity tester (see Table 22). Friction reductions quoted are versus a baseline of water. The first four data points are using particles comprising cellulose alone at varying concentrations. The last two samples are using particles comprising cellulose in combination with a commonly used liquid lubricant. The lubricity system circulates fluid between a stationary piece of Teflon and a rotating shaft. The shaft is connected to a force meter and the force required to turn at constant RPM is back-calculated to produce a coefficient of friction. Different additives may increase or decrease the friction coefficient. The meter used as an OFITE Extreme Pressure and Lubricity Tester at 60 RPM and 150 in-lb of torque.

TABLE 22

| Water | | [particles comprising cellulose] (wt %) | [Lubricant] (wt %) | % Friction reduction vs. water | | | Actual coefficients | | |
|---|---|---|---|---|---|---|---|---|---|
| | | | | 5 min | 10 min | 15 min | | | |
| 5 min | 0.33 | 2.5 | 0 | 15.5 | 11.5 | 17.1 | 0.270 | 0.308 | 0.290 |
| 10 min | 0.348 | 4.29 | 0 | 29.4 | 35.3 | 38.6 | 0.233 | 0.225 | 0.215 |
| 15 min | 0.35 | 5.63 | 0 | 41.0 | 46.5 | 48.6 | 0.195 | 0.186 | 0.180 |

TABLE 22-continued

| Water | [particles comprising cellulose] (wt %) | [Lubricant] (wt %) | % Friction reduction vs. water 5 min | 10 min | 15 min | Actual coefficients | | |
|---|---|---|---|---|---|---|---|---|
| | 7.1 | 0 | 58.2 | 61.2 | 63.1 | 0.138 | 0.135 | 0.129 |
| | 7.1 | 3 | 63.9 | 72.1 | 74.3 | 0.119 | 0.097 | 0.09 |
| | 7.1 | 5 | 76.4 | 75.9 | 77.4 | 0.078 | 0.084 | 0.079 |

The data show that aqueous solutions of cellulose particles are effective as lubricants, with lubricity increasing with increasing levels of the cellulose particles.

Example 13I: Bacteriostatic Properties

The bacteriostatic properties of the composition (aqueous solution of cellulose particles, 16% solids suspension) were evaluated as detailed below and as shown in Table 23. Briefly, a sample was inoculated with a known quantity of each organism. The sample was then measured and reported at t=0 to demonstrate that the organism got inoculated properly. The sample continued to be measured at periodic intervals and the quantity of each organism reported as time progressed.

TABLE 23

| | Control Growth | Sample Growth | % Decrease | Innoculum Level |
|---|---|---|---|---|
| Day 0 | | | | |
| Escherichia Coli | $154^4$ | $138^4$ | 10.39 | OK |
| Staphylococcus Aureus | $152^4$ | $144^4$ | 5.26 | OK |
| Pseudomonas Aeruginosa | $169^4$ | $162^4$ | 4.14 | OK |
| Candida Albicans | $100^4$ | $83^4$ | 17.00 | OK |
| Aspergillus Niger | $95^4$ | $71^4$ | 25.26 | OK |
| Day 7 | | | | |
| Escherichia Coli | | $119^4$ | 22.73 | |
| Staphylococcus Aureus | | $94^4$ | 38.16 | |
| Pseudomonas Aeruginosa | | $120^4$ | 28.99 | |
| Candida Albicans | | $69^4$ | 31.00 | |
| Aspergillus Niger | | $69^4$ | 27.37 | |
| Day 14 | | | | |
| Escherichia Coli | | $87^4$ | 43.51 | |
| Staphylococcus Aureus | | $90^4$ | 40.79 | |
| Pseudomonas Aeruginosa | | $114^4$ | 32.54 | |
| Candida Albicans | | $68^4$ | 32.00 | |
| Aspergillus Niger | | $70^4$ | 26.32 | |
| Day 21 | | | | |
| Escherichia Coli | | $74^4$ | 51.95 | |
| Staphylococcus Aureus | | $85^4$ | 44.08 | |
| Pseudomonas Aeruginosa | | $110^4$ | 34.91 | |
| Candida Albicans | | $67^4$ | 33.00 | |

TABLE 23-continued

| | Control Growth | Sample Growth | % Decrease | Innoculum Level |
|---|---|---|---|---|
| Aspergillus Niger | | $69^4$ | 27.37 | |
| Day 28 | | | | |
| Escherichia Coli | | $66^4$ | 57.14 | |
| Staphylococcus Aureus | | $72^4$ | 52.63 | |
| Pseudomonas Aeruginosa | | $74^4$ | 56.21 | |
| Candida Albicans | | $60^4$ | 40.00 | |
| Aspergillus Niger | | $68^4$ | 28.42 | |

The bacteria grow initially, but are not increasing in population, in fact they are actually decreasing (but not fast enough to be considered to act as a biocide). The cellulose particles are considered to be bacteriostatic, since the particles neither support the growth of bacteria, nor kill the bacteria fast enough to be considered to act as a biocide.

Example 14: Personal Care Applications

The particles comprising cellulose can be used, either alone or in combination with other components (e.g., in the form of the various other types of compositions described herein, such as a thickened composition, suspension, emulsion, and the like), as a personal care, beauty, or cosmetic product. The cellulose particles themselves can provide an exfoliating, softening, or other desirable property (such as a feeling of rejuvenation) to a composition containing them (e.g., as a suspension in water) when such a composition is applied to the skin (e.g., face, hands, feet, arms, legs, or any other skin on the body of a human or animal). In embodiments where the particles comprising cellulose further comprise lignin, or where lignin is present in the composition containing the particles comprising cellulose, the lignin also can provide (in conjunction with the cellulose particles) an exfoliating, softening, or other desirable property (such as a feeling of rejuvenation) to a composition containing such components.

The following formulations (Table 24) were assessed as cosmetic formulations, particularly as body scrub or facial scrub formulations:

TABLE 24

| Ingredient | 1 | 2 | 3 | 4 | 5 | 6 | 7 | 8 |
|---|---|---|---|---|---|---|---|---|
| Cellulose Particles (15% solids) | 99.00 | 98.85 | 80.05 | 78.05 | 95.00 | 95.00 | 57.55 | 63.05 |
| Glycerin | | | 10.00 | 10.00 | | 1.00 | 3.00 | 3.00 |
| Glycolic Acid (70%) | | | 2.85 | 2.85 | | | 2.85 | 2.85 |
| Potassium Hydroxide | | | 0.70 | 0.70 | | | 0.70 | 0.70 |
| Deionized Water | | | 5.00 | 5.00 | | | | |
| Xanthan Gum | | 0.15 | 0.40 | 0.40 | 0.15 | 0.15 | 0.40 | 0.40 |
| Sodium Hyaluronate | | | | | | | 2.00 | 2.00 |
| Algae Extract | | | | | | 1.00 | 4.00 | 4.00 |
| Trehalose | | | | | | 0.25 | 5.00 | 0.50 |
| Urea | | | | | | 0.25 | | |
| Caffeine | | | | | | | 0.50 | 0.50 |
| Acrylic Polymer | | | | | 0.30 | 0.30 | | |
| Argan Oil | | | | | | | 1.00 | 1.00 |
| Shea Butter | | | | | | | 5.00 | 2.00 |
| Coconut Oil | | | | | | | 10.00 | 10.00 |
| Caprylic Capric Trigyceride | | | | | | | 5.00 | 5.00 |
| Squalane | | | | | 3.55 | 1.05 | | |
| BT Resveratrol | | | | | | | 1.00 | 1.00 |
| BT White Tea | | | | | | | 1.00 | 1.00 |
| Biocide | 1.00 | 1.00 | 1.00 | 1.00 | 1.00 | 1.00 | 1.00 | 1.00 |
| Jojoba Esters | | | | 2.00 | | | | 2.00 |
| Ingredient | 1 | 2 | 3 | 4 | 5 | 6 | 7 | 8 |
| Total | 100.00 | 100.00 | 100.00 | 100.00 | 100.00 | 100.00 | 100.00 | 100.00 |
| pH | 3.62 | 3.62 | (~3.5) | 3.56 | (~3.5) | (~3.5) | (~3.5) | 3.42 |

Formulations 1-8 represent cosmetic formulations for skin, which, for example, may be used as skin conditioners, moisturizing lotions/creams and/or exfoliant formulations, such as a body scrub or facial scrub. Formulations 1 and 2 represent minimally formulated cosmetic formulations comprising the cellulose particles in aqueous suspension (15% solids). These formulations add only a biocide (at 1% level) or a biocide (1% level) and minor quantity of a thickener (at 0.15% level). Indeed, the suspension of cellulose particles functions as an exfoliant without additional compositional ingredients. Not shown above, the minimally formulated cosmetic formulations comprising the cellulose particles in aqueous suspension (similar to Formulations 1 and 2) were repeated with elevated levels of the occlusive agent squalane (e.g., at 25% w/w of squalane on the total composition), both with and without additional glycerin (at 10% w/w glycerin on the total composition). Formulations 3 and 4 add a chemical peel agent (glycolic acid), believed to generate an immune response that helps promote the growth of new skin cells for a rejuvenated skin, and formulation 4 additionally comprises a type of microbead which acts as a coarser exfoliant. Formulations 5-8 represent more fully formulated cosmetic formulations for skin comprising the cellulose particles and additional formulation ingredients including one or more of chemical peel agents (as in formulations 3 and 4), moisturizers (such as humectants), occlusive agents (such as oils and emollients, which act to prevent water from leaving the skin), antioxidants, and other ingredients known in the art for fine-tuning (such as texturizers/thickeners, and skin firming agents).

All of the formulations are suitable as skin care formulations, particularly as body wash, body scrub or facial scrub formulations. Formulations 5-8 (as well as the high squalane content formulations) successfully incorporated oils as occlusive agents without an added emulsifier; the particles comprising cellulose functioned as an emulsifier. Testers concluded that the formulations feel lighter and less greasy on the skin.

As discussed herein above, BB creams and CC creams are effectively lightly formulated moisturizers. The cellulose particles in aqueous suspension can be used in such formulations. Table 25, below, shows examples of BB creams with a sun protection factor (SPF) of approximately 20.

TABLE 25

| Ingredient | 1 | 2 | 3 | 4 | 5 |
|---|---|---|---|---|---|
| Cellulose Particles (15% solids) | 20.00 | 25.00 | 25.00 | 25.00 | 50.00 |
| Deionized Water | 41.67 | 36.67 | 35.07 | 36.37 | 9.87 |
| Glycerin | 2.00 | 2.00 | 2.00 | 2.00 | 2.00 |
| Butylene Glycol | 5.00 | 5.00 | 5.00 | 5.00 | 5.00 |
| Disodium EDTA | 0.10 | 0.10 | 0.10 | 0.10 | 0.10 |
| Ascorbyl Glucoside | 0.10 | 0.10 | 0.10 | 0.10 | 0.10 |
| Xanthan Gum | 0.40 | 0.40 | 0.40 | 0.70 | 0.70 |
| Sodium Polyacrylate | | 0.40 | 0.60 | | |
| Sodium Stearoyl Glutamate | 0.40 | | 0.40 | 0.40 | 0.40 |
| Caffeine | 0.10 | 0.10 | 0.10 | 0.10 | 0.10 |
| Hydrocarbon Emollients [1] | 8.00 | 8.00 | 8.00 | 8.00 | 8.00 |
| Octinoxate (OTC Drug Active Sunscreen) | 4.00 | 4.00 | 4.00 | 4.00 | 7.50 |
| Oil Phase Thickeners [2] | 3.00 | 3.00 | 3.00 | 3.00 | 3.00 |
| Nylon-12 | 2.00 | 2.00 | 2.00 | 2.00 | |
| Silicone Emollients [3] | 3.00 | 3.00 | 3.00 | 3.00 | 6.00 |
| Titanium Dioxide based OTC Drug Active Sunscreen | 3.00 | 3.00 | 3.00 | 3.00 | |
| Titanium Dioxide | 4.00 | 4.00 | 4.00 | 4.00 | 4.00 |
| Sodium Hyaluronate | 1.00 | 1.00 | 1.00 | 1.00 | 1.00 |
| Polysorbate 20 [4] | | 1.00 | | | |

US 12,558,303 B2

127

TABLE 25-continued

| Ingredient | 1 | 2 | 3 | 4 | 5 |
|---|---|---|---|---|---|
| Iron Oxide Pigments [5] | 1.23 | 1.23 | 1.23 | 1.23 | 1.23 |
| Biocide | 1.00 | 1.00 | 1.00 | 1.00 | 1.00 |
| Total | 100.00 | 100.00 | 100.00 | 100.00 | 100.00 |

[1] Hydrocarbon Emollients: equal parts Diisopropyl Adipate and Isohexadecane.
[2] Oil Phase Thickeners: 1% Cetyl Palmitate and 2% Stearyl Alcohol (% w/w of total composition).
3 Silicone Emollients: Dimethicone, except sample 5 (equal parts Dimethicone and a mixture of Cyclopentasiloxane and Dimethiconol).
[4] Non-ionic surfactant/emulsifier.
[5] Iron Oxide Pigments: 0.362% Red Iron Oxide, 0.684 Yellow Iron Oxide, 0.180 Black Iron Oxide (% w/w of total composition).

Samples 2 and 3 suffered a small amount of separation; without wishing to be bound by theory, it would seem that in this particular case the combination of solid pigment particles and the polyacrylate compromise the ability of the cellulose particles to stabilize the emulsion. Formulations 1, 4 and 5 are suitable as skin care formulations, particularly as BB Cream formulations. Advantageously, these BB Creams require only minimal amounts of an emulsifier/wetting agent (0.4% w/w sodium stearoyl glutamate), instead of the usual 5-10% levels traditionally required. These formulations may also be suitable as CC Cream formulations (generally intended as color correcting creams), either as currently formulated or with only minor tweaking (primarily with respect to the pigment content).

Although the BB Creams (and CC Creams) described above do provide some sun protection (SPF-20), they are generally not intended to be used as sunscreen lotions because they are generally tinted and may be applied in too thin a layer to be optimal for sun protection. However, appropriately formulated, the cellulose particles in aqueous suspension can also be used advantageously as sunscreen lotions or sprays. Table 26 shows formulations for SPF-30 sunscreen lotions.

128

The SPF-30 sunscreens were formulated by preparing, in two separate vessels and with rapid mixing, the aqueous phase ingredients (deionized water, disodium EDTA, AAVP and/or xanthan gum thickeners, glycerin, butylene glycol and aqueous suspension of cellulose particles) and the oil phase ingredients (by combining all sunscreen actives with mild heating to 60-80° C., followed by cooling to room temperature before adding the remaining oil phase ingredients, except the silicones, dimethicone and dimethiconol, and the biocide). At room temperature, the oil phase ingredients were added to the aqueous phase ingredients and immediately homogenized until uniform. Finally, the silicones and biocide were added.

Formulations 4 and 4PT were formulated and functioned as spray applied sunscreen lotions (with a viscosity of approximately 4700 mPa·s, TE at 3 rpm), whereas all of the other formulations were prepared as lotions to be hand-applied (with a viscosity of approximately 786000 mPa·s, TE at 3 rpm).

Formulations 4PT and 6PT were identical to formulations 4 and 6, respectively, except the cellulose particles described herein were replaced with commercially available microcrystalline cellulose having a broad particle size distribution and $d_{50}$ of about 35 μm. Both of these Comparative formulations (4PT and 6PT) failed the stability test—4PT separated catastrophically within 1 hour even prior to any heat or freeze-thaw stability tests; and 6PT separated during the mild heat stability test, the emulsions breaking upon mild heat in the oven (50° C.) almost immediately. All of the inventive samples passed the stability tests. Evidently, the small particle size cellulose particles act to stabilize the emulsion.

Table 27 shows formulations for SPF-50 mineral sunscreen lotions.

TABLE 26

| Ingredient | 1 | 2 | 3 | 4 | 4PT | 5 | 6 | 6PT |
|---|---|---|---|---|---|---|---|---|
| Cellulose Particles (15% solids) | 20.00 | 15.00 | 15.00 | 20.00 | | 20.00 | 20.00 | |
| Commercial MCC [1] (100% solids) | | | | | 3.00 | | | 3.00 |
| Deionized Water | 30.10 | 37.90 | 37.50 | 33.80 | 50.80 | 33.00 | 32.80 | 49.80 |
| Glycerin | 3.00 | 3.00 | 3.00 | 3.00 | 3.00 | 3.00 | 3.00 | 3.00 |
| Butylene Glycol | 5.00 | 5.00 | 5.00 | 5.00 | 5.00 | 5.00 | 5.00 | 5.00 |
| Disodium EDTA | 0.10 | 0.10 | 0.10 | 0.10 | 0.10 | 0.10 | 0.10 | 0.10 |
| AAVP Copolymer [2] | 0.80 | | | | | 0.50 | 0.70 | 0.70 |
| Xanthan Gum | | | 0.40 | 0.10 | 0.10 | 0.40 | 0.40 | 0.40 |
| Sunscreen Actives [3] | 32.00 | 27.00 | 27.00 | 27.00 | 27.00 | 27.00 | 27.00 | 27.00 |
| Phenyl Trimethicone | | 3.00 | 3.00 | | | | | |
| PPG-12/SMDI Copolymer | | | | 3.00 | 3.00 | 3.00 | 3.00 | 3.00 |
| Diisopropyl Adipate | 5.00 | 5.00 | 5.00 | 5.00 | 5.00 | 5.00 | 5.00 | 5.00 |
| Dimethicone | | | | 2.00 | 2.00 | 2.00 | 2.00 | 2.00 |
| Dimethicone and Dimethiconol | 3.00 | 3.00 | 3.00 | | | | | |
| Biocide | 1.00 | 1.00 | 1.00 | 1.00 | 1.00 | 1.00 | 1.00 | 1.00 |
| Total | 100.00 | 100.00 | 100.00 | 100.00 | 100.00 | 100.00 | 100.00 | 100.00 |

[1] Commercial MCC: Microcrystalline Cellulose from Blackburn Distributions (Nelson, Lancashire, UK), having a broad particle size distribution and $d_{50}$ of about 35 μm
[2] AAVP Copolymer Thickener: A copolymer of Ammonium Acryloyldimethyltaurate and vinylpyrrolidone (100% active ingredient).
[3] Sunscreen Actives: 10.00% Homomenthyl Salicylate, 3.00% Avobenzone, 5.00% Octyl Salicylate, 5.00% Octocrylene (except sample 1 has 10.00% Octocrylene), and 4.00% Isoamyl Laurate (% w/w of total composition).

129

TABLE 27

| Ingredient | 1 | 2 |
|---|---|---|
| Cellulose Particles (15% solids) | 20.00 | 20.00 |
| Deionized Water | 28.50 | 27.30 |
| Glycerin | 3.00 | 3.00 |
| Butylene Glycol | 5.00 | 5.00 |
| Disodium EDTA | 0.10 | 0.10 |
| AAVP Copolymer [1] | 0.50 | 0.50 |
| Xanthan Gum | 0.40 | 0.40 |
| Polysorbate 20 | | 0.50 |
| PPG-12/SMDI Copolymer | 3.00 | 3.00 |
| Diisopropyl Adipate | 5.00 | 5.00 |
| Sunscreen Mixture (1) [2] | 8.00 | 8.00 |
| Sunscreen Active Mixture (2) [3] | 20.00 | |
| Sunscreen Actives (3) [4] | | 11.00 |
| Caprylyl Methicone | 3.00 | 3.00 |

130

Higher SPF formulations generally have a higher organic content or a higher pigment content, or both, all of which present difficulties in formulating (higher levels of emulsifiers or dispersants are usually required and these result in a greasy or waxy feel to the applied skin surface). The use of the cellulose particles as emulsifier negates the need for a conventional emulsifier and the SPF-50 lotions are unusually light and do not leave a greasy or waxy feel after application to the skin. However, these formulations were not optimized for stability and they did separate during the heat aging stability test (50° C.).

Table 28, below, shows formulations for SPF-50 mineral sunscreen lotions.

TABLE 28

| Ingredient | 1 | 2 | 3 | 4 | 5 | 6 |
|---|---|---|---|---|---|---|
| Cellulose Particles (15% solids) | 20.00 | 20.00 | 20.00 | 20.00 | 34.10 | 39.10 |
| Deionized Water | 14.10 | 13.60 | 19.10 | 47.10 | | |
| Glycerin | 3.00 | 3.00 | 3.00 | 3.00 | 3.00 | 3.00 |
| Butylene Glycol | 5.00 | 5.00 | 5.00 | 5.00 | 5.00 | 5.00 |
| Disodium EDTA | 0.10 | 0.10 | 0.10 | 0.10 | 0.10 | 0.10 |
| Xanthan Gum | 0.50 | 0.50 | 0.50 | 0.50 | 0.50 | 0.50 |
| Sunscreen Mixture (1) [1] | 8.00 | 8.00 | 8.00 | | 8.00 | 8.00 |
| Sunscreen Mixture (2) [2] | 20.00 | 20.00 | 20.00 | | 20.00 | 20.00 |
| Sodium Stearoyl Glutamate | | 0.50 | | | | |
| Emollients [3] | 13.00 | 13.00 | 13.00 | 13.00 | 13.00 | 13.00 |
| Potassium Hydroxide | 0.05 | 0.05 | 0.05 | 0.05 | 0.05 | 0.05 |
| Citric Acid | 0.25 | 0.25 | 0.25 | 0.25 | 0.25 | 0.25 |
| Dimethicone | 2.00 | 2.00 | 2.00 | 2.00 | 2.00 | 2.00 |
| Dimethicone and Dimethiconol | 3.00 | 3.00 | 3.00 | 3.00 | 3.00 | 3.00 |
| Cyclopentasiloxane | | | 5.00 | 5.00 | | 5.00 |
| Cyclopentasiloxane and Polysilicone-11 | 10.00 | 10.00 | | | 10.00 | |
| Biocide | 1.00 | 1.00 | 1.00 | 1.00 | 1.00 | 1.00 |
| Total | 100.00 | 100.00 | 100.00 | 100.00 | 100.00 | 100.00 |

[1] Sunscreen Mixture (1): Titanium Dioxide, Silica, Glycerin - (70% TiO2)
[2] Sunscreen Mixture (2): Zinc Oxide, Water, Glycerin, Sodium Polyacrylate, Phenoxyethanol, Xanthan Gum, and Chlorphenesin - (50% ZnO)
[3] Emollients: 5.00% Caprylic/Capric Triglyceride, and 5.00% Diisopropyl Adipate, and 3.00% Isostearyl Palmitate.

TABLE 27-continued

| Ingredient | 1 | 2 |
|---|---|---|
| Potassium Hydroxide | 0.20 | 0.10 |
| Citric Acid | 0.30 | 0.10 |
| Dimethicone | 2.00 | 2.00 |
| Cyclopentasiloxane and Polysilicone-11 | | 10.00 |
| Biocide | 1.00 | 1.00 |
| Total | 100.00 | 100.00 |

[1] AAVP Copolymer Thickener: A copolymer of Ammonium Acryloyldimethyltaurate and vinylpyrrolidone (100% active ingredient).
[2] Sunscreen Mixture (1): Titanium Dioxide, Alumina, and Triethoxycaprylylsilane.
[3] Sunscreen Active Mixture (2): Zinc Oxide, Neopentyl Glycol Diheptanoate, Glyceryl Isostearate, Polyhydroxystearic acid, and Cetyl PEG/PPG-10/1 Dimethicone.
[4] Sunscreen Actives (3): Zinc Oxide and Hydrogen Dimethicone.

The SPF-50 sunscreen lotions were formulated in a manner similar to that described above by preparing, in two separate vessels and with rapid mixing, the aqueous phase ingredients and the oil phase ingredients, followed by adding the oil phase ingredients to the aqueous phase ingredients and immediately homogenizing until uniform. Finally, the silicones and biocide were added.

The SPF-50 mineral sunscreens were formulated as generally discussed above. The higher content of insoluble solids presents challenges in terms of achieving stable formulations free of traditional emulsifiers. However, stable formulations are possible by combining low levels of wetting agents/emulsifiers with the particles of cellulose described herein.

The SPF-50 mineral sunscreens were formulated as generally discussed above. The higher content of insoluble solids presents challenges in terms of achieving stable formulations free of traditional emulsifiers. However, stable formulations are possible by combining low levels of wetting agents/emulsifiers with the particles of cellulose described herein.

Table 29, below, shows formulations for re-texturizing eye cream formulations.

TABLE 29

| Ingredient | 1 | 2 | 3 | 4 | 5 | 6 |
|---|---|---|---|---|---|---|
| Cellulose Particles (15% solids) | 25.00 | 20.00 | 20.00 | 20.00 | 30.00 | 20.00 |
| Deionized Water | 18.10 | 21.60 | 20.05 | 19.80 | 10.10 | 19.10 |
| Glycerin | 6.00 | 6.00 | 6.00 | 6.00 | 6.00 | 6.00 |
| Butylene Glycol | 5.00 | 5.00 | 5.00 | 5.00 | 5.00 | 5.00 |
| Disodium EDTA | 0.10 | 0.10 | 0.10 | 0.10 | 0.10 | 0.10 |
| Sodium Benzoate | 0.20 | 0.20 | 0.20 | 0.20 | 0.20 | 0.20 |
| Potassium Sorbate | 0.10 | 0.10 | 0.10 | 0.10 | 0.10 | 0.10 |
| Sodium Stearoyl Glutamate | | 0.50 | 0.75 | 1.00 | 1.00 | |
| Caffeine | 0.50 | 0.50 | 0.50 | 0.50 | 0.50 | 0.50 |
| Skin Firming Active [1] | 5.00 | 5.00 | 5.00 | 5.00 | 5.00 | 5.00 |
| Titanium Dioxide | | 1.00 | 1.00 | 1.00 | 1.00 | 1.00 |
| Sodium Hyaluronate | 2.00 | 2.00 | 2.00 | 2.00 | 2.00 | 2.00 |
| Niacinamide | 1.00 | 1.00 | 1.00 | 1.00 | 1.00 | 1.00 |
| Hydrogenated Phospholipids | | | | | | 2.00 |
| Ethylhexyl Hydroxystearate | 3.00 | 3.00 | 3.00 | 3.00 | 3.00 | 3.00 |
| Silicone Emollients [2] | 31.50 | 31.50 | 31.50 | 31.50 | 31.50 | 31.50 |
| Cetyl PEG/PPG-10/ Dimethicone | 1.50 | 1.50 | 1.50 | 1.50 | 1.50 | 1.50 |
| Sodium Polyacrylate | | | 0.30 | 0.30 | | |
| Wetting Agent | | | 1.00 | 1.00 | 1.00 | 1.00 |
| Biocide | 1.00 | 1.00 | 1.00 | 1.00 | 1.00 | 1.00 |
| Total | 100.00 | 100.00 | 100.00 | 100.00 | 100.00 | 100.00 |

[1] Skin Firming Active: a mixture of glycols and synthetic peptides.
[2] Silicone Emollients: a mixture of cyclopentasiloxane, polysilicone-11, and dimethicone.

All of the retexturizing eye cream formulations shown in Table 29 were stable and appeared to have the appropriate texture and feel for eye cream products.

Table 30, below, shows formulations for a rejuvenating cellular serum.

TABLE 30

| Ingredient | 1 | 2 | 3 | 4 | 5 |
|---|---|---|---|---|---|
| Cellulose Particles (15% solids) | 20.00 | 20.00 | 20.00 | 20.00 | 20.00 |
| Deionized Water | 28.55 | 23.55 | 22.55 | 28.55 | 27.55 |
| Xanthan Gum | 0.20 | 0.20 | 0.20 | 0.20 | 0.20 |
| Glycerin | 10.00 | 10.00 | 10.00 | 10.00 | 10.00 |
| Butylene Glycol | 6.00 | 6.00 | 6.00 | 6.00 | 6.00 |
| Disodium EDTA | 0.10 | 0.10 | 0.10 | 0.10 | 0.10 |
| Glycolic Acid (70%) | 1.45 | 1.45 | 1.45 | 1.45 | 1.45 |
| Caffeine | 0.50 | 0.50 | 0.50 | 0.50 | 0.50 |
| Sodium Hyaluronate | 1.00 | 1.00 | 1.00 | 1.00 | 1.00 |
| Ascorbic Acid | 2.00 | 2.00 | 2.00 | 2.00 | 2.00 |
| Titanium Dioxide | | | 1.00 | | 1.00 |
| Hydrocarbon Emollients [1] | 10.00 | 10.00 | 10.00 | 10.00 | 10.00 |
| Squalane | 2.00 | 4.00 | 4.00 | 4.00 | 4.00 |
| Coconut Alkanes | 10.00 | | | | |
| Silicone Emollient (A) [2] | | 15.00 | 15.00 | | |
| Silicone Emollient (B) [3] | | | | 10.00 | 10.00 |
| Dimethyl Isosorbide | 5.00 | 3.00 | 3.00 | 3.00 | 3.00 |
| Salicylic Acid | 1.00 | 1.00 | 1.00 | 1.00 | 1.00 |
| Sodium Lactate | 1.20 | 1.20 | 1.20 | 1.20 | 1.20 |
| Biocide | 1.00 | 1.00 | 1.00 | 1.00 | 1.00 |
| Total | 100.00 | 100.00 | 100.00 | 100.00 | 100.00 |

[1] Hydrocarbon Emollients: diisopropyl adipate and ethylhexyl palmitate.
[2] Silicone Emollient (A): polysilicone-11 and coconut alkanes.
[3] Silicone Emollient (B): cyclopentasiloxane and polysilicone-11.

The rejuvenating cellular serum formulations shown in Table 30 were stable and appeared to have the appropriate texture and feel for cellular serum products. These products all contained 1% by weight, based on total weight of formulation, of salicylic acid (which is below the 2% by weight level that is normally considered useful for anti-acne type formulations). However, the formulation also contains glycolic acid, 1.45% level (so, greater than 2% level in combination), where the combination may provide the same effect or better than salicylic acid alone.

Table 31 shows formulations for an anti-acne serum.

TABLE 31

| Ingredient | 1 | 2 | 2B | 2C | 3 |
|---|---|---|---|---|---|
| Cellulose Particles (15% solids) | 20.00 | 20.00 | | | 20.00 |
| Traditional Emulsifier [1] | | | 5.00 | | |
| MCC (100% solids) [2] | | | | 3.00 | |
| Deionized Water | 28.60 | 37.50 | 52.50 | 54.50 | 40.10 |
| Xanthan Gum | 0.40 | 0.30 | 0.30 | 0.30 | 0.40 |
| Copolymer Thickener [3] | 0.40 | 0.40 | 0.40 | 0.40 | 0.70 |
| Glycerin | 3.00 | 3.00 | 3.00 | 3.00 | 3.00 |
| Butylene Glycol | 11.00 | 12.00 | 12.00 | 12.00 | 9.00 |
| Disodium EDTA | 0.10 | 0.10 | 0.10 | 0.10 | 0.10 |
| Glycolic Acid (70%) | 1.00 | | | | |
| Caffeine | 0.50 | 0.50 | 0.50 | 0.50 | 0.50 |
| Sodium Hyaluronate | 1.00 | 1.00 | 1.00 | 1.00 | 1.00 |
| Salicylic Acid | 2.00 | 2.00 | 2.00 | 2.00 | 2.00 |
| Hydrocarbon Emollients [4] | 9.00 | 9.00 | 9.00 | 9.00 | 9.00 |
| Silicone Emollient [5] | 20.00 | 10.00 | 10.00 | 10.00 | 10.00 |
| Dimethicone | 2.00 | 2.00 | 2.00 | 2.00 | 2.00 |
| Sodium Lactate | | 1.20 | 1.20 | 1.20 | 1.20 |
| Biocide | 1.00 | 1.00 | 1.00 | 1.00 | 1.00 |
| Total | 100.00 | 100.00 | 100.00 | 100.00 | 100.00 |

[1] Traditional Emulsifier: potassium cetyl phosphate and hydrogenated palm glycerides.
[2] Commercial MCC: Microcrystalline Cellulose from Blackburn Distributions (Nelson, Lancashire, UK), having a broad particle size distribution and $d_{50}$ of about 35 μm.
[3] Copolymer Thickener:
[4] Hydrocarbon Emollients: diisopropyl adipate and isoamyl laurate.
[5] Silicone Emollient: cyclopentasiloxane and polysilicone-11.

In Table 31, each of the five formulations contained 2% by weight, based on total weight of formulation, of salicylic acid, which is characteristic of an anti-acne serum. Formulation 1 separated during the heat aging stability test (50° C.). Formulations 2 and 3 were stable to separation, even through the heat aging stability test, and appeared to be suitable as anti-acne products. Formulations 2B and 2C were identically formulated to formulation 2, except the particles comprising cellulose of the invention (about 1 μm particle size) were replaced in 2B with a traditional emulsifier (5% by weight), and in 2C with a larger particle size microcrystalline cellulose (about 35 μm) at the same weight by solids as that used in formulation 2. Both 2B and 2C failed to form an emulsion, and were essentially separated immediately.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A personal care formulation comprising particles, wherein the particles:

comprise cellulose having a degree of polymerization ($DP_w$) of from 16 to 120;

have at least one selected from:

(a) a $d_{75}$ of less than 8 microns; and (b) a $d_{50}$ of 0.4 microns to 3 microns;

have an aspect ratio of 1 to 1.5; and have a non-spherical shape, wherein at least a portion of the cellulose is type-II cellulose, and wherein the ratio of type-II cellulose to type-I cellulose is at least 0.2.

2. The personal care formulation of claim 1, wherein the particles are present at a level of at least about 0.5 wt. % of particles based on the total weight of the personal care formulation.

3. The personal care formulation of claim 1, wherein the cellulose particles are present at a level of from about 0.5 to about 40.0 wt % of particles based on the total weight of the personal care formulation.

4. The personal care formulation of claim 1, wherein the personal care formulation further comprises pigment particles, filler or extender particles, polymer particles, beads, or a combination thereof.

5. The personal care formulation of claim 1, further comprising one or more additional thickeners, and wherein the resulting viscosity of the personal care formulation is at least 10% greater than the sum of: the viscosity of an otherwise identical personal care formulation comprising only the particles; and the viscosity of an otherwise identical personal care formulation comprising only the one or more additional thickeners.

6. The personal care formulation of claim 1, wherein the personal care formulation is a lotion, a cream, a serum, an ointment, a shampoo, a conditioner, a hairspray, a hair gel, a deodorant, a facial or body wash, a facial or body scrub, an exfoliant, an emollient, a moisturizer, a liquid soap, a bar soap, a foundation make-up, a BB cream, a CC cream, an eye cream, a sunscreen, an anti-acne serum or cream or lotion, a cellular serum or cream or lotion, a facial or body mask, a blush, an eyeshadow, a mascara, a lipstick, a lip balm, or a clay suspension, a kaolin suspension, or a mud suspension.

7. The personal care formulation of claim 1, wherein the personal care formulation further comprises one or more occlusive agents.

8. The personal care formulation of claim 7, wherein the one or more occlusive agents comprises one or more oils.

9. The personal care formulation of claim 1, wherein the personal care formulation further comprises an emollient.

10. The personal care formulation of claim 1, wherein the personal care formulation further comprises lignin.

11. The personal care formulation of claim 1, wherein the particles comprise:

at least about 70 wt % cellulose, and at least about 5% lignin.

12. The personal care formulation of claim 1, wherein the personal care formulation further comprises less than 1% lignin.

13. The personal care formulation of claim 1, wherein the personal care formulation is a skin care formulation.

14. The personal care formulation of claim 1, wherein the personal care formulation is a body scrub or a facial scrub formulation.

15. The personal care formulation of claim 1, wherein the personal care formulation is a lotion or a serum.

16. The personal care formulation of claim 1, wherein the personal care formulation is a moisturizer.

17. The personal care formulation of claim 1, wherein the personal care formulation is a facial or body wash.

18. The personal care formulation of claim 1, wherein the personal care formulation is an eye cream.

19. The personal care formulation of claim 1, wherein the personal care formulation is a facial or body mask.

20. A foam comprising particles, wherein the particles:

comprise cellulose having a degree of polymerization ($DP_w$) of from 16 to 120;

have at least one selected from:

(a) a $d_{75}$ of less than 8 microns; and (b) a $d_{50}$ of 0.5 microns to 3.0 microns;

have an aspect ratio of 1 to 1.5; and have a non-spherical shape, wherein at least a portion of the cellulose is type-II cellulose, wherein the ratio of type-II cellulose to type-I cellulose is at least 0.2, and wherein the foam is incorporated into a composition to provide structure to the composition.

21. The foam of claim 20, wherein the structure composition further comprises personal care ingredients selected from conditioners, moisturizers, emollients, occlusive agents, soaps, detergents, exfoliants, pigment particles, filler or extender particles, polymer particles, beads, and combinations thereof.

22. The foam of claim 20, wherein the structured composition is a cream, an ointment, a shampoo, a conditioner, a mousse hair treatment, a facial or body wash, an exfoliant, an emollient, a moisturizer, a liquid soap, a foundation make-up, a BB cream, a CC cream, an eye cream, a sunscreen, an anti-acne serum cream, a cellular cream, a facial or body mask, a blush, an eyeshadow, a lipstick, or a lip balm.

* * * * *